US008765404B2

(12) United States Patent
Stephanopoulos et al.

(10) Patent No.: US 8,765,404 B2
(45) Date of Patent: Jul. 1, 2014

(54) MICROBIAL ENGINEERING FOR THE PRODUCTION OF FATTY ACIDS AND FATTY ACID DERIVATIVES

(75) Inventors: Gregory Stephanopoulos, Winchester, MA (US); Syed Hussain Imam Abidi, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 374 days.

(21) Appl. No.: 13/039,227

(22) Filed: Mar. 2, 2011

(65) Prior Publication Data

US 2011/0223641 A1 Sep. 15, 2011

Related U.S. Application Data

(60) Provisional application No. 61/309,782, filed on Mar. 2, 2010.

(51) Int. Cl.
| | |
|---|---|
| C12P 7/64 | (2006.01) |
| C12P 1/02 | (2006.01) |
| C12P 1/04 | (2006.01) |
| C12P 1/06 | (2006.01) |
| C12N 15/81 | (2006.01) |
| C12N 1/00 | (2006.01) |
| C12N 15/63 | (2006.01) |
| C12N 5/10 | (2006.01) |

(52) U.S. Cl.
USPC ........... 435/41; 435/70.1; 435/71.1; 435/170; 435/171; 435/252.1; 435/252.8; 435/253.3; 435/253.5; 435/255.1; 435/255.2; 435/255.5; 435/255.6; 435/256.1; 435/256.7

(58) Field of Classification Search
None
See application file for complete search history.

(56) References Cited

U.S. PATENT DOCUMENTS

| | | | |
|---|---|---|---|
| 5,057,419 A | 10/1991 | Martin et al. | |
| 2006/0035351 A1 | 2/2006 | Zhu et al. | |
| 2008/0153141 A1 | 6/2008 | Seip et al. | |
| 2011/0177564 A1 | 7/2011 | Stephanopoulos | |
| 2013/0143282 A1 | 6/2013 | Stephanopoulos et al. | |
| 2013/0344548 A1 | 12/2013 | Stephanopoulos et al. | |

FOREIGN PATENT DOCUMENTS

| | | |
|---|---|---|
| CN | 1653174 A | 8/2005 |
| WO | WO 03/095655 A2 | 11/2003 |
| WO | WO 2004/104167 A2 | 12/2004 |
| WO | WO 2005/118814 A2 | 12/2005 |
| WO | WO 2006/052814 A2 | 5/2006 |
| WO | WO 2008/025068 A1 | 3/2008 |
| WO | WO 2011/109548 A2 | 9/2011 |

OTHER PUBLICATIONS

Chellappa et al. (J. Biol. Chem, 2001, 276: 43548-43556).*
Cadoret et al., [Lipid biofuel production with microalgae: potential and challenges]. J Soc Biol. 2008;202(3):201-11. doi: 10.1051/jbio:2008022. Epub Nov. 4, 2008. French. English abstract provided.
Cao et al., Increasing unsaturated fatty acid contents in *Escherichia coli* by coexpression of three different genes. Appl Microbiol Biotechnol. Jun. 2010;87(1):271-80. doi: 10.1007/s00253-009-2377-x. Epub Feb. 5, 2010.
Gouveia et al., Microalgae as a raw material for biofuels production. J Ind Microbiol Biotechnol. Feb. 2009;36(2):269-74. doi: 10.1007/s10295-008-0495-6. Epub Nov. 4, 2008.
Grimard et al., siRNA screening reveals JNK2 as an evolutionary conserved regulator of triglyceride homeostasis. J Lipid Res. Nov. 2008;49(11):2427-40. doi:10.1194/jlr.M800168-JLR200. Epub Jul. 8, 2008.
Holz et al., Aconitase overexpression changes the product ratio of citric acid production by *Yarrowia lipolytica*. Appl Microbiol Biotechnol. Jan. 2009;81(6):1087-96. doi: 10.1007/s00253-008-1725-6. Epub Oct. 11, 2008.
Jones et al., Adipose tissue stearoyl-CoA desaturase mRNA is increased by obesity and decreased by polyunsaturated fatty acids. Am J Physiol. Jul. 1996;271(1 Pt 1):E44-9. Abstract only.
Kerscher et al., The complete mitochondrial genome of *Yarrowia lipolytica*. Comp Funct Genomics. 2001;2(2):80-90.
Laoteng et al., *Mucor rouxii* delta9-desaturase gene is transcriptionally regulated during cell growth and by low temperature. Mol Cell Biol Res Commun. Apr. 1999;1(1):36-43. Abstract only.
Laoteng et al., delta(6)-desaturase of *Mucor rouxii* with high similarity to plant delta(6)-desaturase and its heterologous expression in *Saccharomyces cerevisiae*. Biochem Biophys Res Commun. Dec. 9, 2000;279(1):17-22.
Lasserre et al., First complexomic study of alkane-binding protein complexes in the yeast *Yarrowia lipolytica*. Talanta. Feb. 15, 2010;80(4):1576-85. doi:10.1016/j.talanta.2009.07.016. Epub Jul. 10, 2009. Abstract only.
Lee-Young et al., Carbohydrate ingestion does not alter skeletal muscle AMPK signaling during exercise in humans. Am J Physiol Endocrinol Metab. Sep. 2006;291(3):E566-73. Epub May 2, 2006.
Li et al. Perspectives of microbial oils for biodiesel production. Appl Microbiol Biotechnol. Oct. 2008;80(5):749-56. Epub Aug. 9, 2008.
Li et al., Partial characterization of a cDNA for human stearoyl-CoA desaturase and changes in its mRNA expression in some normal and malignant tissues. Int J Cancer. May 1, 1994;57(3):348-52.
Lu et al., Overproduction of free fatty acids in *E. coli*: implications for biodiesel production. Metab Eng. Nov. 2008;10(6):333-9. doi:10.1016/j.ymben.2008.08.006. Epub Sep. 9, 2008.
Martin et al., Regulation of long chain unsaturated fatty acid synthesis in yeast. Biochim Biophys Acta. Mar. 2007;1771(3):271-85. Epub Jul. 13, 2006.

(Continued)

Primary Examiner — Suzanne M Noakes
Assistant Examiner — Jae W Lee
(74) Attorney, Agent, or Firm — Wolf, Greenfield & Sacks, P.C.

(57) ABSTRACT

Some aspects of this invention relate to methods useful for the conversion of a carbon source to a biofuel or biofuel precursor using engineered microbes. Some aspects of this invention relate to the discovery of a key regulator of lipid metabolism in microbes. Some aspects of this invention relate to engineered microbes for biofuel or biofuel precursor production.

22 Claims, 14 Drawing Sheets

(56) References Cited

OTHER PUBLICATIONS

Ntambi et al., Regulation of stearoyl-CoA desaturases and role in metabolism. Prog Lipid Res. Mar. 2004;43(2):91-104.

Ntambi, Regulation of stearoyl-CoA desaturase by polyunsaturated fatty acids and cholesterol. J Lipid Res. Sep. 1999;40(9):1549-58.

Papanikolaou et al., Single cell oil production by *Yarrowia lipolytica* growing on an industrial derivative of animal fat in batch cultures. Appl Microbiol Biotechnol. Mar. 2002;58(3):308-12. Epub Dec. 11, 2001.

Ratledge, Regulation of lipid accumulation in oleaginous micro-organisms. Biochem Soc Trans. Nov. 2002;30(Pt 6):1047-50.

Schweizer et al., Genetic control of *Yarrowia lipolytica* fatty acid synthetase biosynthesis and function. J Basic Microbiol. 1988;28(5):283-92. Abstract only.

Sessler et al., Regulation of stearoyl-CoA desaturase 1 mRNA stability by polyunsaturated fatty acids in 3T3-L1 adipocytes. J Biol Chem. Nov. 22, 1996;271(47):29854-8.

Shimano, Sterol regulatory element-binding protein family as global regulators of lipid synthetic genes in energy metabolism. Vitam Horm. 2002;65:167-94. Abstract only.

Sokolova et al., Laser-induced liquid bead ion desorption-MS of protein complexes from blue-native gels, a sensitive top-down proteomic approach. Proteomics. Apr. 2010;10(7):1401-7. Epub Feb. 1, 2010.

Tabor et al., Identification of conserved cis-elements and transcription factors required for sterol-regulated transcription of stearoyl-CoA desaturase 1 and 2. J Biol Chem. Jul. 16, 1999;274(29):20603-10.

Tehlivets et al., Fatty acid synthesis and elongation in yeast. Biochim Biophys Acta. Mar. 2007;1771(3):255-70. Epub Jul. 21, 2006.

Zanghellini et al., Quantitative modeling of triacylglycerol homeostasis in yeast—metabolic requirement for lipolysis to promote membrane lipid synthesis and cellular growth. FEBS J. Nov. 2008;275(22):5552-63. doi: 10.1111/j.1742-4658.2008.06681.x.

Zhang et al., Human stearoyl-CoA desaturase: alternative transcripts generated from a single gene by usage of tandem polyadenylation sites. Biochem J. May 15, 1999;340 ( Pt 1):255-64.

Zhang et al., Isolation and characterization of the human stearoyl-CoA desaturase gene promoter: requirement of a conserved CCAAT cis-element. Biochem J. Jul. 1, 2001;357(Pt 1):183-93.

Aguilar et al., Control of fatty acid desaturation: a mechanism conserved from bacteria to humans. Mol Microbiol. Dec. 2006;62(6):1507-14.

Andreishcheva et al., Adaptation to salt stress in a salt-tolerant strain of the yeast *Yarrowia lipolytica*. Biochemistry (Mosc). Sep. 1999;64(9):1061-7.

Beopoulos et al., Control of lipid accumulation in the yeast *Yarrowia lipolytica*. Appl Environ Microbiol. Dec. 2008;74(24):7779-89. Epub Oct. 24, 2008.

Beopoulos et al., *Yarrowia lipolytica* as a model for bio-oil production. Prog Lipid Res. Nov. 2009;48(6):375-87. Epub Aug. 29, 2009.

Frey et al., Bacterial hemoglobins and flavohemoglobins: versatile proteins and their impact on microbiology and biotechnology. FEMS Microbiol Rev. Oct. 2003;27(4):525-45.

Martin et al., Yeast desaturases. Biochem Soc Trans. Nov. 2002;30(Pt 6):1080-2.

Miyazaki et al., Identification of mouse palmitoyl-coenzyme A Delta9-desaturase. J Lipid Res. Apr. 2006;47(4):700-4. Epub Jan. 27, 2006.

Polashock et al., Expression of the Yeast Delta-9 Fatty Acid Desaturase in *Nicotiana tabacum*. Plant Physiol. Oct. 1992;100(2):894-901.

Rodríguez-Vargas et al., Fluidization of membrane lipids enhances the tolerance of *Saccharomyces cerevisiae* to freezing and salt stress. Appl Environ Microbiol. Jan. 2007;73(1):110-6. Epub Oct. 27, 2006.

Sheehan et al., A look back at the U.S. Department of Energy's Aquatic Species Program: biodiesel from algae. Close-out report. National Renewable Energy Laboratory. Jul. 1998: i-294. Accessed from www.nrel.gov/biomass/pdfs/24190.pdf on Oct. 19, 2011.

Stukey et al., The OLE1 gene of *Saccharomyces cerevisiae* encodes the delta 9 fatty acid desaturase and can be functionally replaced by the rat stearoyl-CoA desaturase gene. J. Biol Chem. Nov. 25, 1990;265(33):20144-9.

\* cited by examiner

A

B

MICROBIAL ENGINEERING FOR THE PRODUCTION OF FATTY ACIDS AND FATTY ACID DERIVATIVES

RELATED APPLICATION

This application claims priority under 35 U.S.C. §119(e) to U.S. provisional patent application Ser. No. 61/309,782, filed Mar. 2, 2010, the entire contents of which are incorporated herein by reference.

FEDERALLY SPONSORED RESEARCH

This invention was made with government support under Grant No. DE-FC36-07GO17058 awarded by the Department of Energy. The government has certain rights in this invention.

FIELD OF THE INVENTION

The invention, at least in part, relates to the field of converting a carbohydrate source into a biofuel or a biofuel precursor, for example, a fatty acid or fatty acid derivative, such as a triacylglycerol, using an engineered cell or microbe.

BACKGROUND OF THE INVENTION

Sustainably produced biofuels are an alternative to fossil fuels and may help to alleviate the depletion of easily accessible fossil fuel stocks while avoiding fossil fuel-associated pollution and greenhouse gas emission, thus satisfying a rising demand for affordable energy in a sustainable way. However, the widespread implementation of biofuel production has been thwarted by several drawbacks of current production methods, for example the competition of biofuel-producing plants with food crops for agriculturally valuable acreage, or the use of industrial substrates with only limited supply as carbon sources.

SUMMARY OF THE INVENTION

The growing concerns over the sustainability and renewability of fossil fuels have led to the development of a wide spectrum of alternative biofuels of various origins, including lipids synthesized from renewable resources by microbes such as bacteria or yeast. Lipids useful as biofuel or biofuel precursors include, for example, fatty acids and their derivatives (e.g., triacylglycerols).

The economical viability of microbe-synthesized biofuels or biofuel precursors is dependent on employing a suitable microbe of a phenotype including a combination of multiple beneficial traits, for example, a metabolism allowing for efficient carbon to biofuel or biofuel precursor conversion, high biomass formation rate, high productivity of biofuel or biofuel precursor, high levels of intracellular accumulation or secretion of biofuel or biofuel precursor, good tolerance to feedstock (carbon source and associated substances) and synthesized product (e.g., fatty acid or triacylglycerol), and stability of the biofuel or biofuel precursor, for example, at low carbon source concentrations. The conversion yield (gram of oil produced per gram of substrate, e.g., glucose) is of particular importance. Microbes commonly employed in biofuel or biofuel precursor production do not conform to the required phenotype in a way sufficient to allow for economical industrial-scale production of biofuel.

Some aspects of this invention relate to the engineering of required traits in a microorganism for biofuel or biofuel precursor production. While lipid and fatty acid metabolism has been studied in microbes from the 1930s and 1940s onward (see, e.g. Woodbine, M. 1959, *Microbial fat: Microorganisms as potential fat producers*. Prog. Ind. Microbiol. 1:181), little progress has been made toward engineering desirable phenotypes related to biofuel production in microbes despite numerous efforts to genetically engineer a microbe or to optimize the conditions of the production process. So far, genetic engineering efforts have mainly been directed to the manipulation of a gene target upstream of or within the fatty acid synthesis pathway and the optimization of fermentation or growth conditions, for example, by supplementing growth media with fatty acids.

One major obstacle to genetic engineering of microbes is the lack of genomic information and annotation of key metabolic pathway regulators in target microbes, for example, in oleaginous yeast. As a result, functional identification and annotation of a key regulator governing carbohydrate to lipid conversion is still lacking in microbes for biofuel production.

Some aspects of this invention relate to the identification of the oleaginous yeast *Y. lipolytica* as a microbe for biofuel or biofuel precursor production. Some aspects of this invention relate to the discovery of a key regulator of fatty acid metabolism in a microbe. Some aspects of this invention relate to the discovery of stearoyl-CoA desaturase (SCD) as a key regulator of carbohydrate to lipid conversion in a microbe. Some aspects of this invention relate to an isolated nucleic acid encoding a key regulator of fatty acid metabolism in a microbe. Some aspects of this invention provide an isolated nucleic acid encoding a key regulator of fatty acid metabolism, for example, a SCD gene product, of an oleaginous microbe.

Some aspects of this invention relate to the engineering of a microbe for the production of biofuel by manipulating the activity of a regulator of fatty acid metabolism, for example, by genetic manipulation. Some aspects of this invention relate to an isolated microbe engineered for biofuel or biofuel precursor production. Some aspects of this invention relate to an isolated microbe optimized for the conversion of a carbohydrate source to a biofuel or biofuel precursor, for example, an oleaginous microbe comprising an increased activity of a SCD gene product. Some aspects of this invention relate to a culture of a microbe engineered for biofuel or biofuel precursor production. Some aspects of this invention relate to methods of converting a carbohydrate source into a fatty acid or fatty acid derivative using a microbe engineered for biofuel production. Some aspects of this invention relate to a bioreactor for carbohydrate to fatty acid or fatty acid derivative conversion using a microbe engineered for biofuel production. Some aspects of this invention provide a method to convert a carbohydrate source, at least partially, into a biofuel or biofuel precursor using an engineered microbe.

Some aspect of this invention relate to an isolated oleaginous cell, comprising a genetic modification that increases expression of one or more genes chosen from the group of Hemoglobin, Cytochrome, GLUT, Malic Enzyme, ACC, SCD, FAA1, ACS, ACS2, FAT1, FAT2, PCS60, ACLY, FAS, Acyl-CoA synthetase, Pyruvate carboxylase, and AMPK genes, and/or a genetic modification that reduces expression of a gene chosen from the group of JNK2 and delta-12 desaturase. In some embodiments, the isolated oleaginous cell comprises a nucleic acid construct comprising (a) an expression cassette comprising a nucleic acid encoding the gene product under the control of a suitable homologous or heterologous promoter; (b) an expression cassette comprising a nucleic acid encoding an interfering RNA targeting the gene product under the control of a heterologous promoter; and/or (c) a nucleic acid construct inserted into the genome of the cell, the construct comprising a nucleic acid sequence that increases or decreases the expression of the gene product. In some embodiments, the heterologous promoter is an inducible or a constitutive promoter. In some embodiments, the nucleic acid construct inhibits or disrupts the natural regulation of a native gene encoding the gene product resulting in overexpression of the native gene. In some embodiments, the nucleic acid construct inhibits or abolishes expression of the native gene. In some embodiments, inhibition or disruption of the natural regulation of the native gene is mediated by deletion, disruption, mutation and/or substitution of a regulatory region, or a part of a regulatory region regulating expression of the gene, or inhibition or abolition of the expression of a native gene is mediated by deletion, disruption, mutation and/or substitution of a coding sequence of the native gene, or of a regulatory region, or a part of a regulatory region regulating expression of the native gene. In some embodiments, the decreased expression of the JNK2 and/or delta-12 desaturase gene is mediated by constitutive or inducible expression of a nucleic acid targeting a JNK2 and/or delta-12 desaturase gene product and inhibiting the expression of the gene. In some embodiments, the nucleic acid targeting the JNK2 and/or delta-12 desaturase transcript inhibits expression of the transcript via an RNAi pathway. In some embodiments, the nucleic acid targeting the JNK2 and/or delta-12 desaturase transcript is an siRNA, an shRNA, or a microRNA. In some embodiments, a decrease of expression of JNK2 or delta-12 desaturase is achieved by knocking out the wild type gene in the microbe, for example, by homologous recombination of a nucleic acid construct, e.g., a targeting vector, with the genomic JNK2 or delta-12 desaturase locus, thus disrupting the expression of the wild type gene. In some embodiments, the nucleic acid construct is inserted into the genome of the cell. In some embodiments, the increased or decreased expression of the gene product confers a beneficial phenotype for the conversion of a carbohydrate source to a fatty acid, fatty acid derivative and/or TAG to the cell. In some embodiments, the beneficial phenotype is a modified fatty acid profile, a modified triacylglycerol profile, an increased fatty acid and/or triacylglycerol synthesis rate, an increase conversion yield, an increased triacylglycerol accumulation in the cell, and an increased tolerance of osmotic stress, an increased proliferation rate, an increased cell volume, and/or an increased tolerance of a substance at a concentration lethal to and/or inhibiting proliferation of unmodified cells of the same cell type, by the cell. In some embodiments, the modified fatty acid profile or the modified triacylglycerol profile of the cell exhibits at least a 2-fold increase of the ratio of C18 fatty acids over C16 fatty acids as compared to unmodified cells of the same cell type. In some embodiments, the modified fatty acid profile or the modified triacylglycerol profile of the cell exhibits at least an 2.5-fold increase of the ratio of C18 fatty acids over C16 fatty acids as compared to unmodified cells of the same cell type. In some embodiments, the modified fatty acid profile or the modified triacylglycerol profile of the cell exhibits at least a 5-fold increase of the ratio of C18 fatty acids over C16 fatty acids as compared to unmodified cells of the same cell type. In some embodiments, the modified fatty acid profile or the modified triacylglycerol profile of the cell exhibits at least a 6.5-fold increase of the ratio of C18 fatty acids over C16 fatty acids as compared to unmodified cells of the same cell type. In some embodiments, the cell is viable under conditions of osmotic stress lethal to unmodified cells. In some embodiments, the cell is viable under conditions of osmotic stress at a level of 200% of the highest level tolerated by unmodified cells. In some embodiments, the cell is viable under conditions of osmotic stress at a level of 300% of the highest level tolerated by unmodified cells. In some embodiments, the cell is viable under conditions of osmotic stress at a level of 400% of the highest level tolerated by unmodified cells. In some embodiments, the cell proliferation rate is at least 5-fold, at least 10-fold, at least 20-fold, at least 25-fold, or at least 30-fold increased as compared to unmodified cells of the same cell type. In some embodiments, the volume of the cell is at least 2-fold increased as compared to unmodified cells of the same cell type. In some embodiments, the cell tolerates a substance at a concentration lethal to and/or inhibiting proliferation of unmodified cells of the same cell type. In some embodiments, the substance is a fermentable sugar and the concentration is at least 80 g/l, at least 100 g/l, at least 150 g/l, at least 200 g/l, at least 300 g/l. In some embodiments, the synthesis rate of a fatty acid or a triacylglycerol of the cell is at least 5-fold, or at least 10-fold, increased as compared to unmodified cells of the same cell type. In some embodiments, the cell converts a carbohydrate source to a fatty acid or a triacylglycerol at a conversion rate of at least about 20 g/g, at least about 25 g/g, or at least about 30 g/g. In some embodiments, the cell is a prokaryotic cell or a eukaryotic cell. In some embodiments, the cell is a bacterial cell, an algal cell, a fungal cell, or a yeast cell. In some embodiments, the cell is an oleaginous yeast cell. In some embodiments, the cell is a *Y. lipolytica* cell.

Some aspects of this invention relate to a culture, comprising an isolated oleaginous cell, comprising a genetic modification that increases expression of one or more genes chosen from the group of Hemoglobin, Cytochrome, GLUT, Malic Enzyme, ACC, SCD, FAA1, ACS, ACS2, FAT1, FAT2, PCS60, ACLY, FAS, Acyl-CoA synthetase, Pyruvate carboxylase, and AMPK genes, and/or a genetic modification that reduces expression of a JNK2 and/or delta-12 desaturase gene product, and a carbohydrate source. In some embodiments, the isolated oleaginous cell is an engineered microbe as provided herein. In some embodiments, the carbohydrate source is a fermentable sugar. In some embodiments, the carbohydrate source is a monomeric sugar. In some embodiments, the carbohydrate source is glucose and glycerol. In some embodiments, the carbohydrate source is not sterilized. In some embodiments, the culture is maintained under non-sterile conditions. In some embodiments, the culture does not comprise an antibiotic or antiproliferative agent selective for the isolated oleaginous cell. In some embodiments, the carbohydrate source is derived from plant or algal biomass. In some embodiments, the carbohydrate source is derived from cellulose, hemi-cellulose, starch, glycerol, or a derivative thereof. In some embodiments, the culture further comprises a cellulose- or hemi-cellulose-hydrolyzing enzyme. In some embodiments, the biomass or the cellulose or hemi-cellulose is pretreated in a hot water or dilute acid or ammonia fiber expansion procedure, with a hydrolyzing enzyme, with a steam pre-treatment, and/or a lime pre-treatment. In some embodiments, the culture comprises a substance at a concentration lethal to unmodified wild type, unmodified cells of the same cell type as the isolated oleaginous cell. In some embodiments, the substance is a toxic substance generated during pretreatment of the carbohydrate source such as acetic acid, furfural or aromatic compounds. In some embodiments, the substance is the carbohydrate source. In some embodiments, the substance is a fermentable sugar. In some embodiments, the substance is a monomeric sugar. In some embodiments, the culture comprises the fermentable sugar at a concentration of at least 80 g/l, at least 100 g/l, at least 150 g/l, at least 200 g/l, at least 250 g/l, or at least 300 g/l.

Some aspects of this invention relate to a method, comprising contacting a carbohydrate source with an isolated oleaginous cell, the cell comprising a genetic modification that increases expression of one or more genes chosen from the group of Hemoglobin, Cytochrome, GLUT, Malic Enzyme, ACC, SCD, FAA1, ACS, ACS2, FAT1, FAT2, PCS60, ACLY, FAS, Acyl-CoA synthetase, Pyruvate carboxylase, and AMPK gene products, and/or a genetic modification that reduces expression of a JNK2 and/or a delta-12 desaturase gene, and incubating the carbohydrate source contacted with the cell under conditions suitable for at least partial conversion, of the carbohydrate source into a fatty acid or a triacylglycerol by the cell. In some embodiments, the isolated oleaginous cell is an engineered microbe as provided herein. In some embodiments, the carbohydrate source is a sugar, such as glucose, xylose etc or starches derived from plant or algal biomass. In some embodiments, the carbohydrate source is derived from cellulose or hemi-cellulose. In some embodiments, the carbohydrate source is contacted with the cell in the presence of a cellulose- or hemi-cellulose-hydrolyzing enzyme. In some embodiments, the carbohydrate source is contacted with the cell in the presence of about 15 IU of cellulose- or hemi-cellulose-hydrolyzing enzyme per g of biomass at 55° C. for 48 hours. In some embodiments, the biomass or the cellulose or hemi-cellulose is pretreated with hot water or dilute acid or ammonia fiber expansion procedure and/or a hydrolyzing enzyme. In some embodiments, the carbohydrate source contacted with the isolated oleaginous cell comprises a substance at a concentration lethal to unmodified cells of the same cell type as the isolated oleaginous cell. In some embodiments, the substance is a toxic substance generated during pretreatment of the carbohydrate source, for example, acetic acid. In some embodiments, the substance is the carbohydrate source. In some embodiments, the carbohydrate source is a fermentable sugar and the concentration of the fermentable sugar is at least 80 g/l, at least 100 g/l, at least 200 g/l, or at least 300 g/l after contacting with the oleaginous cell. In some embodiments, the carbohydrate source is contacted with the isolated oleaginous cell under non-sterile conditions. In some embodiments, the carbohydrate source contacted with the isolated oleaginous cell is incubated under non-sterile conditions. In some embodiments, the carbohydrate source contacted with the isolated oleaginous cell is incubated in an open reactor. In some embodiments, the carbohydrate source is contacted with the isolated oleaginous cell and incubated for conversion of the carbohydrate source to a fatty acid or a triacylglycerol in a fed batch process. In some embodiments, the carbohydrate source is contacted with the isolated oleaginous cell and incubated for conversion of the carbohydrate source to a fatty acid or a triacylglycerol in a continuous process. In some embodiments, the fatty acid or the triacylglycerol is extracted from the carbohydrate source contacted with the isolated oleaginous cell by solvent extraction. In some embodiments, the solvent extraction is a solvent hexane extraction. In some embodiments, the fatty acid or the triacylglycerol is separated from the carbohydrate source contacted with the isolated oleaginous cell and subsequently refined by transesterification.

Some aspects of this invention relate to a method, comprising modifying the fatty acid profile, the triacylglycerol profile, the fatty acid synthesis rate, the triacylglycerol synthesis rate, the extent of fatty acid derivative accumulation in the cell, the rate of fatty acid derivative secretion, the rate of carbohydrate to fatty acid or fatty acid derivative conversion, the efficient yield of carbohydrate to fatty acid or fatty acid derivative conversion, the tolerance of osmotic stress, the proliferation rate, the cell volume, or the tolerance of a toxic substance of a cell for use in the conversion of a carbohydrate source into a fatty acid or triacylglycerol by increasing the expression of one or more gene product(s) chosen from the group of Hemoglobin, Cytochrome, GLUT, Malic Enzyme, ACC, SCD, FAA1, ACS, ACS2, FAT1, FAT2, PCS60, ACLY, FAS, and AMPK gene products, and/or decreasing expression of a JNK2 and/or a delta-12 desaturase gene. In some embodiments, modifying the fatty acid profile, the triacylglycerol profile, the fatty acid synthesis rate, the triacylglycerol synthesis rate, the extent of fatty acid derivative accumulation in the cell, or the rate of fatty acid derivative secretion of the cell is increasing the amount of a fatty acid, a fatty acid derivative, and/or a triacylglycerol is synthesized, accumulated, or secreted by the cell. In some embodiments, modifying the efficiency of carbohydrate to fatty acid or fatty acid derivative conversion of the cell is increasing the efficiency of conversion by at least 2-fold, at least 3-fold, at least 4-fold, or at least 5-fold. In some embodiments, the fatty acid derivative is a triacylglycerol. In some embodiments, modifying the tolerance of osmotic stress, or the tolerance of a toxic substance of the cell is conferring tolerance of osmotic stress or of a toxic substance at a level lethal to unmodified cells of the same cell type. In some embodiments, modifying the proliferation rate is increasing the proliferation rate at least 2-fold, at least 5-fold, at least 10-fold, at least 20-fold, or at least 30-fold. In some embodiments, modifying the cell volume is increasing the cell volume at least 2-fold. In some embodiments, the cell is a yeast cell. In some embodiments, the yeast is an oleaginous yeast. In some embodiments, the oleaginous yeast is *Y. lipolytica*.

Some aspects of this invention relate to an isolated nucleic acid molecule comprising a) a nucleotide sequence that encodes SEQ ID NO:1 (*Y. lipolytica* SCD), or b) a nucleotide sequence that is at least 85% identical to the nucleotide sequence of (a). In some embodiments, the nucleotide sequence that encodes SEQ ID NO:1 is SEQ ID NO:2. In some embodiments, the nucleotide sequence is at least 85% identical to the nucleotide sequence of SEQ ID NO:2. In some embodiments, the nucleotide sequence is at least 90% identical to the nucleotide sequence of SEQ ID NO:2. In some embodiments, the nucleotide sequence is at least 95% identical to the nucleotide sequence of SEQ ID NO:2. In some embodiments, the nucleotide sequence is at least 97.5% identical to the nucleotide sequence of SEQ ID NO:2. In some embodiments, the nucleotide sequence is at least 99% identical to the nucleotide sequence of SEQ ID NO:2. In some embodiments, a nucleic acid construct is provided that comprises an isolated nucleic acid molecule as described herein, for example, an isolated nucleic acid molecule as described in this paragraph, and a heterologous isolated promoter. In some embodiments, the promoter is a constitutive promoter or an inducible promoter. In some embodiments, the constitutive promoter is a Translation Elongation Factor (TEF) promoter. In some embodiments, the inducible promoter is a drug-inducible promoter. In some embodiments, the isolated nucleic acid molecule includes a modified SCD promoter. In some embodiments, the modification is a deletion, complete or partial, and/or a mutation of a wild-type SCD promoter sequence resulting in a disruption of the feedback inhibition of said SCD promoter in response to high levels of a fatty acid, a fatty acid derivative, and/or a triacylglycerol. In some embodiments, the modification is an insertion of a heterologous sequence into a wild-type SCD promoter region, optionally associated with a deletion, complete or in part, and/or a mutation of a wild-type SCD promoter sequence, resulting in a disruption of the feedback inhibition of said SCD promoter in response to high levels of a fatty acid, a fatty acid derivative, and/or a triacylglycerol.

Some aspects of this invention relate to a vector comprising an expression cassette, for example any of the expression cassettes mentioned herein. Some aspects of this invention relate to a cell comprising an expression cassette as described herein or at least a part of a vector as described herein.

The subject matter of this application may involve, in some cases, interrelated products, alternative solutions to a particular problem, and/or a plurality of different uses of a single system or article.

Other advantages, features, and uses of the invention will become apparent from the following detailed description of non-limiting embodiments of the invention when considered in conjunction with the accompanying drawings In cases where the present specification and a document incorporated by reference include conflicting disclosure, the present specification shall control.

DETAILED DESCRIPTION

Introduction

Figure 1:
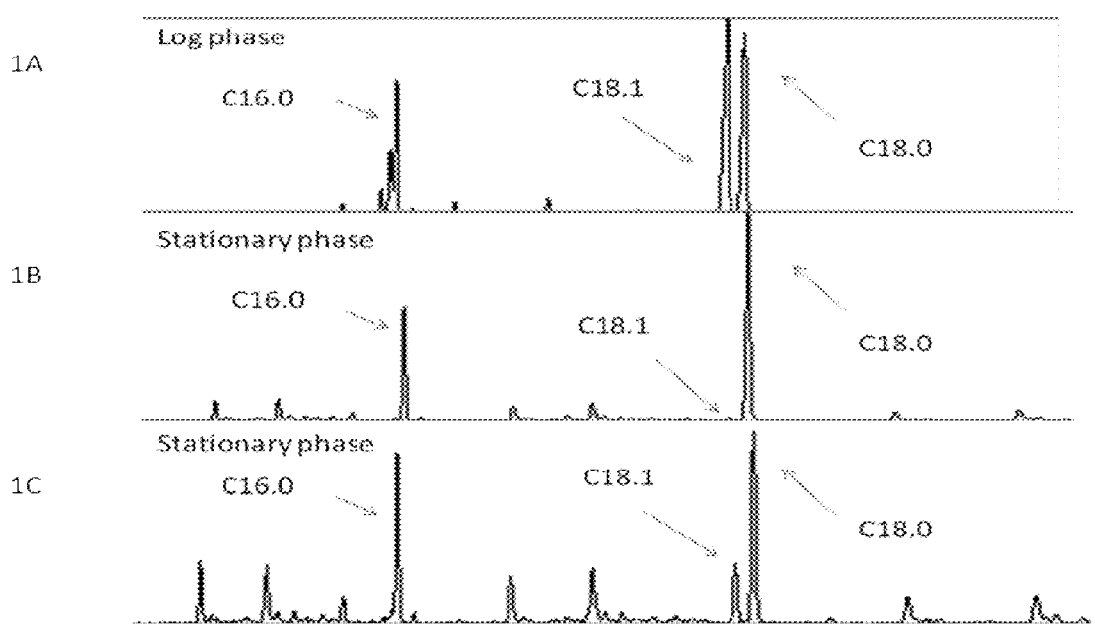
FIG. 1: Fatty acid profiling of *Yarrowia lipolytica*. A) a log phase culture of *Y. lipolytica* grown in minimal media was assayed for total free fatty acid (FFA) using gas chromatography-mass spectroscopy (GC-MS) in a shake flask experiment. B) Total FFA was assayed in the same culture under same conditions during the stationary growth phase. C) Total lipids (FFA and esterified fatty acids) were assayed in the same culture during stationary phase.

In view of diminishing fossil fuel resources, numerous research efforts have been directed to develop renewable alternatives. One promising approach is to engineer microbes for the production of biofuels, for example, biodiesel or biodiesel precursors, such as triacylglycerols, from renewable carbon sources, for example, by using microbes that produce fatty acids or fatty acid derivatives Microalgae as a raw material for biofuels production (Gouveia L, Oliveira A C. J Ind Microbiol Biotechnol. 2009 February; 36(2):269-74). While some aspects of this invention relate to the use of photosynthetic microbes, such as algae, for biofuel or biofuel precursor production, the use of photosynthetic microbes creates a set of technological challenges (Cadoret J P, Bernard O. J *Lipid biofuel production with microalgae: potential and challenges* Soc Biol. 2008; 202(3):201-11). The focus of research efforts is shifting towards the engineering of microbes for converting renewable carbon sources, for example, biomass-derived fermentable sugars (e.g., glucose or sugars from corn or sugarcane) or non-fermentable carbohydrate polymers (e.g. cellulose or hemicellulose) to biofuel or biofuel precursors in dark fermentation processes Economically viable production of biofuel requires (i) the identification of a suitable microbe, and (ii) the engineering of a required and/or desirable phenotype, which may include multiple traits, in the microbe. Examples of such required and/or desirable traits in such a phenotype include, but are not limited to, rapid and efficient biomass production, growth advantage over undesired microbes, efficient, ideally near-theoretical carbohydrate to oil conversion, and high substrate and end-product tolerance. Some of these traits are prerequisites for economically viable, microbe-based biofuel production at an industrial-scale. Ideally, the engineered microbe should display a combination of beneficial traits conferring a phenotype allowing for efficient conversion of an abundant carbon source to a biofuel or biofuel precursor in a scalable, cost-efficient manner.

Microbial Production of a Biofuel or Biofuel Precursor

Some aspects of this invention relate to microbe-mediated production of biofuel or biofuel precursor. The term "biofuel" refers to a fuel that is derived from a biological source, such as a living cell, microbe, fungus, or plant. The term includes, for example, fuel directly obtained from a biological source, for example, by conventional extraction, distillation, or refining methods, and fuel produced by processing a biofuel precursor obtained from a biological source, for example by chemical modification, such as transesterification procedures. Examples of biofuels that are directly obtainable are alcohols such as ethanol, propanol, and butanol, fat, and oil. Examples of biofuels that are obtained by processing of a biofuel precursor (e.g., a lipid), are biodiesel (e.g., produced by transesterification of a lipid), and green diesel/modified oil fuels (e.g., produced by hydrogenation of an oil). Biodiesel, also referred to as fatty acid methyl (or ethyl) ester, is one of the economically most important biofuels today and can be produced on an industrial scale by transesterification of lipids, in which sodium hydroxide and methanol (or ethanol) reacts with a lipid, for example, a triacylglycerol, to produce biodiesel and glycerol. Feedstocks for industrial-scale production of biodiesel include animal fats, vegetable oils, palm oil, hemp, soy, rapeseed, flax, sunflower, and oleaginous algae. In other approaches, biomass is converted by a microbe into a biofuel precursor, for example, a lipid, that is subsequently extracted and further processed to yield a biofuel. The term "biomass" refers to material produced by growth and/or propagation of a living cell or organism, for example, a microbe. Biomass may contain cells, microbes and/or intracellular contents, for example cellular fatty acids and TAGS, as well as extracellular material. Extracellular material includes, but is not limited to, compounds secreted by a cell, for example, secreted fatty acids or TAGs. Important types of biomass for biofuel production are algal biomass and plant-derived biomass, for example, corn stover and wood fiber. In some embodiments, biomass for biofuel or biofuel precursor production may comprise plant derived sugars, for example, sugarcane or corn derived sugars.

Some aspects of this invention relate to the identification, engineering, and development of a microbial source of lipids for economically viable, industrial-scale biodiesel production, none of which has previously been reported. The term "lipid" refers to fatty acids and their derivatives. Accordingly, examples of lipids include fatty acids (FA, both saturated and unsaturated); glycerides or glycerolipids, also referred to as acylglycerols (such as monoglycerides (monoacylgycerols), diglycerides (diacylglycerols), triglycerides (triacylglycerols, TAGs, or neutral fats); phosphoglycerides (glycerophospholipids); nonglycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid droplets.

Some aspects of this invention relate to the identification of a microbe for biofuel or biofuel precursor production based on a suitable lipid metabolism of the microbe. The term "lipid metabolism" refers to the molecular processes that involve the creation or degradation of lipids. Fatty acid synthesis, fatty acid oxidation, fatty acid desaturation, TAG synthesis, TAG storage and TAG degradation are examples of processes that are part of the lipid metabolism of a cell. Accordingly, the term "fatty acid metabolism" refers to all cellular or organismic processes that involve the synthesis, creation, transformation or degradation of fatty acids. Fatty acid synthesis, fatty acid oxidation, TAG synthesis, and TAG degradation are examples of processes are part of the fatty acid metabolism of a cell.

The term "triacylglycerol" (TAG, sometimes also referred to as triglyceride) refers to a molecule comprising a single molecule of glycerol covalently bound to three fatty acid molecules, aliphatic monocarboxylic acids, via ester bonds, one on each of the glycerol molecule's three hydroxyl (OH) groups. Triacylglycerols are highly concentrated stores of metabolic energy because of their reduced, anhydrous nature, and are a suitable feedstock for biodiesel production.

Many cells and organisms store metabolic energy in the form of fatty acids and fatty acid derivatives, such as TAGs. Fatty acids and their derivatives, such as TAGs, provide an ideal form to store metabolic energy. The energy contained in the C—C bonds can be efficiently released by β-oxidation, a reaction formally equivalent to the reverse of fatty acid biosynthesis, but mediated and regulated by different enzymes constituting a different molecular pathway. Microbes can derive fatty acids from external supply, endogenous turnover, and de novo synthesis. Some aspects of this invention relate to the identification of a microbe for biofuel or biofuel precursor production based on the microbe's ability to synthesize and store fatty acids or fatty acid derivatives, such as TAGs, efficiently from an externally supplied carbon source.

A Microbe for Biofuel Production

Some aspects of this invention relate to the identification of a suitable microbe for industrial-scale carbohydrate-to-lipid conversion for biofuel or biofuel precursor production. No suitable microbe has been identified so far that would allow for economically viable production of biofuel or a biofuel precursor from a carbohydrate source on an industrial scale.

Some aspects of this invention relate to the identification of an oleaginous yeast, *Y. lipolytica*, as an organism for biofuel or biofuel precursor production based on *Y. lipolytica*'s favorable base metabolism.

*Y. lipolytica* is a non-pathogenic oleaginous yeast that can use a variety of carbon sources, including organic acids, hydrocarbons and various fats and oils. The term "oleaginous" refers to a microbe that can accumulate more than 20% of its dry cell weight as lipid (see C. Ratledge et al., *Microbial routes to lipids*. Biochem Soc Trans. 1989 December; 17(6): 1139-41). According to some aspects of this invention, *Y. lipolytica* represents a microbe for biofuel or biofuel precursor production, because *Y. lipolytica* is an obligate aerobe with the ability to assimilate carbohydrates, for example, glucose, or glycerol as a sole carbon source, and, compared to other yeast strains, *Y. lipolytica* has a higher glucose to fatty acid and triacylglycerol (TAG) flux and higher lipid storage capacity. See, e.g., Beopoulos A, Cescut J, Haddouche R, Uribelarrea J L, Molina-Jouve C, Nicaud J M, *Yarrowia lipolytica as a model for bio-oil production*. Prog Lipid Res. 2009 November; 48(6):375-87. Further, *Y. lipolytica* is one of the more intensively studied 'non-conventional' yeast species and genome sequencing, including mitochondrial DNA, of *Y. lipolytica* was completed recently. Kerscher S, Durstewitz G, Casaregola S, Gaillardin C, Brandt U., *The complete mitochondrial genome of Yarrowia lipolytica*. Comp Funct Genomics. 2001; 2(2):80-90. The availability of genomic sequence data makes genetic manipulation more accessible., even though functional annotation of genomic sequences is not complete. See, e.g., Sokolova L, Wittig I, Barth H D, Schägger H, Brutschy B, Brandt U., *LILBID-mass spectrometry of protein complexes from blue-native gels, a sensitive top-down proteomic approach*. Proteomics. Published online 2010 Feb. 1, PMID: 20127694.

In wild type *Y. lipolytica*, fatty acid and TAG synthesis from a carbon source is triggered during the stationary growth phase, suggesting a tight regulatory mechanism in place to control lipid metabolism. This regulatory mechanism controls the amount of lipids that can be synthesized and stored, which significantly limits the conversion yield of feedstock to lipids. Accordingly, the metabolic parameters of wild type *Y. lipolytica* are not suitable for economically viable industrial-scale biofuel or biofuel precursor production.

A Microbial Key Regulator of Fatty Acid Metabolism

Some aspects of this invention relate to the surprising discoveries that (i) saturated fatty acids inhibit de novo fatty acid synthesis and TAG storage via a feedback loop, and (ii) that overexpression of SCD, a Δ9-desaturase, in a microbe suitable for biofuel or biofuel precursor production, for example, *Y. lipolytica*, is sufficient to override this feedback inhibition of fatty acid synthesis and TAG storage, resulting in significantly increased synthesis, storage of fatty acids and/or TAGs.

Some aspects of this invention relate to the surprising discovery that, in addition to effecting increased synthesis and storage of fatty acids and/or TAGs, overexpression of SCD in a microbe further confers a beneficial phenotype for biofuel or biofuel precursor production to a microbe, for example, *Y. lipolytica*, including but not limited to: (i) hyperactivation of the TAG storage pathway, (ii) growth advantage, (iii) continuous oil production, (iv) elevated tolerance to carbohydrate source substances (e.g. glucose and other sugars) in the culture medium and (v) fatty acid profile modification, e.g. a shift of the ratios of saturated to unsaturated fatty acids favorable for biofuel or biofuel precursor production.

The discovery of SCD as a key regulator of fatty acid metabolism and TAG synthesis in oleaginous microbes according to this invention has major implication for processes aiming to convert renewable carbon sources into biofuel or biofuel precursor with the help of engineered cells. Based on some aspects of this invention it is now possible to modify the fatty acid and/or TAG profile of a microorganism, for example an oleaginous yeast such as *Y. lipolytica*, in a way that confers highly desirable phenotypes for industrial-scale carbohydrate to biofuel or biofuel precursor conversion, such as remarkable increases in fatty acid synthesis, TAG synthesis, fatty acid and TAG, biomass production, and elevated tolerance of high substrate, product, and/or toxin concentration in the culture medium.

According to some aspects of this invention, modifying the lipid or fatty acid metabolism in a microbe in accordance with methods provided herein, for example by overexpressing SCD alone or in combination with other genetic or non-genetic modifications provided herein, allows for the generation of a microbe optimized for use in biofuel or biofuel precursor production processes. Some aspects of this invention relate to the engineering of the fatty acid metabolism in a microbe, resulting in increased synthesis rate and accumulation of fatty acids and fatty acid derivatives in the microbe.

Natural fatty acid molecules commonly have an unbranched, aliphatic chain, or tail, of 4 to 28 carbon atoms. Fatty acids are referred to as "saturated", if all carbon atoms of the aliphatic chain are connected via a C—C single bond, or as "unsaturated", if two or more carbon atoms are connected via a C—C double bond. Unsaturated fatty acids play important roles in the regulation of membrane fluidity, cellular activity, metabolism and nuclear events governing gene transcription.

The spectrum of fatty acids in yeast consists mostly of C16 and C18 fatty acids, for example palmitic acid (C16), palmitoleic acid (C16), stearic acid (C18) and oleic acid (C18). Palmitic acid is an unbranched, saturated fatty acid, with an aliphatic chain of 16 carbon atoms (carbon atoms/unsaturated bonds: 16.0). Stearic acid is an unbranched, saturated fatty acid with an aliphatic chain of 18 carbon atoms (18.0). Palmitoleic acid is a monounsaturated fatty acid with an aliphatic chain of 16 carbon atoms (16.1). Oleic acid is a monounsaturated fatty acid with an aliphatic chain of 18 carbon atoms (18.1). Minor fatty acid species in yeast include C14 and C26 fatty acids, which play essential functions in protein modification or as components of sphingolipids and GPI anchors, respectively.

De novo synthesis of fatty acids utilizes substantial amounts of metabolites, acetyl-CoA, ATP and NADPH, and thus competes with other cellular processes that are dependent on these compounds. NADPH is required for two reduction steps in the fatty acid elongation cycle, linking fatty acid synthesis to the metabolic state of the cell and results in fatty acid synthesis being restricted to conditions of high energy load of the cells, indicated by increased ATP/AMP ratio, elevated reduction equivalents and elevated acetyl-CoA pool. Almost all subcellular organelles are involved in fatty acid metabolism, indicating that maintenance of fatty acid homeostasis requires regulation at multiple levels.

Most organisms, including yeast, are able to synthesize fatty acids de novo from a variety of carbon sources. In an initial step, acetyl-CoA is carboxylated by the addition of $CO_2$ to malonyl-CoA, by the enzyme acetyl-CoA carboxylase (ACC; encoded by ACC1 and HFA1 in yeast). Biotin is an essential cofactor in this reaction, and is covalently attached to the ACC apoprotein, by the enzyme biotin:apoprotein ligase (encoded by BPL1/ACC2 in yeast). ACC is a trifunctional enzyme, harboring a biotin carboxyl carrier protein (BCCP) domain, a biotin-carboxylase (BC) domain, and a carboxyl-transferase (CT) domain. In most bacteria, these domains are expressed as individual polypeptides and assembled into a heteromeric complex. In contrast, eukaryotic ACC, including mitochondrial ACC variants (Hfa1 in yeast) harbor these functions on a single polypeptide. Malonyl-CoA produced by ACC serves as a two carbon donor in a cyclic series of reactions catalyzed by fatty acid synthase, FAS, and elongases.

In yeast, the individual functions involved in cytosolic fatty acid synthesis are represented as discrete domains on a single or on two different polypeptide chains, respectively. Yeast cytosolic fatty acid synthase (FAS) is a complex composed of two subunits, Fas1 (β subunit) and Fas2 (α subunit) which are organized as a hexameric α6β6 complex. Fas1 harbors acetyl transferase, enoyl reductase, dehydratase, and malonyl-palmitoyl transferase activities; Fas2 contains acyl carrier protein, 3-ketoreductase, 3-ketosynthase and the phosphopantheteine transferase activities.

Mitochondrial fatty acid synthesis in yeast is carried out by a type II FAS system, harboring the individual enzymatic activities on distinct polypeptides: Acp1, acyl-carrier protein which carries the prosthetic phosphopantetheine group; Cem1, β-ketoacyl-ACP synthase; Oar1, 3-oxoacyl-[acyl-carrier-protein] reductase; Htd2, 3-hydroxyacyl-thioester dehydratase; Etr1, enoyl-ACP reductase. Ppt2 functions as the phosphopantetheine: protein transferase, catalyzing the attachment of the phosphopantetheine prosthetic group to the apoACP.

The immediate product of de novo fatty acid synthesis are saturated fatty acids. Saturated fatty acids are known to be the precursors of unsaturated fatty acids in eukaryotes, including yeast. Unsaturated fatty acids are generally produced by desaturation of C—C single bonds in saturated fatty acids by specialized enzymes, called desaturases. The control mechanisms that govern the conversion of saturated fatty acids to unsaturated fatty acids are not well understood. In eukaryotes, unsaturated fatty acids play important roles in the regulation of membrane fluidity, cellular activity, metabolism and nuclear events that govern gene transcription. Typically, about 80% of yeast fatty acids are monounsaturated, meaning that they contain one unsaturated bond in their aliphatic chain.

A critical committed step in the biosynthesis of monounsaturated fatty acids is the introduction of the first cis-double bond in the Δ9 position (between carbons 9 and 10). This oxidative reaction is catalyzed by stearoyl-CoA desaturase (SCD, also known as delta-9-desaturase, or Δ9-desaturase). Although the insertion of the double bond occurs in several different methylene-interrupted fatty acyl-CoA substrates, the preferred substrates of SCD are palmitoyl (16.0)- and stearoyl (18.0)-CoA which are converted to palmitoleoyl (16.1)- and oleoyl(18.1)-CoA, respectively (Ntambi, J. Lipid Res., 1999, 40, 1549-1558).

In *S. cerevisiae*, a stearoyl-CoA desaturase gene was identified as Ole1 in 1990 (Stukey J E, et al., J Biol. Chem., 1990, 265(33):20144-9). The human stearoyl-CoA desaturase gene was partially characterized in 1994 via isolation of a 0.76 kb partial cDNA from human adipose tissue (Li et al., Int. J. Cancer, 1994, 57, 50 348-352). The gene was fully characterized in 1999 and it was found that alternative usage of polyadenylation sites generates two transcripts of 3.9 and 5.2 kb (Zhang et al., Biochem. J., 1999, 340, 255-264). In *S. cerevisiae*, fatty acid monodesaturation is catalyzed by the endoplasmic reticulum (ER)-resident and essential Δ9-desaturase, Ole1 (Martin C E, Oh C S, Jiang Y, *Regulation of long chain unsaturated fatty acid synthesis in yeast*. Biochim Biophys Acta. 2007 March; 1771(3):271-85. Epub 2006 Jul. 13.

Some aspects of this invention relate, at least in part, to the identification of the *S. cerevisiae* Ole1 homologue SCD in *Y. lipolytica*, as described herein.

Non-limiting examples of representative sequences of *Y. lipolytica* SCD are given below:

```
>gi|50548053|ref|XP_501496.1|YALI0C05951p
[Yarrowia lipolytica]
                                          (SEQ ID NO: 1)
MVKNVDQVDLSQVDTIASGRDVNYKVKYTSGVKMSQGAYDDKGRHISEQP

FTWANWHQHINWLNFILVIALPLSSFAAAPFVSFNWKTAAFAVGYYMCTG

LGITAGYHRMWAHRAYKAALPVRIILALFGGGAVEGSIRWWASSHRVHHR

WTDSNKDPYDARKGFWFSHFGWMLLVPNPKNKGRTDISDLNNDWVVRLQH

KYYVYVLVFMAIVLPTLVCGFGWGDWKGGLVYAGIMRYTFVQQVTFCVNS

LAHWIGEQPFDDRRTPRDHALTALVTFGEGYHNFHHEFPSDYRNALIWYQ

YDPTKWLIWTLKQVGLAWDLQTFSQNAIEQGLVQQRQKKLDKWRNNLNWG

IPIEQLPVIEFEEFQEQAKTRDLVLISGIVHDVSAFVEHHPGGKALIMSA

VGKDGTAVFNGGVYRHSNAGHNLLATMRVSVIRGGMEVEVWKTAQNEKKD

QNIVSDESGNRIHRAGLQATRVENPGMSGMAA

>gi|50548052|ref|XM_501496.1|Yarrowia lipolytica
YALI0C05951p (YALI0C05951g) mRNA, complete cds
                                          (SEQ ID NO: 2)
ATGGTGAAAAACGTGGACCAAGTGGATCTCTCGCAGGTCGACACCATTGC

CTCCGGCCGAGATGTCAACTACAAGGTCAAGTACACCTCCGGCGTTAAGA

TGAGCCAGGGCGCCTACGACGACAAGGGCCGCCACATTTCCGAGCAGCCC

TTCACCTGGGCCAACTGGCACCAGCACATCAACTGGCTCAACTTCATTCT

GGTGATTGCGCTGCCTCTGTCGTCCTTTGCTGCCGCTCCCTTCGTCTCCT

TCAACTGGAAGACCGCCGCGTTTGCTGTCGGCTATTACATGTGCACCGGT

CTCGGTATCACCGCCGGCTACCACCGAATGTGGGCCCATCGAGCCTACAA

GGCCGCTCTGCCCGTTCGAATCATCCTTGCTCTGTTTGGAGGAGGAGCTG

TCGAGGGCTCCATCCGATGGTGGGCCTCGTCTCACCGAGTCCACCACCGA

TGGACCGACTCCAACAAGGACCCTTACGACGCCCGAAAGGGATTCTGGTT

CTCCCACTTTGGCTGGATGCTGCTTGTGCCCAACCCCAAGAACAAGGGCC

GAACTGACATTTCTGACCTCAACAACGACTGGGTTGTCCGACTCCAGCAC

AAGTACTACGTTTACGTTCTCGTCTTCATGGCCATTGTTCTGCCCACCCT

CGTCTGTGGCTTTGGCTGGGGCGACTGGAAGGGAGGTCTTGTCTACGCCG

GTATCATGCGATACACCTTTGTGCAGCAGGTGACTTTCTGTGTCAACTCC

CTTGCCCACTGGATTGGAGAGCAGCCCTTCGACGACCGACGAACTCCCCG

AGACCACGCTCTTACCGCCCTGGTCACCTTTGGAGAGGGCTACCACAACT

TCCACCACGAGTTCCCCTCGGACTACCGAAACGCCCTCATCTGGTACCAG

TACGACCCCACCAAGTGGCTCATCTGGACCCTCAAGCAGGTTGGTCTCGC

CTGGGACCTCCAGACCTTCTCCCAGAACGCCATCGAGCAGGGTCTCGTGC

AGCAGCGACAGAAGAAGCTGGACAAGTGGCGAAACAACCTCAACTGGGGT

ATCCCCATTGAGCAGCTGCCTGTCATTGAGTTTGAGGAGTTCCAAGAGCA
```

```
-continued
GGCCAAGACCCGAGATCTGGTTCTCATTTCTGGCATTGTCCACGACGTGT

CTGCCTTTGTCGAGCACCACCCTGGTGGAAAGGCCCTCATTATGAGCGCC

GTCGGCAAGGACGGTACCGCTGTCTTCAACGGAGGTGTCTACCGACACTC

CAACGCTGGCCACAACCTGCTTGCCACCATGCGAGTTTCGGTCATTCGAG

GCGGCATGGAGGTTGAGGTGTGGAAGACTGCCCAGAACGAAAAGAAGGAC

CAGAACATTGTCTCCGATGAGAGTGGAAACCGAATCCACCGAGCTGGTCT

CCAGGCCACCCGGGTCGAGAACCCCGGTATGTCTGGCATGGCTGCTTAG
```

Stearoyl-CoA desaturase, or SCD, introduces a double bond at the Δ9-C of its substrate fatty acids esterified with CoA. This activity affects the ratio of saturated to unsaturated fatty acids, for example of stearic acid to oleic acid. Stearic acid is the primary substrate for SCD, however other chain length fatty acids can be processed as well by SCD. In humans, Stearoyl-CoA desaturase has been viewed as a lipogenic enzyme not only for its key role in the biosynthesis of monounsaturated fatty acids, but also for its pattern of regulation by diet and insulin (Ntambi, Lipid Res., 1999, 40, 1549-1558). The regulation of stearoyl-CoA desaturase is, therefore, of considerable physiologic importance and its activity is sensitive to dietary changes, hormonal imbalance, developmental processes, temperature changes, metals, alcohol, peroxisomal proliferators and phenolic compounds (Ntambi, Lipid Res., 1999, 40, 1549-1558).

Animal models have been very useful in investigations of the regulation of stearoyl-CoA desaturase by polyunsaturated fatty acids (PUFAs). For example, in adipose tissue of lean and obese Zucker rats, Jones et al. observed a 75% decrease in stearoyl-CoA desaturase mRNA when both groups were fed a diet high in PUFAs relative to a control diet (Jones et al, Am. J. Physiol., 1996, 271, E44-49). Similar results have been obtained with tissue culture systems. In the murine 3T3-L1 adipocyte cell line, arachidonic, linoleic, linolenic, and eicosapentanenoic acids decreased stearoyl-CoA desaturase expression in a dose-dependent manner (Sessler et al, J. Biol. Chem., 1996, 271, 29854-29858).

The molecular mechanisms by which PUFAs regulate stearoyl-CoA desaturase gene expression in different tissues are still poorly understood. The current understanding of the regulatory mechanism involves binding of PUFAs to a putative PUFA-binding protein, after which repression of transcription occurs via binding of the PUFA-binding protein to a cis-acting PUFA response element of the stearoyl-CoA desaturase gene (SREBP) (Ntambi, Lipid Res., 1999, 40, 1549-1558; Zhang et al, Biochem. J., 2001, 357, 183-193).

While the regulation of the catalytic activity of the SCD gene has been investigated in different organisms, the implications of SCD gene expression and regulation on lipid metabolism itself have not been the subject of extensive study. It has been stated that SCD affects the ratio of saturated to unsaturated fatty acids, for example of stearic acid to oleic acid.

Some aspects of this invention relate to the surprising discovery that SCD also functions as a key regulator of fatty acid and TAG metabolism in microbes, for example, in *Y. lipolytica*. Some aspects of this invention relate to the surprising discovery that overexpression of a SCD gene product alone not only skews the ratio of saturated to unsaturated fatty acids in the affected cells, but is sufficient to trigger remarkable and unexpected increases in fatty acid and/or TAG synthesis rates and/or storage. The unexpected finding that manipulation of desaturase expression alone confers highly desirable phenotypes to microbes, for example, oleaginous yeast cells, for industrial-scale carbohydrate to lipid conversion has far-reaching implications for the efficient production of biofuels or biofuel precursors from renewable carbon sources by microbe-mediated fermentation processes. Overriding down-regulation of fatty acid synthesis and storage by overexpressing SCD in a microbe not only confers increased fatty acid synthesis rate and accumulation in the microbe, but also overrides the restriction of FA/TAG synthesis to the stationary phase of a microbe in culture. Surprisingly, overexpression of SCD in a microbe, for example, a microbe for biofuel or biofuel precursor production, also confers increased tolerance to high concentrations of substrate, for example, of fermentable sugars, and to substrate-associated toxic substances, for example, by-products of substrate pre-treatment procedures, to the microbe. The phenotypes conferred by SCD overexpression, for example the improved tolerance phenotypes described above, allow for obtaining high concentrations of lipids in industrial fermentation processes converting sugars to lipids. (See FIG. 11 for override of negative FA synthesis regulation by SCD over-expression)

According to some aspects of this invention, the manipulation of additional genes may be beneficial for the large-scale production of biofuel or biofuel precursor from a carbon source by microbial fermentation. For example, genes that effect the diversion of carbon-containing substrates, for example, sugars, to fatty acid synthesis. Accordingly, some aspects of this invention provide methods to manipulate the expression of genes involved in regulating carbon flux into or out of lipid synthesis pathways to achieve an improvement in lipid production parameters.

Some aspects of this invention provide a method for the manipulation of the expression and/or activity of other gene products regulating the lipid metabolism of microbes for biofuel or biofuel precursor production. Manipulations according to aspects of this invention are targeted to increase carbohydrate to fatty acid and/or TAG conversion in order to optimize the manipulated organism for large-scale production of lipids from carbohydrate sources. Manipulations provided according to some aspects of this invention, for example, overexpression, knockout, knock-down, activation and/or inhibition of specific gene products, may be effected alone or in combination, and/or in combination with other manipulations known to those of skill in the art. The term "manipulation" refers to both genetic manipulation, for example, overexpression, knockout, knock-down, activation and/or inhibition of specific gene products, and non-genetic manipulation, for example, manipulation of the growth media, substrate, substrate pretreatment, pH, temperature, conversion process, etc.

A manipulation of gene expression, also referred to herein as a modulation of gene expression, can be a disruption or inhibition of the natural regulation of expression, an overexpression, an inhibition of expression, or a complete abolishment of expression of a given gene. The insertion of a heterologous promoter upstream of a native gene sequence, for example the native SCD gene sequence, or the deletion of regulatory sequences within a promoter, for example regulatory sequences that mediate the feedback inhibition of the SCD gene by saturated fatty acids, are examples of a disruption or inhibition of the natural regulation of expression. Strategies for the modulation of gene expression may include genetic alterations, for example by recombinant technologies, such as gene targeting or viral transductions, or non-genetic alterations, for example environmental alterations known to result in the up- or down-regulation of gene expression, or transient delivery of modulators, for example drugs or small RNA molecules to the target cells. Methods for genetic and non-genetic alterations of microbes are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology*, Part A, Volume 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

The term "overexpression", as used herein, refers to an increased level of expression of a given gene in a given cell, cell type or cell state, as compared to a reference cell, for example, a wild type cell of the same cell type or a cell of the same cell type but lacking a specific modification, for example, a genetic modification. Forced, continuous expression of the SCD gene in *Y. lipolytica* cells exhibiting concentrations of saturated fatty acids that would inhibit SCD gene expression in wild-type cells is an example of gene overexpression.

The term "knockout", as used herein, refers to the functional disruption of the expression of a gene product, for example a RNA or protein. This is normally achieved by targeting a respective genomic region with a targeting construct, which recombines with a specific part of said genomic region and either deletes a part of said region and/or inserts a heterologous nucleotide or nucleotide sequence, resulting in a complete inhibition of expression of a gene product, for example a mRNA or protein, from the recombined gene. In diploids, such homologous recombination events normally only affect one of the two alleles. Homozygosity can be achieved by various strategies, for example by breeding heterozygotes and screening the offspring. In diploid organisms, for example yeast, the term "knockout strain" generally refers to a strain homozygous for a non-functional allele.

The term "knock-down", as used herein, refers to the partial inhibition of the expression of a gene product, for example a mRNA or protein. Various strategies for gene knockdown known in the art can be used to inhibit gene expression (for example expression of a gene inhibiting or diverting resources away from lipid synthesis pathways, such as ACS2, FAT1, PCS60, and/or AMPK in oleaginous yeast, for example in *Y. lipolytica*). For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA or shRNA-mir expression constructs) are used to reduce expression of a gene (for example of a gene inhibiting or diverting resources away from lipid synthesis pathways, such as ACS2, FAT1, PCS60, and/or AMPK) in a cell (for example in an oleaginous yeast cell, such as a *Y. lipolytica* cell). Isolated plasmids according to aspects of this invention may comprise a promoter operably linked to a gene encoding a small interfering nucleic acid, for example an shRNA. In some embodiments, an isolated plasmid vector may be employed to generate a viral particle, for example a retrovirus or bacteriophage, capable of infecting a cell, for example a yeast cell or bacterial cell. Exemplary viruses include adenovirus, retrovirus, lentivirus, adeno-associated virus, phages and others that are known in the art and disclosed herein.

Some aspects of this invention provide a method for the manipulation of the activity of a stearoyl-CoA-desaturase (SCD) in a microbe for biofuel or biofuel precursor production. SCD is a Δ9 desaturase that inserts a double bond between C9 and C10 of stearic acid coupled to CoA, a key step in the generation of desaturated fatty acids and their derivatives, as described in more detail elsewhere herein. In some embodiments, the manipulation is an overexpression. In some embodiments, the manipulation is effected by contacting a microbe for biofuel or biofuel precursor production with an expression construct comprising a nucleic acid coding for a SCD gene product, for example, a SCD protein, operably linked to a heterologous promoter, for example, a constitutive or an inducible promoter. In some embodiments, the nucleic acid coding for a SCD gene product comprises the coding sequence of SEQ ID NO: 2. In some embodiments, the SCD is *Y. lipolytica* SCD, for example, *Y. lipolytica* SCD comprising the amino acid sequence of SEQ ID NO: 1. In some embodiments, the microbe is *Y. lipolytica*. In some embodiments, manipulation of the activity of a SCD in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. Stearoyl-CoA Desaturase gene and gene product sequences are well known to those of skill in the art. Exemplary, representative gene and gene product sequences can be found under the entry for GeneID: 852825 in the NCBI database (www.ncbi.nlm.nih.gov).

Some aspects of this invention provide a method for the manipulation of the activity of a c-Jun N-terminal kinase 2 (JNK2) gene product in a microbe for biofuel or biofuel precursor production. JNK2 is localized to the cytoplasm and catalyzes the breakdown of fatty acids for energy and carbon block generation during starvation. JNK2 is required for energy homoeostasis and plays a crucial role in lipase activation in response to low cellular sugar levels. See, Grimard V, Massier J, Richter D, Schwudke D, Kalaidzidis Y, Fava E, Hermetter A, Thiele C., *siRNA screening reveals JNK2 as an evolutionary conserved regulator of triglyceride homeostasis.* J Lipid Res. 2008 November; 49(11):2427-40. Epub 2008 Jul. 8. In some embodiments, JNK2 activity is abolished or decreased in a microbe for biofuel or biofuel precursor production, for example, by knockout or knockdown, respectively. In some embodiment, JNK2 activity is decreased in a microbe for biofuel or biofuel precursor production in order to increase product stability and/or decrease product catabolism. In some embodiments, a conditional repression system is used and JNK2 activity is repressed during a phase in the production process in which the carbohydrate source, for example, a fermentable sugar, is very low. In some embodiments, manipulation of the activity of a JNK2 gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. JNK2 gene and gene product sequences are well known to those of skill in the art. Exemplary, representative gene and gene product sequences can be found under the entry for GeneID: 5601 in the NCBI database (www.ncbi.nlm.nih.gov).

Some aspects of this invention provide a method for the manipulation of the activity of a delta-12 desaturase gene product in a microbe for biofuel or biofuel precursor production. Delta-12 desaturase is involved in the conversion of oleic acid containing lipids to higher chain lipids. In some embodiments, it is desirable to avoid or minimize the production of long-chain fatty acids for the production of biofuel, for example, in view of the cold flow properties of the resulting biofuel. In some embodiments, delta-12 desaturase activity is abolished or decreased in a microbe for biofuel or biofuel precursor production, for example, by complete (e.g., knockout) or partial gene deletion or knockdown, respectively. In some embodiments, delta-12 desaturase activity is decreased in a microbe for biofuel or biofuel precursor production in order to increase product stability, achieve a desirable TAG profile in the microbe and/or decrease product catabolism. In some embodiments, a conditional repression system is used for the repression of delta-12 desaturase activity. In some embodiments, manipulation of the activity of a delta-12 desaturase gene product in a microbe is effected to confer a beneficial phenotype for large-scale carbohydrate to lipid conversion, for example increased lipid synthesis rate, increased carbohydrate to lipid conversion efficiency, increased lipid storage, increased content of C18 fatty acids, increased percentage of C18 fatty acids of the whole fatty acid pool in the microbe, improved cold flow properties of the produced lipids, oils, or TAGs, increased growth rate, increased tolerance to elevated concentrations of a carbon source or a lipid product. Delta-12 desaturase gene and gene product sequences are well known to those of skill in the art. Exemplary, representative gene and gene product sequences can be found under the entry for GeneID: 2909806 in the NCBI database (www.ncbi.nlm.nih.gov).

Some aspects of this invention provide a method for the manipulation of the activity of a hemoglobin gene product in a microbe for biofuel or biofuel precursor production. For an overview of hemoglobin gene products, including hemoglobin gene products useful in some embodiments of this invention, see, Frey A D, Kallio P T. *Bacterial hemoglobins and flavohemoglobins: versatile proteins and their impact on microbiology and biotechnology*. FEMS Microbiol Rev. 2003 October; 27(4):525-45. In some embodiments, the activity of a hemoglobin gene product, for example, a hemoglobin protein, is increased in the microbe, for example, by overexpression of a hemoglobin protein-encoding nucleic acid. In some embodiments, overexpression of hemoglobin in the microbe effects increased oxygen transfer in the microbe. In some embodiments, increased hemoglobin activity results in improved biofuel or biofuel precursor synthesis, due to increased flux of oxygen into a highly oxygen demanding synthesis pathway, for example, the fatty acid synthesis pathway. In some embodiments, manipulation of the activity of a hemoglobin gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. Hemoglobin gene and gene product sequences are well known to those of skill in the art. Exemplary, representative gene and gene product sequences can be found under the entry for GeneID: 7738539 (Deide_12990) in the NCBI database (www.ncbi.nlm.nih.gov).

Some aspects of this invention provide a method for the manipulation of the activity of a cytochrome gene product in a microbe for biofuel or biofuel precursor production, such as a cytochrome B gene product, more specifically a cytochrome B5 gene product. In some embodiments, the activity of a cytochrome gene product, for example, a cytochrome protein, is increased in the microbe, for example, by overexpression of a cytochrome protein-encoding nucleic acid. In some embodiments, overexpression of cytochrome in the microbe effects increased oxygen transfer in the microbe. In some embodiments, increased cytochrome activity results in improved biofuel or biofuel precursor synthesis, due to increased flux of oxygen into a highly oxygen demanding synthesis pathway, for example, the fatty acid synthesis pathway. In some embodiments, manipulation of the activity of a cytochrome gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. Cytochrome gene and gene product sequences are well known to those of skill in the art. An exemplary, representative gene sequence c an be found under the entry for GeneID: 1528 in the NCBI database (www.ncbi.nlm.nih.gov).

Some aspects of this invention provide a method for the manipulation of the activity of a glucose transporter (GLUT) gene product, for example, a Glut1 gene product, in a microbe for biofuel or biofuel precursor production. In some embodiments, the activity of a GLUT gene product, for example, a GLUT protein, is increased in the microbe, for example, by overexpression of a GLUT protein-encoding nucleic acid. In some embodiments, overexpression of a GLUT protein encoding nucleic acid in the microbe effects increased glucose uptake by the microbe. In some embodiments, increased GLUT activity results in improved biofuel or biofuel precursor synthesis, due to increased uptake of glucose. In some embodiments, manipulation of the activity of a GLUT gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. GLUT gene and gene product sequences are well known to those of skill in the art. Exemplary, representative gene and gene product sequences can be found under the entry for GeneID: 38109 in the NCBI database (www.ncbi.nlm.nih.gov).

Some aspects of this invention provide a method for the manipulation of the activity of a Pyruvate Carboxylase (PC) gene product in a microbe for biofuel or biofuel precursor production. In some embodiments, the activity of a PC gene product, for example, a PC protein, is increased in the microbe, for example, by overexpression of a PC protein-encoding nucleic acid. In some embodiments, overexpression of a PC protein encoding nucleic acid in the microbe effects increased glucose uptake by the microbe. In some embodiments, increased PC activity results in improved biofuel or biofuel precursor synthesis, due to increased uptake of glucose. In some embodiments, manipulation of the activity of a PC gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. PC gene and gene product sequences are well known to those of skill in the art. Exemplary, representative gene and gene product sequences can be found under the entry for GeneID:5091 in the NCBI database (www.ncbi.nlm.nih.gov).

Some aspects of this invention provide a method for the manipulation of the activity of a malic enzyme (ME) gene product in a microbe for biofuel or biofuel precursor production. ME catalyzes the oxidative decarboxylation of (S)-malate to pyruvate, with the concomitant release of carbon dioxide and conversion of NADP+ to NADPH. In some embodiments, the activity of a ME gene product, for example, a ME protein, is increased in the microbe, for example, by overexpression of a ME protein-encoding nucleic acid. In some embodiments, overexpression of a ME protein encoding nucleic acid in the microbe effects increased NADPH levels in the microbe, resulting in sufficient levels of reducing metabolites, for example, NADPH, for increased fatty acid synthesis. In some embodiments, increased ME activity results in improved biofuel or biofuel precursor synthesis, due to increased NADPH levels. In some embodiments, manipulation of the activity of a ME gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. ME gene and gene product sequences are well known to those of skill in the art. Exemplary, representative gene and gene product sequences can be found under the entry for GeneID: 17436 in the NCBI database (www.ncbi.nlm.nih.gov).

Some aspects of this invention provide a method for the manipulation of an acetyl-CoA carboxylase (ACC) gene product in a microbe for biofuel or biofuel precursor production, for example, in *Y. lipolytica*. ACC gene products mediate the conversion of acetyl-CoA, the main C2-precursor in fatty acid synthesis, to malonyl-CoA, which is considered the first committed step in fatty acid synthesis and has been suggested to also be the rate-limiting step in fatty acid synthesis (see Cao Y, Yang J, Xian M, Xu X, Liu W. *Increasing unsaturated fatty acid contents in Escherichia coli by coexpression of three different genes*. Appl Microbiol Biotechnol. 2010). In some embodiments, ACC activity manipulation is ACC overexpression. In some embodiments, ACC overexpression in a microbe increases fatty acid synthesis rate and/or confers a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. ACC gene and gene product sequences are well known to those of skill in the art. Exemplary, representative gene and gene product sequences can be found under the entry for GeneID: 855750 in the NCBI database (www.ncbi.nlm.nih.gov).

Some aspects of this invention provide a method for the manipulation of the activity of an Acyl-CoA synthetase (ACS) in a microbe for biofuel or biofuel precursor production. ACSs are a family of enzymes catalyzing the thioesterification of fatty acids with CoA to form activated intermediates (see Lu X, Vora H, Khosla C., *Overproduction of free fatty acids in E. coli: implications for biodiesel production* Metab Eng. 2008 November; 10(6):333-9). These intermediates are the precursors for phospholipids, fatty acid choles-terol esters, or fatty acid alcohol esters, such as TAGs. *Y. lipolytica* contains two known and two predicted Acyl-CoA synthetases. In some embodiments of this invention, overexpression of an ACS enzyme in a lipid producing organism is effected to confer a beneficial phenotype for large-scale carbohydrate to lipid conversion, for example increased lipid synthesis rate, increased carbohydrate to lipid conversion efficiency, increased lipid storage and/or secretion, increased growth rate, increased tolerance to elevated concentrations of a carbon source or a lipid product. ACS gene and gene product sequences are well known to those of skill in the art. Exemplary, representative gene and gene product sequences can be found under the entry for GeneID: 851245 in the NCBI database (www.ncbi.nlm.nih.gov).

Some aspects of this invention provide a method for the manipulation of the activity of acetyl-CoA synthetase 2 (ACS2), an enzyme localized in the peroxisome and involved in the degradation of fatty acids, in a microbe for biofuel or biofuel precursor production. In some embodiments, inhibition of ACS2 prevents or inhibits degradation of fatty acids by yeast catabolic metabolism and, I some embodiments, such inhibition complements an increase in FAA1 gene product activity for increased fatty acid secretion into the medium. *Y. lipolytica* contains ACS2 acetyl-CoA synthetase (see Beopoulos A, Cescut J, Haddouche R, Uribelarrea J L, Molina-Jouve C, Nicaud J M., *Yarrowia lipolytica as a model for bio-oil production*. Prog Lipid Res. 2009 November; 48(6):375-87). In some embodiments, knockout, knockdown, and/or inhibition of ACS2 gene product expression or activity in a microbe is effected to confer a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. ACS2 gene and gene product sequences are well known to those of skill in the art. Exemplary, representative gene and gene product sequences can be found under the entry for GeneID: 850846 in the NCBI database (www.ncbi.nlm.nih.gov).

Some aspects of this invention provide a method for the manipulation of the activity of a FAA1 gene product in a microbe for biofuel or biofuel precursor production. The FAA1 gene product catalyzes the cytoplasmic thioesterification of long-chain fatty acids with CoA to produce activated intermediates. *Y. lipolytica* FAA1 is a homologue of *S. cerevisiae* P30624 FAA1 long-chain-fatty-acid-CoA ligase. This enzyme is involved in the generation of the free fatty acid pool and fatty acid secretion. In some embodiments, overexpression of a FAA1 gene product in a microbe for biofuel or biofuel precursor production is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. FAA1 gene and gene product sequences are well known to those of skill in the art. Exemplary, representative gene and gene product sequences can be found under the entry for GeneID: 854495 in the NCBI database (www.ncbi.nlm.nih.gov).

Some aspects of this invention provide a method for the manipulation of very long-chain-fatty-acid-CoA synthetase (FAT1) activity in a microbe for biofuel or biofuel precursor production. FAT1 is thought to control the fatty acid transport and thioesterification of very long chain fatty acids with CoA. *Y. lipolytica* contains a FAT1 very-long-chain-fatty-acid-CoA synthetase. In some embodiments, inhibition of FAT1 activity, for example, by genetic manipulation, prevents synthesis of very long fatty acid derivatives and/or increases the pool of free fatty acids. In some embodiments, knockout, knock-down, and/or inhibition of FAT1 gene product expression or activity in a microbe is effected to confer a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. FAT1 gene and gene product sequences are well known to those of skill in the art. Exemplary, representative gene and gene product sequences can be found under the entry for GeneID: 852329 in the NCBI database (www.ncbi.nlm.nih.gov).

Some aspects of this invention provide a method for the manipulation of PCS60, also known as FAT2, AMP-binding protein acyl-CoA synthetase, or peroxisomal-CoA synthetase, which is a peroxisomal acyl-CoA synthetase with undefined substrate specificity. *Y. lipolytica* contains a *S. cerevisiae* PCS60 homolog. PCS60 inhibition will prevent synthesis of very long fatty acid derivatives and increase the pool of free fatty acid. In some embodiments of this invention, knockout, knock-down, and/or inhibition of PCS60 gene product expression or activity in a microbe is effected to confer a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. FAT2 gene and gene product sequences are well known to those of skill in the art. Exemplary, representative gene and gene product sequences can be found under the entry for GeneID: 852523 in the NCBI database (www.ncbi.nlm.nih.gov).

Some aspects of this invention provide a method for the overexpression of ATP citrate lyase (ACLY) in a microbe, for example *Y. lipolytica*, for the large-scale production of a biofuel or biofuel precursor. Some microbes suitable for industrial scale biofuel or biofuel precursor production, including *Y. lipolytica*, commonly produce large amounts of citrate. ACLY mediates the conversion of citrate to CoA, a reaction, which, according to some aspects of this invention, can be promoted by ACLY overexpression (see Holz M, Förster A, Mauersberger S, Barth G., *Aconitase overexpression changes the product ratio of citric acid production by Yarrowia lipolytica*. Appl Microbiol Biotechnol. 2009 January; 81(6):1087-96). In some embodiments, ACLY overexpression reduces the production of undesirable citrate and/or provides an additional source of acetyl-CoA for biofuel or biofuel precursor synthesis. In some embodiments, excessive citrate production is inhibited in a microbe for biofuel or biofuel precursor production, including *Y. lipolytica*. In some embodiments, ACLY overexpression in a microbe, for example in *Y. lipolytica*, increases fatty acid synthesis rate and/or confers a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. See also Lasserre J P, Nicaud J M, Pagot Y, Joubert-Caron R, Caron M, Hardouin J. Talanta. *First complexomic study of alkane-binding protein complexes in the yeast Yarrowia lipolytica*. 2010 Feb. 15; 80(4):1576-85. ACLY gene and gene product sequences are well known to those of skill in the art. Exemplary, representative gene and gene product sequences can be found under the entry for GeneID: 108728 in the NCBI database (www.ncbi.nlm.nih.gov).

Some aspects of this invention provide a method for the overexpression of Fatty Acid Synthase complex (FAS). While ACC is likely to be the rate-limiting enzyme in fatty acid synthesis, other steps have also been suggested to exercise control of this pathway, most notably, FAS (see Schweizer E, Köttig H, Regler R, Rottner G. J, *Genetic control of Yarrowia lipolytica fatty acid synthetase biosynthesis and function*. Basic Microbiol. 1988; 28(5):283-92). This complex is a multifunctional polypeptide that elongates the fatty acid chain in the most substrate-intensive process in the entire lipid synthesis pathway. In some embodiments, ACLY overexpression in a microbe, for example in *Y. lipolytica*, increases fatty acid synthesis rate and/or confers a beneficial phenotypes for large-scale carbohydrate to biofuel or biofuel precursor conversion, for example increased lipid synthesis rate, increased carbohydrate to lipid conversion efficiency, increased lipid storage and/or secretion, increased growth rate, increased tolerance to concentrations of a substance, e.g. a carbon source, a biofuel or biofuel precursor, or a toxic substance. FAS gene and gene product sequences are well known to those of skill in the art. Exemplary, representative gene and gene product sequences can be found under the entries for GeneID: 853653 and GeneID: 855845 in the NCBI database (www.ncbi.nlm.nih.gov).

Some aspects of this invention provide a method for the inhibition of AMP activated Protein Kinase (AMPK). AMPK is a regulatory enzyme that regulates the activity of other proteins by phosphorylation in response to cellular AMP:ADP ratio (see Lee-Young R S, Palmer M J, Linden K C, LePlastrier K, Canny B J, Hargreaves M, Wadley G D, Kemp B E, McConell G K. *Carbohydrate ingestion does not alter skeletal muscle AMPK signaling during exercise in humans*. Am J Physiol Endocrinol Metab. 2006 September; 291 (3):E566-73). In yeast, AMPK was shown to target ACC as well as INO1, a gene required for an early step in lipid biosynthesis. Lack of ACC phosphorylation in AMPK knockout mutants results in hyperactive ACC and fatty acid overproduction. In some embodiments, inhibition of AMPK in a microbe leads to hyperactivation of lipid synthesis. In some embodiments, AMPK activity is completely abolished in a microbe, for example, by knockout of the AMPK gene. In some embodiments, AMPK activity is inhibited in a microbe, for example, by genetic or non-genetic manipulation. Inhibition, as opposed to complete abolishment, of AMPK activity might avoid negative effects on other cellular processes regulated by AMPK. In some embodiments, knockout, knock-down, and/or inhibition of AMPK gene product expression or activity in a microbe, for example *Y. lipolytica*, is effected to confer a beneficial phenotype for large-scale carbohydrate to biofuel or biofuel precursor conversion, for example increased lipid synthesis rate, increased carbohydrate to lipid conversion efficiency, increased lipid storage and/or secretion, increased growth rate, increased tolerance to concentrations of a substance, e.g. a carbon source, a biofuel or biofuel precursor, or a toxic substance. AMPK gene and gene product sequences are well known to those of skill in the art. Exemplary, representative gene and gene product sequences can be found under the entry for GeneID: 100145903 in the NCBI database (www.ncbi.nlm.nih.gov).

Isolated Nucleic Acids

Some aspects of this invention provide nucleic acids coding for a gene product conferring a required and/or desired phenotype for biofuel or biofuel precursor production to a microbe, for example, *Y. lipolytica*. In some embodiments, the nucleic acid is a nucleic acid derived from *Y. lipolytica*. In some embodiments, the nucleic acid encodes a desaturase, for example a Δ9 desaturase. In some embodiments, the nucleic acid encodes *Y. lipolytica* Δ9 desaturase. In some embodiments, the nucleic acid comprises SEQ ID NO: 1. In some embodiments, the nucleic acid is SEQ ID NO: 1. In some embodiments, the nucleic acid encodes a gene product, for example, a protein, encoded by SEQ ID NO: 1.

Some aspects of this invention provide a gene product, for example, a protein, conferring a required and/or desirable phenotype for biofuel or biofuel precursor production to a microbe, for example, *Y. lipolytica*. In some embodiments, the protein is a protein from *Y. lipolytica*. In some embodiments, the protein is a desaturase, for example a Δ9 desaturase. In some embodiments, the protein is a *Y. lipolytica* Δ9 desaturase. In some embodiments, the amino acid sequence of the protein is the one provided in SEQ ID NO: 2.

The term "nucleic acid" refers to a molecule comprising multiple linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) and yeast artificial chromosomes (YACs) can also be used in accordance with some aspects of this invention.

Some aspects of this invention relate to the use of nucleic acid derivatives. As will be described herein, the use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects of this invention may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives according to some aspects of this invention may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine.

In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Some aspects of this invention relate to nucleic acids encoding a gene product conferring a required or desirable phenotype to a microbe for biofuel or biofuel precursor production which are linked to a promoter or other transcription activating element. In some embodiments, the nucleic acid encoding the gene product and linked to a promoter is comprised in an expression vector or expression construct. As used herein, the terms "expression vector" or "expression construct" refer to a nucleic acid construct, generated recombinantly or synthetically, with a series of specified nucleic acid elements that permit transcription of a particular nucleic acid in a host microbe, for example, an oleaginous yeast. In some embodiments, the expression vector may be part of a plasmid, virus, or nucleic acid fragment. In some embodiments, the expression vector includes the coding nucleic acid to be transcribed operably linked to a promoter. A promoter is a nucleic acid element that facilitates transcription of a nucleic acid to be transcribed. A promoter is typically located on the same strand and upstream (or 5') of the nucleic acid sequence the transcription of which it controls. In some embodiments, the expression vector includes the coding nucleic acid to be transcribed operably linked to a heterologous promoter. A heterologous promoter is a promoter not naturally operably linked to a given nucleic acid sequence. For example, the SCD gene in *Y. lipolytica* is naturally operably linked to the *Y. lipolytica* SCD gene promoter. Any promoter other than the wildtype *Y. lipolytica* SCD gene promoter operably linked to the SCD gene, or parts thereof, for example in an expression construct, would, therefore, be a heterologous promoter.

In some embodiments, the expression vector includes the coding nucleic acid, for example, a nucleic acid encoding a SCD gene product, operably linked to a constitutive promoter. The term "constitutive promoter" refers to a promoter that allows for continual transcription of its associated gene. In some embodiments, the expression vector includes the coding nucleic acid, for example, a nucleic acid encoding a SCD gene product, operably linked to an inducible promoter. The term "inducible promoter", interchangeably used herein with the term "conditional promoter", refers to a promoter that allows for transcription of its associated gene only in the presence or absence of biotic or abiotic factors. Drug-inducible promoters, for example tetracycline/doxycycline inducible promoters, tamoxifen-inducible promoters, as well as promoters that depend on a recombination event in order to be active, for example the cre-mediated recombination of loxP sites, are examples of inducible promoters that are well known in the art.

Methods to deliver expression vectors or expression constructs into microbes, for example, into yeast cells, are well known to those of skill in the art. Nucleic acids, including expression vectors, can be delivered to prokaryotic and eukaryotic microbes by various methods well known to those of skill in the relevant biological arts. Methods for the delivery of nucleic acids to a microbe in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an SCD expression construct, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

In some embodiments, the native promoter of a gene encoding a gene product conferring a required or desirable phenotype to a microbe, for example, the native SCD promoter, is modified in the microbe to alter the regulation of its transcriptional activity. In some embodiment, the modified promoter exhibits an increased transcriptional activity as compared to its unmodified counterpart. The term "modified promoter", as used herein, refers to a promoter the nucleotide sequence of which has been artificially altered. Nucleotide deletion(s), insertion(s) or mutation(s), alone or in combination, are examples of such artificial alterations. Artificial promoter alterations can be effected in a targeted fashion, for example by homologous recombination approaches, such as gene targeting, knockout, knock in, site-directed mutagenesis, or artificial zinc finger nuclease-mediated strategies. Alternatively, such alterations may be effected by a random or quasi-random event, such as irradiation or non-targeted nucleotide integration an subsequent selection. Promoter modifications, in general, are fashioned in order to modulate the transcriptional activation properties of the respective promoter. For example, the disruption or deletion of a regulatory element mediating the repression of a SCD promoter in response to elevated intracellular fatty acid levels would lead to continued transcriptional activation of the SCD gene even under conditions of elevated intracellular fatty acid levels. Similarly, the insertion of a constitutively active transcriptional activator element into a conditional promoter region may effect overexpression of the respective gene under normally inhibitive conditions. Methods for the targeted disruption of a native promoter, for example, a native SCD promoter, in a microbe, for example, for targeted disruption resulting in an increased transcription rate, are well known to those of skill in the art.

In some embodiments, a nucleic acid construct is provided that is useful for the knockout of a delta-12 desaturase gene in a microbe for biofuel or biofuel precursor production. In some embodiments, the knockout construct comprises genomic sequences of a microbial delta-12 desaturase gene that flank a nucleotide sequence that, when inserted into the delta-12 desaturase gene, disrupts the expression of a delta-12 desaturase gene product. In some embodiments, the nucleic acid disrupting the delta-12 desaturase gene product expression is an antibiotic resistance marker, for example, a phleomycin resistance gene. In some embodiments, the delta-12 desaturase knockout vector comprises a sequence as provided in SEQ ID NO: 28. Methods of delivering knockout vectors to microbes are well known to those of skill in the art and methods to effect homologous recombination in microbes, for example, in yeasts, are well known to the skilled artisan as well. The invention is not limited in this respect.

Microbe Engineering Methods

Some aspects of this invention relate to engineering of a microbe, for example, *Y. lipolytica*, to exhibit a required and/or desirable phenotype for large-scale production of a biofuel or biofuel precursor. Some aspects of this invention relate to the metabolic engineering of the SCD pathway in order to yield a microbe optimized for biofuel production. Some aspects of this invention relate to the metabolic engineering of a gene regulating carbon flux into or out of a fatty acid synthesis pathway in order to yield a microbe optimized for biofuel production.

Some aspects of this invention provide methods to greatly increase the efficiency of *Y. lipolytica* mediated carbon source to lipid conversion by modulating *Y. lipolytica*'s native lipid metabolism. Some aspects of this invention relate to the discovery that an overexpression of a gene increasing fatty acid or triacylglycerol accumulation, such as SCD, not only results in an increase in lipid accumulation, but also an increase of lipid synthesis rate, lipid content, and/or growth rate. Remarkably and unexpectedly, lipid metabolism modulation according to some methods provided by this invention also confers other beneficial characteristics, for example an increased tolerance to feedstock substances, including high concentrations of substrate (e.g., glucose) and/or of toxic substances commonly found to contaminate feedstock, for example, pretreated feedstock. Some non-limiting examples of such contaminating substances are furfural, 5-hydroxymethylfurfural and acetic acid. Some non-limiting examples of feedstock materials that generate contaminating, toxic substances upon pre-treatment, are wood-derived feedstocks, corn stover, and bagasse.

Some aspects of this invention relate to engineering required and/or desirable phenotypes in *Y. lipolytica* via overriding transcriptional inhibition of a key regulator of lipid metabolism, for example via overriding transcriptional inhibition of SCD. The manipulation of a key regulator of lipid metabolism, for example SCD, in other biofuel producing microbes, for example yeast, bacteria, fungi, or algae, is also contemplated.

In order to engineer an organism, for example an oleaginous yeast, to be useful in the industrial-scale production of biofuels, a detailed understanding of the molecular mechanisms governing fatty acid and lipid metabolism in the respective organism is essential. Until the present invention, the identification and functional annotation of fatty acid and lipid metabolism regulators in oil producing microorganisms for biofuel production, e.g. oleaginous yeast, remained unsolved. Some aspects of this invention provide the identification and functional annotation of key regulator gene, SCD, in the oleaginous yeast *Y. lipolytica*. Isolated SCD nucleic acid and protein molecules are also provided.

Some aspects of this invention relate to the engineering of a desirable phenotype for biofuel or biofuel precursor production in a microbe by genetic engineering. Some aspects of this invention relate to the manipulation of a gene involved in the production of biofuel or a biofuel precursor, for example, a fatty acid or a triacylglycerol, in a microbe. Some aspects of this invention relate to the manipulation of a plurality of genes involved in the production of biofuel or a biofuel precursor in parallel in a microbe.

In some embodiments, a microbe is engineered for biofuel or biofuel precursor production by manipulating a single gene according to methods provided by aspects of this invention, for example, a Δ9 desaturase (e.g., SCD), GLUT (e.g., Glut1), hemoglobin, cytochrome (e.g., cytochrome B5), malic enzyme, ACC, ACS, ACS2, FAA1, FAT1, FAT2, ACLY, FAS, AMPK, JNK2, or delta-12 desaturase. In some embodiments, a microbe is engineered for biofuel or biofuel precursor production by manipulating a plurality of genes according to methods provided by aspects of this invention, for example, any combination of two or more of a Δ9 desaturase (e.g., SCD), GLUT (e.g., Glut1), hemoglobin, cytochrome (e.g., cytochrome B5), malic enzyme, ACC, ACS, ACS2, FAA1, FAT1, FAT2, ACLY, FAS, JNK2, delta-12 desaturase, and/or AMPK. In some embodiments, a microbe is engineered to comprise an increased level of a SCD gene product and an additional manipulation, for example, a genetic manipulation, of the expression of an additional gene product, for example, a GLUT (e.g., Glut1), hemoglobin, cytochrome (e.g., cytochrome B5), malic enzyme, ACC, ACS, ACS2, FAA1, FAT1, FAT2, ACLY, FAS, JNK2, delta-12 desaturase, or AMPK gene product. In some embodiments, a microbe is engineered to comprise an increased level of a SCD gene product and of a hemoglobin gene product. In some embodiments, a microbe is engineered to comprise an increased level of a SCD gene product and of a GLUT gene product, for example, a Glut1 gene product. In some embodiments, a microbe is engineered to comprise an increased level of a SCD gene product, of a GLUT gene product, for example, a Glut1 gene product, and of a hemoglobin and/or a cytochrome gene product. In some embodiments, a microbe is engineered to comprise an increased level of a SCD gene product and of Glut1, hemoglobin and cytochrome b5, and optionally a delta-12 desaturase knockout. In some embodiments, the microbe is *Y. lipolytica*.

Engineered Microbes for Biofuel Production

Some aspects of this invention relate to a microbe engineered and/or optimized for large-scale biofuel or biofuel precursor production. In some embodiments, an engineered microbe is provided that has been manipulated by a method or using a nucleic acid or protein provided by some aspects of this invention. In some embodiments, an engineered microbe is provided, that overexpresses a gene product that, according to some aspects of this invention, confers a required and/or desirable phenotype for biofuel or biofuel precursor production to the microbe. In some embodiments, a microbe comprising an increased SCD gene product activity is provided. In some embodiments, the microbe exhibits an increased fatty acid synthesis rate, an increased TAG storage, and/or an additional required or desirable trait.

In some embodiments, the engineered microbe is an oleaginous yeast, for example, *Y. lipolytica*. In some embodiments, an engineered yeast provided by this invention exhibits one or more highly desirable and unexpected phenotypic characteristics, for example: increased carbon to oil conversion, e.g., at a rate approaching theoretical values, robust growth, continuous oil production, remarkable biomass production, and increased tolerance of the carbon source and associated substances.

In some embodiments, the engineered microbe, for example, the engineered yeast, provided by aspects of this invention exhibits a carbon to oil conversion rate within the range of about 0.02 g/g (g oil, lipid, or TAG produced/g Glucose consumed) to about 0.3 g/g. In some embodiments, the engineered microbe, for example, the engineered yeast, provided by aspects of this invention exhibits a carbon to oil conversion of about 0.010 g/g (g TAG produced/g Glucose consumed), about 0.02 g/g, about 0.025 g/g, about 0.03 g/g, about 0.04 g/g, about 0.05 g/g, about 0.06 g/g, about 0.07 g/g, about 0.075 g/g, about 0.08 g/g, about 0.09 g/g, about 0.1 g/g, about 0.11 g/g, about 0.12 g/g, about 0.13 g/g, about 0.14 g/g, about 0.15 g/g, about 0.16 g/g, about 0.17 g/g, about 0.18 g/g, about 0.19 g/g, about 0.2 g/g, about 0.21 g/g, about 0.22 g/g, about 0.23 g/g, about 0.24 g/g, about 0.25 g/g, about 0.26 g/g, about 0.27 g/g, about 0.28 g/g, about 0.29 g/g, or about 0.3 g/g, or approaching theoretical values. In some embodiments, the engineered microbe, for example, the engineered yeast, provided by aspects of this invention exhibits a carbon to oil conversion rate of at least about 0.010 g/g (g TAG produced/g Glucose consumed), at least about 0.02 g/g, at least about 0.025 g/g, at least about 0.03 g/g, at least about 0.04 g/g, at least about 0.05 g/g, at least about 0.06 g/g, at least about 0.07 g/g, at least about 0.075 g/g, at least about 0.08 g/g, at least about 0.09 g/g, at least about 0.1 g/g, at least about 0.11 g/g, at least about 0.12 g/g, at least about 0.13 g/g, at least about 0.14 g/g, at least about 0.15 g/g, at least about 0.16 g/g, at least about 0.17 g/g, at least about 0.18 g/g, at least about 0.19 g/g, at least about 0.2 g/g, at least about 0.21 g/g, at least about 0.22 g/g, at least about 0.23 g/g, at least about 0.24 g/g, at least about 0.25 g/g, at least about 0.26 g/g, at least about 0.27 g/g, at least about 0.28 g/g, at least about 0.29 g/g, or at least about 0.3 g/g, or approaching theoretical values.

In some embodiments, the engineered yeast provided by aspects of this invention exhibits a biomass production that is increased about 2-fold, about 2.5-fold, about 5-fold, about 7.5-fold, about 10-fold, about 15-fold, about 20-fold, about 25-fold, about 30-fold, about 32-fold, about 35-fold, or about 40-fold as compared to wild type yeast. In some embodiments, the engineered yeast provided by aspects of this invention exhibits tolerance to the carbon source and/or associated substances at concentrations of up to about 150%, up to about 175%, up to about 200%, up to about 225%, up to about 250%, up to about 275%, up to about 300%, up to about 325%, up to about 350%, up to about 375%, up to about 400%, or up to about 500% of that of the highest concentrations tolerated by wild type yeast. Non-limiting examples of carbon source associated substances include toxic substances contaminating the carbon source, for example, substances that are generated or used during pretreatment of the carbon source (e.g. acidic substances, such as acetic acid, or ammonia).

The data presented herein identify a novel rate-limiting step of lipid accumulation in oleaginous yeast, the engineering of which results in greatly improved characteristics of the manipulated microbe in respect to biofuel generation from carbohydrate sources (e.g. glucose). Accordingly, methods and manufactures provided by the instant invention represent a significant advance towards an alternative production of biofuels from renewable carbohydrate sources using microbial, for example yeast, fermentation.

Microbial Cultures for Biofuel Production

Some aspects of this invention relate to a culture of a microbe provided herein or engineered according to aspects of this invention or comprising an isolated nucleic acid or protein provided herein.

In some embodiments, the culture comprises a microbe provided herein or engineered according to aspects of this invention or comprising an isolated nucleic acid or protein from the list provided herein and a medium, for example, a liquid medium.

In some embodiments, the culture comprises a microbe provided herein or engineered according to aspects of this invention or comprising an isolated nucleic acid or protein provided herein and a carbohydrate source.

In some embodiments, the culture comprises a microbe provided herein or engineered according to aspects of this invention or comprising an isolated nucleic acid or protein provided herein and a salt and/or buffer establishing conditions of salinity, osmolarity, and pH, that are amenable to survival, growth, and/or carbohydrate to biofuel or biofuel precursor conversion by the microbe.

In some embodiments, the culture comprises an additional component, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions.

While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); and Christine Guthrie and Gerald R. Fink, *Guide to Yeast Genetics and Molecular and Cell Biology, Part C, Volume* 351, Academic Press; 1st edition (Jul. 9, 2002), all of which are incorporated by reference herein. For oil production, the cultures of engineered microbes described herein are cultured under conditions suitable for oil accumulation, as known in the art.

In some embodiments, an engineered microbe is provided that exhibits a growth advantage over wild type microbes of the same kind and/or over other microbes, for example, microbes commonly found to contaminate microbial cultures for carbon source to biofuel or biofuel precursor conversion. For example, in some embodiments, a microbe is provided that exhibits an increased proliferation rate as compared to wild type microbes of the same kind or other microbes, and/or an increased tolerance to or viability under conditions that are toxic or restrict growth or proliferation to wild type microbes of the same kind and/or other microbes. In some embodiments, the growth and/or proliferation advantage of an engineered microbe provided by aspects of this invention translates into the possibility of using non-sterile culturing and fermentation conditions for biofuel or biofuel precursor production, because the problem of culture overgrowth by contaminating microbes is mitigated or completely abolished. In some embodiments, an engineered microbe provided by aspects of this invention is cultured under non-sterile conditions for biofuel or biofuel precursor production. For example, in some embodiments, non-sterilized feedstock, non-sterilized culture media, non-sterilized supplements, or a non-sterilized bioreactor (e.g. an open reactor under non-sterile conditions) is used for biofuel or biofuel precursor production.

Methods for Biofuel Production/Feedstock/Bioreactors

Some aspects of this invention relate to methods for the production of biofuel or biofuel precursor using modified microbes in accordance with this invention. In some embodiments, methods for biofuel or biofuel precursor production on an industrial scale are provided.

A variety of carbon sources can be converted into a biofuel or biofuel precursor using a method provided by some aspects of this invention. Sugars, starches, and fibers are non-limiting examples of carbohydrate sources suitable for conversion methods provided by some aspects of this invention. According to some aspects of this invention, a carbohydrate source may comprise a refined and/or unrefined sugar, starch, and/or fiber, or a combination of any of these. Non-limiting examples of sugars are fermentable sugars, such as glucose, fructose, sucrose, xylose, and lactose. Non-limiting examples of starches are amylase and amylopectin. Non-limiting examples of fibers are plant fibers, such as cellulose, hemicellulose and wood fibers. Some aspects of this invention relate to the use of industrial byproducts, intermediates, or waste products, for example raw plant extracts, molasses, stover, or sewage as a carbon source. In some embodiments, the carbon source is derived from algae. In some embodiments, algal biomass is produced specifically for use as a carbon source in microbe-mediated biofuel or biofuel precursor production.

In some embodiments, methods for the production of biofuel or biofuel precursor are provided that include the use of a cheap, abundant, and readily available carbon source feedstock as the carbon source. In some embodiments, cellulose or hemicellulose is used as the carbon source. In some embodiments, the cellulose or hemicellulose is derived from industrial by- or waste products. In some embodiments, the cellulose or hemicellulose is derived directly from plant or algal biomass. Plant or algal biomass is one of the most abundant feedstocks and comprises a significant amount of non-fermentable sugars and fibers, for example, cellulose and hemi-cellulose. In some embodiments, biomass feedstock is pretreated to convert a non-fermentable sugar or fiber into a fermentable sugar, thus making them available for microbe growth and microbe-mediated biofuel or biofuel precursor production. In some embodiments, the pretreatment of biomass feedstock includes depolymerizing cellulose and/or hemicellulose components to monomeric sugars using a pretreatment method known to those of skill in the art, for example, a dilute acid or ammonia fiber expansion (AFEX) method (see, e.g., Yang B, Wyman C E. *Dilute acid and autohydrolysis pretreatment*. Methods Mol. Biol. 2009; 581: 103-14; Balan V, Bals B, Chundawat S P, Marshall D, Dale B E, *Lignocellulosic biomass pretreatment using AFEX Methods* Mol Biol. 2009; 581:61-77). Other methods for depolymerization of biomass polymers to monomeric sugars are well known to those of skill in the art and are contemplated to be used in some embodiments of this invention.

In some embodiments, a biomass feedstock containing non-fermentable sugars is pretreated using a dilute acid method to depolymerize a non-fermentable sugar to a monomeric, fermentable sugar. In some embodiments, biomass is treated with dilute sulphuric acid at moderately mild temperatures for a defined period of time. For example, in some embodiments, the biomass is treated with about 0.5%, about 1%, about 2%, about 3%, about 4%, about 5%, or about 6% sulphuric acid. In some embodiments, the biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C.

In some embodiments, the resulting hydrolysate contains insoluble lignin and solubilized cellulosic and hemicellulosic polymers. The latter products can be further treated to generate hexose and pentose sugars such as glucose and xylose monomers by methods well known to those of skill in the art, for example, by treatment with cellulase or other hydrolyzing enzymes. In some embodiments, the pretreatment of non-fermentable sugars with dilute acid results in the generation of by-products that include toxic compounds which inhibit growth, decrease viability, and/or inhibit biofuel or biofuel precursor production of microbes not engineered according to aspects of this invention. In some embodiments, the pretreated feedstock is washed, supplemented with media supporting microbial growth and biofuel or biofuel precursor production, and/or over-limed for detoxification.

In some embodiments, a biomass feedstock containing non-fermentable sugars is pretreated using an AFEX method to depolymerize a non-fermentable sugar to a monomeric, fermentable sugar. In some embodiments, biomass is treated with liquid ammonia at high temperature and pressure for a defined period of time. In some embodiments, biomass is treated for about 10 minutes, about 20 minutes, about 30 minutes, about 40 minutes, about 50 minutes, about 60 minutes, about 70 minutes, about 80 minutes, about 90 minutes, or longer. In some embodiments, biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C. In some embodiments, the AFEX pretreatment results in the conversion of crystalline cellulose contained in the feedstock into an amorphous, fermentable form. In some embodiments, the AFEX pre-treated biomass feedstock does not contain significant amounts of toxic byproducts that inhibit microbial growth and/or biofuel or biofuel precursor production, and is used without prior detoxification for microbial biofuel or biofuel precursor production.

In some embodiments, biomass feedstock, with or without pre-treatment, is treated with an enzyme that hydrolyzes or depolymerizes sugar polymers, for example, with a cellulase or hemicellulase enzyme. In some embodiments, the feedstock is contacted with the enzyme in a liquid phase and incubated at a temperature allowing for the enzyme to catalyze a depolymerization or hydrolyzation reaction for a time sufficient to hydrolyze or depolymerize a significant amount of the non-fermentable sugar or fiber in the biomass feedstock. In some embodiments, the liquid phase of the feedstock contacted with the enzyme, which contains the soluble, fermentable sugar fraction, is separated from the solid phase, including non-fermentable sugars and fibers, after incubation for hydrolyzation and depolymerization, for example, by centrifugation. In some embodiments, the liquid fraction of the feedstock is subsequently contacted with a microbe, for example, a microbe provided by aspects of this invention, for conversion to biofuel or biofuel precursor. In some embodiments, enzymatic conversion of non-fermentable sugars or fiber occurs in a consolidated bioprocess, for example, at the same time and/or in the same reactor as microbial conversion of the produced fermentable sugars to biofuel or biofuel precursor. In some embodiments, the enzymatic conversion is performed first, and the feedstock contacted with enzyme is subsequently contacted with the microbe for biofuel or biofuel precursor production. In some embodiments, enzymatic and microbial conversion are performed at the same time and in the same reactor.

In some embodiments, an engineered microbe as provided herein, for example, a *Yarrowia lipolytica* overexpressing an SCD gene and, optionally, carrying additional modifications as described herein, is grown on acetate as the main carbon source. For example, in some embodiments, the microbe is grown in a solution of acetic acid with a concentration of about 1%, about 2%, about 3%, about 4%, about 5%, about 6%, about 7%, about 8%, about 9%, or about 10%. In some embodiments, the acetate concentration is between about 3%-10%. In some embodiments, cell cultures comprising engineered microbes as provided herein that are cultured on acetate as the main carbon source are contacted, or "spiked" with glycerol. In some embodiments, the microbes are intermittently contacted with glycerol. In some embodiments, the microbes are continuously or semi-continuously contacted with glycerol. In some embodiments, the microbes are contacted with glycerol at a concentration of about 0.5%, about 1%, about 2%, about 3%, about 4%, or about 5%. Contacting the engineered microbes provided herein with glycerol provides much needed metabolites for the production of TAGs, as well as reducing moieties needed in the production of fatty acids from carbohydrates. In some embodiments, glycerol spiking is performed in biofuel or biofuel precursor production methods using a carbon source other than acetate, for example, any carbon source described herein.

In some embodiments, fermentation processes for large-scale microbe-mediated carbohydrate to lipid conversion may be carried out in bioreactors. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate a product, for example a biofuel or biofuel precursor, for example a fatty acid and/or TAG, on a commercial or quasi-commercial scale. Large scale bioreactors typically have volumes in the range of liters, hundreds of liters, thousands of liters, or more.

A bioreactor in accordance with aspects of this invention may comprise a microbe or a microbe culture. In some embodiments, a bioreactor may comprise a spore and/or any kind of dormant cell type of any isolated microbe provided by aspects of this invention, for example, in a dry state. In some embodiments, addition of a suitable carbohydrate source to such bioreactors may lead to activation of the dormant cell, for example to germination of a yeast spore, and subsequent conversion of the carbohydrate source, at least in part, to a biofuel or biofuel precursor.

Some bioreactors according to aspects of this invention may include cell culture systems where microbes are in contact with moving liquids and/or gas bubbles. Microbes or microbe cultures in accordance with aspects of this invention may be grown in suspension or attached to solid phase carriers. Non-limiting examples of carrier systems include microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

Industrial-scale carbohydrate to lipid conversion processes in accordance with aspects of this invention may be operated in continuous, semi-continuous or non-continuous modes. Non-limiting examples of operation modes in accordance with this invention are batch, fed batch, extended batch, repetitive batch, draw/fill, rotating-wall, spinning flask, and/or perfusion mode of operation.

In some embodiments, bioreactors may be used that allow continuous or semi-continuous replenishment of the substrate stock, for example a carbohydrate source and/or continuous or semi-continuous separation of the product, for example a secreted lipid, an organic phase comprising a lipid, and/or cells exhibiting a desired lipid content, from the reactor.

Non-limiting examples of bioreactors in accordance with this invention are: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multiwell plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

Bioreactors and fermentors according to aspects of this invention may, optionally, comprise a sensor and/or a control system to measure and/or adjust reaction parameters. Non-limiting examples of reaction parameters are: biological parameters, for example growth rate, cell size, cell number, cell density, cell type, or cell state, chemical parameters, for example pH, redox-potential, concentration of reaction substrate and/or product, concentration of dissolved gases, such as oxygen concentration and CO2 concentration, nutrient concentrations, metabolite concentrations, glucose concentration, glutamine concentration, pyruvate concentration, apatite concentration, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products, physical/mechanical parameters, for example density, conductivity, degree of agitation, pressure, and flow rate, shear stress, shear rate, viscosity, color, turbidity, light absorption, mixing rate, conversion rate, as well as thermodynamic parameters, such as temperature, light intensity/quality etc.

Sensors able to measure parameters as described herein are well known to those of skill in the relevant mechanical and electronic arts. Control systems able to adjust the parameters in a bioreactor based on the inputs from a sensor as described herein are well known to those of skill in the art of bioreactor engineering.

A variety of different microbes as provided by aspects of this invention can be cultured in a suitable bioreactor to perform large-scale carbohydrate to biofuel or biofuel precursor conversion in accordance with aspects of the invention, for example, microbes from various sources of yeast, such as oleaginous yeast, bacteria, algae and fungi.

Non-limiting examples of yeast cells are cells from *Yarrowia lipolytica, Hansenula polymorpha, Pichia pastoris, Saccharomyces cerevisiae, S. bayanus, K. lactis, Waltomyces lipofer, Mortierella alpine, Mortierella isabellina, Hansenula polymorpha, Mucor rouxii, Trichosporon cutaneu, Rhodotorula glutinis, Saccharomyces diastasicus, Schwanniomyces occidentalis, S. cerevisiae, Pichia stipitis*, and *Schizosaccharomyces pombe*.

Non-limiting examples of bacteria are *Bacillus subtilis, Salmonella, Escherichia coli, Vibrio cholerae, Streptomyces, Pseudomonas fluorescens, Pseudomonas putida, Pseudomonas* sp, *Rhodococcus* sp, *Streptomyces* sp, and *Alcaligenes* sp.

Fungal cells can, for example, be cultured from species such as *Aspergillus shirousamii, Aspergillus niger* and *Trichoderma reesei*.

Non-limiting examples of algal cells are cells from *Neochloris oleoabundans, Scenedesmus obliquus, Nannochloropsis* sp., *Dunaliella tertiolecta, Chlorella vulgaris, Chlorella emersonii*, and *Spirulina maxima*.

The type of carbohydrate source to be employed for conversion to a biofuel or biofuel precursor according to aspects of this invention depends on the specific microbe employed. Some microbes provided by aspects of this invention may be able to efficiently convert a specific carbohydrate source, while a different carbohydrate source may not be processed by the same microbe at high efficiency or at all. According to aspects of this invention, the oleaginous yeast *Y. lipolytica*, for example, can efficiently convert sugars, such as glucose, fructose, sucrose, and/or lactose, and carbohydrate sources high in sugars, for example molasses, and plant fibers into fatty acids and their derivatives.

In some embodiments, a biofuel or biofuel precursor, for example, a fatty acid or a triacylglycerol, generated from a carbon source feedstock is secreted, at least partially, by a microbe provided by aspects of this invention, for example, an oleaginous yeast, such as a *Y. lipolytica* cell. In some embodiments, a microbe provided by aspects of this invention is contacted with a carbohydrate source in an aqueous solution in a bioreactor, and secreted biofuel or biofuel precursor forms an organic phase that can be separated from the aqueous phase. The term organic phase, as used herein, refers to a liquid phase comprising a non-polar, organic compound, for example a fatty acid, TAG, and/or other non-polar lipid. And organic phase in accordance to this invention might further contain a microbe, a carbohydrate, or other compound found in other phases found in a respective bioreactor. Methods useful for industrial scale phase separation are well known to those of ordinary skill in the art. In some embodiments, the organic phase is continuously or semi-continuously siphoned off. In some embodiments, a bioreactor is employed, comprising a separator, which continuously or semi-continuously extracts the organic phase.

In some embodiments, a biofuel or biofuel precursor is accumulated in cells according to aspects of this invention. In some embodiments, cells that have accumulated a desirable amount of biofuel or biofuel precursor, are separated continuously or semi-continuously from a bioreactor, for example, by centrifugation, sedimentation, or filtration. Cell separation can further be effected, for example, based on a change in physical cell characteristics, such as cell size or density, by methods well known to those skilled in the art. The accumulated biofuel or biofuel precursor can subsequently be extracted from the respective cells using standard methods of extraction well known to those skilled in the art, for example, solvent hexane extraction. In some embodiments, microbial cells are collected and extracted with 3 times the collected cell volume of hexane. In some embodiments, the extracted biofuel or biofuel precursor are further refined. In some embodiments, a biofuel precursor, for example a triacylglycerol is converted to a biofuel, for example, biodiesel, using a method well known to those of skill in the art, for example, a transesterification procedure.

The function and advantage of these and other embodiments of the present invention will be more fully understood from the examples below. The following examples are intended to illustrate the benefits of the present invention, but do not exemplify the full scope of the invention.

EXAMPLES

Materials and Methods

Figure 12:
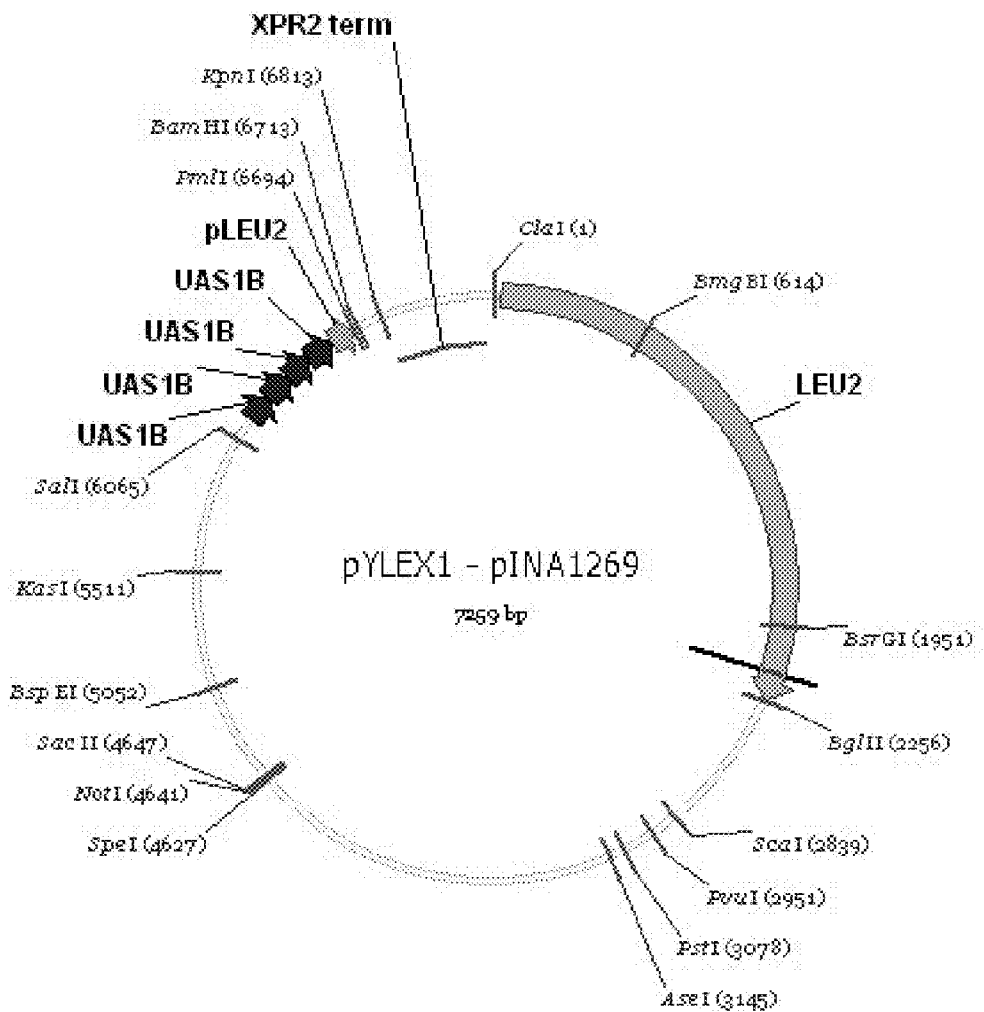
FIG. 12: pYLEX1, an expression vector useful for transgene expression in *Y. lipolytica* (A). The vector, which is well known to those of skill in the art, may include a selection marker, or a defective URA3 marker, which is derived from the URA3 gene of *Y. lipolytica*, which allows complementation of auxotrophy for uracil, such as the URA3d markers described by LE DALL et al., Curr. Genet., 26, 38-44 (1994). The sequences for controlling the expression are, for example, promoter and terminator sequences which are active in *Yarrowia*. In some embodiments, the vector comprises an inducible or constitutive promoter. In some embodiments, genes can be overexpressed in microbes from pYLEX1, for example, by cloning a construct of interest, e.g., a SCD cDNA under the control of a promoter, into pYLEX1. Exemplary cloning of cytochrome B and hemoglobin cDNAs under the control of a TEF promoter are shown (B, C).
Figure 12:
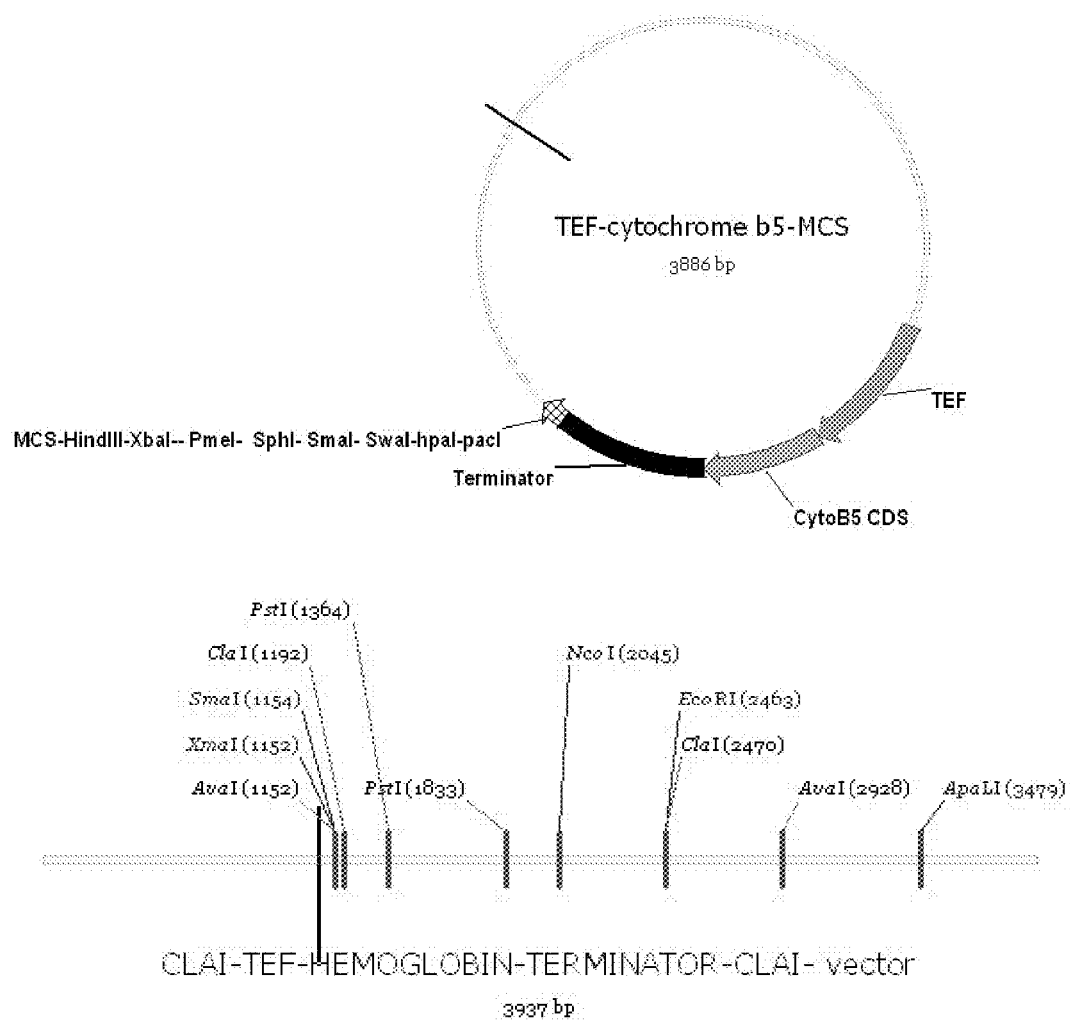

Gene constructs: The respective genes, for example, GLUT1, hemoglobin, cytochrome, pyruvate carboxylase, SCD, etc., were cloned into plasmid YLEX (FIG. 12) between PmlI and Kpn sites. The restrictions sites used were PmlI and KpnI. All cDNA were sequenced and mapped to genomic databases. Exemplary, representative sequence database entries that the cloned cDNAs were mapped to include: GLUT1: GeneID: 6513; Hemoglobin: *Vitreoscilla stercoraria* bacterial hemoglobin gene, ACCESSION L77863; Cytochrome: GeneID: 1528, CYB5A cytochrome b5 type A; Pyruvate carboxylase: GeneID: 5091; SCD stearoyl-CoA desaturase (SCD): GeneID: 710155.

Representative sequences, for example coding sequences, useful for the generation of overexpressing microbes are, for example:

```
HEMOGLOBIN (bacterial)
                                                                      (SEQ ID NO: 3)
ATGTTAGACCAACAAACCGTAGACACCAGCAAAGCCACTGTTCCTGTATTGAAAGAGCATGGCGTGACCATTACCACGACGTT TTACCAAAATTTGTTTGCCAAACATCCTGAAGTACGACCTTTGTTTGACATGGGTCGCCAAGCATCTTTGGAACAGCCTAAGG CTTTGGCGATGACGGTTGGGGCGGCGGCACAAAACATTGAAAATTTACCTGCAATTTTGCCTGCAGTACAAAAAATTGCCGTC AAACATTGTCAAGCAGGCGTGGCGGCACGACATTATCCGATTGTGGGTCAAGAATTGTTGGGTGCGATTAAAGAATTATTGGG TGATGCGGCGACCGATGATATTTTGGATGCGTGGGGCAAGGCTTATGGCGTGATTGCCGATGTTTTTATTCAAGTGGAAGCGG

ATTTGTACGCTCAAGACGCTGAATAA

CYTOCROME B (Yarrowia)
                                                                      (SEQ ID NO: 4)
ATGATCATCAACGGCAAGGTCTACGACATCTCCAGCTTCGTTGACGAGCATCCCGGTGGAGAGGAGGTTCTTCTTGATGCCGG TGGAACTGAGGCCACCAACGCTTTCGACGACGTTGGACACTCTGAGGACGCTTACGGCATCCTTAACGACCTCTATGTCGGTG AGGTTGACCCCAGCGAGGACGTTATCCGAAAGACTCACACTGTCAAGACTTCTTACGAGGACGGCGAGTCTGTTGGTGATGAC CACGGATCTTCTTCCATGATCTTCCTCATTGTTGCTGCTGCTGTTGCCGCCGCTGCTTTCTTCTACCTCCAGGGTCAGAAATA
A GLUT (rat)
                                                                      (SEQ ID NO: 5)
ATGGAGCCCAGCAGCAAGAAGGTGACGGGCCGCCTTATGTTGGCCGTGGGAGGGGCAGTGCTCGGATCCCTGCAGTTCGGCTA TAACACCGGTGTCATCAACGCCCCCCAGAAGGTAATTGAGGAGTTCTACAATCAAACATGGAACCACCGCTATGGAGAGTCCA TCCCATCCACCACACTCACCACACTCTGGTCTCTCTCCGTGGCCATCTTCTCTGTCGGGGGCATGATTGGTTCCTTCTCTGTG GGCCTCTTTGTTAATCGCTTTGGCAGGCGGAACTCCATGCTGATGATGAACCTGTTGGCCTTTGTGTCTGCCGTGCTTATGGG
```

-continued

```
TTTCTCCAAACTGGGCAAGTCCTTTGAGATGCTGATCCTGGGCCGCTTCATCATTGGAGTGTACTGTGGCCTGACCACCGGCT

TTGTGCCCATGTATGTGGGGGAGGTGTCACCCACAGCTCTTCGTGGAGCCCTGGGCACCCTGCACCAGCTGGGCATCGTCGTT

GGGATCCTTATTGCCCAGGTGTTCGGCTTAGACTCCATCATGGGCAATGCAGACTTGTGGCCTCTACTGCTCAGTGTCATCTT

CATCCCAGCCCTGCTACAGTGTATCCTGTTGCCCTTCTGCCCTGAGAGCCCCCGCTTCCTGCTCATCAATCGTAACGAGGAGA

ACCGGGCCAAGAGTGTGCTGAAAAAGCTTCGAGGGACAGCCGATGTGACCCGAGACCTGCAGGAGATGAAAGAAGAGGGTCGG

CAGATGATGCGGGAGAAGAAGGTCACCATCTTGGAGCTGTTCCGCTCACCCGCCTACCGCCAGCCCATCCTCATCGCCGTGGT

GCTGCAGCTGTCCCAGCAGCTGTCGGGCATCAATGCTGTGTTCTACTACTCAACGAGCATCTTCGAGAAGGCAGGTGTGCAGC

AGCCTGTGTATGCCACCATCGGCTCGGGTATCGTCAACACGGCCTTCACTGTGGTGTCGCTGTTCGTCGTGGAGCGAGCTGGC

CGTCGGACCCTGCACCTCATTGGTCTGGCTGGCATGGCGGGCTGTGCTGTGCTCATGACCATCGCCCTGGCCCTGCTGGAGCA

GCTGCCCTGGATGTCCTATCTGAGTATCGTGGCCATCTTTGGCTTTGTGGCCTTCTTTGAAGTAGGCCCTGGTCCTATTCCAT

GGTTCATTGTGGCCGAGCTGTTCAGCCAGGGGCCCCGACCTGCTGCTGTTGCTGTGGCTGGCTTCTCTAACTGGACCTCAAAC

TTCATCGTGGGCATGTGCTTCCAATATGTGGAGCAACTGTGTGGCCCCTACGTCTTCATCATCTTCACGGTGCTGCTGGTACT

CTTCTTCATCTTCACCTACTTCAAAGTTCCTGAGACCAAAGGCCGGACCTTCGATGAGATCGCTTCCGGCTTCCGGCAGGGGG

GTGCCAGCCAGAGCGACAAGACACCTGAGGAGCTCTTCCACCCTCTGGGGGCTGACTCCCAAGTGTGA
```

Malic enzyme (Yarrowia)

(SEQ ID NO: 6)

```
ATGTTACGACTACGAACCATGCGACCCACACAGACCAGCGTCAGGGCGGCGCTTGGGCCCACCGCCGCGGCCCGAAACATGTC

CTCCTCCAGCCCCTCCAGCTTCGAATACTCGTCCTACGTCAAGGGCACGCGGGAAATCGGCCACCGAAAGGCGCCCACAACCC

GTCTGTCGGTTGAGGGCCCCATCTACGTGGGCTTCGACGGCATTCGTCTTCTCAACCTGCCGCATCTCAACAAGGGCTCGGGA

TTCCCCCTCAACGAGCGACGGGAATTCAGACTCAGTGGTCTTCTGCCCTCTGCCGAAGCCACCCTGGAGGAACAGGTCGACCG

AGCATACCAACAATTCAAAAAGTGTGGCACTCCCTTAGCCAAAAACGGGTTCTGCACCTCGCTCAAGTTCCAAAACGAGGTGC

TCTACTACGCCCTGCTGCTCAAGCACGTTAAGGAGGTCTTCCCCATCATCTATACACCGACTCAGGGAGAAGCCATTGAACAG

TACTCGCGGCTGTTCCGGCGGCCCGAAGGCTGCTTCCTCGACATCACCAGTCCCTACGACGTGGAGGAGCGTCTGGGAGCGTT

TGGAGACCATGACGACATTGACTACATTGTCGTGACTGACTCCGAGGGTATTCTCGGAATTGGAGACCAAGGAGTGGGCGGTA

TTGGTATTTCCATCGCCAAGCTGGCTCTCATGACTCTATGTGCTGGAGTCAACCCCTCACGAGTCATTCCTGTGGTTCTGGAT

ACGGGAACCAACAACCAGGAGCTGCTGCACGACCCCCTGTATCTCGGCCGACGAATGCCCCGAGTGCGAGGAAAGCAGTACGA

CGACTTCATCGACAACTTTGTGCAGTCTGCCCGAAGGCTGTATCCCAAGGCGGTGATCCATTTCGAGGACTTTGGGCTCGCTA

ACGCACACAAGATCCTCGACAAGTATCGACCGGAGATCCCCTGCTTCAACGACGACATCCAGGGCACTGGAGCCGTCACTTTG

GCCTCCATCACGGCCGCTCTCAAGGTGCTGGGCAAAAATATCACAGATACTGAATTCTCGTGTACGGAGCTGGTTCGGCCGG

CATGGGTATTGCTGAACAGGTCTATGATAACCTGGTTGCCCAGGGTCTCGACGACAAGACTGCGCGACAAAACATCTTTCTCA

TGGACCGACCGGGTCTACTGACCACCGCACTTACCGACGAGCAGATGAGCGACGTGCAGAAGCCGTTTGCCAAGGACAAGGCC

AATTACGAGGGAGTGGACACCAAGACTCTGGAGCACGTGGTTGCTGCCGTCAAGCCCATATTCTCATTGGATGTTCCACTCA

GCCCGGCGCCTTTAACGAGAAGGTCGTCAAGGAGATGCTCAAACACACCCCTCGACCCATCATTCTCCCTCTTTCCAACCCCA

CACGTCTTCATGAGGCTGTCCCTGCAGATCTGTACAAGTGGACCGACGGCAAGGCTCTGGTTGCCACCGGCTCGCCCTTTGAC

CCAGTCAACGGCAAGGAGACGTCTGAGAACAATAACTGCTTTGTTTTCCCCGGAATCGGGCTGGGAGCCATTCTGTCTCGATC

AAAGCTCATCACCAACACCATGATTGCTGCTGCCATCGAGTGCCTCGCCGAACAGGCCCCCATTCTCAAGAACCACGACGAGG

GAGTACTTCCCGACGTAGCTCTCATCCAGATCATTTCGGCCCGGGTGGCCACTGCCGTGGTTCTTCAGGCCAAGGCTGAGGGC

CTAGCCACTGTCGAGGAAGAGCTCAAGCCCGGCACCAAGGAACATGTGCAGATTCCCGACAACTTTGACGAGTGTCTCGCCTG

GGTCGAGACTCAGATGTGGCGGCCCGTCTACCGGCCTCTCATCCATGTGCGGGATTACGACTAG
```

-continued

Yarrowia Delta(9)-desaturase (Stearoyl-CoA desaturase)
(SEQ ID NO: 7)
ATGGTGAAAAACGTGGACCAAGTGGATCTCTCGCAGGTCGACACCATTGCCTCCGGCCGAGATGTCAACTACAAGGTCAAGTA
CACCTCCGGCGTTAAGATGAGCCAGGGCGCCTACGACGACAAGGGCCGCCACATTTCCGAGCAGCCCTTCACCTGGGCCAACT
GGCACCAGCACATCAACTGGCTCAACTTCATTCTGGTGATTGCGCTGCCTCTGTCGTCCTTTGCTGCCGCTCCCTTCGTCTCC
TTCAACTGGAAGACCGCCGCGTTTGCTGTCGGCTATTACATGTGCACCGGTCTCGGTATCACCGCCGGCTACCACCGAATGTG
GGCCCATCGAGCCTACAAGGCCGCTCTGCCCGTTCGAATCATCCTTGCTCTGTTTGGAGGAGGAGCTGTCGAGGGCTCCATCC
GATGGTGGGCCTCGTCTCACCGAGTCCACCACCGATGGACCGACTCCAACAAGGACCCTTACGACGCCCGAAAGGGATTCTGG
TTCTCCCACTTTGGCTGGATGCTGCTTGTGCCCAACCCCAAGAACAAGGGCCGAACTGACATTTCTGACCTCAACAACGACTG
GGTTGTCCGACTCCAGCACAAGTACTACGTTTACGTTCTCGTCTTCATGGCCATTGTTCTGCCCACCCTCGTCTGTGGCTTTG
GCTGGGGCGACTGGAAGGGAGGTCTTGTCTACGCCGGTATCATGCGATACACCTTTGTGCAGCAGGTGACTTTCTGTGTCAAC
TCCCTTGCCCACTGGATTGGAGAGCAGCCCTTCGACGACCGACGAACTCCCCGAGACCACGCTCTTACCGCCCTGGTCACCTT
TGGAGAGGGCTACCACAACTTCCACCACGAGTTCCCCTCGGACTACCGAAACGCCCTCATCTGGTACCAGTACGACCCCACCA
AGTGGCTCATCTGGACCCTCAAGCAGGTTGGTCTCGCCTGGGACCTCCAGACCTTCTCCCAGAACGCCATCGAGCAGGGTCTC
GTGCAGCAGCGACAGAAGAAGCTGGACAAGTGGCGAAACAACCTCAACTGGGGTATCCCCATTGAGCAGCTGCCTGTCATTGA
GTTTGAGGAGTTCCAAGAGCAGGCCAAGACCCGAGATCTGGTTCTCATTTCTGGCATTGTCCACGACGTGTCTGCCTTTGTCG
AGCACCACCCTGGTGGAAAGGCCCTCATTATGAGCGCCGTCGGCAAGGACGGTACCGCTGTCTTCAACGGAGGTGTCTACCGA
CACTCCAACGCTGGCCACAACCTGCTTGCCACCATGCGAGTTTCGGTCATTCGAGGCGGCATGGAGGTTGAGGTGTGGAAGAC
TGCCCAGAACGAAAAGAAGGACCAGAACATTGTCTCCGATGAGAGTGGAAACCGAATCCACCGAGCTGGTCTCCAGGCCACCC
GGGTCGAGAACCCCGGTATGTCTGGCATGGCTGCTTAG Pyruvate carboxylase (human)
(SEQ ID NO: 8)
ATGCTGAAGTTCCGAACAGTCCATGGGGGCCTGAGGCTCCTGGGAATCCGCCGAACCTCCACCGCCCCCGCTGCCTCCCCAAA
TGTCCGGCGCCTGGAGTATAAGCCCATCAAGAAAGTCATGGTGGCCAACAGAGGTGAGATTGCCATCCGTGTGTTCCGGGCCT
GCACGGAGCTGGGCATCCGCACCGTAGCCATCTACTCTGAGCAGGACACGGGCCAGATGCACCGGCAGAAAGCAGATGAAGCC
TATCTCATCGGCCGCGGCCTGGCCCCCGTGCAGGCCTACCTGCACATCCCAGACATCATCAAGGTGGCCAAGGAGAACAACGT
AGATGCAGTGCACCCTGGCTACGGGTTCCTCTCTGAGCGAGCGGACTTCGCCCAGGCCTGCCAGGATGCAGGGGTCCGGTTTA
TTGGGCCAAGCCCAGAAGTGGTCCGCAAGATGGGAGACAAGGTGGAGGCCCGGGCCATCGCCATTGCTGCGGGTGTTCCCGTT
GTCCCTGGCACAGATGCCCCCATCACGTCCCTGCATGAGGCCCACGAGTTCTCCAACACCTACGGCTTCCCCATCATCTTCAA
GGCGGCCTATGGGGGTGGAGGCGTGGCATGAGGGTGGTGCACAGCTACGAGGAGCTGGAGGAGAATTACACCCGGGCCTACT
CAGAGGCTCTGGCCGCCTTTGGGAATGGGGCGCTGTTTGTGGAGAAGTTCATCGAGAAGCCACGGCACATCGAGGTGCAGATC
TTGGGGGACCAGTATGGGAACATCCTGCACCTGTACGAGCGAGACTGCTCCATCCAGCGGCGGCACCAGAAGGTGGTCGAGAT
TGCCCCCGCCGCCCACCTGGACCCGCAGCTTCGGACTCGGCTCACCAGCGACTCTGTGAAACTCGCTAAACAGGTGGGCTACG
AGAACGCAGGCACCGTGGAGTTCCTGGTGGACAGGCACGGCAAGCACTACTTCATCGAGGTCAACTCCCGCCTGCAGGTGGAG
CACACGGTCACAGAGGAGATCACCGACGTAGACCTGGTCCATGCTCAGATCCACGTGGCTGAGGGCAGGAGCCTACCCGACCT
GGGCCTGCGGCAGGAGAACATCCGCATCAACGGGTGTGCCATCCAGTGCCGGGTCACCACCGAGGACCCCGCGCGCAGCTTCC
AGCCGGACACCGGCCGCATTGAGGTGTTCCGGAGCGGAGAGGGCATGGGCATCCGCCTGGATAATGCTTCCGCCTTCCAAGGA
GCCGTCATCTCGCCCCACTACGACTCCCTGCTGGTCAAAGTCATTGCCCACGGCAAAGACCACCCCACGGCCGCCACCAAGAT
GAGCAGGGCCCTTGCGGAGTTCCGCGTCCGAGGTGTGAAGACCAACATCGCCTTCCTGCAGAATGTGCTCAACAACCAGCAGT
TCCTGGCAGGCACTGTGGACACCCAGTTCATCGACGAGAACCCAGAGCTGTTCCAGCTGCGGCCTGCACAGAACCGGGCCCAA
AAGCTGTTGCACTACCTCGGCCATGTCATGGTAAACGGTCCAACCACCCCGATTCCCGTCAAGGCCAGCCCCAGCCCCACGGA
CCCCGTTGTCCCTGCAGTGCCCATAGGCCCGCCCCCGGCTGGTTTCAGAGACATCCTGCTGCGAGAGGGGCCTGAGGGCTTTG -continued CTCGAGCTGTGCGGAACCACCCGGGGCTGCTGCTGATGGACACGACCTTCAGGGACGCCCACCAGTCACTGCTGGCCACTCGT GTGCGCACCCACGATCTCAAAAAGATCGCCCCCTATGTTGCCCACAACTTCAGCAAGCTCTTCAGCATGGAGAACTGGGGAGG AGCCACGTTTGACGTCGCCATGCGCTTCCTGTATGAGTGCCCCTGGCGGCGGCTGCAGGAGCTCCGGGAGCTCATCCCCAACA TCCCTTTCCAGATGCTGCTGCGGGGGGCCAATGCTGTGGGCTACACCAACTACCCAGACAACGTGGTCTTCAAGTTCTGTGAA GTGGCCAAAGAGAATGGCATGGATGTCTTCCGTGTGTTTGACTCCCTCAACTACTTGCCCAACATGCTGCTGGGCATGGAGGC GGCAGGAAGTGCCGGAGGCGTGGTGGAGGCTGCCATCTCATACACGGGCGACGTGGCCGACCCCAGCCGCACCAAGTACTCAC TGCAGTACTACATGGGCTTGGCCGAAGAGCTGGTGCGAGCTGGCACCCACATCCTGTGCATCAAGGACATGGCCGGGCTGCTG AAGCCCACGGCCTGCACCATGCTGGTCAGCTCCCTCCGGGACCGCTTCCCCGACCTCCCACTGCACATCCACACCCACGACAC GTCAGGGGCAGGCGTGGCAGCCATGCTGGCCTGTGCCCAGGCTGGAGCTGATGTGGTGGATGTGGCAGCTGATTCCATGTCTG GGATGACTTCACAGCCCAGCATGGGGGCCCTGGTGGCCTGTACCAGAGGGACTCCCCTGGACACAGAGGTGCCCATGGAGCGC GTGTTTGACTACAGTGAGTACTGGGAGGGGGCTCGGGGACTGTACGCGGCCTTCGACTGCACGGCCACCATGAAGTCTGGCAA CTCGGACGTGTATGAAAATGAGATCCCAGGGGGCCAGTACACCAACCTGCACTTCCAGGCCCACAGCATGGGGCTTGGCTCCA AGTTCAAGGAGGTCAAGAAGGCCTATGTGGAGGCCAACCAGATGCTGGGCGATCTCATCAAGGTGACGCCCTCCTCCAAGATC GTGGGGGACCTGGCCCAGTTTATGGTGCAGAATGGATTGAGCCGGGCAGAGGCCGAAGCTCAGGCGGAAGAGCTGTCCTTTCC CCGCTCCGTGGTGGAGTTCCTGCAGGGCTACATCGGTGTCCCCATGGGGGGTTCCCCGAACCCTTTCGCTCTAAGGTACTGA AGGACCTGCCAAGGGTGGAGGGGCGGCCTGGAGCCTCCCTCCCTCCCCTGGATCTGCAGGCACTGGAGAAGGAGCTGGTAGAC CGGCATGGGAGGAGGTGACGCCGGAAGATGTGCTCTCAGCAGCTATGTACCCCGATGTGTTTGCCCACTTCAAGGACTTCAC TGCCACCTTTGGCCCCCTGGATAGCCTGAATACTCGCCTCTTCCTGCAGGGACCCAAGATCGCAGAGGAGTTTGAGGTGGAGC TGGAGCGGGGCAAGACGCTGCACATCAAAGCCCTGGCCGTGAGCGACCTGAACCGGGCCGGCCAGAGGCAGGTCTTCTTTGAG CTCAATGGGCAGCTGCGGTCCATCTTGGTCAAGGACACCCAGGCCATGAAGGAGATGCACTTCCACCCCAAGGCCCTAAAGGA CGTGAAGGGCCAGATCGGGGCGCCCATGCCTGGGAAGGTGATAGACATCAAAGTGGTGGCAGGGGCCAAGGTGGCCAAGGGCC AGCCCCTGTGTGTGCTCAGTGCCATGAAGATGGAGACTGTGGTGACCTCACCCATGGAGGGTACTGTCCGCAAGGTTCATGTG

ACCAAGGACATGACACTGGAAGGTGACGACCTCATCCTGGAGATCGAGTGA

ACC (Saccharomyces cerevisiae)

(SEQ ID NO: 9)
TTATTTCAAAGTCTTCAACAATTTTTCTTTATCATCGGTAGATAACATCTTGATAACTTCAGATAATCCATCAATAGCATTGT

CATGGTCGCTTCTGATCTTTTTAGCTAAGTCTTGAGCGAATGACTCTAATTTCAAACCCTTTAGTTTATCGTCCAAAGTTTTG

TAGTTTTCTTCAATCCATGTTGCGACTTGCCTATCATCTTCATGGTCCACTGAAGCAGGGTACCACGATCTAATTCTTGCGAT

CTTTTCTAATCTTGATGCTTCGCCTACCTGATGGCTCAACCTTTTAATCAAATATTCTTCGTTCAATCTTCTTCTCAATCTCC

AGAAGAAGAAACGACGTGCCTCGGTCCATTCCAGTTCCTTAGAAATAACACCCTTGGCCACCATACGTGAAGACCTATCGTGC

AAATCAGCAAATTGAAGACTGATTTGTCCGTAAATTGGCAATAGTTCTCTCTCACGATCAGCTAATTGCTTGGATATTTGCTG

ATGTACTTCTGGAGCCAAACTCTTGTTGGATAATTGAGATCTCAATTCTCTGTACTTGTCATCCAATCTGTTCATGGTGTCCA

GCAATTTTTCTCTACGGAACTTGATACCAACCATACCTTGTGGTTCCAAAACACCAGCTCTAGCGTTGACGTCGGCATACATT

TCCATTTGGTCAGCGTTGATAGTTGGATCGACAACAACCCATGAACCACCTCTTAGTTCACCGGTAGGTGGGATATAGATAAT

AATTGGTTGTTTGTAATCCACCAATGCGTCAACAATAAACGAACCATACTTCAAGACTTCGTTGAACATATCACGTTGACCAC

CAGAGAAACCTCTCCAGTTGGCCAAAATCATCATTGGCAATTGTTCACCGTTGTTAAAGTCATTGATAGCTTGAGCAGTCTTG

AAGGCGGAGTTTGGATGCCAAACTTGACCAGGTTCTTGAATTAATGTTTCAGCACTATTTGGATTAGCTGGATCAGCAGGAAT

CAAGTTCTCGACAGTTCTTGTTTCAACACCAATAACACCCAGTGGAATACCACCAAGACGGGCTCTACCAACGACAACACCTT

TGGCCCATCCTGACAAAGTTTCAAAGAAAGACCCTTTATCAAACAAACCATATTCAAATCCACTTTCAGTCTCACGACCTTCA

ATCATCCATCTTACATCGTAAGTTTCATCATTAGTTGGAGTGAAATCAACTGGTCTATCCCATGTGTCTTTAGTTTCCAAGAT

AGGAACTGGCATATTACGCTTGGCTGGAACATAAGACATCCATTCAACAATCTTCTCTACACCAGCTAAATCGTCAACAGCAG

TCAAATGTGAAACACCGTTGTTATACATGATTTGAGTACCACCCAATTGTAAGTTAGAAGTATAAACTTCTCTACCCAGCATT

-continued

```
TTGTTGATTGCAGGAGCACCAGTTAAAATAATTGGCTGGCCTTCGACCTGAATAGCTCTTTGACCCAAACGAACCAAATAAGC

ACCGATACCGACGGATCTACAAGTGACTAAGGTGATAGTGAAGATATCGTGGTAAGCCCTTGACGTTGCACCAGCAATTAAAC

CAGATCCACGTAGACATTCGACACCTAACCCATCTTCAGAACCAATAATTGTCTTGATGACAAATCTTTCTTCACCGTTTATA

ACAGTACGTTCAGTGAGAACAGAATTTTCTTTGTCAAATTTCTTTAAAGTTTCCATACCTTCACTTGTTAAGTATAAGTATTG

GAAGCCCTTGTCCGGATTGGCAGCATCATTCCATGCAACTTGAAATAGTGGAACAATCTCTTCAGCCATACCAATTCTGGCAC

CTGAGTTTGCAGCCAAGTAAATTCTTGGGATACCACGCTTTCTAGCATATTCAGTAACCTTATTGAAGAATTCGTCTTCTTGT

GGACCAAAGGAACCGATCTTGAATGTGATATCGTTAGCAACAACAACAAATTGACGGCCTCTTGGATATTCAGGAGTCTTTAC

AGTAATCTTAAAGGCAACCATACCAATAGCGTTGGCACCAGGTTCTCTTTCCACCTCAGTTAATTCGCCGTTTTCATCTTCAA

TCAACTCGTTGGAAATAAAGAAATCATCTGTTAACTTAACATCTGCAGAGAAATTTTTCCATTGGGATGACGATGCTTGGCGG

AATAATTCTGGGAAGTCATAGACATATGTGGTACCCATCAAGTGTGCCTTATAACGTTTTGGTTGCAACCATTCCTTAACAGG

GTAAGGAGTAGCAATAGGTCTTAAATGCATGGATCCAGGTTTACCCAAAGACTTAAATACCCATTCACCTTTTGCGTTCTTGA

CTTCGGTGTACATTTCTGTTTTGATAACATAACCAGAAACGTTATTGATCAAGGCACGCAATGGTACTGGGGCACCTGTTTGA

GGATCTTTGATGATGATTCTAATTTCGGCAGAAGAAACACGCAATCTCAACAATCTCTTACCAAATCTTTCTAAGAAACCACC

GAAGGCGGCTTCGACATCTTCTGGAGAGATATCAAACACCGCAATGAAGTTGATGAAGATATGATTCAAATCAGAATTTGAAG

TGTCGGTGACTTCTAAATTATCCAATATATCACTCATCAATCTGTTAGCTTCAGAAGTCAGATATTCTTGAATAGAAATGTCA

TCACGGATATGACCCGTTCTAATAATACCTCTTGTAAAGAATCTCTTATCCAATGGAGAAGTCTTACTAACAGCTTCGTAGAC

ATGGATGTTTCTATTATCAGTGAAAATTGGTTTAATGTTGAAGTTGGACAATCTTCCTAATTCCAGTTGGAAGGCCAAAGCCG

GCTCAATGTGACGAATTGTTTCATTTTCGTTATAATTTGGACCGTTAAAAGTATAATACTTTGGATAAGACCCATCTTTAAAA

CCGAACATAAATGTGATACGACGGATAGAAGCATTGATTAATTCCTGCTTATTCAAATCCAAAATTTCTCTCAACCTTACCAA

AATTTCCTCTTCAGATTCGAAACCTTCTGTAGAAGCAACACAAACATTAGCAACATTACTCAACGATGCGGAGCTACCAGAAC

GATCAGGAGCAGGTCCGTTAGAAGAAGATTGGTGACGAGGAATAACTTCCAAACTTTGTGACAAAATTTCATCAACATCATCT

AAATGATCCACAGCCATCAAAATACCTTCTCTTAACGGAGATGACTGACTGTTTGCAACATATGACAAATCTGAAACAGAAAC

AGCCCTGTTCATACCCATTTTAGATTTAACAGTTGGAAAGGTGGAGAACGCAGCTGAAGGTAGTTGGAATTTCCATTCAACAA

TTGGAACTGTGACACCTTCGTGAACTCTAATATCTCCTATGGTGTAAGCACGATAAGCACGACGAATATAGACTTGAGCAGCT

GCAGCAGTCACAACTGGGTCTTGATGGGTTAGGAATTGAAGTAAAACATCGAACACAACGTAATTAGAATCGATCAAGTCCTT

CAAGATATTCAAATCTGGTTCAGAGCGCTTTGGATTGGATGAGCCATAGGCAACCTTCACAACAGAGGATTTTAAGATATGTT

CAATTTGTTCAGTTCTTTCCTTGACCGAAGGTAAAGCGCCTTGAATCAAAATTTCTCTTGCTTGTAGAGCGACCTTAGCGGTA

GCCTTAGATTCTAGTTCAACAATATGTTGTAGAGGAGTAGAGAAAATGGCAGAAACTTTAGAAGATAACTTGCACAATGGTTG

ATAATGTTTCAAGATAGCTAGGATCAGGTTATTCTTCGCTGAAACTTTCGAATGAGACAAAACAGTTAGCGCAACTTTATCTA

GATCTTTAGGGTTTTCATCACGCAATTTCAGAATGATATTTTCCTCACGAACATTTGGACCATTGAATAACTTTTCAACTTCG

TAATATTCTTCCAAGAAATGGACAAATATAGAATGTTCATGGGCTTCTAACCCGTTAGAGTACTTATGAGCAATATCCGCCAA

TGGTTCCACGACGGCGCCCAGCAATTTGTCGGGGTTGTATTCAGGATTCTTCACGGCCATATCAATCAATTTACTTAATTGTC

TAGCTGGGAAAACAGCACCACGTCTCAAAGAACGTGCAACTAACTCTTCCATTTGTTCATCTAGCTTAGCAGGCAATCTTGAA

TGTAAAGCAGAGATGTGTAGTTTCCATTCTGAGTAAGGCAGTTTTGGATTTCTCAAAACCTCTATCAATTGTTGCAAGGAAGC

GTTCATAATAACTTGGTTGTCATAACCCTTCAAAATGTTTTCCAAAGTAGACACTAATGACTTGAATTTATAGGCAGGTTTGG

TTCCTTCGATAACTGGAGAACCAAAATCTGGCAGCATACCTTCAAATGGTAGAGCGTGCTTGACCTTGGATGGATCGTCAAGA

GTCATAATAGCCATGATATCACCTGCAACAATGGTAGAACCAGGTTGCTTTAATAACTGGACGATACCATTTTCTTGAGAAAC

CAAAGGCATTTGCATTTTCATAACTTCAATTTCTGCATATGGTTGGCCCTTGATAATGTGTTCACCATTTTCCACCAAGAATT

TAACCAATTTACCAGGGGATGGAGTACGCAACTGGGTTGATCGTTTTCAACTTCCAACAAAGTAGTCATAGAGTCAACGGAT

AATCTTGTAGCAGCAACTTCTTCTTTCCAATAGATGGTATGCGATTTACCGCCTATGGCAATCAAAAGACCACCATCAGATAG
```

-continued

```
TTGACGCAGTATGATATCACATTTAGAACCATTGATAAATAATGTGTAACGGTCATTACCGGATTTAGCTACGGTGAACTTGT

ATCTTTTACCCTCATGGATAAAATCTACAGGGAACATAGTTTGCAGTAGGTCTTTAGATAGAACTTGTCCCTTTTGTAAGGAT

TCGATATACTTGTGGCGGGCTTCTTCAGATGCTAAGAAAGCCTTTGTAGCGGCACCGCAAATGACGGCAAGAGTTGGATCAGG

CTTTTCAGCGGTCATTTTATGAGTAATCAAATCGTCCAACCAACCGGTGGTAATAGTGTTATCCTCGAAATCTTCAGTTTCCA

AAAGTTTGATCAAGTATTCCACAGTAGTTCTGAAATCACCCCTAATGGACAATTCCTTCAGGGCAACAACCATGTGTTTCCTG

GAAGCTTGTCTATTTTCACCAAAAGCAAAATATGGCCGAACTGAGAGTCCGAAAAGGAGTGAATATTACCATTGTTACCCAC

GGAGAAGTAACCCCAAACATTAGAGGAAGAACGGAAGTTTAGTTCATGCAAAGTACCACCCGATGGCTTGAATCCATCGTTTG

GATCTTCTGATGTGATACGACAAGCGGTACAATGACCCTTTGGAATAGGTCTTCTTTGTTTCTTGGTGGCATCTTGAGTTTTG

AATTCGAAATCGATTTCTGAGGCAGAATGAGGATTCATACCATATAAAGTTCTAATGTCACTTATTCTATGCATAGGGATACC

CATAGCGATTTGTAATTGAGCTGCAGGTAAGTTAACACCGGAGACCATTTCCGTTGTTGGATGCTCGACTTGTAATCTTGGGT

TCAATTCTAAAAAGTAGAATTTTCCATCATCATGAGAATATAGATACTCCACGGTACCGGCAGAGACATAACCGACTAGTTTC

CCCAGTCTGACGGCAGCCTTTTCCATCTCGTGAAATGTTTCAGCCTTGGCAATTGTAACTGGTGCTTCTTCGATAATTTTTTG

ATGACGTCTCTGAACGGAACAGTCTCTACCGAACAAGGAAATATTTGTACCGTACTGATCTGCTAGCAGTTGAACTTCCAAGT

GACGCGCTCTACCGGCCAACTTCATGATGAAAATGGGGGAGCCTGGAATTTCGTTGGCTGCCTGGTGGTATAAAGCGATGAAA

TCTTCTTCACGTTCAACTTGTCTGATACCTTTACCACCACCACCTTCGGATGCCTTAATCATGACAGGAAAACCAATACGCTT

GGCCTTTTGTAAACCATCTTCAGGAGAGGTACAACAACCCTTTTGATAGATGTCATCGTCGACAGAGACCAGACCGGTTTTCT

CGTCCACGTGAACGGTGTCAACACCGGTACCAGACCATGGAATACATGGACTTTAGCACTTTGAGCGACAATGGTAGAGGAG

ATTTTATCACCTAAAGACCTCATGGCGTTACCTGGAGGCCCAATAAAGATGACTTTCCTCTTAGACTGGGACAATTTTTCAGG

CAATAGTGGATTCTCGGAGGCGTGACCCCAGCCAGCCCATACGGCGTCTACGTCTGCTCTTTCGGCGATGTCTACGATCAAGT

CTACGTTAGCGTAGTTGTTATTATTAGTACCACCTGGCACTTCAATGTATTGATCGGCCATACGGATATATTCTGCGTTGGCC

TCCAGATCTTCTGGGGTGGCCATGGCGACGAATTGGACGGTTCTGTCATCGCCGAACGTCTCGTATGCCCATTTTCTGACGGA

TCTAATTTCTTTCACGGCGGCAATACCATTATTTGCTATCAGGATCTTGGATATGACCGTGTGACCACCGTGACTCTTAACAA

AGTCCCTTAACGGGACTCCTCTAGTTTATCTACTGTATTGAGGCCAATGAAATGACCTGGAAGTTCTGTATGTCTTTCTGAG

TAGTTTGTAATTTCGTACTCCATCTTCTGTGGAGAAGACTCGAATAAGCTTTCTTCGCTCAT
```

FAA (S. cerevisiae)

(SEQ ID NO: 10)

```
ATGGTTGCTCAATATACCGTTCCAGTTGGGAAAGCCGCCAATGAGCATGAAACTGCTCCAAGAAGAAATTATCAATGCCGCGA

GAAGCCGCTCGTCAGACCGCCTAACACAAAGTGTTCCACTGTTTATGAGTTTGTTCTAGAGTGCTTTCAGAAGAACAAAAATT

CAAATGCTATGGGTTGGAGGGATGTTAAGGAAATTCATGAAGAATCCAAATCGGTTATGAAAAAGTTGATGGCAAGGAGACT

TCAGTGGAAAAGAAATGGATGTATTATGAACTATCGCATTATCATTATAATTCATTTGACCAATTGACCGATATCATGCATGA

AATTGGTCGTGGGTTGGTGAAAATAGGATTAAAGCCTAATGATGATGACAAATTACATCTTTACGCAGCCACTTCTCACAAGT

GGATGAAGATGTTCTTAGGAGCGCAGTCTCAAGGTATTCCTGTCGTCACTGCCTACGATACTTTGGGAGAGAAAGGGCTAATT

CATTCTTTGGTGCAAACGGGGTCTAAGGCCATTTTTACCGATAACTCTTTATTACCATCCTTGATCAAACCAGTGCAAGCCGC

TCAAGACGTAAAATACATAATTCATTTCGATTCCATCAGTTCTGAGGACAGGAGGCAAAGTGGTAAGATCTATCAATCTGCTC

ATGATGCCATCAACAGAATTAAAGAAGTTAGACCTGATATCAAGACCTTTAGCTTTGACGACATCTTGAAGCTAGGTAAAGAA

TCCTGTAACGAAATCGATGTTCATCCACCTGGCAAGGATGATCTTTGTTGCATCATGTATACGTCTGGTTCTACAGGTGAGCC

AAAGGGTGTTGTCTTGAAACATTCAAATGTTGTCGCAGGTGTTGGTGGTGCAAGTTTGAATGTTTTGAAGTTTGTGGGCAATA

CCGACCGTGTTATCTGTTTTTTGCCACTAGCTCATATTTTTGAATTGGTTTTCGAACTATTGTCCTTTTATTGGGGGGCCTGC

ATTGGTTATGCCACCGTAAAAACTTTAACTAGCAGCTCTGTGAGAAATTGTCAAGGTGATTTGCAAGAATTCAAGCCCACAAT

CATGGTTGGTGTCGCCGCTGTTTGGGAAACAGTGAGAAAAGGGATCTTAAACCAAATTGATAATTTGCCCTTCCTCACCAAGA

AAATCTTCTGGACCGCGTATAATACCAAGTTGAACATGCAACGTCTCCACATCCCTGGTGGCGGCGCCTTAGGAAACTTGGTT

TTCAAAAAAATCAGAACTGCCACAGGTGGCCAATTAAGATATTTGTTAAACGGTGGTTCTCCAATCAGTCGGGATGCTCAGGA
```

-continued

ATTCATCACAAATTTAATCTGCCCTATGCTTATTGGTTACGGTTTAACCGAGACATGCGCTAGTACCACCATCTTGGATCCTG

CTAATTTTGAACTCGGCGTCGCTGGTGACCTAACAGGTTGTGTTACCGTCAAACTAGTTGATGTTGAAGAATTAGGTTATTTT

GCTAAAAACAACCAAGGTGAAGTTTGGATCACAGGTGCCAATGTCACGCCTGAATATTATAAGAATGAGGAAGAAACTTCTCA

AGCTTTAACAAGCGATGGTTGGTTCAAGACCGGTGACATCGGTGAATGGAAGCAAATGGCCATTTGAAAATAATTGACAGGA

AGAAAAACTTGGTCAAAACAATGAACGGTGAATATATCGCACTCGAGAAATTAGAGTCCGTTTACAGATCTAACGAATATGTT

GCTAACATTTGTGTTTATGCCGACCAATCTAAGACTAAGCCAGTTGGTATTATTGTACCAAATCATGCTCCATTAACGAAGCT

TGCTAAAAAGTTGGGAATTATGGAACAAAAAGACAGTTCAATTAATATCGAAAATTATTTGGAGGATGCAAAATTGATTAAAG

CTGTTTATTCTGATCTTTTGAAGACAGGTAAAGACCAAGGTTTGGTTGGCATTGAATTACTAGCAGGCATAGTGTTCTTTGAC

GGCGAATGGACTCCACAAAACGGTTTTGTTACGTCCGCTCAGAAATTGAAAAGAAAAGACATTTTGAATGCTGTCAAAGATAA

AGTTGACGCCGTTTATAGTTCGTCTTAA

Acyl-CoA synthetase (SEQ ID NO: 11)
ATGACTGTTACCCCACAGCACCAAGTCGTCCACGAGGCCAACGGTGTCACCCCAAGACCCACTCCTAAGGAGTTTTTTGACAA ACAGCCCCGTCCTGGCCATATCACCTCCATCGAACAGTACCAGGAATTATACCAGAAGTCCATCGCCGACCCTGAAGGATTCT TTGGTCCTATGGCCAAGGAGTTGTTGTCGTGGGACAGAGACTTCGACAAGGTCAAGTCCGGTTCTTTGAAGGACGGTGACGTT GCCTGGTTCATTGGCGGCCAGTTGAACGCTTCCTACAACTGTGTAGACAGATGGGCCTATGCGACTCCAGACAAGACTGCCAT CATCTACGAAGCTGACGAAGAAAGGACTCGTACAAGTTGACCTACGCCGAGTTGTTGAGAGAAGTCTCCAAGGTAGCTGGTG TGTTGAAGAGCTGGGGCATCAAAAAGGGTGATACTGTTGCTATCTACTTGCCAATGACTCCTCAAGCTGTTATTGCTATGCTC GCTGTAGCCAGATTAGGTGCCATCCACTCGGTTATCTTTGCAGGTTTCTCTTCTGGTTCCATCAGAGACAGAGTCAACGATGC TTCTTGTAAGGCTCTTATTACCTGTGACGAAGGTAGAAGAGGTGGTAAGACCGTTAACATCAAGAAATTGTGCGACGAAGCCT TGAAGAGCTGTCCTACTGTAGAAAAGGTGCTTGTTTTCAAGAGAACCGGAAACGAAAATATTGAATTGGAAGAGGGTAGAGAT TTCTGGTGGGATGAAGAAACCGCCAAGTTCTCGGGTTACTTGCCACCTGTTCCAGTCAATTCTGAAGACCCATTGTTCTTGTT GTATACATCTGGTTCCACTGGTACTCCTAAGGGTGTTGTCCACACCACTGGGGGCTACCTCTTAGGTGCTGCCATGACCACCA AGTACATTTTCGACGTCCACCCAGAAGACATCTTGTTCACTGCCGGTGATGTCGGTTGGATTACTGGTCACACCTATGCTTTG TACGGACCTTTGGCTCTCGGTATCCCAACAATCGTTTTTGAAGGTACTCCAGCCTACCCAGACTTTGGTAGATTCTGGCAAAT TGTCGAAAAGCACAAGGCTACCCACTTCTACGTAGCTCCTACTGCCCTCAGATTGTTGAGAAAGAGTGGCGAGCAAGAGATTC CAAAGTACGACTTGTCTTCTTTGAGAACATTGGGCTCTGTTGGTGAACCTATCTCCCCTGATATCTGGGAATGGTACAACGAG CACGTTGGACAAGGCAGATGCCACATCTCCGACACCTACTGGCAAACTGAGTCTGGTTCTCACTTCATTGCTCCAATTGCCGG TGTCACTCCAAACAAACCTGGTTCAGCCTCTTTGCCATTCTTTGGTATCGAGACCGCTCTTATTGATCCAGTTTCCGGCCACG AACTCGAAGGTAACGACATCGAAGGTGTTCTTGCCATCAAGAGCACCTGGCCATCTATGGCTAGATCTGTCTGGAACAACCAC ACCAAGTACATGGACACATACTTGAACCCATACCCAGGCTACTACTTTACCGGCGACGGTGCTGCCAGAGATCACGACGGCTA CTACTGGATTAGAGGTAGAGTCGATGATGTCGTCAATGTGTCTGGTCACAGATTGTCTACTGCTGAAATAGAAGCTGCCCTCA TCGAACACAACGGTGTTTCTGAAGCTGCTGTGGTTGGTATTACCGACGACTTAACTGGTCAAGCCGTAGTTGCCTACGTTGCT CTCAAGAACGAATACGTCGACAAGATCGCCGGCAAGGAAACCAGCGACGAAGCCTTTGCCTTGAGAAAGGAATTGATCATGAC CGTCAGAAAGGAAATCGGACCTTTCGCAGCTCCAAAGAGCGTCATCATTGTCGCCGACTTGCCAAAGACCAGATCTGGTAAGA TCATGAGAAGAATCTTGAGAAAGATCTCTGCCAACGAAGCAGACCAATTGGGTGACATCACCACTTTGTCCAACCCTCAGTCT

GTCGTTGGTATAATCGACTCCTTTGCTGCTCAATTTGCTAAGAAATAA

FAT (SEQ ID NO: 12)
ATGGGGAGACACTTGGCCTTGCTTCTGCTTCTGCTCTTCTTCCTCCAGCATTTTGGAGATGGTGATGGAAGCCAAAGACTTGA

ACCGACCCCTTCCCTCCAGTTTACACACGTCCAGTACAATGTCACTGTGCACGAAAACTCGGCCGCAAAGACCTATGTCGGCC

ACCCTAGAAAAATGGGCATCTACATCTTAGACCCCTCGTGGGAAATAAGGTACAAAATCATCTCAGGAGACAACGAAAACCTA

-continued

```
TTCAAAGCGGAAGAGTATGTTCTCGGAGACTTTTGCTTTCTAAGGATAAGAACCAAGGGAGGGAATACTGCCATCCTGAACCG

AGAAGTGAGAGACCATTACACACTGGTAATCAAAGCAGTTGAAAAAGTCACAGATGCCGAGGCCCGAGCCAAGGTCAGGGTGC

AAGTGCTGGATACAAACGACTTACGGCCGTTGTTCTCACCCACGTCCTACAGCGTTTCTCTGCCGGAAAACACAGCCATAAGG

ACCAGTATCGCAAGAGTCAGTGCCACGGATGCGGACATTGGAACCAACGGCGAATTTTACTACAGCTTTAAAGACAGAACGGA

CATGTTTGCCATCCACCCAACCAGTGGTGTGGTTGTTTTGACTGGCAGGCTTGATGTCCTGGAGACCCAGCGCTATGAGCTGG

AGATCTTGGCTGTGGACCGGGGAATGAAGCTGTACGGTAGCAGTGGGGTCAGCAGTCTGGCCAAGCTGACGGTTCACGTGGAG

CAGGCTAACGAGTGTGCACCCGGGATAACCGCCGTGACGTTATCACCATCTGAGCTGGACAAGGACCCAACGTACGCCATTAT

CACTGTGGAGGACTGCGATCAGGGTGCCAACGGGGAGATAGCATCTTTGAGCATTGTGGCTGCGACCTCCTTCAGCAGTTTA

AAACGGTGAGGTCTTTCCCAGGGAGTAAAGCATTCAAAGTGAAAGCCGTCGGGGCGTCGACTGGGACAGCCATCCTTATGGC

TACAACCTGACAGTGCAGGCTAAAGACAAAGGAACTCCTCCGCAGTTTTCCCCTGTGAAAGTCATTCACGTCATTTCTCCTCA

GTTCAGAGCTGGCCCGGTCAAGTTTGAAATGGATGTTTACAGAGCTGAGATCAGTGAGTTTGCCCCTCCACATACACCCGTGG

TCCTGGTCAAGGCTATTCCTAGTTATTCCCATTTGAGGTACGTTTTTAAAAGCACTCCTGGAAAACCCAAATTCGGTTTAAAT

CACAACACGGGTCTCATTTCCATTTTAGAACCAATTAAAAGGCAGCACACATCCCATTTTGAGCTTGAGGTGACAACAAGTGA

CAGACGAGCCTCCACCAAAGTCGTGGTCAAAGTTGTAGGTACAAACAGCAACCCCCCGGAGTTTACACAGACCTCGTACAAAG

CATCCTTTGATGAGAATGCACCCGTCGGTACCCCGGTCATGAGGGTGAGCGCGGTTGACCCTGACGAGGGGGAGAATGGCTAC

GTGACTTACAGTATTGCAAACTTAAATCACGTGCCATTTGTCATCGACCACTTTACGGGTGCTGTGAGTACCTCTGAGAATCT

GGACTATGAACTGATGCCTCGAGTCTACACGCTGAGGATTCGTGCTTCCGACTGGGCTTACCGTACCGCCGGGAAGTTGAAG

TCCTTGCCACAATTACTCTGAATAACCTGAATGACAACACCCCCCTGTTTGAGAAGACAAACTGTGAAGGGACAATTCCCCGA

GACCTGGGTGTAGGGGAGCAGATAACCACGGTTTCTGCCATTGACGCTGATGAGCTGCAGTTGGTCCGGTACCAGATTGAAGC

TGGAAATGAGTTGGATTTGTTTGGCTTAAACCCCAGCTCTGGTGTGCTGTCATTGAAGCACTCGCTCATGGACGGCTTGGGTG

CAAAGGTTTCCTTTCACAGCTTGAGAATCACAGCTACAGACGGAGAAAATTTTGCCACACCATTATATATCAACCTAACGGTG

GCTGCCAGTCGCAAGCCAGTAAACTTGCGGTGTGAGGAGACCGGTGTTGCCAAAATGCTGGCAGAGAAACTCCTGCAGGCGAA

TAAATTACACCATCAGGGGACGCGGAGGATATTTTCTTTGATTCTCACTCCGTCAACGCCCATGCCCCACAGTTTAGGGGTT

CTCTTCCAACAGGAATTGAGGTAAAGGAGGACCTCCCAGTGGGCGCCAGTATACTATTCATGAATGCTACTGACCTTGACTCT

GGCTTCAATGGGAAACTGGTCTATGCTATCTCTGGAGGGAATGATGACAGTTGCTTTACTGTTGACATGGAAACAGGAATGCT

GAAAGTCCTCTCTCCACTTGACCGAGAAGTAACGGACAAATACACACTGAACATTACCGTGTATGACCTTGGTATACCCCAGA

GGGCTGCCTGGCGCCTTCTGGATGTCACCGTCCTGGATGCCAATGACAACGCGCCCGAGTTTTTACAGGAGAGCTATTTTGTC

GAAGTGAGCGAAGACAAGGAGATAAACAGTGAAATCATCCAGGTAGAGGCCACCGATAAAGACCTGGGCCCCAGCGGACACGT

GACATACGCCATCCTCACGGACACAGAGAAGTTTGCGATCGACAGGGTGACCGGTGTGGTGAAAATTATCCAGCCTTTGGATC

GTGAAGTGCAGCGTGTACATTACCTGAAGATCGAGGCCAGGGACCAAGCCACAGAGGAACCCTGGCTGTCCTCCACTGTGCTT

CTGAAAGTGTCACTCGATGATGTTAATGACAACCCACCTAGGTTCATTCCACCCAGTTACTCCGTGAAGGTTCGAGAAGACCT

ACCGGAAGGAACCATCATCATGTGGTTAGAAGCCCATGACCCTGATGTAGGTCAGTCCAGTCAGGTGAGATACAGCCTCCTGG

ACCACGGAGAAGGCCACTTCGATGTGGATAAACTCAGCGGGGCAGTGAGAATTGTCCAGCAGCTGGACTTTGAAGAAGCAA

CTGTATAATCTCACCGTGAGGGCCAAAGACAAAGGGAAGCCGGCGTCTCTGTCTTCCACTGGCTACGTGGAAGTGGAGGTCGT

GGACGTGAATGAGAACTTACACGCGCCAGTGTTCTCCAGCTTCGTGGAGAAGGGCACAGTGAAAGAAGACGTCCCTATGGGCT

CATCAGTAATGACCGTGTCAGCTCACGATGAGGACACCGGGAGAGATGGAGAGATCCGGTATTCCATCAGAGATGGCTCTGGT

GTTGGTGTTTTCAGGATAGATGAAGAAACAGGTGTCATAGAGACCTCAGATCGACTGGACCGAGAGTCGACTTCCCACTACTG

GCTCACCGTCTACGCCACAGATCAGGGTGTGGTGCCTCTGTCATCCTTCATAGAGGTCTACATAGAGGTTGAGGATGTCAATG

ACAACGCACCACAGACATCAGAGCCTGTGTATTATCCTGAAATAATGGAGAATTCACCCAAGGATGTATCTGTGGTCCAGATT

GAGGCATTTGACCCGGATTCCAGCTCCAGTGACAAGCTGACGTACAGAATTACAAGTGGAAATCCCCAAGGGTTCTTCTCAAT

ACACCCTAAAACAGGTCTCATCACAACCACATCGAGGAAGCTGGACCGAGAGCAGCAGGATGAACACATTCTGGAAGTTACTG
```

```
TGACAGACAATGGTGTACCTCCCAGATCCACCATTGCCAGGGTCATTGTGAAAATCCTGGATGAGAACGACAACAGGCCTCAG

TTCCTTCAGAAGTTTTATAAAATCAGGCTCCCGGAGCGAGAAAAAGCTGATGGAGACCGGAGCGCGAAGCGCGAGCCTCTCTA

CCGAGTCATAGCCGCAGATAAGGATGAAGGGCCCAATGCCGAGCTCTCCTACAGCATCGAGGAAGGGAACGAGCACGGCCGGT

TTTCCATTGAACCCAAGACAGGAGTGGTCTCATCCAAAAAGTTCTCTGCGGCTGGAGAATACGACATTCTTTCTATTAAGGCA

ATTGACAATGGGCGCCCCCAGAAGTCATCGACCACCAGACTCCATATTGAATGGATCTCCAAACCCAAGCCGTCCTTGGAGCC

GATTTCGTTTGAGGAATCGGTTTTCTCGTTTACTGTAATGGAGAGTGATCCGGTGGCTCACATGATCGGCGTGATCTCCGTTG

AGCCTCCTGGCATGCCTCTGTGGTTTGACATCATCGGGGGCAACTATGACAGTCACTTTGATGTGGACAAGGGCACTGGAACC

ATCATTGTGGCCAAGCCCCTTGACGCAGAGCAGAAGTCCAGCTATAACCTCACAGTGGAGGCGACAGACGGGACCTCCACTAT

CCTCACCCAGGTACTCATCAAAGTAATAGATACCAATGACCACCGCCCTCAGTTTTCTACCTCGAAATACGAAGTCTCTGTTC

CCGAAGACACAGAGCCAGAAACAGAGATTCTGCAAATCAGCGCCGTAGACAGGGACGAGAAAAACAAACTGATCTACACCCTC

CAGAGCAGCATAGATCCAGCAAGTCTCAAGAAATTCCGCCTCGATCCTGCAACAGGCGCTCTCTACACATCTGAGAAGCTCGA

TCACGAAGCCATTCACCAGCACGTCCTCACAGTCATGGTCCGGGATCAGGATGTCCCTGTGAAACGCAACTTTGCCAGAATCA

TTGTGAATGTCAGTGACATGAATGACCACTCTCCGTGGTTCACCAGTTCGTCCTATGAAGGGCGGGTTTATGAGTCGGCAGCC

GTGGGCTCGGTCGTGCTACAGGTTACAGCTCTGGACAGAGACAAAGGGAGAAATGCTGAAGTGCTCTACTCCATCGAGTCAGG

AAACATTGGAAATTCCTTTACAATCGACCCCATCTTGGGCTCTATAAAAACTGCCAGAGAATTGGATCGAAGTCACCAAGTAG

ACTATGATTTAATGGTAAAAGCTACAGACAAAGGGGAGCCACCAATGAGCGAAATGACCTCCGTGCGGATCTCTGTCACCGTC

GCCGACAATGCCTCTCCTAAGTTCACATCCAAGGAGTACTCGGCTGAGATTAGTGAAGCCATCAGGATTGGGAGTTTTGTTGG

AATGGTCTCTGCTCACAGTCAGTCATCAGTGATGTATGAAGTAAAAGATGGAAATATAGGCGATGCATTTAATATCAATCCAC

ATTCAGGAAGCATCGTCACTCAGAGAGCCTTGGATTTTGAGACACTGCCCATTTATACATTGACAGTACAAGGGACCAACATG

GCCGGCTTGTCCACCAATACAACGGTGGTAGTGCACATACAGGATGAGAATGACAACCCTCCAGCTTTCACACGGGCGGAATA

TTCAGGATTCATTAGTGAATCAGCCTCAGTCAACAGCGTGGTGCTAACGGATAAGAATGTTCCGCTCGTGATCCGAGCCACCG

ACGCTGATCGGGAATCCAATGCTCTGCTCGTCTATCAAATTGTCGAGCCATCTGTGCACAACTATTTTGCCATTGATCCCACC

ACCGGTGCCATCCATACCGTACTGAGTCTGGACTATGAAGAGACACGTGTCTTTCACTTCACCGTCCAAGTGCATGACATGGG

GACGCCTCGTCTGTTTGCTGAGTATGCAGCAAATGTGACCGTGCATGTGATTGACATCAATGACTGCCCCCCTGTCTTCTCTA

AGTCACTGTACGAAGCATCCCTCCTATTGCCGACGTACAAAGGCGTGAACGTCATCACAGTGAATGCCACAGATGCCGACTCC

AGGGCGTTCTCCCAGTTAATATACTCCATCACCAAAGGCAACATTGGGGAGAAGTTCTCCATGGACCACAAGACTGGCACCAT

AGCAATTCAGAACACAACCCAGTTACGGACCGCTATGAGCTGACCGTCCGCGCCTCCGATGGCCGGTTTACAAGCGTGGCCT

CCGTGAGAATCAACGTGAAGGAAAGCAGAGAGAGTCCTCTCAAGTTTACCCAAGATGCCTACTCTGCGGTGGTGAAGGAGAAC

TCCACCGAAGCCAAAACCTTAGCTGTCATTACCGCGATAGGGAACCCGATTAACGAGCCTTTGTTTTACCGTATCCTCAACCC

AGACCGCAGATTTAAAATCAGCCACACCTCAGGCGTGTTGTCAACCACTGGGATACCATTTGATCGGGAGCAACAGGAGACGT

TTGTTGTGGTGGTAGAGGTGACTAAAGAACGGGAGCCGTCGGCCGTGGCCCACGTTGTGGTGAAGGTCACCGTGAAGACCAG

AATGATAATGCACCCGTGTTTGTCAACCTTCCCTACTATGCTGTGGTGAAGGTGGATGCTGAGGTGGGCCATGTCATCCGCCA

CGTCACTGCCATTGACAGAGACAGTGGCAGAAACGGTGACGTTCACTACTACCTTAAGGAGCATCATGACCACTTTGAGATTG

GACCCTCTGGTGACATTTCTCTGAAAAAGCAATTTGAGCACGACACCTTGAATAAAGAATACCTTGTCACAGTGGTTGCGAAG

GACGGGGGAACCCAGCTTTCTCCGCAGAAGTTCTAGTTCCCATCACCGTCATGAACAAAGCCATGCCCGTGTTTGAAAAGGC

TTTCTACAGTGCAGAGATTCCCGAGAACGTCCAGACGCACAGCCCAGTGGTCCACGTCCAAGCCAACAGCCCAGAAGGGTTGA

AAGTGTTCTACAGTATCACAGACGGGGACCCTTTTAGTCAGTTTACTATCAACTTCAACACTGGGGTGATAAACGTCATCGCA

CCGCTGGACTTTGAGTCCCACCCAGCCTATAAGCTAAGCATACGGGCCACTGACTCCCTGACTGGCGCCCACGCTGAAGTGTT

TGTTGACATCGTAGTAGAAGACATCAATGACAACCCTCCCGTGTTTGTGCAACAGTCTTACTCGACAACCCTGTCTGAAGCAT

CTGTCATCGGAGCGCCTATCCTTCAAGTTAGAGCCACCGACTCTGACTCGGAACCAAATAGAGGGATTTCCTACCAGCTGATT
```

```
GGAAATCACAGCAAAAGCCACGATCACTTTCACATAGATAGTCACACTGGGCTGATTTCACTGGTGAGGGCTTTGGATTACGA
ACAGTTCCAGCAGCACAAGCTGCTCGTAAGGGCTGTTGATGGAGGAATGCCGCCACTGAGCAGCGATGTGGTCGTCACTGTGG
ATGTCACCGACCTCAACGATAACCCGCCTCTGTTTGAACAACAGGTTTACGAAGCTAGGATCAGTGAGCACGCTGCCCACGGG
CATTTTGTGATGTGCGTAAAGGCCTGTGATGCAGATCGCTCAGACCTAGACAGGCTGGAGTACTCCATTCTGTCCGGCAATGA
TCACAAGAGCTTTGTCATTGACGGGGAGACAGGAATCATCACGCTCTCCAACCCGCGCCGCCACACCTTGAAGCCGTTCTATA
GTCTCAACGTTTCTGTGTCTGATGGGGTTTTCCGAAGCTCGGCTCGGGTGAATGTCACCGTGATGGGAGGGAATTTGCACAGC
CCTGTCTTTCACCAGAATGAGTATGAGGTAGAGCTGGCTGAAAACGCCCCCTTGCACACCCTGGTGGTCCAAGTGAAGGCTAC
TGACAGAGATTCCGGTATCTACGGCCACCTGACTTACCACCTTGTAAATGACTTTGCCAAAGACAGGTTTTACGTGAACGACG
GAGGGCAGGTCTTCACTCTGGAGAGACTTGATCGAGAGGCTCCAGCAGAGAAAGTGATCTCAGTCCGTTTAATGGCTAAGGAT
GCTGGGGGGAAGGTCGCCTTCTGCACTGTCAACGTCATCCTCACGGACGACAATGACAACGCACCACAGTTTCGCTCAACCAA
GTACGAGGTGAACGTGGGGTCCAGCGCCGCCAAAGGGACGTCGGTCGTCAAGGTCTTCGCGAGTGATGCCGATGAGGGGTCGA
ATGCTGACGTCACCTACGCCATCGAGGCAGATTCGGAAAGTGTCGAGGAGAACTTGGAAATCAACCAACTGACCGGCCTCATT
ACTACAAAGGAAAGCTTAATAGGTTTAGAGAATGAATTCTTCACTTTCTTCGTTAGAGCTGTGGATAACGGGTCTCCGCCCAA
AGAGTCTGTTGTTCCTGTCTATGTTAAAATACTTCCCCCGGAAGTGCAGCTTCCTAGGTTCTCAGAGCCCTTTTATACCTATT
CCATTTCAGAAGACATGCCTATTGGCACAGAGATTGACCTCATCCGGGTAGAGCATAGCGGGACTGTTCTCTACACCCTGGTC
AAAGGCAATACTCCCGAGAGTAACAGGGACGAGTTCTTTGTGATTGACCGGCAGAGTGGGAGACTGAAGCTGGAGAAGAGCCT
TGACCACGAGACCACTAAGTGGTATCAGTTTTCCATCCTGGCCAGGTGTACTCTGGATGACTACGAGGTGGTGGCTTCTATAG
ATGTCAGTATCCAGGTGAAAGACGCTAATGATAACAGCCCAGTTTTGGAGTCCAATCCATACGAGGCATTTATTGTCGAAAAC
CTGCCAGCAGGGAGTAGGGTCATCCAGGTCAGAGCATCTGACCTAGACTCAGGAGTCAACGGCCAAGTCATGTACAGTCTAGA
TCAGTCCCAAGATGCAGACATCATCGAGTCTTTTGCCATTAACATGGAAACAGGCTGGATTACAACCCTCAAGGAGCTTGACC
ATGAAGAGAGCCAGTTACCAGATTAAAGTGGTTGCCTCAGACCATGGTGAAAAGGTGCAGCTGTCTTCCACCGCCATTGTG
GATGTCACCGTCACTGACGTCAACGACAGCCCGCCTCGATTCACAGCTGAGATTTATAAAGGGACAGTGAGTGAGGATGACCC
CCCAGGGGGTGTGATCGCCATCTTGAGCACCACTGACGCCGACTCTGAAGAGATTAACCGACAAGTGTCGTACTTCATAACAG
GAGGGGATGCATTGGGACAGTTTGCTGTGGAAAATATGCAGAATGACTGGAGGGTGTACGTGAAGAAACCTCTCGACAGGGAA
CAAAAGGACAGTTACCTTCTGACCGTCACTGCAACAGATGGGACCTTCTCTTCCAAAGCTAGAGTTGAAGTCAAGGTTCTCGA
TGCCAATGATAACAGTCCAGTGTGTGAGAGGACCGCATATTCTGATGCCATTCCCGAAGACGCTCTTCCGGGGAAGCTGGTCA
TGCAGGTCTCTGCCACAGATGCAGATATCCGGTCCAACGCGGAGATCACTTACACTTTATTTGGCTCAGGTGCAGAAAAGTTT
AAACTGAATCCAGACACAGGTGAACTGAGAACATTAGCCCTCCTTGATCGTGAGGAGCAAGCAGTTTATCATCTTCTGGTCAA
GGCCACAGACGGAGGGGGCAGATCCTGTCAGGCAACTATTGTGCTCACGTTAGAAGATGTAAATGACAACACCCCCGAGTTCA
CCGCGGATCCATACGCCATCACGGTATTTGAAAACACAGAGCCTGGGACACCGTTGACCAGAGTGCAGGCCACCGATGCAGAC
GCAGGGTTGAATCGGAAGATTTCCTACTCACTGCTTGACTCTGCTGACGGGCAGTTCTCCATTAACGAGCAGTCCGGAATTCT
TCAGTTGGAAAAGCATTTGGACAGGGAACTACAGGCAGTCTATACTCTCACTTTGAAAGCAGCGGACCAAGGATTGCCAAGGA
AATTGACAGCCACTGGCACGGTGGTTGTGTCTGTTTTGGATATAAATGACAACCCACCTGTGTTTGAGTACCGTGAATATGGT
GCCACCGTGTCAGAGGACATTGTCATCGGGACCGAAGTTCTCCAGGTGTACGCAGCCAGTCGGGATATCGAGGCGAATGCAGA
AATCACATACGCAATCATAAGTGGGAACGAACACGGAAAATTCAGCATCGATTCTAAGACAGGGGCCATATTTATCATTGAGA
ACCTGGATTATGAAAGCTCCCATGGCTATTACCTGACTGTGGAAGCCACTGATGGAGGCACGCCCTCGTTGAGTGACGTGGCG
ACCGTGAACATCAACATCACAGATATTAACGATAACAGCCCAGTGTTCAGCCAGGACAGCTACACCACAGTGGTCAGCGAAGA
CGCGGCCCTGGAGCAGCCCGTCATTACAATTATGGCTGATGATGCTGATGGCCCTTCAAACAGCCACATCCTCTACTCCATTA
TAGAGGGTAACCAAGGAAGTCCATTCACAATCGACCCTGTCAGAGGAGAAATCAAAGTAACGAAGCCCCTAGACCGCGAAACG
ATCTCAGGTTATACGCTCACGGTGCAGGCTGCCGACAACGGCAATCCACCCAGAGTCAACACCACCACAGTGAACATCGATGT
CTCCGATGTCAACGACAATGCTCCCCTCTTCTCCAGAGACAACTACAGTGTCATCATCCAGGAAAACAAGCCCGTGGGTTTCA
```

```
GCGTCCTGAAGCTAGTAGTGACAGACAAGGACTCGTCCCACAACGGCCCCCTTTCTCCTTTGCTATTGTGAGTGGAAATGAT
GACAACATGTTTGAGGTGAACCAGCACGGGGTCCTCCTGACAGCGGCAACAGTCAAGAGGAAAGTGAAGGACCATTACCTTCT
GCACGTTAAGGTGGCTGACAATGGAAAGCCTCAGCTGTCTTCGTTGACACACATTGACATCAGGGTTATTGAGGAGAGCATCC
ACCCTCCTGCCATTTTGCCACTGGAGATTTTCATCACTGCTTCTGGAGAGGAATACTCAGGCGGGGTCATAGGAAAGATCCAT
GCCACAGACCAGGATGTGTATGACACCTTGACGTACAGTCTGGATCCCCACATGGATGGCCTGTTCTCTGTTTCCAGCACGGG
GGGTAAACTGATTGCACACAGAAAGCTGGATATAGGCCAGTACCTTCTTAATGTCAGCGTGACAGACGGGAAGTTTACAACGG
TGGCTGACATCACCGTGCACATCCAGCAAGTGACCCAGGAGATGCTGAACCACACCATCGCTATCCGATTTGCAAATCTCACC
CCGGAAGAGTTTGTCGGCGACTACTGGCGCAACTTCCAGCGAGCTTTACGCAACATCCTGGGCATCCGGAAGAACGACATACA
GATTGTCAGCTTGCAGCCCTCCGAACCCCACTCCCACCTTGACGTCTTACTCTTTGTAGAGAAATCAGGGGGCACCCAGATCT
CAACGAAACAACTTCTGCACAAGATCAATTCTTCCGTCACGGACATCGAGGAAATCATTGGCGTGAGGATACTGGATGTGTTC
CAGAAACTCTGTGCAGGGCTGGATTGCCCGTGGAAATTCTGTGATGAGAAGGTTTCTGTGGATGAAAACATTATGTCAACTCA
TAGCACAGCCAGACTGAGTTTTGTGACTCCCCGGCACCATAGAACAGCCGTGTGTCTCTGCAAAGATGGGACATGCCCGCCTG
TCCACCAAGGGTGCGAAGATAACCCCTGTCCTGCAGGATCCGAATGTGTCGCTGATCCCCGAGAAGAGAAGTACAGCTGTGTG
TGTCCTGGTGGCGGGTTCGCCAAATGTCCAGGGAGTTCATCCATAACTTTTACCGGCAGCAGCTTTGTGAAATATCGTCTGAT
GGAAAATGAAAACCGACTGGAGATGAAGTTGACCATGCGCCTGAGAACCTACTCTTCCCACGCGGTTGTGATGTACGCTCGAG
GAACTGACTACAGTATCCTGGAGATTCATACTGGGAGACTGCAGTACAAATTTGACTGTGGAAGTGGCCCTGGGATCGTCTCT
GTTCAGAGCATTCAAGTCAACGATGGGCAGTGGCATGCAGTGTCCCTGGAAGTGGAGGGGAATTATGCAAAATTGGTTCTAGA
TGAAGTCCACACTGCCTCGGGCACAGCCCCAGGAGCTCTGAAAACCCTCAACCTGGATAACTACGTAATTTTTGGTGGCCACC
TCCGCCAGCAAGGGACAAAACATGGACGAAACACCCAGGTGGCCAATGGTTTCAGGGGCTGCATGGACTCTATTTATTTGAAT
GGGCAGGAGCTACCTTTGAACAACAAACCAAGAGCCTATGCACACATCGAAGAATGGGTGGACCTAGCTCATGGGTGCTTGTT
AACTGCCACCGAAGACTGTTCCAGCAACCCTTGTCAGAATGGAGGCGTCTGCAATCCCTCGCCCACTGGAGGTTATTACTGCA
AGTGCAGTGCATTGACACGCAGGGACGTACTGTGAGGTGAGCGTCAACCCGTGCTCCTCCAACCCCTGCCTCTACGGAGGAACG
TGCATGGTAGACAACGGAGGTTTTGTTTGCCAGTGCAGGGGCTGTACACTGGCCAGAGATGTCAGCTTAGTCCGTACTGCAA
AGATGAACCCTGTAAAAATGGTGGAACGTGTTTTGACAGTTTGGATGGTGCTGTCTGTCAGTGTGACTCAGGCTTTAGGGGAG
AAAGATGTCAGAGTGACATTGACGAGTGTGCTGGGAACCCCTGTCGGAACGGGGCCCTTTGCGAGAACACGCATGGCTCCTAT
CACTGTAACTGCAGCCAGGAGTACAGAGGGAAGCACTGTGAGGATGCCACTCCCAACCACTACGTGTCCACCCCGTGGAACAT
CGGACTGGCCGAAGGAATCGGAATTATTGTGTTTATAGCCGGGATATTCTTACTGGTGGTGGTGTTTGTCCTCTGCCGAAAGA
TGATCAGTCGGAAGAAGAAACACCAGGCGGAACCTGAAGACAAGCGTTTGGGGCCAACCACGGCTTTCTTACAGAGACCTTAC
TTTGATTCCAAGCCGAGCAAGAACATTTACTCTGACATCCCGCCCCAGGTGCCCGTGCGTCCCATTTCCTACACTCCGAGCAT
TCCCAGTGACTCTAGAAACAATCTGGACCGGAACTCGTTTGAAGGCTCGGCAATCCCAGAGCACCCAGAATTCAGCACTTTTA
ACCCCGAGTCTATGCACGGACATCGGAAAGCCGTGGCTGTGTGCAGCGTGGCTCCAAACTTGCCTCCCCCACCCCCTTCCAAC
TCTCCCTCAGACAGCGACTCCATTCAGAAGCCCAGCTGGGACTTCGACTACGACGCTAAAGTGGTGGATCTTGACCCTTGTCT
TTCCAAGAAGCCCCTGGAGGAAAAACCCTCTCAGCCATACAGTGCCCGGGAGAGCCTGTCCGAGGTGCAGTCCCTTAGCTCCT
TCCAGTCAGAGTCCTGTGATGACAATGGGTACCACTGGGATACATCAGACTGGATGCCCAGTGTTCCTCTGCCAGACATACAA
GAGTTCCCCAATTACGAGGTTATCGATGAGCACACGCCCCTCTACTCAGCTGATCCAAATGCCATCGACACTGACTATTACCC
TGGGGGTTATGACATTGAAAGTGACTTTCCACCCCCACCAGAGGACTTCCCTGCACCCGATGAACTGCCACCATTGCCTCCAG
AATTCAGCGACCAGTTCGAGTCCATACACCCACCCAGAGACATGCCCGCAGCAGGTAGCTTGGGGTCTTCCTCCAGGAATCGT
CAGAGGTTCAACCTGAATCAGTACCTGCCCAATTTCTACCCCGTCGATATGTCTGAACCTCAGAAACAAGGCGCTGGTGAGAA
CAGTACCTGTAGAGAACCCTACACTCCCTACCCTCCAGGGTATCAAAGAAACTTCGAGGCGCCCACCATAGAAAACATGCCCA
```

TGTCTGTGTACACCTCTACGGCTTCCTGCTCCGATGTGTCAGCGTGCTGCGAAGTGGAGTCTGAGGTCATGATGAGTGACTAC

GAGAGCGGGGACGACGGCCACTTTGAAGAGGTGACCATTCCCCCGCTAGATTCCCAGCAGCATACGGAAGTGTGA

FAT (SEQ ID NO: 13)
ATGAAGATTAAAAAATATGTAACTCCTGTAAAAAGAAAAGCTTTCACCATACTCCAATGGATTTCACTACTGTGTAGTCTATG

GTTGATCCCCACTGTACAAAGCAAGGCCGATGAGAAGCACACGGCGACCCTGGAGTATAGACTAGAGAACCAACTGCAAGATC

TATATAGGTTTAGCCATAGTGTATATAATGTTACCATACCAGAAAATAGTCTGGGCAAGACTTACGCCAAGGGAGTATTGCAT

GAAAGACTGGCCGGCCTGAGAGTTGGCTTGAACGCAGAGGTTAAGTATAGGATAATTAGTGGCGATAAGGAGAAGCTATTTAA

GGCCGAGGAGAAACTGGTCGGAGATTTTGCCTTCTTAGCGATTCGAACGCGGACAAATAACGTTGTGCTAAACAGAGAAAAAA

CTGAGGAATACGTTATAAGAGTGAAGGCACATGTACATTTGCACGACCGAAATGTATCAAGCTATGAAACGGAGGCGAATATC

CACATCAAAGTACTGGATCGCAATGACCTGAGTCCGCTGTTTTATCCGACCCAGTACACCGTTGTTATTCCGGAGGACACGCC

CAAATATCAAAGTATTTTAAAGGTCACAGCTGACGATGCTGACCTCGGCATCAATGGGGAAATCTACTACAGCCTCCTGATGG

ATAGTGAATACTTTGCTATCCATCCAACAACTGGCGAAATTACTCTCCTGCAGCAGCTTCAGTATGCGGAGAACTCGCACTTC

GAGCTCACGGTGGTGGCCTACGATCGGGATCATGGGTGAACCATCAGAACCACCAGGCCAGCAAGACGAAGGTTAGTATTTC

GGTGAAACAGGTTAACTTTTACGCTCCAGAGATTTTCACGAAAACCTTCTCGAGCGTGACGCCAACATCAAACCCTTTGATTT

ATGGAATTGTACGAGTAAACGACAAAGACACTGGGATAAATGGCAACATAGGGCGATTGGAAATCGTCGATGGAAATCCGGAT

GGCACGTTTCTTCTGAAGGCGGCGGAGACCAAAGACGAGTACTACATCGAATTGAATCAGTTTGCCCATCTTAACCAGCAACA

TTTCATTTACAACTTAACCCTACTGGCGGAGGACCTCGGAACTCCCCGTCGATTCGCCTACAAATCCGTTCCGATTCAAATCA

AGCCCGAGAGCAAAAATATACCCATATTCACACAGGAGATTTACGAAGTATCCATTCCAGAAACGGCACCCATTAACATGCCT

GTGATAAGGCTCAAAGTAAGCGATCCAGATTTGGGCAAAAATGCATTGGTCTACTTGGAAATCGTGGGTGGAAATGAGGGCGA

CGAGTTCCGAATTAATCCCGATTCGGGAATGTTGTACACAGCAAAGCAACTGGATGCCGAAAAGAAGTCAAGTTATACCTTAA

CAGTCTCCGCCATTGATCAGGCAAATGTTGGGTCGCGGAAACAATCTTCAGCCAAGGTGAAAATCAGCGTACAGGATATGAAC

GACAATGATCCCATTTTTGAGAATGTCAATAAGGTCATTAGTATCAATGAGAACAACTTGGCTGGCTCGTTTGTTGTGAAGCT

TACTGCCAAGGACAGGGATTCTGGTGAAAATTCATACATATCGTATAGTATTGCCAATCTAAATGCGGTTCCATTTGAAATCG

ATCACTTTAGCGGTATAGTTAAGACCACATCACTGCTTGACTTTGAAACAATGAAGCGTAACTATGAGCTGATAATCCGTGCA

TCCGATTGGGGATTGCCGTACAGAAGACAGACGGAAATCAAACTGTCCATCGTCGTCAAGGATATCAACGATAATCGGCCGCA

GTTTGAACGTGTGAACTGCTATGGCAAAGTGACCAAATCGGCGCCGATGGGCACCGAGGTATTCGTTACCTCAGCCATTGACT

TGATGCAGGCGATATAATATCCTATAGGTTGAGCGACGGCAACGAGGATGGCTGCTTTAACTTGGACCCCACATCGGGTTCC

CTGTCTATTTCCTGCGACCTGAAGAAAACAACCTTAACAAACCGTATTCTCAAAGTTTCCGCCACGGACGGCACCCACTTTTC

CGATGACTTGATCATCAATGTACACCTAATGCCCGAAGATTTGGGTGGAGATTCCAGTATTCTACATGGTTTTGGATCCTTTG

AGTGCCGGGAAACCGGCGTGGCCAGGAGATTGGCGGAAACATTATCGTTGGCCGAAAAAAACAATGTAAAGAGTGCATCGCCA

TCCGTTTTCAGTGACTTGTCTCTAACACCCAGTCGATATGGCCAAAATGTGCATAGACCAGAGTTCGTGAACTTCCCTCAGGA

GCTGTCCATTAACGAAAGTGTCCAATTGGGCGAAACAGTTGCTTGGATAGAGGCCAAAGATCGCGATTTGGGCTACAATGGAA

AGCTGGTATTTGCAATTTCAGACGGGGACTACGATTCGGTTTTTCGTATTGATCCAGACCGCGGTGAACTGCAGATTATTGGA

TATTTGGATAGAGAGCGTCAAAATGAATATGTTCTCAACATCACCGTCTACGATCTGGGTAACCCGACCAAATCGACGTCAAA

AATGTTGCCAATAACGATCCTCGACGTGAACGATAATCGCCCGGTTATTCAGAAGACGTTGGCCACCTTCCGGCTGACTGAGA

GCGCCAGGATAGGAACTGTGGTACACTGCCTTCATGCCACGGATGCGGATTCTGGAATCAATGCTCAGGTGACATATGCCCTG

TCGGTTGAGTGCAGCGATTTCACAGTAAATGCTACTACGGGATGTCTTCGTCTGAACAAACCACTGGATCGCGAGAAGCAGGA

TAACTACGCTCTTCACATAACTGCCAAGGATGGTGGCAGTCCCGTGCTATCCTCGGAGGCATTGGTTTACGTCCTGGTCGACG

ATGTCAACGACAACGCGCCCGTTTTCGGAGTGCAAGAGTACATATTTAAGGTGCGCGAAGATCTGCCCCGTGGAACAGTGTTG

GCCGTAATCGAGGCGGTGGACGAAGATATTGGACCCAATGCCGAGATCCAATTCTCTTTGAAAGAGGAGACCCAGGATGAGGA

```
ACTATTCAGAATCGATAAGCACACGGGTGCAATTAGGACTCAAGGATATCTGGACTATGAGAACAAACAAGTGCACAACCTTA
TTGTCAGTGCCATCGATGGCGGAGATCCCTCTCTAACTTCGGACATGTCCATCGTAATAATGATCATCGACGTCAACGAGAAC
CGATTTGCGCCCGAATTCGACGACTTTGTGTACGAGGGAAAGGTAAAGGAGAACAAGCCGAAGGGAACGTTCGTAATGAATGT
CACAGCACGGGATATGGACACGGTGGACCTGAACTCCAAGATCACGTACTCAATAACAGGTGGCGATGGACTGGGAATTTTTG
CGGTTAACGACCAAGGTTCAATAACTTCCTTGTCGCAACTCGATGCGGAGACGAAAAACTTTTACTGGCTGACGCTCTGTGCA
CAGGATTGCGCAATAGTTCCCCTCAGCAATTGTGTGGAAGTTTACATACAAGTCGAAAACGAAAACGATAACATTCCTCTTAC
GGACAAACCAGTGTACTACGTTAATGTCACGGAAGCCAGTGTGGAAAATGTGGAGATCATTACCCTAAAGGCTTTCGATCCCG
ATATAGATCCCACTCAGACTATAACATATAACATAGTTTCCGGAAATCTTGTCGGGTACTTTGAAATTGATTCGAAAACAGGA
GTGATTAAGACGACAGAACGCAAATTGGATAGAGAAAATCAAGCGGAACATATTTTGGAGGTGGCTATATCAGATAACGGATC
TCCAGTACTATCTTCTACATCGCGAATCGTTGTGTCAGTACTGGATATTAACGATAACAGCCCCGAGTTTGACCAAAGGGTCT
ACAAGGTGCAAGTTCCGTCTTCAGCCACAGTCAATCAATCTATTTTTCAGGTTCACGCTATCGACAGCGACAGTGGCGAAAAT
GGTCGAATTACCTACTCAATTAAGTCCGGAAAGGGTAAGAATAAATTTCGCATCGATAGCCAAAGGGGCCATATACATATAGC
AAAACCATTGGACTCCGACAATGAGTTTGAGATTCACATCAAGGCTGAGGACAACGGAATTCCTAAAAAGAGTCAAACTGCTA
GAGTTAATATTGTTGTAGTTCCTGTAAATCCTAATTCCCAAAATGCACCGTTGATAGTCAGAAAGACATCCGAAAATGTCGTT
GATCTTACGGAAAATGACAAGCCTGGATTTTTGGTCACTCAAATTTTAGCTGTCGATGATGACAACGACCAGCTGTGGTACAA
CATTTCCAATGGCAATGACGACAATACCTTTTACATTGGCCAAGACAACGGAAACATACTGCTTTCAAAATATTTGGACTACG
AGACCCAACAGTCCTATAATCTGACTATCAGCGTCACTGATGGCACATTCACAGCGTTTACTAATCTTTTGGTTCAAGTGATC
GATATTAATGACAACCCCCCTCAGTTCGCTAAAGATGTGTATCATGTCAATATATCCGAAAATATTGAAGAGGAATCAGTTAT
AATGCAACTCCACGCCACTGACAGAGATGAGGACAAGAAGCTATTCTATCACCTGCACGCAACTCAGGATCCGTCGTCGCTGG
CATTGTTCCGAATCGATTCCATAAGTGGAAATGTCATTGTCACTCAGAGATTGGATTTTGAAAAGACTGCGCAGCATATACTC
ATCGTTTTTGTTAAGGATCAAGGAGCGCCTGGAAAAAGAAACTATGCCAAGATAATTGTAAACGTGCATGACCACAACGACCA
TCATCCAGAATTTACTGCTAAAATAATTCAAAGTAAGGTTCCCGAAAGCGCAGCTATTGGCTCTAAGTTAGCCGAAGTGAGGG
CCATAGATAGAGATAGTGGTCACAATGCCGAGATCCAGTACTCGATTATCACGGGTAACGTGGGTAGTGTGTTTGAGATTGAT
CCGACTTTCGGTATAATCACATTGGCTGGCAACTTGAATATCAACAAGATCCAGGAGTACATGCTTCAAGTGAAGGCCGTAGA
TCTGGGAAATCCACCGCTGTCATCGCAGATTCCGGTACACATCATTGTCACCATGTCCGAGAACGATCCTCCGAAGTTCCCAA
CCAACAACATTGCCATTGAAATATTCGAAAACCTGCCCATCGGAACATTTGTTACTCAAGTCACCGCTCGGTCGTCGTCATCC
ATATTCTTCAATATTATTTCCGGCAACATCAACGAAAGCTTCCGCATTAACCCATCTACTGGAGTTATTGTTATCAATGGAAA
TATCGACTATGAATCCATCAAAGTATTCAACCTTACGGTTAAAGGAACCAATATGGCAGCCGAGTCATCCTGCCAAAATATAA
TTATACATATCCTAGATGCTAACGATAATATTCCGTATTTCGTTCAAAATGAATATGTTGGAGCATTACCCGAATCCGCCGCT
ATTGGATCTTACGTACTGAAAGTACACGACTCATCAAAAGATCATTTAACATTACAAGTTAAGGATGCGGATGTCGGAGTAAA
CGGAATGGTTAATACCACATAGTTGACGATCTGGCAAAAAACTTTTTTAAAATAGATTCGACAACTGGCGCTATTGAACTGT
TACGACAATTGGACTATGAAACAAACGCTGGTTATACCTTTGACGTTACGGTTAGTGATATGGGAAAGCCCAAACTACATTCC
ACTACAACTGCACATGTGACGATTCGTGTCATAAATGTTAACGATTGTCCTCCAGTATTTAATGAGCGTGAACTCAATGTAAC
TTTGTTCCTTCCAACTTTTGAGAATGTGTTTGTAAGACAAGTTAGCGCAAAGGATGCTGATAACGATACCTTAAGGTTTGATA
TTGTGGATGGAAACACCAACGAATGTTTCCAGATCGAAAAATACACCGGAATAATTACAACACGAAATTTTGAAATACTAAAT
AACGAAAATGATCGGGACTATGCCTTGCACGTCCGTGCCTCCGACGGAATTTTCTCTGCAATTTTAATAGTTAAAATTAAGGT
TTTGTCCGCCATCGATTCGAATTTCGCATTCCAACGTGAATCGTACAGATTTTCTGCATTTGAAAATAACACAAAGGTAGCTA
CCATTGGATTGGTGAACGTAATAGGAAACACACTGGACGAAAACGTTGAGTATCGCATCCTGAACCCAACACAATTGTTTGAT
ATTGGAATCAGTTCGGGAGCCCTAAAAACCACTGGAGTTATTTTCGATCGCGAAGTAAAGGATTTGTACAGACTCTTCGTGGA
AGCAAAGTCAATGCTATACGACGGCATGAATTCAAATGTTCGCAGAGCAGTAACGTCCATAGATATATCCGTCTTGGATGTGA
ACGACAATTGCCCCTTGTTTGTCAATATGCCCTATTATGCCACAGTCTCTATTGACGATCCAAAAGGAACGATTATTATGCAG
```

-continued

```
GTCAAGGCCATTGACTTGGACAGTGCAGAAAACGGCGAAGTTCGGTACGAACTTAAGAAGGGCAATGGGGAGTTGTTCAAACT

GGACCGCAAATCTGGGGAGTTATCCATAAAGCAGCATGTCGAAGGTCATAACCGAAACTATGAATTGACAGTGGCTGCCTATG

ATGGCGCCATAACACCATGCTCCTCGGAAGCTCCTCTGCAGGTTAAGGTTATAGATCGTTCGATGCCCGTTTTTGAAAAGCAG

TTTTATACTGTTAGCGTCAAGGAAGACGTGGAAATGTACTCAGCCCTTTCCGTATCCATTGAAGCAGAAAGTCCCCTGGGAAG

GAGTTTAATTTACACAATATCTTCCGAGAGTCAATCGTTTGAAATTGATTACAACACGGGATCAATTTTTGTCGTAAATGAAT

TGGATTACGAGAAAATAAGCTCACACGATGTTTCCATTCGAGCGACTGACAGTCTTTCTGGTGTTTATGCTGAAGTCGTTTTA

TCTGTTTCCATTATGGATGTCAATGACTGCTATCCAGAAATTGAGAGTGATATATACAACCTAACCATTCCGGAAAATGCATC

GTTTGGAACACAAATTCTGAAGATTAATGCAACTGATAACGACTCGGGAGCAAATGCAAAACTTTCCTATTACATTGAGTCCA

TTAATGGGCAAAATAATTCAGAACTGTTTTACATTGACGTCACAGACGGAAATCTGTATTTAAAGACTCCATTGGACTATGAA

CAAATCAAGTATCATCATATAGTCGTTAACGTAAAGGACCATGGATCGCCATCATTAAGTTCCCGATCAAACGTATTTATAAC

AGGTAGAATTCTATGTCGCTTTATCTCTTACAAACTAATTTATGATTCTATTATTCCAGTTAAAGACTTAAACGACAACGCTC

CATGTTTCGTTGAGCCGTCGTACTTCACCAAAGTGTCAGTGGCAGCTGTTCGTGGACAATTTGTTGCTTTACCTAAAGCATAC

GATAAGGATATTTCCGATACCGATTCTCTGGAATACAAAATTGTTTACGGAAATGAATTGCAAACCTATAGTATTGATAAGCT

AACAGGAGTGATTTCCCTTCAAAATATGTTAAATTTCACTGATAAAAGTAGCACAGTCTTGAATATTTCCGTCTCCGATGGAG

TTCATACGGCATATGCCCGGCTCAAAATATCCTTATTGCCAGAAAACGTTTACAGTCCACTGTTTGATCAAAGTACTTATGAG

GCTCAAGTACCTGAAAACTTGCTACACGGTCATAATATAATCACGGTAAAAGCATCGGATGGAGACTTTGGCACCTACGCCAA

TCTTTACTACGAAATAGTTTCGGAGGAAATGAAAAAAATCTTTCTCATCGACCAAACGACGGGTGTAATAACCTCAAAAGTAA

CTTTCGACCGTGAAAAAAAGGATGAGTACGTGGTGCTACTGAAGGTGTCCGACGGTGGCGGAAAATTCGGATTTGCCTCTCTC

AAGGTCATAGTCGTCGACGTGAACGATAACGTTCCTTACTTCCTATTGAAGGAATACAAAATGGTTGTTAGCACAACAGTGGA

AGCAAACCAAACTATCCTGACGGTCAAAGCCAAAGACGACGATATTGTTGATAATGGATCGGTGCATTTCCAAATTGTTCAAA

AATCCAACGATAAGGCAGTAAAGGATGTAATCGAAATCAACGAGAAAACTGGGGATATTGTGTTTAAAAGCAAGGCGGAATCT

TACGGAGTGAACTCATATCAGTTTTTCGTTCGCGCTTCCGATCGCGGTGAACCTCAATTTCATTCGGAAGTTCCAGTGTCAAT

CGAAATAATCGAGACTGATGCCAATATTCCCACTTTTGAGAAATCGTCAGTTCTACTAAAGATCATAGAGTCAACGCCACCAG

GAACCGTGCTAACGAAGCTACATATGATTGGAAACTATACGTTCAAATTCTCAATAGCAGCGGATCAGGATCACTTCATGATA

TCCGATAGTGGTGAACTGATCCTTCAGCAGACATTGGACAGGGAGCAGCAAGAGTCGCACAATTTGATTGTAGTGGCGGAAAC

TTCCACGGTTCCCGTTTTTTTCGCCTACGCTGATGTTTTGATTGACGTTAGGGACGAAAATGATAACTATCCCAAGTTTGACA

ACACATTCTACAGTGCCAGTGTTGCGGAAAACAGTGAAAAGGTGATATCCTTGGTGAAAGTATCGGCCACAGATGCGGACACT

GGGCCAAATGGCGACATTCGCTACTACTTGGAAAGTGATACTGAAAACATTCAAAATATTTTTGACATTGACATTTACTCTGG

CTGGATCACCTTGCTAACCTCCTTGGACAGAGAAGTTCAGTCCGAGTACAATTTCAAAGTAATTGCTGCCGATAATGGCCACC

CAAAGCATGATGCAAAAGTACCTGTAACTATCAAAATCGTAGACTATAATGATAACGCACCAGTATTTAAGTTGCCTATCGAA

GGGCTTTCTGTTTTCGAAAACGCGCTGCCTGGCACGGTTTTAATCAACTTACTCCTAATTGATCCCGATATCGAGAAACAGGA

AATGGATTTCTTTATCGTTTCTGGGGACAAGCAAGCCCAGTTTCAGATCGGTAAGAGCGGAGAGTTATTTATTGCCAAACCAT

TAGATCGCGAACAACTCATGTTCTACAACTTAAGCATAATAGCCACTGATGGAAAATTCACTGCCAAAGCCAATGTGGAAATA

GATGTAAAAGACATAAACGACAATACGCCTTACTGCCTAAAACCCCGCTATCATATCTCCACTAATGAATCAATCTCGATTGG

AACTACACTCGTTGAGGTCAAGGCGATTGACTTTGATTTTCAAAGCAAACTGCGCTTCTATCTTTCGGGCAAAGGTGCGGACG

ACTTCAGTATAGGAAAGGAAAGTGGCATCCTGAAGGTGGCAAGCGCACTGGATCGGGAGACAACCCCCAAGTACAAATTGGTC

GCACATGTACAGGATGGCAAGGACTTTACGCAAGAGTGTTTCTCGGAAATAATCATCACGGTCAATGACATAAATGACAATAT

GCCCATTTTCTCAATGGCTCAATATAGAGTGAGTGTACCCGAGGATGCACAACTGAACACATTGATCACGAAAGTGCACGCGA

TGGATAAGGATTTCGGGGTAAATAGACAAATCAAATACTCGCTAATGGGTGAAAACCATGATTATTTCAAAATATCAAAATCG

ACTGGTATCATAAGGCTGCACAAAAGTCTCGATCGTGAAACAATTTCATTGTTTAATCTCACTGTGAAGGCGGAGGACTGTGG
```

```
CGTTCCAAAACTACACTCCATTGCAACAGTTGCTGTGAACATATTGGACATTAATGACAATCCACCCGAGTTCAGTATGCGTC
AGTATTCGTGCAAAATTCTGGAAAACGCCACACACGGCACAGAAGTGTGCAAAGTTTATGCCACTTCGATAGATATTGGGGTA
AATGCGGATATTCACTACTTCATAATGAGTGGCAACGAGCAGGGGAAGTTCAAAATGGATTCCACGACGGGCGACTTGGTGCT
AAATGCAACCTTGGACTATGAAATGTCCAAGTTTTACTTCTTGACCATTCAAGCAATCGATGGCGGCACTCCACCGCTTAGCA
ACAATGCATATGTGAACATCTCTATTCTGGACATTAATGACAACAGTCCCACGTTTCTGCAAAACCTGTACCGCATTAATGTC
AATGAAGATATTTTCGTGGGCTCCAAGATTCTGGACGTCAAAGCCACGGACGAAGATTCAGATGTAAATGGTCTTGTAACTTA
CAACATTGAAAGAGGCGACAATATAGGCCAGTTTTCAATAGATCCGAAAAACGGAACAATTAGCGTTTCGAGGCCATTAGATC
GTGAGACTATTTCGCACTACACTCTTGAAATTCAAGCCTGTGATCAGGGAGATCCTCAGAGATGCAACAGTGTTCCAATCAAT
ATAAACATTTTGGACACTAACGATAATGCACCCATATTTTCCAGCTCTAACTACAGTGTAGTACTTCAAGAAAACCGACTTCT
GGGCTATGTATTCCTTACCTTCAAGATATCAGACGCAGACGAAACACCCAATACCACGCCATACACCTTCGATATTAGGTCTG
GAAATGAGGGTGGGCTTTTCCGGCTGGAGCAAGATGGTTCCTTGAGAACGGCCTCGCGATTTAATCACAATCTGCAGGACGAA
TTCGTGATTCAAGTTCGAGTTTTCGACAACGGCACACCTCCATTATATTCCGATGCCTGGGTGGTTGTGAAAATAATTGAAGA
AAGCCAATACCCGCCCATTGTCACACCCCTAGAAGTAACCATAAATTCATTCGAGGACGATTTTTCGGGCGCATTCATTGGCA
AAGTTCATGCCTCGGATCAGGACAAGTATGATGAATTGAACTTTAGTTTGGTGTCCGGTCCCGATGACATGTATCAGAGCTCG
AAGCTGTTCAACATTTCCAACAACACGGGAAAGATCTATGCCATATCCAACCTGGATATTGGTCTGTACAAGCTAAATGTGTC
CGTTTCGGATGGTAAATTTCATGTGTTCTCCATTGTCAAAATCAACGTGGAACTGGTAACCAATGATATGCTAAAAGAGTCGG
TTGTCATTCGATTCAGAAGGATTTCAGCATCTGAGTTTCTGCTGAGTCACAGGAAAACCTTTATGCGCTCCATTCGCAATATA
ATGCGATGTCGCCAAAAGGATGTAATTCTCATCACCCTTCAATCGGATTATCAAAAAGCATCACAACATGCTGTGGGTAATCG
ACGAGCCAGGTCCATTGACTCCGATTTGAACGTGGTGTTTGCAGTGCGAAAGCAGCAAATAATACCCGATTCCGATGAATTCT
TCACAAGTGATGAAATTCGGCAGACACTGATAGACAAGAAGAACGAGATTGAAAACGAAACCAACCTGGTGGTGGAGGATGTA
CTACCATCCACCTGTCAAAGCAACAAAAACGACTGCGTTCACGGGGAATGCAAACAGATATTACAGATCCTGAAGAACAACGT
TACCACCACCTTTACGGATGTGATTAGTTTTGCTGCTCCATCTTACATTCCGGTGAATACGTGTGTCTGTCGACCAGGATTCG
ATGGAAAGCACTGCAAAGAGACTGTGAATGCCTGCTCCACGGATCCATGTTCCCCGCAGAGGATCTGCATGCCGTCTGGCTCG
GCTTTGGGTTACCAATGTGTGTGTCCCAAGGGATTTTCAGGAACCTACTGCGAGCGGAAGTCTTCGAAGTGCAGCAATGAGTC
CTGTGACATGGGTCTATTCACTGCGGTGTCCTTTGGCGGAAAGAGCTATGCCCACTACAAGATCAACAAGGTGAAGGCGAAGT
TCACGCTGGAAAACGGGTTTTCCTACTCCCTGCAGATAAGAACTGTGCAACAAACTGGGACTCTGCTGTATGCCAGCGGCAAG
GTGGACTACAACATCCTGGAGATCATAAACGGAGCTGTTCAGTACAGATTCGATTTGGGCTCGGGCGAGGGAGTCATCAGTGT
GTCCAGCATTAACATCTCTGACGGCGAGTGGCATCAAATCAGCCTAGAGCGGTCCCTCAATAGTGCCAAAGTGATGGTGGACA
ACAAGCACGTCTCCCATGGCAGTGCTCCGGGTGTGAATGGCATCCTGAACATCCAGTCGAACGATATCTTTGTAGGCGCCGAG
GTTCGTCCGCATCCATCGATAATTGGCTACGAGGATATTCAGCGTGGCTTCATCGGTTGCATGGCAAACATCAAAATAGCCAA
AGAGTGCTGCCATTGTACATTTCCGGTGGGAGTACCATTGCTGCCTTGAAACGTTTTACGAATGTCGAGTTCAAGTGCGATC
CGTCGAATGTTCTGGTGCGCCTGGGCATTTGCGGATCTCAGCCGTGTGCCAATAGTGGAATCTGCAAGGAACTCGATACGGAC
GTGTTTGAATGCGCCTGTCAGCCCCGATATTCCGGCAAGCATTGCGAGATTGATTTGGACCCTTGCTCATCGGGACCCTGCTT
GTTTGGCGGCAGGTGCGACTACCACGGACCGAACAACTACAGCTGCACGTGTCCCATCCACTTATCCGGAAAGAGGTGTGAGT
ACGGCAAGTTCTGCACGCCGAACCCGTGCAAAAACGGTGGCATTTGCGAGGAAGGCGATGGAATATCGCACTGCATGTGCCGC
GGCTACACGGGACCCACTTGTGAGATCGATGTGGATGAGTGCGAGAACCAGCCGTGCGGCAATGGAGCGACCTGCATCAATGA
ACCCGGAAGTTTCCGTTGCATTTGTCCATCTTATCTCACAGGAGCCAGCTGCGGCGATCCCCTGTATTCGAACTCTATTTCTA
CAAAGCTGAAGAACTTTTCTATAGAGCACATTAGCGGGATCATTTCCGGCGTGGCCGTGGTACTGGTCATCATCAGTTGTGTC
CTGTGTTGCGTGGTGTTGAAGAGGAGTTCCTCTTCAAAGCGAAGGAACCGACTAGAAAAGGACAAGAACAAGTCGTCGTACAA
GGAGGCGAACTTGAACTCACTGGTGGACAAGGACAATTACTGCAAACCAAACGTAAAGTTGAGTAACTTGGAGGTTAACCAGC
GTCCAATTAGCTACACAGCAGTTCCAAATGACAACCTAGTCCTGAGCAATAGGAATTTTGTAAATAACTTAGACATCTTGCGT
```

AGCTACGGTTCGGCCGGCGATGAACTGGAAAATGTGCCATTCGAGTACCAGAAGGTTAATCGAAACAAACAGCATGTGAACAT

AAACTCCTGCCATTCAACCGATGCAGATAATGCCTACAAACAAGAATGGTGCGAGCAAATGCATTTAAGAACCTTCAGTGAAA

ATAAACTGAACAATGAACTTAAACGGGATTTCGGACCATCTGTGAGTCGCTTTTCAACTGGGAAACTAATCCAAGTTGAAATG

CCCAACGTGTGCCACTCTTCCAGTGCGAATTTCGTTGATTATTCAGCTCTTGCCAATGGTCAGTATCATTGGGACTGTTCCGA

CTGGGTTCGCAAAAGCCATAATCCCTTGCCAGATATAACCGAAGTTCCTGGAGCAGAAATAGCTGATTCGTCGAGCTTACACA

GCAACGATAGCAACGAGTCCAAGTCGAAGAAAGCCTTTTTCGTGCACAGGGAAGACGGAGATGTTGATCCGACGAGGGATATA

GCCGCGTTGAATGAGGATATCGGATCGGAGTATTTGGACTCGGAGGCAGAGAGCTGCTTGGAGCCGTTTATGTTGCCAAGATC

AAGTAATCAGCCACTTTCAAGACTGAGTTCTTTTAATAATATCGAGAATGAAGACTATAAATCAAATACAGGCAAAGTATATT

TAAGACATCCTGATTCGTATTTACCGACGATGCATTTTCCAAGTGAGACCGATGGGGAAAGCTCTATGACCGAGGGGCCGATT

TCTAGGATGGAAATAAAAACCAGGAGGACGATAAGTGAAAATTCAGAGGAGGCATACCTATTTCCATGCACTGTCGGAGAAAT

TGGATCCAACAGCAACATTTCGGTTCGACTGTGTGAAATTGAAGATTCTGAGTTGGAGGAGTTTTTACCACAACAACAAACAA

ACAATTAA

PCS (*Saccharomyces cerevisiae*)
(SEQ ID NO: 14)
CTACAACTTACTCTTATTTCTGCTGCTCTTAGCAAAAGTTTCTGCGATAACTCTTCTCTGGATTTTACCTGTAGCGGTTTTTG GTAGCTTATCAACAAAGTACACCTTGGTTGGAATTTTGAAAGAGGCTAGGTGCTTCTTTAAGAAGTTCACCAGTTCTTCGTAG GTCATTTTTTCTCCCTTCTTCAAAACAATGGCGGCTTGAACTACTTGGCCGTACATATCGTCGGGAACACCAAATGCAACGGC TTCATCGATCTTTGGATGCGATAGCATAATGCCGTCGAGCTCAATGGGTGAAATCTTTTCACCACCCCTGTTGATAAGCTCTT TGATTCTGCCTGTAAGGACCAAAAACCCCTCAGGGTCGAAATAACCTTGGTCACCGGTTCTGAAATAGTTCTCTCTCTTGGTG AAGTTCTCCTTGTTAGCTTTTGGATTATTAGCATACCCCAAAGTGACGTTTTCGCCTCTGATGGAAACTTCGCCGACTTTGCC CGGGGGCAAGACATTGTCATTGTCATCTAGAATGACGACGGTGACTCCTTGTGGCTGGCCCACAGTACCAGGCTTTCTCTTTC CTGGAGGCAGATTGTTTGAGGTCATTTGATGTGATGCTTCGGTCATCGCATAGGCCTCCAAGACAGGTGCATTGAATTCCTTC TCCAGCTTATGGAACGTTGCTGGAGCCAAAGCAGAAGAACACGATCTGATGAATCTAATGTGTGGGAAAGGGTTTGGTTTGGG CATGTTCAGCATAATCATGCTTATTGTGGGAACGCAACTGAACCAATTACAGTTGTACTTAACAAATTGGTCCCAGAATAACT TTGGATGGAATCCATCGGGAACCACAACAGAACCCTGAGTTCTAAAAGTGGAAAGTAAAACACCAATTAACCCATGGACGTGG AAAAGAGGCATCACGACATAAGATCTGTCCAAGGGCGTTAGCTTGTAAGTGTTAGCAATGTTCAACGTGCTTCTCACAATGTT CAAATGTAACAAAGGCACCGTTTTTGGAGTGGAGGTGGTACCACTGGTATGCAAAATCAGGGCAACGTCACTGGAACGGGCAA ACCCAGGGAATTTAACGGGATTTGTGTTGACAAATTTGGCGTTGTTCAAAGACCGGTAAATAACCCTTTTGTAGTTGTCCTCT GGAGAGTATATATCATACTCTACCCTAAACCTGGTCGCATCGAAGGCCAGCTCTACGATAAAACATCCAAACGTGGAGGCAGA TTTTAGAATTTCAGAACTCTGTAACTTTGTGGTACCCTTTGGGACGCAAATCGCCTTAGATTTCAGGTCATTCAAATAAAAAT TGAACTCCTTTTCCTTATAATTGGGATTCAAGGGCGCGCCAATTTTAGCGTCCATAGTAGCACCGAGGAAAGCGACGATAAAT TCCAGCCCATTACGCATGGATATCGCCACTGTATCTTGTCTGAAAACAGCTCCGTACAATGGAGAATTAGGATTTGTGAACAT GGTCTGGAAGTGACCCACCATGTGGGATAGATCCCTGTAGGTCACCTGAGTGTCCGTTTCAGGAACAATAACGGCGACATTAT

CGGATACGCTAAAAGTATCGTTGAACGAAGCAGTAACAGTAGCGGCACTTGTCAT

ACLY (*Homo sapiens*):
(SEQ ID NO: 15)
GCGAGCCGATGGGGCGGGAAAAGTCCGGCTGGGCCGGGACAAAAGCCGGATCCCGGGAAGCTACCGGCTGCTGGGGTGCTC CGGATTTTGCGGGGTTCGTCGGGCCTGTGGAAGAAGCTGCCGCGCACGGACTTCGGCAGAGGTAGAGCAGGTCTCTCTGCAGC CATGTCGGCCAAGGCAATTTCAGAGCAGACGGGCAAAGAACTCCTTTACAAGTTCATCTGTACCACCTCAGCCATCCAGAATC GGTTCAAGTATGCTCGGGTCACTCCTGACACAGACTGGGCCCGCTTGCTGCAGGACCACCCCTGGCTGCTCAGCCAGAACTTG GTAGTCAAGCCAGACCAGCTGATCAAACGTCGTGGAAAACTTGGTCTCGTTGGGGTCAACCTCACTCTGGATGGGGTCAAGTC CTGGCTGAAGCCACGGCTGGGACAGGAAGCCACAGTTGGCAAGGCCACAGGCTTCCTCAAGAACTTTCTGATCGAGCCCTTCG -continued

```
TCCCCCACAGTCAGGCTGAGGAGTTCTATGTCTGCATCTATGCCACCCGAGAAGGGGACTACGTCCTGTTCCACCACGAGGGG

GGTGTGGACGTGGGTGATGTGGACGCCAAGGCCCAGAAGCTGCTTGTTGGCGTGGATGAGAAACTGAATCCTGAGGACATCAA

AAAACACCTGTTGGTCCACGCCCCTGAAGACAAGAAAGAAATTCTGGCCAGTTTTATCTCCGGCCTCTTCAATTTCTACGAGG

ACTTGTACTTCACCTACCTCGAGATCAATCCCCTTGTAGTGACCAAAGATGGAGTCTATGTCCTTGACTTGGCGGCCAAGGTG

GACGCCACTGCCGACTACATCTGCAAAGTGAAGTGGGGTGACATCGAGTTCCCTCCCCCCTTCGGGCGGGAGGCATATCCAGA

GGAAGCCTACATTGCAGACCTCGATGCCAAAGTGGGGCAAGCCTGAAGCTGACCTTGCTGAACCCCAAAGGGAGGATCTGGA

CCATGGTGGCCGGGGGTGGCGCCTCTGTCGTGTACAGCGATACCATCTGTGATCTAGGGGGTGTCAACGAGCTGGCAAACTAT

GGGGAGTACTCAGGCGCCCCCAGCGAGCAGCAGACCTATGACTATGCCAAGACTATCCTCTCCCTCATGACCCGAGAGAAGCA

CCCAGATGGCAAGATCCTCATCATTGGAGGCAGCATCGCAAACTTCACCAACGTGGCTGCCACGTTCAAGGGCATCGTGAGAG

CAATTCGAGATTACCAGGGCCCCCTGAAGGAGCACGAAGTCACAATCTTTGTCCGAAGAGGTGGCCCCAACTATCAGGAGGGC

TTACGGGTGATGGGAGAAGTCGGGAAGACCACTGGGATCCCCATCCATGTCTTTGGCACAGAGACTCACATGACGGCCATTGT

GGGCATGGCCCTGGGCCACCGGCCCATCCCCAACCAGCCACCCACAGCGGCCCACACTGCAAACTTCCTCCTCAACGCCAGCG

GGAGCACATCGACGCCAGCCCCCAGCAGGACAGCATCTTTTTCTGAGTCCAGGGCCGATGAGGTGGCGCCTGCAAAGAAGGCC

AAGCCTGCCATGCCACAAGATTCAGTCCCAAGTCCAAGATCCCTGCAAGGAAAGAGCACCACCCTCTTCAGCCGCCACACCAA

GGCCATTGTGTGGGCATGCAGACCCGGGCCGTGCAAGGCATGCTGGACTTTGACTATGTCTGCTCCCGAGACGAGCCCTCAG

TGGCTGCCATGGTCTACCCTTTCACTGGGGACCACAAGCAGAAGTTTTACTGGGGCACAAAGAGATCCTGATCCCTGTCTTC

AAGAACATGGCTGATGCCATGAGGAAGCACCCGGAGGTAGATGTGCTCATCAACTTTGCCTCTCTCCGCTCTGCCTATGACAG

CACCATGGAGACCATGAACTATGCCCAGATCCGGACCATCGCCATCATAGCTGAAGGCATCCCTGAGGCCCTCACGAGAAAGC

TGATCAAGAAGGCGGACCAGAAGGGAGTGACCATCATCGGACCTGCCACTGTTGGAGGCATCAAGCCTGGGTGCTTTAAGATT

GGCAACACAGGTGGGATGCTGGACAACATCCTGGCCTCCAAACTGTACCGCCCAGGCAGCGTGGCCTATGTCTCACGTTCCGG

AGGCATGTCCAACGAGCTCAACAATATCATCTCTCGGACCACGGATGGCGTCTATGAGGGCGTGGCCATTGGTGGGGACAGGT

ACCCGGGCTCCACATTCATGGATCATGTGTTACGCTATCAGGACACTCCAGGAGTCAAAATGATTGTGGTTCTTGGAGAGATT

GGGGGCACTGAGGAATATAAGATTTGCCGGGGCATCAAGGAGGGCCGCCTCACTAAGCCCATCGTCTGCTGGTGCATCGGGAC

GTGTGCCACCATGTTCTCCTCTGAGGTCCAGTTTGGCCATGCTGGAGCTTGTGCCAACCAGGCTTCTGAAACTGCAGTAGCCA

AGAACCAGGCTTTGAAGGAAGCAGGAGTGTTTGTGCCCCGGAGCTTTGATGAGCTTGGAGAGATCATCCAGTCTGTATACGAA

GATCTCGTGGCCAATGGAGTCATTGTACCTGCCCAGGAGGTGCCGCCCCCAACCGTGCCCATGGACTACTCCTGGGCCAGGGA

GCTTGGTTTGATCCGCAAACCTGCCTCGTTCATGACCAGCATCTGCGATGAGCGAGGACAGGAGCTCATCTACGCGGGCATGC

CCATCACTGAGGTCTTCAAGGAAGAGATGGGCATTGGCGGGGTCCTCGGCCTCCTCTGGTTCCAGAAAAGGTTGCCTAAGTAC

TCTTGCCAGTTCATTGAGATGTGTCTGATGGTGACAGCTGATCACGGGCCAGCCGTCTCTGGAGCCCACAACACCATCATTTG

TGCGCGAGCTGGGAAAGACCTGGTCTCCAGCCTCACCTCGGGGCTGCTCACCATCGGGGATCGGTTTGGGGGTGCCTTGGATG

CAGCAGCCAAGATGTTCAGTAAAGCCTTTGACAGTGGCATTATCCCCATGGAGTTTGTGAACAAGATGAAGAAGGAAGGGAAG

CTGATCATGGGCATTGGTCACCGAGTGAAGTCGATAAACAACCCAGACATGCGAGTGCAGATCCTCAAAGATTACGTCAGGCA

GCACTTCCCTGCCACTCCTCTGCTCGATTATGCACTGGAAGTAGAGAAGATTACCACCTCGAAGAAGCCAAATCTTATCCTGA

ATGTAGATGGTCTCATCGGAGTCGCATTTGTAGACATGCTTAGAAACTGTGGGTCCTTTACTCGGGAGGAAGCTGATGAATAT

ATTGACATTGGAGCCCTCAATGGCATCTTTGTGCTGGGAAGGAGTATGGGGTTCATTGGACACTATCTTGATCAGAAGAGGCT

GAAGCAGGGGCTGTATCGTCATCCGTGGGATGATATTTCATATGTTCTTCCGGAACACATGAGCATGTAA
```

FAS (*Mycobacterium bovid* subsp. *bovis*):

(SEQ ID NO: 16)
```
ATGAGTCAGACGGTGCGCGGTGTGATCGCACGACAAAAGGGCGAACCCGTTGAGCTGGTGAACATTGTCGTCCCGGATCCCGG

ACCCGGCGAGGCCGTGGTCGACGTCACCGCCTGCGGGGTATGCCATACCGACCTGACCTACCGCGAGGGCGGCATCAACGACG

AATACCCTTTTCTGCTCGGACACGAGGCCGCGGGCATCATCGAGGCCGTCGGGCGGGTGTAACGCAGTCGAGCCCGGCGAC

TTCGTGATCCTGAACTGGCGTGCCGTGTGCGGCCAGTGCCGGGCCTGCAAACGCGGACGGCCCCGCTACTGCTTCGACACCTT
```

-continued

```
TAACGCCGAACAGAAGATGACGCTGACCGACGGCACCGAGCTCACTGCGGCGTTGGGCATCGGGGCCTTTGCCGATAAGACGC
TGGTGCACTCTGGCCAGTGCACGAAGGTCGATCCGGCTGCCGATCCCGCGGTGGCCGGCCTGCTGGGTTGCGGGGTCATGGCC
GGCCTGGGCGCCGCGATCAACACCGGCGGGGTAACCCGCGACGACACCGTCGCGGTGATCGGCTGCGGCGGCGTTGGCGATGC
CGCGATCGCCGGTGCCGCGCTGGTCGGCGCCAAACGGATCATCGCGGTCGACACCGATGACACGAAGCTTGACTGGGCCCGCA
CCTTCGGCGCCACCCACACCGTCAACGCCCGCGAAGTCGACGTCGTCCAGGCCATCGGCGGCCTCACGGATGGATTCGGCGCG
GACGTGGTGATCGACGCCGTCGGCCGACCGGAAACCTACCAGCAGGCCTTCTACGCCCGCGATCTCGCCGGAACCGTTGTGCT
GGTGGGTGTTCCGACGCCCGACATGCGCCTGGACATGCCGCTGGTCGACTTCTTCTCTCACGGCGGTGCGCTGAAGTCGTCGT
GGTACGGCGATTGCCTGCCCGAAAGCGACTTCCCCACGCTGATCGACCTTTACCTGCAGGGCCGGCTGCCGCTGCAGCGGTTC
GTTTCCGAACGCATCGGGCTCGAAGACGTCGAGGAGGCGTTCCACAAGATGCATGGCGGCAAGGTATTGCGTTCGGTGGTGAT
GTTGTGA
```

AMPK (*Homo sapiens*):
(SEQ ID NO: 17)
```
AGTTCCTGGAGAAAGATGGCGACAGCCGAGAAGCAGAAACACGACGGGCGGGTGAAGATCGGCCACTACATTCTGGGTGACAC
GCTGGGGGTCGGCACCTTCGGCAAAGTGAAGGTTGGCAAACATGAATTGACTGGGCATAAAGTAGCTGTGAAGATACTCAATC
GACAGAAGATTCGGAGCCTTGATGTGGTAGGAAAAATCCGCAGAGAAATTCAGAACCTCAAGCTTTTCAGGCATCCTCATATA
ATTAAACTGCACCAGGTCATCAGTACACCATCTGATATTTTCATGGTGATGGAATATGTCTCAGGAGGAGAGCTATTTGATTA
TATCTGTAAGAATGGAAGGAAATCTGATGTACCTGGAGTAGTAAAAACAGGCTCCACGAAGGAGCTGGATGAAAAAGAAAGTC
GGCGTCTGTTCCAACAGATCCTTTCTGGTGTGGATTATTGTCACAGGCATATGGTGGTCCATAGAGATTTGAAACCTGAAAAT
GTCCTGCTTGATGCACACATGAATGCAAAGATAGCTGATTTTGGTCTTTCAAACATGATGTCAGATGGTGAATTTTTAAGAAC
AAGTTGTGGCTCACCCAACTATGCTGCACCAGAAGTAATTTCAGGAAGATTGTATGCAGGCCCAGAGGTAGATATATGGAGCA
GTGGGGTTATTCTCTATGCTTTATTATGTGGAACCCTTCCATTTGATGATGACCATGTGCCAACTCTTTTTAAGAAGATATGT
GATGGGATCTTCTATACCCCTCAATATTTAAATCCTTCTGTGATTAGCCTTTTGAAACATATGCTGCAGGTGGATCCCATGAA
GAGGGCCACAATCAAAGATATCAGGGAACATGAATGGTTTAAACAGGACCTTCCAAAATATCTCTTTCCTGAGGATCCATCAT
ATAGTTCAACCATGATTGATGATGAAGCCTTAAAAGAAGTATGTGAAAAGTTTGAGTGCTCAGAAGAGGAAGTTCTCAGCTGT
CTTTACAACAGAAATCACCAGGATCCTTTGGCAGTTGCCTACCATCTCATAATAGATAACAGGAGAATAATGAATGAAGCCAA
AGATTTCTATTTGGCGACAAGCCCACCTGATTCTTTTCTTGATGATCATCACCTGACTCGGCCCCATCCTGAAAGAGTACCAT
TCTTGGTTGCTGAAACACCAAGGGCACGCCATACCCTTGATGAATTAAATCCACAGAAATCCAAACACCAAGGTGTAAGGAAA
GCAAAATGGCATTTAGGAATTAGAAGTCAAAGTCGACCAAATGATATTATGGCAGAAGTATGTAGAGCAATCAAACAATTGGA
TTATGAATGGAAGGTTGTAAACCCATATTATTTGCGTGTACGAAGGAAGAATCCTGTGACAAGCACTTACTCCAAAATGAGTC
TACAGTTATACCAAGTGGATAGTAGAACTTATCTACTGGATTTCCGTAGTATTGATGATGAAATTACAGAAGCCAAATCAGGG
ACTGCTACTCCACAGAGATCGGGATCAGTTAGCAACTATCGATCTTGCCAAAGGAGTGATTCAGATGCTGAGGCTCAAGGAAA
ATCCTCAGAAGTTTCTCTTACCTCATCTGTGACCTCACTTGACTCTTCTCCTGTTGACCTAACTCCAAGACCTGGAAGTCACA
CAATAGAATTTTTTGAGATGTGTGCAAATCTAATTAAAATTCTTGCACAATAA
```

The vector was transformed in Po1 g *Yarrowia lipolytica* strain and selected on leucine deficient agar plates. The colonies were screened for the correct insert in the genome using PCR.

Δ9-FW
AATGGTGAAAAACGTGGACCAAGTGGA (SEQ ID NO: 18)

Δ9-REV
ATGGATCCCTAAGCAGCCATGCCAGACATAC (SEQ ID NO: 19)

GLUT1-FW
AATGGAGCCCAGCAGCAAGAAGGTGA (SEQ ID NO: 20)

GLUT1-REV
AATGGGTACCTCACACTTGGGAGTCAGCC (SEQ ID NO: 21)

Hemoglobin FW
AGAGACCGGGTTGGCGGCGCA (SEQ ID NO: 22)

Hemoglobin REV
CAGCGTCTTGAGCGTACAAA (SEQ ID NO: 23)

Cytochrome FW
AATGATCATCAACGGCAAGGTCT (SEQ ID NO: 24)

-continued

```
Cytochrome REV
TTATTTCTGACCCTGGAGGTAGAAG          (SEQ ID NO: 25)

Pyruvate Carboxylase FW
AATGCTGAAGTTCCGAACAGT              (SEQ ID NO: 26)

Pyruvate Carboxylase REV
CGATGGTACCTCACTCGATCTCCAGGATG      (SEQ ID NO: 27)
```

The resulting colony was grown in YPD media (full media: yeast extract, peptone, dextrose) and YNB media (minimal media, containing all nutrients, but no amino acids, and no nitrogen or carbon source). When grown in YNB media was used, nitrogen was provided as ammonium sulphate and carbon was provided as glucose at a Carbon to Nitrogen ratio of 150. This C/N ratio is necessary for triggering oil accumulation. Upon depletion of nitrogen excess sugar is channeled to oil accumulation in yeast.

Oil Harvesting: The cells were grown in nitrogen-restricted growth media. After 72 hours the cells are harvested and dried at 60° C. for 2 days. The cells were directly treated with 1% sulphuric acid and methanol for 24 hours at 90° C. The oil was converted to FAME (fatty acid methyl esters) and extracted by hexane. The hexane extraction is repeated twice to recover 95% of FAME. The hexane fraction is evaporated and re-suspended in 5 ml of hexane. 10 ul of the fraction is injected into GC-MS to quantify FAME.

Cell cultures were harvested and prepared for fatty acid analysis, as described earlier (Voelker and Davies, 1994). The fatty acid content of each sample was quantified by GC-MS using a single quadrupole MS with an electron impact ionization source. The GC column was a 30 m long HP-5 MS (5% phenyl)-methylpolysiloxane with a ID of 0.25 mm and a film thickness of 25 µm. The GC elution conditions were as follows: 100° C. as the starting temperature (5 min), a 15 min ramp to 250° C., hold at 250° C. for 10 min.

Example 1

A qualitative profile of total free fatty acid (FFA) pool was probed in *Y. lipolytica* culture grown in the log and stationary growth phases using GC-MS (FIG. 1A-C). The major FFA pool is comprised of saturated palmitic and stearic acids and unsaturated oleic acid. A comparison of the FFA profiles in the two growth phases revealed absence of oleic acid in the stationary phase while similar peak intensities of stearic and oleic acid were observed in the log phase (FIG. 1A, B). Analysis of the total lipids (FFA+lipids) during stationary phase recovered partial amount of the oleic acid suggesting that oleic acid is being routed for TAG formation (FIG. 1C). The remaining pool of oleic acid is utilized for downstream poly-unsaturated fatty acids and therefore cannot be rescued. Therefore, oleic acid is channeled to TAG formation in a temporal fashion during stationary growth phase that coincides with the timing of activation of intracellular TAG storage pathway. This suggests a checkpoint mechanism may exist to monitor oleic acid levels to regulate oil accumulation.

Example 2

Figure 2:
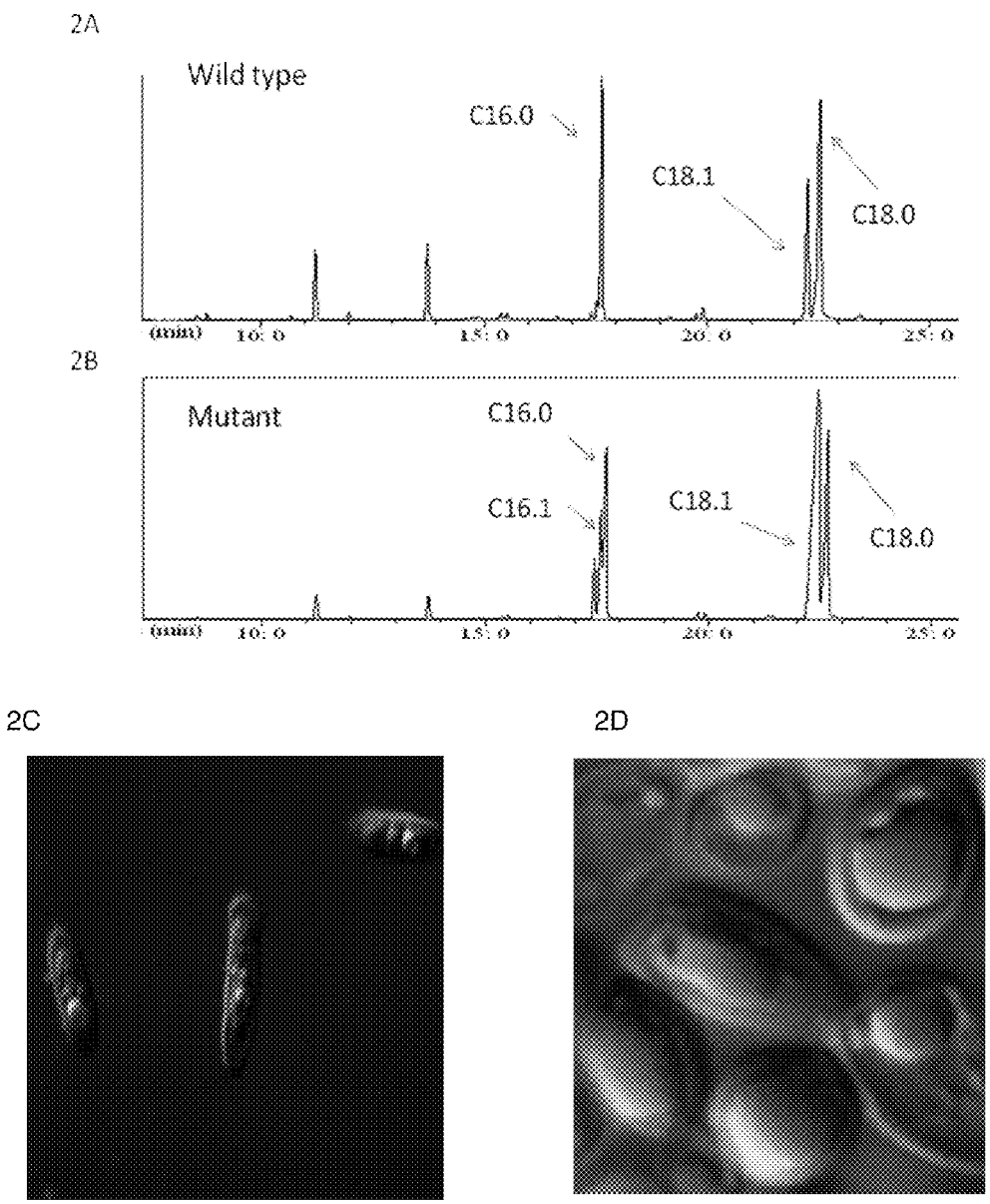
FIG. 2: Analysis of total lipids in *Yarrowia lipolytica*. A) Wild type *Y. lipolytica* strain grown in minimal media until 72-hour stationary phase culture and assayed for total lipids using GC-MS in a shake flask experiment. B) Total lipids were assayed in the mutant strain grown to stationary phase (72 hours) and over-expressing SCD, a native Δ9 desaturase under the control of a quasi-constitutive promoter. C) Confocal microscopy on wild type strain grown to stationary phase was stained with Nile red. D) Mutant strain grown to stationary phase was stained with Nile red and analyzed with confocal microscope.

Since in mouse SCD is essential for lipogenesis (see, e.g. *Regulation of stearoyl-CoA desaturases and role in metabolism*. Prog Lipid Res. 2004 March; 43(2):91-104) and is reported to be important for the synthesis of unsaturated fatty acids in most organisms, we tested the role of *Y. lipolytica* SCD as a rate limiting step in TAG accumulation. Protein sequence analysis of *Saccharomyces cerevisiae* OLE1 gene encoding SCD against *Y. lipolytica* protein sequences revealed a protein with 51% identity. The *Y. lipolytica* desaturase contains three histidine boxes and a cytochrome b5 domain typical to other stearoyl-CoA desaturases. Since desaturase enzymes are highly regulated at gene transcription level (see e.g., *Regulation of stearoyl-CoA desaturase by polyunsaturated fatty acids and cholesterol*. James M. Ntambi. Journal of Lipid Research, Vol. 40, 1549-1558, September 1999) and during the log and stationary phase of cell growth (see Mol Cell Biol Res Commun. 1999 April; 1(1): 36-43), we modulated the native *Y. lipolytica* desaturase gene expression with a quasi-constitutive promoter. A single copy of the modified gene was stably integrated into the genome. GC-MS profile between the mutant and wild type strain showed a significant increase in the ratio between unsaturated to saturated fatty acids (FIG. 2 A, B). Confocal microscopy of intracellular lipids stained with Nile red showed a correlation between elevated unsaturated fatty acids and excess accumulation of TAG (FIG. 2C: wild type, FIG. 2D: SCD overexpressor). In most cases the entire cell volume of the SCD overexpressor cells is completely filled with TAG (FIG. 2D). These findings provide evidence of a key regulator gene that surprisingly is sufficient to induce over-accumulation of intracellular TAG by altering the ratio of unsaturated fatty acids to saturated fatty acids.

The confocal imaging of the growing and stationary cells revealed a striking difference in the pattern of oil accumulation. We tested the intracellular TAG mobility of stationary phase oil-rich mutant cells upon re-entry to mitotic cell cycle. We fed-batch stationary phase cells with minimal media containing higher concentration of sugars (300 g/l). The cells efficiently re-enter the log phase and followed rapid growth and biomass production consuming all of the sugars within 96 hours. Interestingly, image analysis showed the mutant strain accumulating excess intracellular oil even during log phase, which is atypical to oleaginous yeast. Although the wild type cells were unable to grow in high sugar concentration, the continuous oil production and yeast-like bodies were absent in log phase even at sugar concentrations favorable to growth.

Taken together, these results establish a continuous fed-batch process using high concentration of sugars, and suggest that the engineered yeast strain is able to accumulate oil continuously during the log and stationary growth phases.

Example 3

Two types of mutant yeast were generated, which overexpressed the following genes: Mutant 1: SCD, Hemoglobin, Glut1, Cytochrome; Mutant 2: Hemoglobin, Glut1, Cytochrome. The respective genes were cloned into plasmid YLEX between PmlI and Kpn sites. The vector was transformed in Po1 g *Yarrowia lipolytica* strain and selected on Leucine-deficient agar plates. The colonies were screened for the correct insert in the genome using PCR. The resulting colony was grown in YPD media and YNB media with a carbon to nitrogen (C/N) ratio of 150. This C/N ratio is necessary for triggering oil accumulation. Upon depletion of nitrogen excess sugar is channeled to oil accumulation in yeast.

In order to measure maximum oil accumulation, the cells were grown in nitrogen restricted growth media. After 72 hours the cells were harvested and dried at 60° C. for 2 days. The cells were directly treated with 1% sulphuric acid and methanol for 24 hours at 90° C. The oil was converted to FAME (fatty acid methyl esters) and extracted by hexane. The hexane extraction was repeated twice to recover 95% of FAME. The hexane fraction was evaporated and re-suspended in 5 ml of hexane. 10 ul of the fraction was injected into GC-MS to quantify FAME. The maximum oil accumulation in the mutant strains was 80 grams/l.

Figure 3:
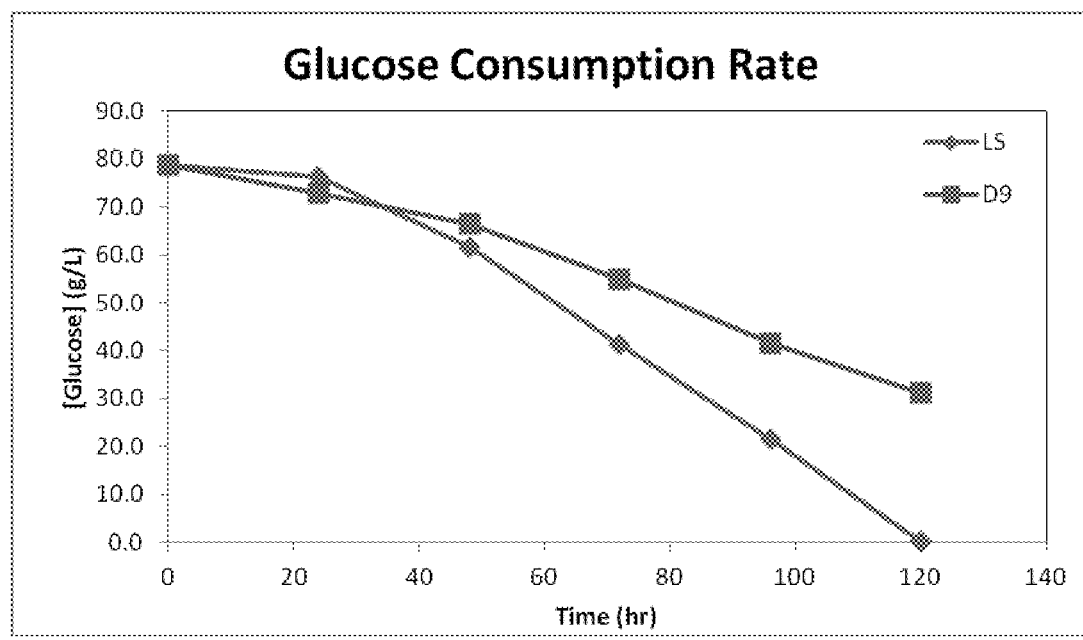
FIG. 3: Glucose consumption of *Y. lipolytica* mutant-1 (overexpressing cytochrome B, hemoglobin, Glut1, and Δ9-desaturase (SCD), (D9, ■)); and the wild type (LS, ♦) on pure glucose in shake flask. *Y. lipolytica* mutant-1 exhibits a faster glucose consumption characteristics as compared to wild type *Y. lipolytica* and also a complete glucose consumption as compared to the incomplete consumption observed in the wild type.

The glucose uptake kinetics of mutant 1 ("D9") and wild type yeast ("LS") were compared. FIG. 3 shows that mutant 1 consumed all sugar provided after 72 hours, whereas wild type yeast only consumed about 70% of the provided sugar. It was observed that wild type strains did not consume all sugars even at extended period of time.

It was next determined whether the mutant strains could use biomass hydrolyzate as a carbon source. A 2-L bioreactor was set up containing corn stover hydrolyzates (Hz) in the presence of 1% yeast extract. The Hz contains 20 gram of glucose. We added (fed-batch) 180 g of glucose to final conc. of 200 g/l. We determined that the wild type cannot grow in the toxic biomass Hz. Mutant 1 and mutant 2 cells were grown in shake flask to a final OD of 3 in 50 ml. The overnight culture was added to the respective bioreactor and fermentation was carried out for 72 hours at 30° C. The two reactors, one with mutant 1 and the other with mutant 2, were run under identical conditions. The stirring was 800 rpm and the pH was set at 5.5.

Figure 4:
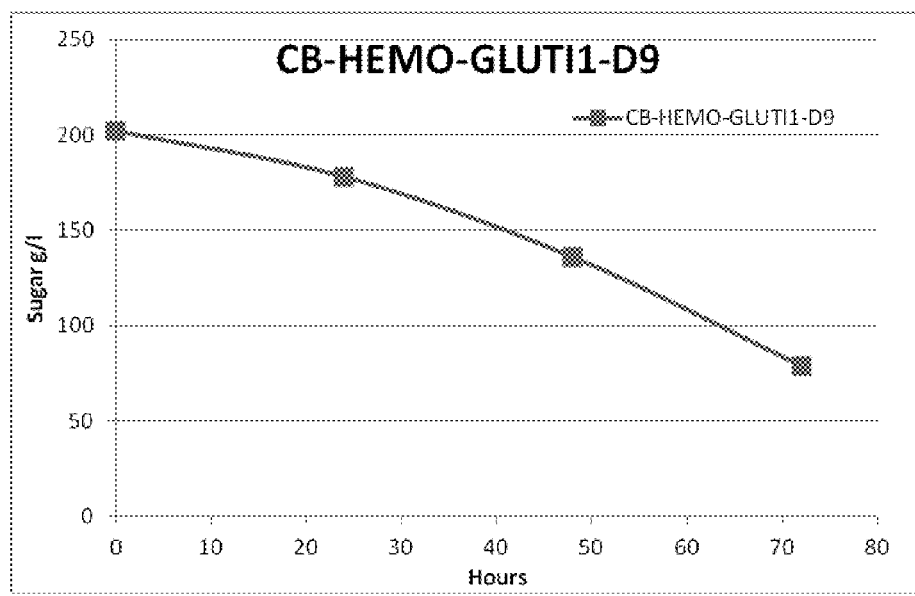
FIG. 4: A) Sugar consumption in *Y. lipolytica* mutant 1 (overexpressing cytochrome B, hemoglobin, Glut1, and Δ9-desaturase (SCD)), and mutant 2 (overexpressing cytochrome B, hemoglobin, and Glut1) in 72 hours in corn stover hydrolyzate (Hz). B) Oil production in mutant 1 and mutant 2 hours in corn stover Hz.
Figure 4:
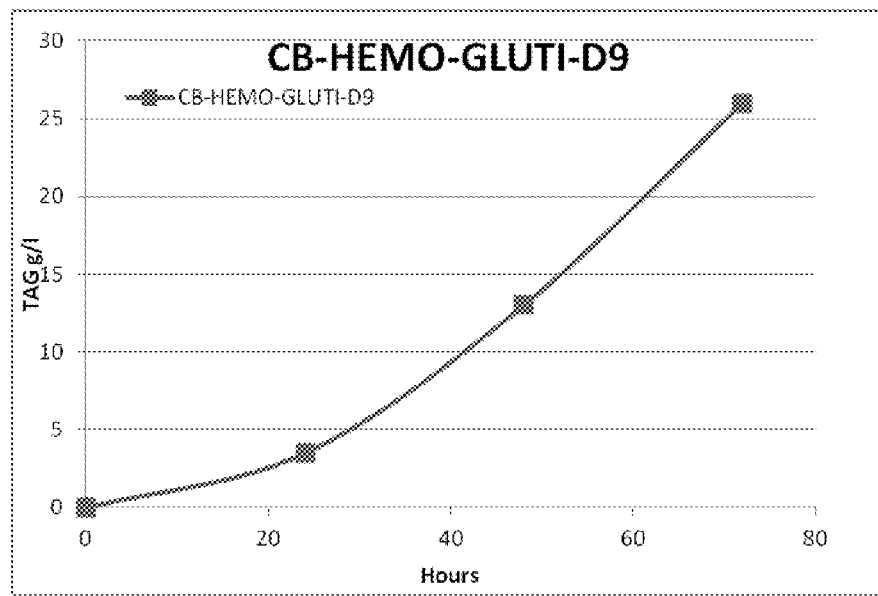
Figure 5:
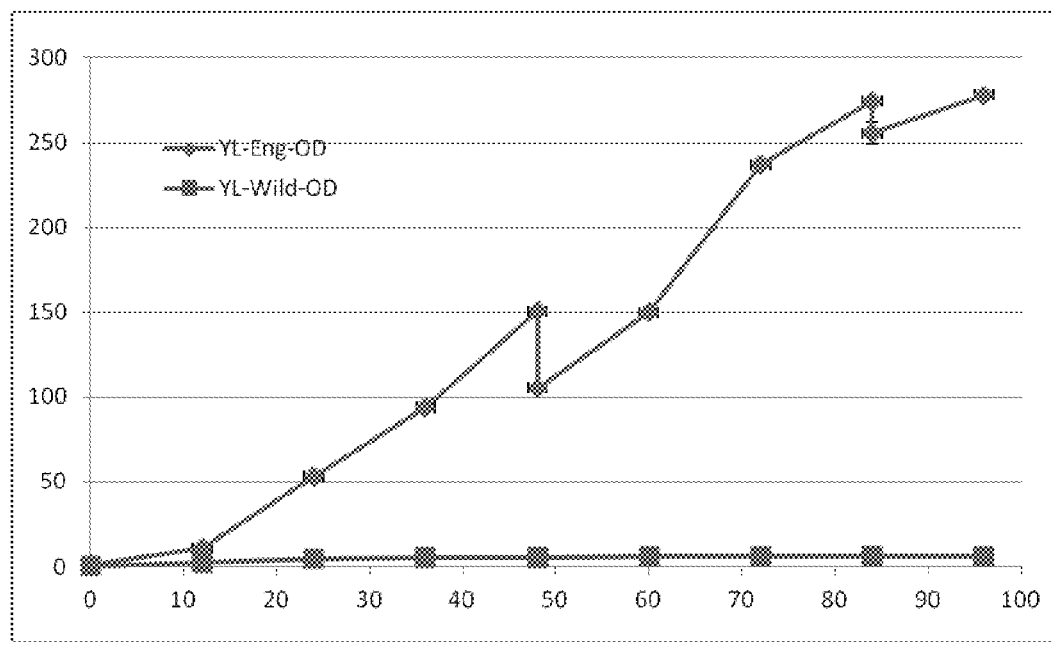
FIG. 5: Comparison of growth characteristics of wild type and engineered microbes. YL-eng: mutant *Y. lipolytica* overexpressing Δ9-desaturase (SCD). YL-wild: wild-type *Y. lipolytica*. Cells were grown in minimal media containing a sugar concentration of 250 g/l. While the wild type cells failed to grow under these conditions, the mutant cells were able to tolerate the high level of sugars and grew well, suggesting that higher biofuel or biofuel precursor productivity can be achieved in processes using mutant strains. Y-axis: OD values. X-axis: time in hours.
Figure 6:
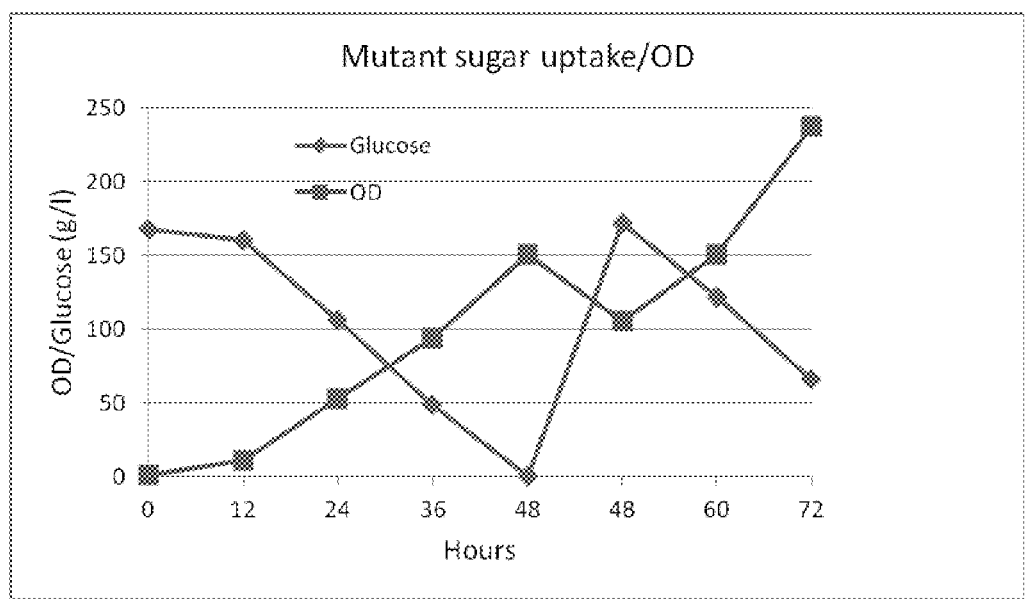
FIG. 6: Sugar consumption and growth characteristics of a *Y. lipolytica* mutant overexpressing Δ9-desaturase (SCD). Cells were grown in media containing 160 g/l sugar and OD and sugar consumption of the culture were monitored. The mutant cells consumed the supplied sugar within 48 hours, and continued to grow after fed-batch replenishment of sugars. This figure exemplifies an embodiment useful for fed-batch operations and semi-continuous biofuel production processes.

Both strains consumed around 50% of the supplied glucose in 72 hours due to limitation of some nutrient factors in the medium (FIG. 4A, showing mutant 1 strain). The reason for 50% sugar consumption in both strains is due to the presence of Glut1 which is known to transport glucose into the cell. Mutant 1 consumed 123 gram of glucose whereas mutant 2 consumed 105 grams of sugar. This result shows that the mutant cells can consume almost 50% of the sugars and resist the toxicity of the Hz very well compared to wild type, which do not grow well and consume less than 10 gram of sugars in earlier experiments. The mutant strains showed robust growth and good consumption of sugars. The leftover sugars were not consumed due to some deprivation of nutrient factors (see FIGS. 5 and 6).

Mutant 1 (with combination of genes overexpressed) displayed increased oil synthesis as compared to mutant 2. Mutant-1 produced 26 grams of oil per liter (FIG. 4B) and mutant-2 produced 14 grams of oil per liter. This suggests that overexpression of a combination of genes not only results in the increased consumption of supplied sugars but also in the increased production of more oil, a useful biofuel precursor.

Example 4

We next measured the growth advantage, total lipid production, conversion efficiency of carbohydrate substrate to lipid and substrate tolerance between the engineered and the wild type strain in a 2 liter fermentor vessel.

Figure 7:
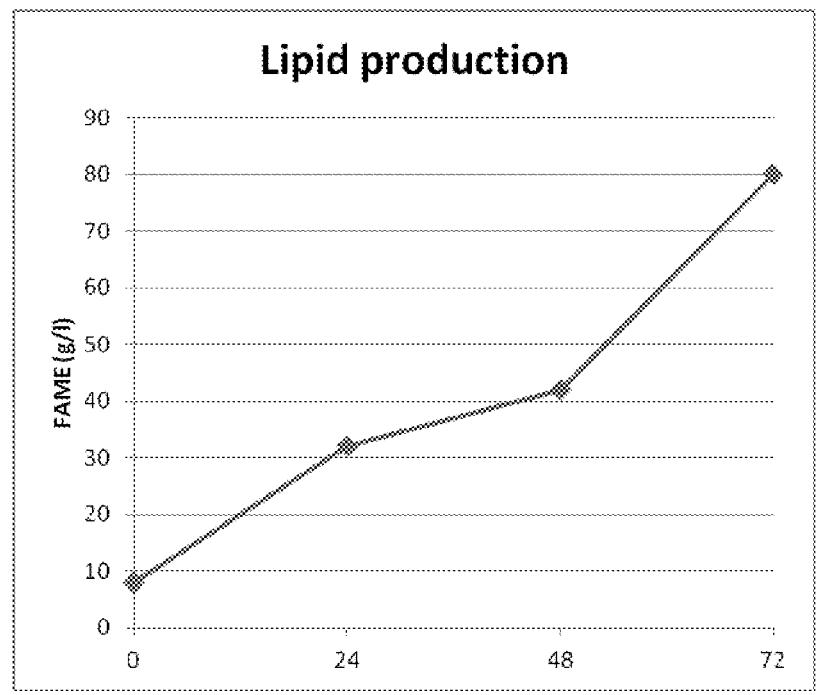
FIG. 7: Lipid production of engineered *Y. lipolytica* (overexpressing Δ9-desaturase (SCD), Cytochrome B and hemoglobin).
Figure 8:
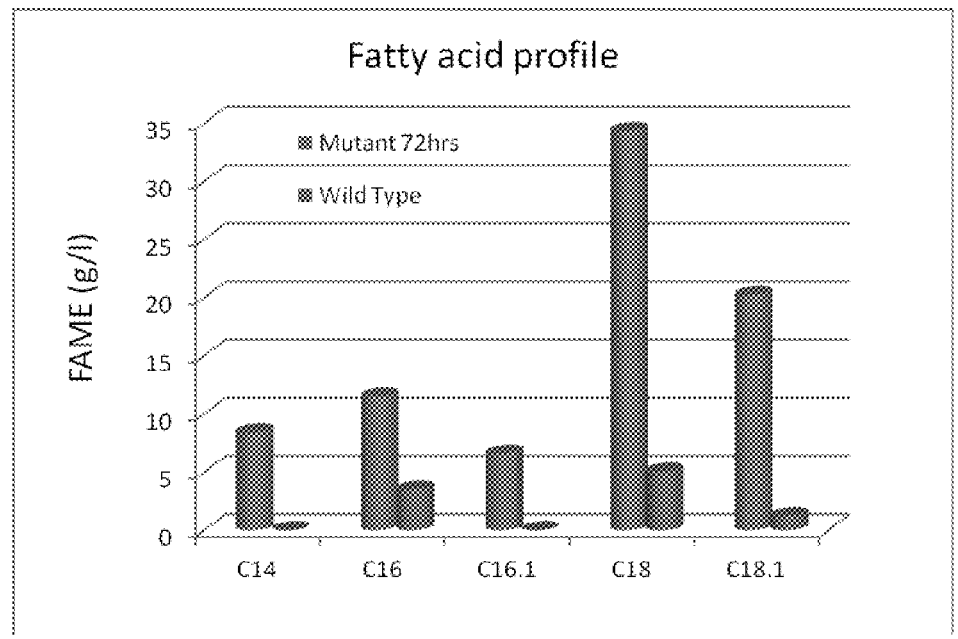
FIG. 8: Fatty acid profiles of mutant strain (overexpressing Δ9-desaturase (SCD), cytochrome B and hemoglobin; left bar in each set) and wild type *Y. lipolytica* strain (right bar in each set) after 72 h of culture.

The total amount of lipid was measured using GC-MS (FIG. 7). A 10 fold higher production of lipid (80 g/l) was observed in the engineered strain as compared to the wild type strain, representing a 20 fold increase over the *Yarrowia lipolytica* strain described by others (S. Papanikolaou I. Chevalot, M. Komaitis, I. Marc G. Aggelis, *Single cell oil production by Yarrowia lipolytica growing on an industrial derivative of animal fat in batch cultures* Appl Microbiol Biotechnol. 2002 March; 58(3):308-12.). The dominant species of mono-unsaturated fatty acid was oleic acid which increased 8.5 times (g/l) as compared to the control strain (FIG. 8). The ratio of total unsaturated to saturated fatty acid was significantly increased, the total unsaturated fatty acids are not increased over saturated ones, however few of them are as in the case of c18.1 (see FIGS. 7 and 8). The sugar to oil conversion efficiency of the mutant strain was determined to be 0.28 g/g, approaching near theoretical values when taking into consideration the sugar utilized for biomass production.

Figure 9:
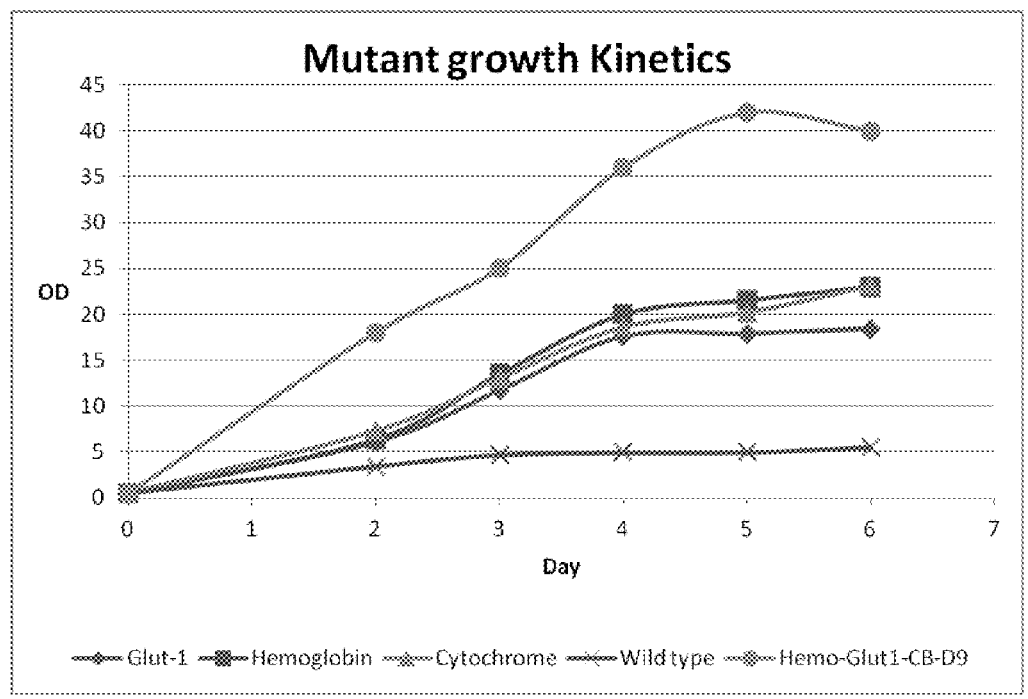
FIG. 9: Growth kinetics of different mutant *Y. lipolytica* strains compared to wild type *Y. lipolytica*. CB: cytochrome B overexpressor. D9: SCD overexpressor.
Figure 10:
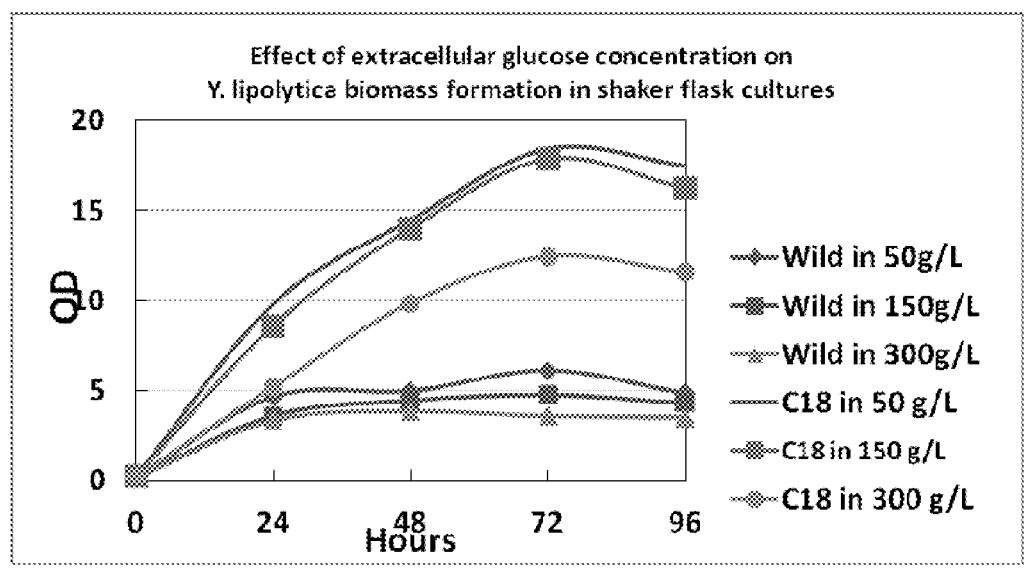
FIG. 10: Growth kinetics of different mutant *Y. lipolytica* strains compared to wild type *Y. lipolytica* at different glucose levels. Wild: wild-type *Y. lipolytica*; C18: mutant *Y. lipolytica* overexpressing Δ9-desaturase (SCD).

A remarkable and unexpected 32-fold growth advantage was observed between the engineered and wild type strain (FIG. 9). The growth characteristic of the mutant strain remains the same at sugar concentrations that were osmotic-lethal to wild type strain (FIG. 10). The higher sugar tolerance is particularly important for high gravity fermentation commonly employed in industrial biofuel production. Previously, an inverse correlation was observed between higher biomass production and lipid accumulation in *Yarrowia lipolytica* culture (Papanikolaou S, Chevalot I, Komaitis M, Marc I, Aggelis G. *Single cell oil production by Yarrowia lipolytica growing on an industrial derivative of animal fat in batch cultures.* Appl Microbiol Biotechnol. 2002 March; 58(3):308-12.). Therefore, the link between higher biomass production and excess lipid accumulation in our engineered strain was unexpected. Since fat storage is primarily used for membrane synthesis and budding activities (FEBS J. 2008 November; 275(22):5552-63), one possibility for the cells in log phase is to re-direct the excess lipid flux towards membrane synthesis via activation of cell division pathway and/or secretion of lipid to extra-cellular medium. This would compensate for excess lipid production early on followed by intracellular accumulation of lipids upon entry to stationary phase of cell cycle. Indeed, the higher biomass production was coupled to secretion of lipid during early growth phase.

Figure 11:
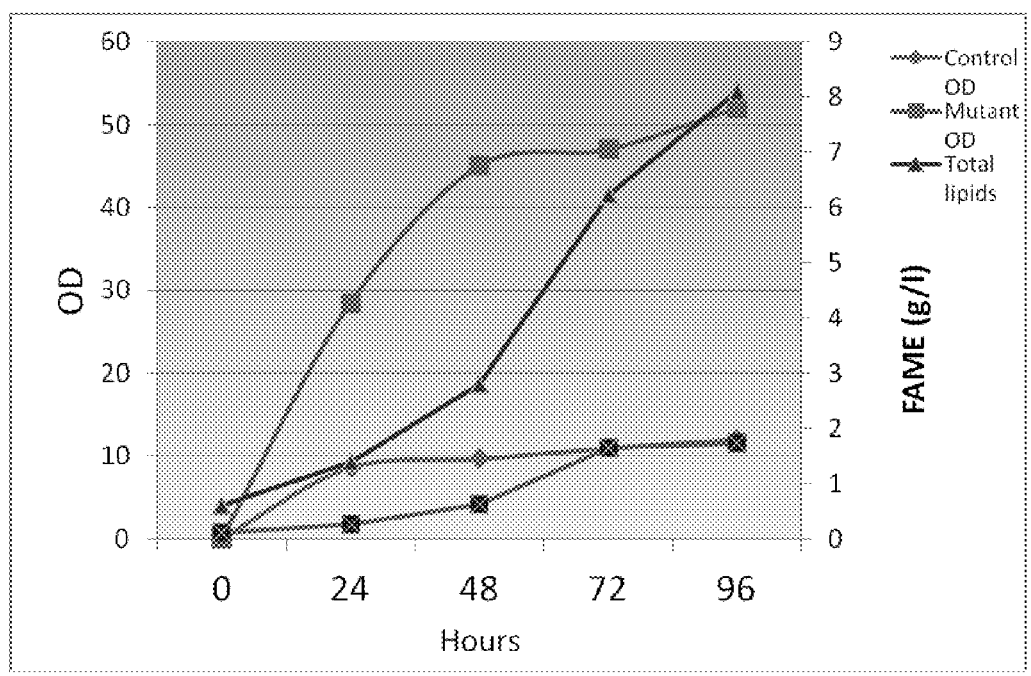
FIG. 11: Growth and lipid production kinetics of mutant (overexpressing 49-desaturase (SCD)) and wild type *Y. lipolytica*.

FIG. 11 shows the growth and lipid production kinetics of mutant and wild type *Y. lipolytica*. Not only does the mutant strain exhibit a strong growth advantage, but it also produces a significantly higher amount of fatty acids as compared to the wild type (control) strain.

Taken together, these results demonstrate efficient metabolic engineering of oleaginous yeast to exhibit highly desirable multiple phenotypes on glucose as a sole carbon source.

Example 5

The regulatory mechanism of SCD underlying the diverse phenotypic traits of the mutant strain was probed. Given the low sequence identity of *Yarrowia lipolytica* desaturase gene to similar functional genes in the nematode *Caenorhabditis elegans* and mouse, the cloned cross-species SCD for fatty acid specificity in *Yarrowia lipolytica* was tested. The SCD in *C. elegans* and mouse has similar specificity toward stearic acid, showed higher biomass production, similar to mutants over-expressing native *Yarrowia* gene. The confocal imaging confirmed excess oil accumulation during stationary growth phase. These results suggest that desaturase activity towards oleic acid synthesis is linked to over-accumulation of TAG. Since SCD in baker's yeast is known to be regulated at the transcriptional and post-transcriptional level (see Tabor D E, Kim J B, Spiegelman B M, Edwards P A, *Identification of conserved cis-elements and transcription factors required for sterol-regulated transcription of stearoyl-CoA desaturase.* J Biol. Chem. 1999 Jul. 16; 274(29):20603-10; Shimano H, *Sterol regulatory element-binding protein family as global regulators of lipid synthetic genes in energy metabolism.* Vitam Horm. 2002; 65:167-94), the feedback inhibition of oleic acid on the desaturase gene was investigated as a possible regulatory niche. We stably integrated a single copy of a native desaturase gene with a 1 kb upstream sequence including the promoter region. The mutant strain accumulated excessive oil and had growth advantage and sugar tolerance as with the earlier mutant. This shows that, unlike in baker's yeast, the oil accumulation is not modulated with promoter sequences driving desaturase expression. This means the negative regulation of desaturase gene in *Yarrowia* is transcriptional independent and possibly occurs at the metabolite level. This data provide the first mechanistic insight of oil regulation via over-riding the inhibitory effects of oleic acid in the oleaginous yeast.

Example 6

Figure 13:
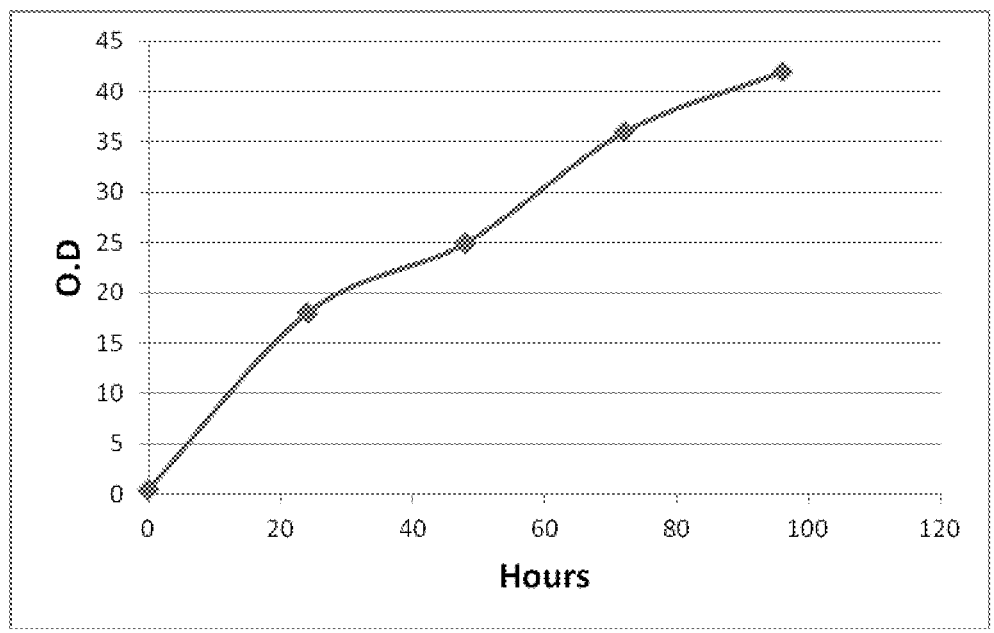
FIG. 13: Growth of engineered microbe on algal biomass. Dried algae was obtained and autoclaved to break cells and gelatinize starches. The autoclaved cells were enzymatically treated with alpha-amylase to release glucose. The resulting media was inoculated with our mutant yeast cells containing Δ9-desaturase and Cytochrome, Glut1, and hemoglobin. The chart shows robust growth of *Yarrowia* mutant in fermentation media without any additive. The cells obtained OD 43 in 4-5 days. This shows there is no inhibition on growth of mutant yeast.
Figure 14:
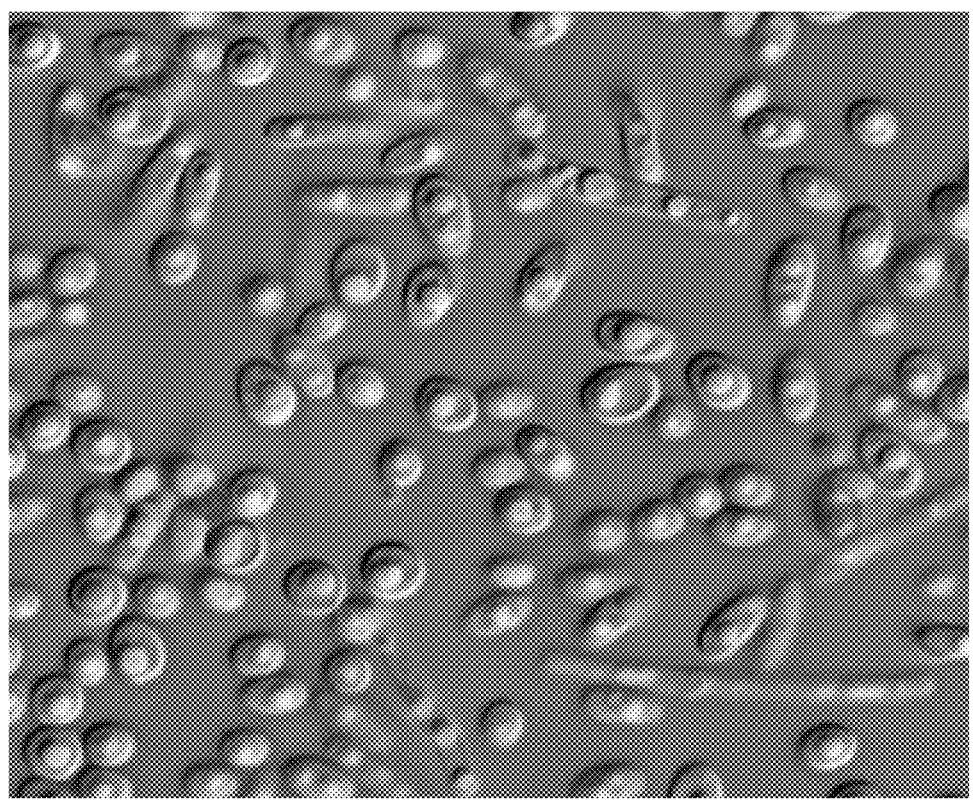
FIG. 14: Microscopy of the yeast cells grown in algae hydrolysates. Cells were grown in the conditions described in FIG. 13. Cells were harvested and stained with Nile Red to identify oil. The droplets inside the yeast cells represents oil.
Figure 15:
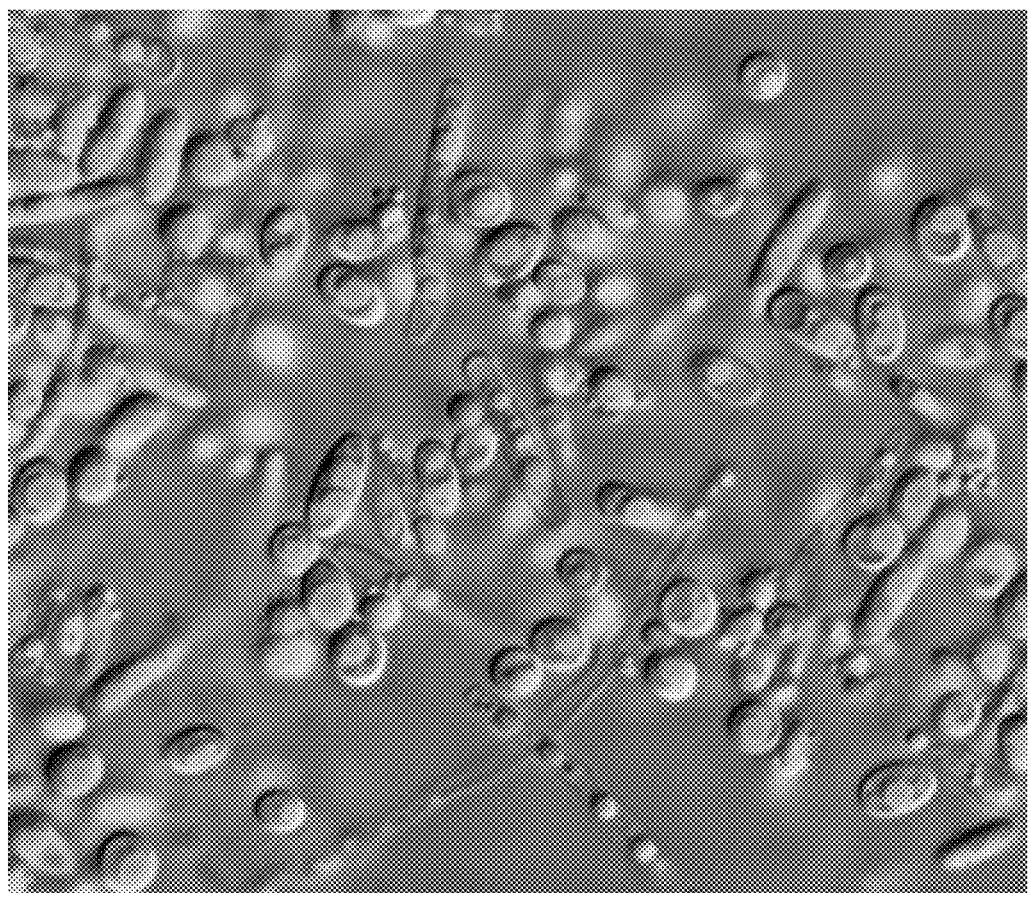
FIG. 15: Microscopy of the yeast cells grown in crude glycerol. Cells were harvested and stained with Nile Red to identify oil. The droplets inside the yeast cells represent oil.

Engineered microbes provided herein can be grown on various substrates. FIG. 13 shows robust growth of a mutant *Y. lipolytica* strain on algal biomass as the carbohydrate source. FIG. 14 shows oil accumulation in engineered microbial cells grown on algal biomass. FIG. 15 shows oil accumulation in engineered cells grown on crude glycerol.

Example 7

Delta-12 desaturase is responsible for converting oleic acid containing lipids to higher chain lipids. For the purpose of producing biofuels, C18 chain fatty acids such as stearic and oleic acids are preferred in view of the cold flow properties of diesel fuel. It is therefore desirable, in some embodiments, to block or inhibit the conversion of C18 fatty acids to longer chain fatty acids.

Figure 16:
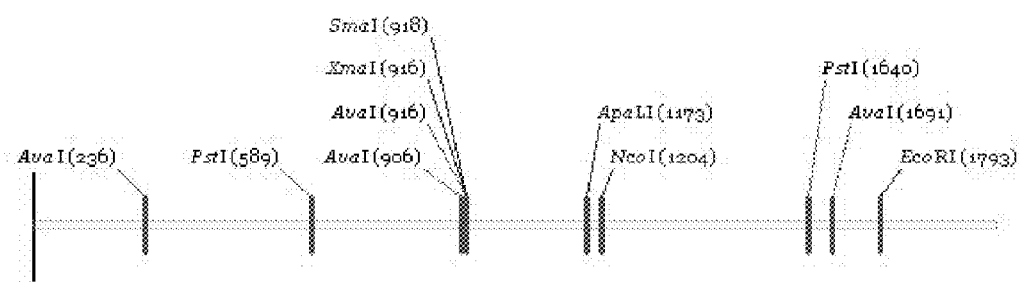
FIG. 16: Schematic structure of a delta-12 desaturase knockout construct containing delta-12 desaturase gene flanking regions and antibiotic resistance sequence, that is used to generate delta-12 desaturase knockout strains.

This can be achieved by inhibiting or blocking the expression of the wild type delta-12 desaturase gene in the host microbe, for example, a microbe overexpressing a Δ9 desaturase (SCD). To this end, a nucleic acid construct was generated to knock out wild type delta-12 desaturase in *Yarrowia lipolytica*. A schematic structure of the knockout construct is shown in FIG. 16. The vector comprises genomic sequences of the delta-12 desaturase gene flanking a phleomycin (e.g., Zeocin™) resistance gene. The sequence of the construct is shown below.

```
delta-12 desaturase Knockout vector sequence:
                               (SEQ ID NO: 28)
CCAACAGACCGACCATAGAAATGGATTCGACCACGCAGACCAACACCGGC

ACCGGCAAGGTGGCCGTGCAGCCCCCCACGGCCTTCATTAAGCCCATTGA

GAAGGTGTCCGAGCCCGTCTACGACACCTTTGGCAACGAGTTCACTCCTC

CAGACTACTCTATCAAGGATATTCTGGATGCCATTCCCCAGGAGTGCTAC

AAGCGGTCCTACGTTAAGTCCTACTCGTACGTGGCCCGAGACTGCTTCTT

TATCGCCGTTTTTGCCTACATGGCCTACGCGTACCTGCCTCTTATTCCCT

CGGCTTCCGGCCGAGCTGTGGCCTGGGCCATGTACTCCATTGTCCAGGGT

CTGTTTGGCACCGGTCTGTGGGTTCTTGCCCACGAGTGTGGCCACTCTGC

TTTCTCCGACTCTAACACCGAGAGACCGGGTTGGCGGCGCATTTGTGTCC

CAAAAAACAGCCCCAATTGCCCCAATTGACCCCAAATTGACCCAGTAGCG

GGCCCAACCCCGGCGAGAGCCCCCTTCACCCCACATATCAAACCTCCCCC

GGTTCCCACACTTGCCGTTAAGGGCGTAGGGTACTGCAGTCTGGAATCTA

CGCTTGTTCAGACTTTGTACTAGTTTCTTTGTCTGGCCATCCGGGTAACC

CATGCCGGACGCAAAATAGACTACTGAAAATTTTTTGCTTTGTGGTTGG

GACTTTAGCCAAGGGTATAAAAGACCACCGTCCCCGAATTACCTTTCCTC
```

```
                               -continued
TTCTTTTCTCTCTCTCCTTGTCAACTCACACCCGAAATCGTTAAGCATTT

CCTTCTGAGTATAAGAATCATTCAAAATGGCCAAGTTGACCAGTGCCGTT

CCGGTGCTCACCGCGCGCGACGTCGCCGGAGCGGTCGAGTTCTGGACCGA

CCGGCTCGGGTTCTCCCGGGACTTCGTGGAGGACGACTTCGCCGGTGTGG

TCCGGGACGACGTGACCCTGTTCATCAGCGCGGTCCAGGACCAGGTGGTG

CCGGACAACACCCTGGCCTGGGTGTGGGTGCGCGGCCTGGACGAGCTGTA

CGCCGAGTGGTCGGAGGTCGTGTCCACGAACTTCCGGGACGCCTCCGGGC

CGGCCATGACCGAGATCGGCGAGCAGCCGTGGGGGCGGGAGTTCGCCCTG

CGCGACCCGGCCGGCAACTGCGTGCACTTCGTGGCCGAGGAGCAGGACTG

ATCCATGGCCTGTCCCCACGTTGCCGGTCTTGCCTCCTACTACCTGTCCA

TCAATGACGAGGTTCTCACCCCTGCCCAGGTCGAGGCTCTTATTACTGAG

TCCAACACCGGTGTTCTTCCCACCACCAACCTCAAGGGCTCTCCCAACGC

TGTTGCCTACAACGGTGTTGGCATTTAGGCAATTAACAGATAGTTTGCCG

GTGATAATTCTCTTAACCTCCCACACTCCTTTGACATAACGATTTATGTA

ACGAAACTGAAATTTGACCAGATATTGTTGTAAATAGAAAATCTGGCTTG

TAGGTGGCAAAATGCGGCGTCTTTGTTCATCAATTCCCTCTGTGACTACT

CGTCATCCCTTTATGTTCGACTGTCGTATTTCTTATTTTCCATACATATG

CAAGTGAGATGCCCGTGTCCTGGCCATCACCTACCTGCAGCACACCGACC

CCACTCTGCCCCACTACCACGCCGACCAGTGGAACTTCACCCGAGGAGCC

GCCGCCACCATCGACCGAGAGTTTGGCTTCATCGGCTCCTTCTGCTTCCA

TGACATCATCGAGACCCACGTTCTGCACCACTACGTGTCTCGAATTCCCT

TCTACAACGCCCGAATCGCCACTGAGAAGATCAAGAAGGTCATGGGCAAG

CACTACCGACACGACGACACCAACTTCATCAAGTCTCTTTACACTGTCGC

CCGAACCTGCCAGTTTGTTGAAGGTAAGGAAGGCATTCAGATGTTTAGAA

ACGTCAATGGAGTCGGAGTTGCTCCTGACGGCCTGCCTTCTAAAAAGTAG

AGCTAGAAATGTTATTTGATTGTGTTTTAACTGAACAGCA
```

A series of genes including Δ9 desaturase, Glut1, hemoglobin and cytochrome b5, were overexpressed in delta-12 desaturase knockout cells of *Yarrowia lipolytica* to further increase the sugar flux into the cell and increase oil content. A marked increase in the size of the cells was observed with up to 95% by volume of cells filled with oil.

Example 8

Figure 17:
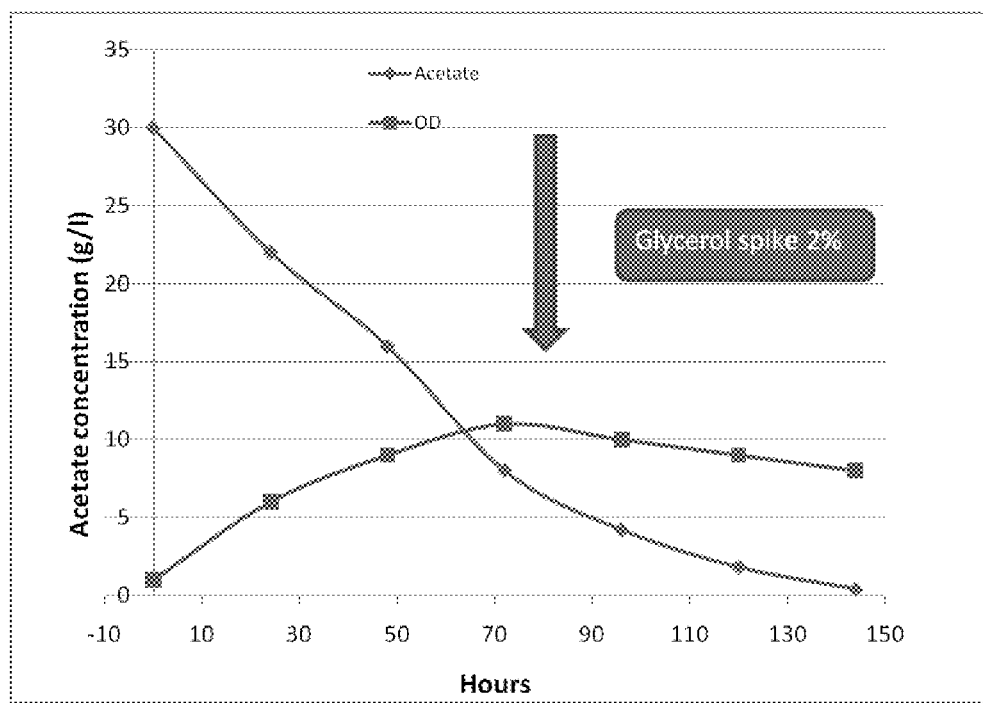
FIG. 17: Growth of engineered microbes on 3% acetate with addition of 2% glycerol at 84 hrs.

*Yarrowia lipolytica* overexpressing SCD was grown in 3% acetic acid solution for 148 hours (FIG. 17). Cell cultures were spiked with 2% glycerol at about 84 hours to provide glycerol to drive fatty acid production. The latter is a bottleneck in the production of oil using acetate as feedstock. A marked increase in oil production was observed by confocal laser microscopy using a glycerol spike on acetate media showing a new process to efficiently produce oils with better economics.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

REFERENCES

1. J. Sambrook and D. Russell, Molecular Cloning: A Laboratory Manual, Cold Spring Harbor Laboratory Press; 3rd edition (Jan. 15, 2001), 978-0879695774
2. David C. Amberg, Daniel J. Burke; and Jeffrey N. Strathern, Methods in Yeast Genetics: A Cold Spring Harbor Laboratory Course Manual, Cold Spring Harbor Laboratory Press (April 2005), 978-0879697280
3. John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004), 978-0121827786
4. Christine Guthrie and Gerald R. Fink, Guide to Yeast Genetics and Molecular and Cell Biology, Part B, Volume 350 (Methods in Enzymology, Vol 350), Academic Press; 1st edition (Jul. 2, 2002), 978-0123106711
5. Christine Guthrie and Gerald R. Fink, Guide to Yeast Genetics and Molecular and Cell Biology, Part C, Volume 351, Academic Press; 1st edition (Jul. 9, 2002), 978-0123106728
6. Gregory N. Stephanopoulos, Aristos A. Aristidou and Jens Nielsen, Metabolic Engineering: Principles and Methodologies, Academic Press; 1 edition (Oct. 16, 1998), 978-0126662603
7. Christina Smolke, The Metabolic Pathway Engineering Handbook: Fundamentals, CRC Press; 1 edition (Jul. 28, 2009), 978-1439802960

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

The invention claimed is:

1. An isolated oleaginous cell, comprising a recombinant stearoyl-CoA desaturase (SCD) gene that increases expression of SCD, and/or at least one additional copy of a SCD gene, relative to an unmodified cell of the same type, that increases expression of SCD, and a genetic modification that decreases expression of delta-12 desaturase.

2. The isolated oleaginous cell of claim 1, wherein the increased or decreased expression of the gene product confers a beneficial phenotype for the conversion of a carbohydrate source to a fatty acid, fatty acid derivative and/or triacylglycerol (TAG) to the cell.

3. The isolated oleaginous cell of claim 2, wherein the beneficial phenotype relative to an unmodified cell of the same type is a modified fatty acid profile, a modified TAG profile, an increased fatty acid and/or triacylglycerol synthesis rate, an increased conversion yield from a carbohydrate source to a fatty acid, fatty acid derivative and/or triacylglycerol (TAG), an increased triacylglycerol accumulation in the cell, and an increased tolerance of osmotic stress, an increased proliferation rate, an increased cell volume, and/or an increased tolerance of a substance at a concentration lethal to and/or inhibiting proliferation of an unmodified cell of the same type.

4. The isolated oleaginous cell of claim 3, wherein the cell is viable under conditions of osmotic stress lethal to unmodified cells of the same type.

5. The isolated oleaginous cell of claim 3, wherein the cell proliferation rate is at least 5-fold increased as compared to unmodified cells of the same cell type.

6. The isolated oleaginous cell of claim 3, wherein the cell tolerates a substance at a concentration lethal to and/or inhibiting proliferation of unmodified cells of the same cell type.

7. The isolated oleaginous cell of claim 3, wherein the synthesis rate of a fatty acid or a TAG of the cell is at least 5-fold increased as compared to unmodified cells of the same cell type.

8. The isolated oleaginous cell of claim 1, wherein said cell comprises a recombinant stearoyl-CoA desaturase (SCD) gene that increases expression of SCD.

9. The isolated oleaginous cell of claim 1, wherein said cell comprises at least one additional copy of a stearoyl-CoA desaturase (SCD) gene, relative to an unmodified cell of the same type, that increases expression of SCD.

10. The isolated oleaginous cell of claim 1, wherein said cell is selected from the group consisting of *Yarrowia lipolytica, Hansenula polymorpha, Pichia pastoris, S. bayanus, K. lactis, Waltomyces lipofer, Mortierella alpine, Mortierella isabellina, Mucor rouxii, Trichosporon cutaneu, Rhodotorula glutinis, Saccharomyces diastasicus, Schwanniomyces occidentalis, Pichia stipitis, Schizosaccharomyces pombe, Bacillus subtilis, Salmonella, Escherichia coli, Vibrio cholerae, Streptomyces, Pseudomonas fluorescens, Pseudomonas putida, Pseudomonas* sp, *Rhodococcus* sp, *Alcaligenes* sp, *Aspergillus shirousamii, Aspergillus niger, Trichoderma reesei, Neochloris oleoabundans, Scenedesmus obliquus, Nannochloropsis* sp, *Dunaliella tertiolecta, Chlorella vulgaris, Chlorella emersonii*, and *Spirulina maxima.*

11. The isolated oleaginous cell of claim 10, wherein said cell is selected from the group consisting of *Yarrowia lipolytica, Hansenula polymorpha, Pichia pastoris, S. bayanus, K. lactis, Waltomyces lipofer, Mortierella alpine, Mortierella isabellina, Mucor rouxii, Trichosporon cutaneu, Rhodotorula glutinis, Saccharomyces diastasicus, Schwanniomyces occidentalis, Pichia stipitis*, and *Schizosaccharomyces pombe.*

12. The isolated oleaginous cell of claim 11, wherein said cell is *Yarrowia lipolytica.*

13. The isolated oleaginous cell of claim 10, wherein said cell is selected from the group consisting of *Bacillus subtilis, Salmonella, Escherichia coli, Vibrio cholerae, Streptomyces, Pseudomonas fluorescens, Pseudomonas putida, Pseudomonas* sp, *Rhodococcus* sp, and *Alcaligenes* sp.

14. The isolated oleaginous cell of claim 10, wherein said cell is selected from the group consisting of *Aspergillus shirousamii, Aspergillus niger*, and *Trichoderma reesei.*

15. The isolated oleaginous cell of claim 10, wherein said cell is selected from the group consisting of *Neochloris oleoabundans, Scenedesmus obliquus, Nannochloropsis* sp, *Dunaliella tertiolecta, Chlorella vulgaris, Chlorella emersonii*, and *Spirulina maxima.*

16. A culture, comprising the oleaginous cell of claim 1.

17. The culture of claim 16, further comprising a carbohydrate source.

18. The culture of claim 16, further comprising acetate.

19. A method, comprising
contacting a carbohydrate source with the isolated oleaginous cell of claim 1
and
incubating the carbohydrate source contacted with the cell under conditions suitable for at least partial conversion of the carbohydrate source into a fatty acid or a triacylglycerol by the cell.

20. The method of claim 19, wherein the carbohydrate source contacted with the oleaginous cell comprises a substance at a concentration lethal to unmodified cells of the same cell type as the oleaginous cell.

21. The method of claim 20, wherein the substance is the carbohydrate source.

22. The method of claim 21, wherein the carbohydrate source is a fermentable sugar and the concentration of the fermentable sugar is at least 80 g/l after contacting with the oleaginous cell.

* * * * *

SEQUENCE LISTING

<160> NUMBER OF SEQ ID NOS: 28

<210> SEQ ID NO 1
<211> LENGTH: 482
<212> TYPE: PRT
<213> ORGANISM: Yarrowia lipolytica

<400> SEQUENCE: 1

```
Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Phe Gln Glu Gln Ala
        355                 360                 365
```

```
Lys Thr Arg Asp Leu Val Leu Ile Ser Gly Ile Val His Asp Val Ser
    370                 375                 380

Ala Phe Val Glu His His Pro Gly Gly Lys Ala Leu Ile Met Ser Ala
385                 390                 395                 400

Val Gly Lys Asp Gly Thr Ala Val Phe Asn Gly Val Tyr Arg His
                405                 410                 415

Ser Asn Ala Gly His Asn Leu Leu Ala Thr Met Arg Val Ser Val Ile
                420                 425                 430

Arg Gly Gly Met Glu Val Glu Val Trp Lys Thr Ala Gln Asn Glu Lys
            435                 440                 445

Lys Asp Gln Asn Ile Val Ser Asp Glu Ser Gly Asn Arg Ile His Arg
    450                 455                 460

Ala Gly Leu Gln Ala Thr Arg Val Glu Asn Pro Gly Met Ser Gly Met
465                 470                 475                 480

Ala Ala
```

<210> SEQ ID NO 2
<211> LENGTH: 1449
<212> TYPE: DNA
<213> ORGANISM: Yarrowia lipolytica

<400> SEQUENCE: 2

```
atggtgaaaa acgtggacca agtggatctc tcgcaggtcg acaccattgc ctccggccga    60
gatgtcaact acaaggtcaa gtacacctcc ggcgttaaga tgagccaggg cgcctacgac   120
gacaagggcc gccacatttc cgagcagccc ttcacctggg ccaactggca ccagcacatc   180
aactggctca acttcattct ggtgattgcg ctgcctctgt cgtcctttgc tgccgctccc   240
ttcgtctcct tcaactggaa gaccgccgcg tttgctgtcg ctattacat gtgcaccggt   300
ctcggtatca ccgccggcta ccaccgaatg tgggcccatc gagcctacaa ggccgctctg   360
cccgttcgaa tcatccttgc tctgtttgga ggaggagctg tcgagggctc catccgatgg   420
tgggcctcgt ctcaccgagt ccaccaccga tggaccgact ccaacaagga cccttacgac   480
gcccgaaagg gattctggtt ctcccacttt ggctggatgc tgcttgtgcc caaccccaag   540
aacaagggcc gaactgacat ttctgacctc aacaacgact gggttgtccg actccagcac   600
aagtactacg tttacgttct cgtcttcatg gccattgttc tgcccaccct cgtctgtggc   660
tttggctggg gcgactggaa gggaggtctt gtctacgccg gtatcatgcg atacaccttt   720
gtgcagcagg tgactttctg tgtcaactcc cttgcccact ggattggaga gcagcccttc   780
gacgaccgac gaactccccg agaccacgct cttaccgccc tggtcacctt ggagagggc   840
taccacaact ccaccacga gttcccctcg gactaccgaa cgccctcat ctggtaccag   900
tacgacccca ccaagtggct catctggacc ctcaagcagg ttggtctcgc ctgggacctc   960
cagaccttct cccagaacgc catcgagcag ggtctcgtgc agcagcgaca agaagctg  1020
gacaagtggc gaaacaacct caactggggt atccccattg agcagctgcc tgtcattgag  1080
tttgaggagt ccaagagca ggccaagacc cgagatctgg ttctcatttc tggcattgtc  1140
cacgacgtgt ctgcctttgt cgagcaccac cctggtggaa aggccctcat tatgagcgcc  1200
gtcggcaagg acggtaccgc tgtcttcaac ggaggtgtct accgacactc caacgctggc  1260
cacaacctgc ttgccaccat gcgagtttcg gtcattcgag gcggcatgga ggttgaggtg  1320
tggaagactg cccagaacga aaagaaggac cagaacattg tctccgatga gagtggaaac  1380
cgaatccacc gagctggtct ccaggccacc cgggtcgaga ccccggtat gtctggcatg  1440
```

```
gctgcttag                                                           1449

<210> SEQ ID NO 3
<211> LENGTH: 441
<212> TYPE: DNA
<213> ORGANISM: Unknown
<220> FEATURE:
<223> OTHER INFORMATION: Bacterial sequence

<400> SEQUENCE: 3
atgttagacc aacaaaccgt agacaccagc aaagccactg ttcctgtatt gaaagagcat    60
ggcgtgacca ttaccacgac gttttaccaa aatttgtttg ccaaacatcc tgaagtacga   120
cctttgtttg acatgggtcg ccaagcatct ttggaacagc ctaaggcttt ggcgatgacg   180
gttggggcgg cggcacaaaa cattgaaaat ttacctgcaa ttttgcctgc agtacaaaaa   240
attgccgtca aacattgtca agcaggcgtg gcggcacgac attatccgat tgtgggtcaa   300
gaattgttgg gtgcgattaa agaattattg ggtgatgcgg cgaccgatga tattttggat   360
gcgtggggca aggcttatgg cgtgattgcc gatgttttta ttcaagtgga agcggatttg   420
tacgctcaag acgctgaata a                                             441

<210> SEQ ID NO 4
<211> LENGTH: 333
<212> TYPE: DNA
<213> ORGANISM: Yarrowia lipolytica

<400> SEQUENCE: 4
atgatcatca acggcaaggt ctacgacatc tccagcttcg ttgacgagca tcccggtgga    60
gaggaggttc ttcttgatgc cggtggaact gaggccacca acgctttcga cgacgttgga   120
cactctgagg acgcttacgg catccttaac gacctctatg tcgtgaggt tgaccccagc    180
gaggacgtta tccgaaagac tcacactgtc aagacttctt acgaggacgg cgagtctgtt   240
ggtgatgacc acggatcttc ttccatgatc ttcctcattg ttgctgctgc tgttgccgcc   300
gctgctttct tctacctcca gggtcagaaa taa                                333

<210> SEQ ID NO 5
<211> LENGTH: 1479
<212> TYPE: DNA
<213> ORGANISM: Rattus norvegicus

<400> SEQUENCE: 5
atggagccca gcagcaagaa ggtgacgggc cgccttatgt tggccgtggg aggggcagtg    60
ctcggatccc tgcagttcgg ctataacacc ggtgtcatca acgcccccca gaaggtaatt   120
gaggagttct acaatcaaac atggaaccac cgctatggag agtccatccc atccaccaca   180
ctcaccacac tctggtctct ctccgtggcc atcttctctg tcgggggcat gattggttcc   240
ttctctgtgg gcctctttgt taatcgcttt ggcaggcgga actccatgct gatgatgaac   300
ctgttggcct ttgtgtctgc cgtgcttatg ggtttctcca aactgggcaa gtcctttgag   360
atgctgatcc tgggccgctt catcattgga gtgtactgtg gcctgaccac cggctttgtg   420
cccatgtatg tggggaggt gtcacccaca gctcttcgtg gagccctggg cacccctgcac   480
cagctgggca tcgtcgttgg gatccttatt gcccaggtgt tcggcttaga ctccatcatg   540
ggcaatgcag acttgtggcc tctactgctc agtgtcatct tcatcccagc cctgctacag   600
tgtatcctgt tgcccttctg ccctgagagc cccgcttcc tgctcatcaa tcgtaacgag   660
gagaaccggg ccaagagtgt gctgaaaaag cttcgaggga cagccgatgt gacccgagac   720
```

```
ctgcaggaga tgaaagaaga gggtcggcag atgatgcggg agaagaaggt caccatcttg      780
gagctgttcc gctcacccgc ctaccgccag cccatcctca tcgccgtggt gctgcagctg      840
tcccagcagc tgtcgggcat caatgctgtg ttctactact caacgagcat cttcgagaag      900
gcaggtgtgc agcagcctgt gtatgccacc atcggctcgg gtatcgtcaa cacggccttc      960
actgtggtgt cgctgttcgt cgtggagcga gctggccgtc ggaccctgca cctcattggt     1020
ctggctggca tggcgggctg tgctgtgctc atgaccatcg ccctggccct gctggagcag     1080
ctgccctgga tgtcctatct gagtatcgtg gccatctttg ctttgtggc cttctttgaa      1140 gtaggccctg gtcctattcc atggttcatt gtggccgagc tgttcagcca ggggcccga      1200 cctgctgctg ttgctgtggc tggcttctct aactggacct caaacttcat cgtgggcatg     1260
tgcttccaat atgtggagca actgtgtggc ccctacgtct tcatcatctt cacggtgctg     1320
ctggtactct tcttcatctt cacctacttc aaagttcctg agaccaaagg ccggaccttc     1380
gatgagatcg cttccggctt ccggcagggg ggtgccagcc agagcgacaa gacacctgag     1440
gagctcttcc accctctggg ggctgactcc caagtgtga                            1479

<210> SEQ ID NO 6
<211> LENGTH: 1890
<212> TYPE: DNA
<213> ORGANISM: Yarrowia lipolytica

<400> SEQUENCE: 6
atgttacgac tacgaaccat gcgacccaca cagaccagcg tcagggcggc gcttgggccc       60
accgccgcgg cccgaaacat gtcctcctcc agcccctcca gcttcgaata ctcgtcctac      120
gtcaagggca cgcggaaat cggccaccga aggcgccca caacccgtct gtcggttgag       180
ggccccatct acgtgggctt cgacggcatt cgtcttctca acctgccgca tctcaacaag      240
ggctcgggat tccccctcaa cgagcgacgg gaattcagac tcagtggtct tctgccctct      300
gccgaagcca ccctggagga acaggtcgac cgagcatacc aacaattcaa aaagtgtggc      360
actcccttag ccaaaaacgg gttctgcacc tcgctcaagt tccaaaacga ggtgctctac      420
tacgccctgc tgctcaagca cgttaaggag gtcttcccca tcatctatac accgactcag      480
ggagaagcca ttgaacagta ctcgcggctg ttccggcggc ccgaaggctg cttcctcgac      540
atcaccagtc cctacgacgt ggaggagcgt ctggagcgt ttggagacca tgacgacatt       600
gactacattg tcgtgactga ctccgagggt attctcggaa ttggagacca aggagtgggc      660
ggtattggta tttccatcgc caagctggct ctcatgactc tatgtgctgg agtcaacccc      720
tcacgagtca ttcctgtggt tctggatacg ggaaccaaca accaggagct gctgcacgac      780
cccctgtatc tcggccgacg aatgcccga gtgcgaggaa agcagtacga cgacttcatc       840
gacaactttg tgcagtctgc ccgaaggctg tatcccaagg cggtgatcca tttcgaggac      900
tttgggctcg ctaacgcaca caagatcctc gacaagtatc gaccggagat ccctgcttc       960 aacgacgaca tccagggcac tggagccgtc actttggcct ccatcacggc cgctctcaag     1020
gtgctgggca aaaatatcac agatactcga attctcgtgt acggagctgg ttcggccggc     1080
atgggtattg ctgaacaggt ctatgataac ctggttgccc agggtctcga cgacaagact     1140
gcgcgacaaa acatctttct catggaccga ccgggtctac tgaccaccgc acttaccgac     1200
gagcagatga gcgacgtgca gaagccgttt gccaaggaca aggccaatta cgagggagtg     1260
gacaccaaga ctctggagca cgtggttgct gccgtcaagc cccatattct cattggatgt     1320
```

| | |
|---|---|
| tccactcagc ccggcgcctt taacgagaag gtcgtcaagg agatgctcaa acacacccct | 1380 |
| cgacccatca ttctccctct ttccaacccc acacgtcttc atgaggctgt ccctgcagat | 1440 |
| ctgtacaagt ggaccgacgg caaggctctg gttgccaccg gctcgccctt tgacccagtc | 1500 |
| aacggcaagg agacgtctga gaacaataac tgctttgttt tccccggaat cgggctggga | 1560 |
| gccattctgt ctcgatcaaa gctcatcacc aacaccatga ttgctgctgc catcgagtgc | 1620 |
| ctcgccgaac aggcccccat tctcaagaac acgacgagg gagtacttcc cgacgtagct | 1680 |
| ctcatccaga tcatttcggc ccgggtggcc actgccgtgg ttcttcaggc caaggctgag | 1740 |
| ggcctagcca ctgtcgagga agagctcaag cccggcacca aggaacatgt gcagattccc | 1800 |
| gacaactttg acgagtgtct cgcctgggtc gagactcaga tgtggcggcc cgtctaccgg | 1860 |
| cctctcatcc atgtgcggga ttacgactag | 1890 |

<210> SEQ ID NO 7
<211> LENGTH: 1449
<212> TYPE: DNA
<213> ORGANISM: Yarrowia lipolytica

<400> SEQUENCE: 7

| | |
|---|---|
| atggtgaaaa acgtggacca agtggatctc tcgcaggtcg acaccattgc ctccggccga | 60 |
| gatgtcaact acaaggtcaa gtacacctcc ggcgttaaga tgagccaggg cgcctacgac | 120 |
| gacaagggcc gccacatttc cgagcagccc ttcacctggg ccaactggca ccagcacatc | 180 |
| aactggctca acttcattct ggtgattgcg ctgcctctgt cgtcctttgc tgccgctccc | 240 |
| ttcgtctcct tcaactggaa gaccgccgcg tttgctgtcg ctattacat gtgcaccggt | 300 |
| ctcggtatca ccgccggcta ccaccgaatg tgggcccatc gagcctacaa ggccgctctg | 360 |
| cccgttcgaa tcatccttgc tctgtttgga ggaggagctg tcgagggctc catccgatgg | 420 |
| tgggcctcgt ctcaccgagt ccaccaccga tggaccgact ccaacaagga cccttacgac | 480 |
| gcccgaaagg gattctggtt ctcccacttt ggctggatgc tgcttgtgcc caaccccaag | 540 |
| aacaagggcc gaactgacat tctgacctc aacaacgact gggttgtccg actccagcac | 600 |
| aagtactacg tttacgttct cgtcttcatg gccattgttc tgcccaccct cgtctgtggc | 660 |
| tttggctggg gcgactggaa gggaggtctt gtctacgccg gtatcatgcg atacaccttt | 720 |
| gtgcagcagg tgactttctg tgtcaactcc cttgcccact ggattggaga gcagcccttc | 780 |
| gacgaccgac gaactccccg agaccacgct cttaccgccc tggtcacctt ggagagggc | 840 |
| taccacaact tccaccacga gttccccctcg gactaccgaa acgccctcat ctggtaccag | 900 |
| tacgacccca ccaagtggct catctggacc ctcaagcagg ttggtctcgc ctgggacctc | 960 |
| cagaccttct cccagaacgc catcgagcag ggtctcgtgc agcagcgaca gaagaagctg | 1020 |
| gacaagtggc gaaacaacct caactggggt atccccattg agcagctgcc tgtcattgag | 1080 |
| tttgaggagt tccaagagca ggccaagacc cgagatctgg ttctcatttc tggcattgtc | 1140 |
| cacgacgtgt ctgcctttgt cgagcaccac cctggtggaa aggccctcat tatgagcgcc | 1200 |
| gtcggcaagg acggtaccgc tgtcttcaac ggaggtgtct accgacactc caacgctggc | 1260 |
| cacaacctgc ttgccaccat gcgagtttcg gtcattcgag gcggcatgga ggttgaggtg | 1320 |
| tggaagactg cccagaacga aaagaaggac cagaacattg tctccgatga gagtggaaac | 1380 |
| cgaatccacc gagctggtct ccaggccacc cgggtcgaga accccggtat gtctggcatg | 1440 |
| gctgcttag | 1449 |

<210> SEQ ID NO 8
<211> LENGTH: 1449
<212> TYPE: DNA
<213> ORGANISM: Homo sapiens

<400> SEQUENCE: 8

```
atggtgaaaa acgtggacca agtggatctc tcgcaggtcg acaccattgc ctccggccga      60
gatgtcaact acaaggtcaa gtacacctcc ggcgttaaga tgagccaggg cgcctacgac     120
gacaagggcc gccacatttc cgagcagccc ttcacctggg ccaactggca ccagcacatc     180
aactggctca acttcattct ggtgattgcg ctgcctctgt cgtcctttgc tgccgctccc     240
ttcgtctcct tcaactggaa gaccgccgcg tttgctgtcg ctattacat gtgcaccggt      300
ctcggtatca ccgccggcta ccaccgaatg tgggcccatc gagcctacaa ggccgctctg     360
cccgttcgaa tcatccttgc tctgtttgga ggaggagctg tcgagggctc catccgatgg     420
tgggcctcgt ctcaccgagt ccaccaccga tggaccgact ccaacaagga cccttacgac     480
gcccgaaagg gattctggtt ctcccacttt ggctggatgc tgcttgtgcc caaccccaag     540
aacaagggcc gaactgacat tctgacctc aacaacgact gggttgtccg actccagcac      600
aagtactacg tttacgttct cgtcttcatg gccattgttc tgcccaccct cgtctgtggc     660
tttggctggg gcgactggaa gggaggtctt gtctacgccg gtatcatgcg ataccctt      720
gtgcagcagg tgactttctg tgtcaactcc cttgcccact ggattggaga gcagcccttc     780
gacgaccgac gaactcccg agaccacgct cttaccgccc tggtcacctt ggagagggc      840
taccacaact ccaccacga gttccccctcg gactaccgaa acgccctcat ctggtaccag     900
tacgacccca ccaagtggct catctggacc ctcaagcagg ttggtctcgc ctgggacctc     960
cagaccttct cccagaacgc catcgagcag ggtctcgtgc agcagcgaca gaagaagctg    1020
gacaagtggc gaaacaacct caactggggt atccccattg agcagctgcc tgtcattgag    1080
tttgaggagt tccaagagca ggccaagacc cgagatctgg ttctcatttc tggcattgtc    1140
cacgacgtgt ctgcctttgt cgagcaccac cctggtggaa aggccctcat tatgagcgcc    1200
gtcggcaagg acgtaccgc tgtcttcaac ggaggtgtct accgacactc caacgctggc     1260
cacaacctgc ttgccaccat gcgagtttcg gtcattcgag gcggcatgga ggttgaggtg    1320
tggaagactg cccagaacga aaagaaggac cagaacattg tctccgatga gagtggaaac    1380
cgaatccacc gagctggtct ccaggccacc cgggtcgaga ccccggtat gtctggcatg    1440
gctgcttag                                                           1449
```

<210> SEQ ID NO 9
<211> LENGTH: 6702
<212> TYPE: DNA
<213> ORGANISM: Saccharomyces cerevisiae

<400> SEQUENCE: 9

```
ttatttcaaa gtcttcaaca attttttctt atcatcggta gataacatct tgataacttc      60
agataatcca tcaatagcat tgtcatggtc gcttctgatc ttttttagcta agtcttgagc    120
gaatgactct aatttcaaac cctttagttt atcgtccaaa gttttgtagt tttcttcaat    180
ccatgttgcg acttgcctat catcttcatg gtccactgaa gcagggtacc acgatctaat    240
tcttgcgatc ttttctaatc ttgatgcttc gcctacctga tggctcaacc ttttaatcaa    300
atattcttcg ttcaatcttc ttctcaatct ccagaagaag aaacgacgtg cctcggtcca    360
ttccagttcc ttagaaataa caccccttggc caccatacgt gaagacctat cgtgcaaatc    420
```

-continued

```
agcaaattga agactgattt gtccgtaaat tggcaatagt tctctctcac gatcagctaa      480
ttgcttggat atttgctgat gtacttctgg agccaaactc ttgttggata attgagatct      540
caattctctg tacttgtcat ccaatctgtt catggtgtcc agcaattttt ctctacggaa      600
cttgatacca accataccct gtggttccaa aacaccagct ctagcgttga cgtcggcata      660
catttccatt tggtcagcgt tgatagttgg atcgacaaca acccatgaac cacctcttag      720
ttcaccggta ggtgggatat agataataat tggttgtttg taatccacca atgcgtcaac      780
aataaacgaa ccatacttca agacttcgtt gaacatatca cgttgaccac cagagaaacc      840
tctccagttg gccaaaatca tcattggcaa ttgttcaccg ttgttaaagt cattgatagc      900
ttgagcagtc ttgaaggcgg agtttggatg ccaaacttga ccaggttctt gaattaatgt      960
ttcagcacta tttggattag ctggatcagc aggaatcaag ttctcgacag ttcttgtttc     1020
aacaccaata acacccagtg aataccacc aagacgggct ctaccaacga caacacctt      1080 ggcccatcct gacaaagttt caaagaaaga cccttatca aacaaaccat attcaaatcc     1140
actttcagtc tcacgacctt caatcatcca tcttacatcg taagtttcat cattagttgg     1200
agtgaaatca actggtctat cccatgtgtc tttagtttcc aagataggaa ctggcatatt     1260
acgcttggct ggaacataag acatccattc aacaatcttc tctacaccag ctaaatcgtc     1320
aacagcagtc aaatgtgaaa caccgttgtt atacatgatt tgagtaccac ccaattgtaa     1380
gttagaagta taaacttctc tacccagcat tttgttgatt gcaggagcac cagttaaaat     1440
aattggctgg ccttcgacct gaatagctct ttgacccaaa cgaaccaaat aagcaccgat     1500
accgacggat ctacaagtga ctaaggtgat agtgaagata tcgtggtaag cccttgacgt     1560
tgcaccagca attaaaccag atccacgtag acattcgaca cctaacccat cttcagaacc     1620
aataattgtc ttgatgacaa atctttcttc accgtttata acagtacgtt cagtgagaac     1680
agaattttct ttgtcaaatt tctttaaagt tccatacct tcacttgtta agtataagta     1740
ttggaagccc ttgtccggat tggcagcatc attccatgca acttgaaata gtggaacaat     1800
ctcttcagcc ataccaattc tggcacctga gtttgcagcc aagtaaattc ttgggatacc     1860
acgctttcta gcatattcag taaccttatt gaagaattcg tcttcttgtg gaccaaagga     1920
accgatcttg aatgtgatat cgttagcaac aacaacaaat tgacggcctc ttggatattc     1980
aggagtcttt acagtaatct taaaggcaac cataccaata gcgttggcac caggttctct     2040
ttccacctca gttaattcgc cgttttcatc ttcaatcaac tcgttggaaa taagaaaatc     2100
atctgttaac ttaacatctg cagagaaatt tttccattgg gatgacgatg cttggcggaa     2160
taattctggg aagtcataga catatgtggt acccatcaag tgtgccttat aacgttttgg     2220
ttgcaaccat tccttaacag ggtaaggagt agcaataggc cttaaatgca tggatccagg     2280
tttacccaaa gacttaaata cccattcacc ttttgcgttc ttgacttcgg tgtacatttc     2340
tgttttgata acataaccag aaacgttatt gatcaaggca cgcaatggta ctggggcacc     2400
tgtttgagga tctttgatga tgattctaat ttcggcagaa gaaacacgca atctcaacaa     2460
tctcttacca aatctttcta agaaaccacc gaaggcggct tcgacatctt ctggagagat     2520
atcaaacacc gcaatgaagt tgatgaagat atgattcaaa tcagaatttg aagtgtcggt     2580
gacttctaaa ttatccaata tatcactcat caatctgtta gcttcagaag tcagatattc     2640
ttgaatagaa atgtcatcac ggatatgacc cgttctaata atacctcttg taaagaatct     2700
cttatccaat ggagaagtct tactaacagc ttcgtagaca tggatgtttc tattatcagt     2760
gaaaattggt ttaatgttga agttggacaa tcttcctaat tccagttgga aggccaaagc     2820
```

```
cggctcaatg tgacgaattg tttcattttc gttataattt ggaccgttaa aagtataata    2880
ctttggataa gacccatctt taaaaccgaa cataaatgtg atacgacgga tagaagcatt    2940
gattaattcc tgcttattca aatccaaaat ttctctcaac cttaccaaaa tttcctcttc    3000
agattcgaaa ccttctgtag aagcaacaca aacattagca acattactca acgatgcgga    3060
gctaccagaa cgatcaggag caggtccgtt agaagaagat tggtgacgag gaataacttc    3120
caaactttgt gacaaaattt catcaacatc atctaaatga tccacagcca tcaaaatacc    3180
ttctcttaac ggagatgact gactgtttgc aacatatgac aaatctgaaa cagaaacagc    3240
cctgttcata cccatttttag atttaacagt tggaaaggtg gagaacgcag ctgaaggtag    3300
ttggaatttc cattcaacaa ttggaactgt gacaccttcg tgaactctaa tatctcctat    3360
ggtgtaagca cgataagcac gacgaatata gacttgagca gctgcagcag tcacaactgg    3420
gtcttgatgg gttaggaatt gaagtaaaac atcgaacaca acgtaattag aatcgatcaa    3480
gtccttcaag atattcaaat ctggttcaga gcgctttgga ttggatgagc cataggcaac    3540
cttcacaaca gaggatttta agatatgttc aatttgttca gttctttcct tgaccgaagg    3600
taaagcgcct tgaatcaaaa tttctcttgc ttgtagagcg accttagcgg tagccttaga    3660
ttctagttca acaatatgtt gtagaggagt agagaaaatg gcagaaactt tagaagataa    3720
cttgcacaat ggttgataat gtttcaagat agctaggatc aggttattct tcgctgaaac    3780
tttcgaatga gacaaaacag ttagcgcaac tttatctaga tctttagggt tttcatcacg    3840
caatttcaga atgatatttt cctcacgaac atttggacca ttgaataact tttcaacttc    3900
gtaatattct tccaagaaat ggacaaatat agaatgttca tgggcttcta acccgttaga    3960
gtacttatga gcaatatccg ccaatggttc cacgacggcg cccagcaatt tgtcggggtt    4020
gtattcagga ttcttcacgg ccatatcaat caatttactt aattgtctag ctgggaaaac    4080
agcaccacgt ctcaaagaac gtgcaactaa ctcttccatt tgttcatcta gcttagcagg    4140
caatcttgaa tgtaaagcag agatgtgtag tttccattct gagtaaggca gttttggatt    4200
tctcaaaacc tctatcaatt gttgcaagga agcgttcata ataacttggt tgtcataacc    4260
cttcaaaatg ttttccaaag tagacactaa tgacttgaat ttataggcag gtttggttcc    4320
ttcgataact ggagaaccaa aatctggcag cataccttca aatggtagag cgtgcttgac    4380
cttggatgga tcgtcaagag tcataatagc catgatatca cctgcaacaa tggtagaacc    4440
aggttgcttt aataactgga cgataccatt ttcttgagaa accaaaggca tttgcatttt    4500
cataacttca atttctgcat atggttggcc cttgataatg tgttcaccat tttccaccaa    4560
gaatttaacc aatttaccag gggatggagt acgcaactgg gttggatcgt tttcaacttc    4620
caacaaagta gtcatagagt caacggataa tcttgtagca gcaacttctt cttttccaata    4680 gatggtatgc gatttaccgc ctatggcaat caaaagacca ccatcagata gttgacgcag    4740
tatgatatca catttagaac cattgataaa taatgtgtaa cggtcattac cggatttagc    4800
tacggtgaac ttgtatcttt taccctcatg gataaaatct acagggaaca tagtttgcag    4860
taggtcttta gatagaactt gtccctttg taaggattcg atatacttgt ggcgggcttc    4920
ttcagatgct aagaaagcct tgtagcggc accgcaaatg acggcaagag ttggatcagg    4980
cttttcagcg gtcattttat gagtaatcaa atcgtccaac caaccggtgg taatagtgtt    5040
atcctcgaaa tcttcagttt ccaaaagttt gatcaagtat tccacagtag ttctgaaatc    5100 accccctaatg gacaattcct tcagggcaac aaccatgtgt ttcctggaag cttgtctatt    5160
```

| | |
|---|---|
| ttcaccaaaa gcaaaaatat ggccgaactg agagtccgaa aaggagtgaa tattaccatt | 5220 |
| gttacccacg gagaagtaac cccaaacatt agaggaagaa cggaagttta gttcatgcaa | 5280 |
| agtaccaccc gatggcttga atccatcgtt tggatcttct gatgtgatac gacaagcggt | 5340 |
| acaatgaccc tttggaatag gtcttctttg tttcttggtg gcatcttgag ttttgaattc | 5400 |
| gaaatcgatt tctgaggcag aatgaggatt cataccatat aaagttctaa tgtcacttat | 5460 |
| tctatgcata gggataccca tagcgatttg taattgagct gcaggtaagt taacaccgga | 5520 |
| gaccatttcc gttgttggat gctcgacttg taatcttggg ttcaattcta aaaagtagaa | 5580 |
| ttttccatca tcatgagaat atagatactc cacggtaccg gcagagacat aaccgactag | 5640 |
| tttccccagt ctgacggcag cctttcccat ctcgtgaaat gtttcagcct tggcaattgt | 5700 |
| aactggtgct tcttcgataa ttttttgatg acgtctctga acggaacagt ctctaccgaa | 5760 |
| caaggaaata tttgtaccgt actgatctgc tagcagttga acttccaagt gacgcgctct | 5820 |
| accggccaac ttcatgatga aaatggggga gcctggaatt tcgttggctg cctggtggta | 5880 |
| taaagcgatg aaatcttctt cacgttcaac ttgtctgata cctttaccac caccaccttc | 5940 |
| ggatgcctta atcatgacag gaaaaccaat acgcttggcc ttttgtaaac catcttcagg | 6000 |
| agaggtacaa caacccttt gatagatgtc atcgtcgaca gagaccagac cggttttctc | 6060 |
| gtccacgtga acgtgtcaa caccggtacc agaccatgga atacatggga ctttagcact | 6120 |
| ttgagcgaca atggtagagg agattttatc acctaaagac ctcatggcgt tacctggagg | 6180 |
| cccaataaag atgactttcc tcttagactg ggacaatttt tcaggcaata gtggattctc | 6240 |
| ggaggcgtga ccccagccag cccatacggc gtctacgtct gctctttcgg cgatgtctac | 6300 |
| gatcaagtct acgttagcgt agttgttatt attagtacca cctggcactt caatgtattg | 6360 |
| atcggccata cggatatatt ctgcgttggc ctccagatct tctggggtgg ccatggcgac | 6420 |
| gaattggacg gttctgtcat cgccgaacgt ctcgtatgcc cattttctga cggatctaat | 6480 |
| ttcttttcacg gcggcaatac cattatttgc tatcaggatc ttggatatga ccgtgtgacc | 6540 |
| accgtgactc ttaacaaagt cccttaacgg ggactcctct agtttatcta ctgtattgag | 6600 |
| gccaatgaaa tgacctggaa gttctgtatg tcttctgag tagtttgtaa tttcgtactc | 6660 |
| catcttctgt ggagaagact cgaataagct ttcttcgctc at | 6702 |

<210> SEQ ID NO 10
<211> LENGTH: 2103
<212> TYPE: DNA
<213> ORGANISM: Saccharomyces cerevisiae

<400> SEQUENCE: 10

| | |
|---|---|
| atggttgctc aatataccgt tccagttggg aaagccgcca atgagcatga aactgctcca | 60 |
| agaagaaatt atcaatgccg cgagaagccg ctcgtcagac cgcctaacac aaagtgttcc | 120 |
| actgtttatg agtttgttct agagtgcttt cagaagaaca aaaattcaaa tgctatgggt | 180 |
| tggagggatg ttaaggaaat tcatgaagaa tccaaatcgg ttatgaaaaa agttgatggc | 240 |
| aaggagactt cagtggaaaa gaaatggatg tattatgaac tatcgcatta tcattataat | 300 |
| tcatttgacc aattgaccga tatcatgcat gaaattggtc gtgggttggt gaaaatagga | 360 |
| ttaaagccta atgatgatga caaattacat ctttacgcag ccacttctca caagtggatg | 420 |
| aagatgttct taggagcgca gtctcaaggt attcctgtcg tcactgccta cgatactttg | 480 |
| ggagagaaag ggctaattca ttcttttggtg caaacggggt ctaaggccat ttttaccgat | 540 |
| aactctttat taccatcctt gatcaaacca gtgcaagccg ctcaagacgt aaaatacata | 600 |

```
attcatttcg attccatcag ttctgaggac aggaggcaaa gtggtaagat ctatcaatct    660
gctcatgatg ccatcaacag aattaaagaa gttagacctg atatcaagac ctttagcttt    720
gacgacatct tgaagctagg taaagaatcc tgtaacgaaa tcgatgttca tccacctggc    780
aaggatgatc tttgttgcat catgtatacg tctggttcta caggtgagcc aaagggtgtt    840
gtcttgaaac attcaaatgt tgtcgcaggt gttggtggtg caagtttgaa tgttttgaag    900
tttgtgggca ataccgaccg tgttatctgt tttttgccac tagctcatat ttttgaattg    960
gttttcgaac tattgtcctt ttattggggg gcctgcattg gttatgccac cgtaaaaact   1020
ttaactagca gctctgtgag aaattgtcaa ggtgatttgc aagaattcaa gcccacaatc   1080
atggttggtg tcgccgctgt ttgggaaaca gtgagaaaag ggatcttaaa ccaaattgat   1140
aatttgccct tcctcaccaa gaaaatcttc tggaccgcgt ataataccaa gttgaacatg   1200
caacgtctcc acatccctgg tggcggcgcc ttaggaaact tggttttcaa aaaaatcaga   1260
actgccacag gtggccaatt aagatatttg ttaaacggtg gttctccaat cagtcgggat   1320
gctcaggaat tcatcacaaa tttaatctgc cctatgctta ttggttacgg tttaaccgag   1380
acatgcgcta gtaccaccat cttggatcct gctaattttg aactcggcgt cgctggtgac   1440
ctaacaggtt gtgttaccgt caaactagtt gatgttgaag aattaggtta ttttgctaaa   1500
aacaaccaag gtgaagtttg gatcacaggt gccaatgtca cgcctgaata ttataagaat   1560
gaggaagaaa cttctcaagc tttaacaagc gatggttggt tcaagaccgg tgacatcggt   1620
gaatgggaag caaatggcca tttgaaaata attgacagga agaaaaactt ggtcaaaaca   1680
atgaacggtg aatatatcgc actcgagaaa ttagagtccg tttacagatc taacgaatat   1740
gttgctaaca tttgtgttta tgccgaccaa tctaagacta gccagttgg tattattgta   1800 ccaaatcatg ctccattaac gaagcttgct aaaaagttgg gaattatgga acaaaaagac   1860
agttcaatta atatcgaaaa ttatttggag gatgcaaaat tgattaaagc tgtttattct   1920
gatcttttga agacaggtaa agaccaaggt ttggttggca ttgaattact agcaggcata   1980
gtgttctttg acggcgaatg gactccacaa aacggttttg ttacgtccgc tcagaaattg   2040
aaaagaaaag acattttgaa tgctgtcaaa gataaagttg acgccgttta tagttcgtct   2100
taa                                                                 2103
```

<210> SEQ ID NO 11
<211> LENGTH: 2040
<212> TYPE: DNA
<213> ORGANISM: Yarrowia lipolytica

<400> SEQUENCE: 11

```
atgactgtta ccccacagca ccaagtcgtc cacgaggcca acggtgtcac cccaagaccc     60
actcctaagg agttttttga caaacagccc cgtcctggcc atatcacctc catcgaacag    120
taccaggaat ataccagaa gtccatcgcc gaccctgaag gattctttgg tcctatggcc    180
aaggagttgt tgtcgtggga cagagacttc gacaaggtca agtccggttc tttgaaggac    240
ggtgacgttg cctggttcat tggcggccag ttgaacgctt cctacaactg tgtagacaga    300
tgggcctatg cgactccaga caagactgcc atcatctacg aagctgacga gaaaaggac    360 tcgtacaagt tgacctacgc cgagttgttg agagaagtct ccaaggtagc tggtgtgttg    420
aagagctggg gcatcaaaaa gggtgatact gttgctatct acttgccaat gactcctcaa    480
gctgttattg ctatgctcgc tgtagccaga ttaggtgcca tccactcggt tatctttgca    540
```

```
ggtttctctt ctggttccat cagagacaga gtcaacgatg cttcttgtaa ggctcttatt    600
acctgtgacg aaggtagaag aggtggtaag accgttaaca tcaagaaatt gtgcgacgaa    660
gccttgaaga gctgtcctac tgtagaaaag gtgcttgttt tcaagagaac cggaaacgaa    720
aatattgaat tggaagaggg tagagatttc tggtgggatg aagaaaccgc caagttctcg    780
ggttacttgc cacctgttcc agtcaattct gaagacccat tgttcttgtt gtatacatct    840
ggttccactg gtactcctaa gggtgttgtc cacaccactg ggggctacct cttaggtgct    900
gccatgacca ccaagtacat tttcgacgtc cacccagaag acatcttgtt cactgccggt    960
gatgtcggtt ggattactgg tcacacctat gctttgtacg accctttggc tctcggtatc   1020
ccaacaatcg ttttttgaagg tactccagcc tacccagact ttggtagatt ctggcaaatt   1080
gtcgaaaagc acaaggctac ccacttctac gtagctccta ctgccctcag attgttgaga   1140
aagagtggcg agcaagagat tccaaagtac gacttgtctt ctttgagaac attgggctct   1200
gttggtgaac ctatctcccc tgatatctgg aatggtaca acgagcacgt tggacaaggc    1260
agatgccaca tctccgacac ctactggcaa actgagtctg ttctcactt cattgctcca    1320 attgccggtg tcactccaaa caaacctggt tcagcctctt tgccattctt tggtatcgag   1380
accgctctta ttgatccagt ttccggccac gaactcgaag gtaacgacat cgaaggtgtt   1440
cttgccatca gagcacctg gccatctatg gctagatctg tctggaacaa ccacaccaag   1500
tacatggaca catacttgaa cccataccca ggctactact ttaccggcga cggtgctgcc   1560
agagatcacg acggctacta ctggattaga ggtagagtcg atgatgtcgt caatgtgtct   1620
ggtcacagat tgtctactgc tgaaatagaa gctgccctca tcgaacacaa cggtgtttct   1680
gaagctgctg tggttggtat taccgacgac ttaactggtc aagccgtagt tgcctacgtt   1740
gctctcaaga acgaatacgt cgacaagatc gccggcaagg aaaccagcga cgaagccttt   1800
gccttgagaa aggaattgat catgaccgtc agaaaggaaa tcggaccttt cgcagctcca   1860
aagagcgtca tcattgtcgc cgacttgcca aagaccagat ctggtaagat catgagaaga   1920
atcttgagaa agatctctgc caacgaagca gaccaattgg gtgacatcac cactttgtcc   1980
aaccctcagt ctgtcgttgg tataatcgac tcctttgctg ctcaatttgc taagaaataa   2040
```

<210> SEQ ID NO 12
<211> LENGTH: 13770
<212> TYPE: DNA
<213> ORGANISM: Yarrowia lipolytica

<400> SEQUENCE: 12

```
atggggagac acttggcctt gcttctgctt ctgctcttct tcctccagca ttttggagat     60
ggtgatggaa gccaaagact tgaaccgacc ccttccctcc agtttacaca cgtccagtac    120
aatgtcactg tgcacgaaaa ctcggccgca aagacctatg tcggccaccc tagaaaaatg    180
ggcatctaca tcttagaccc ctcgtgggaa ataaggtaca aaatcatctc aggagacaac    240
gaaaacctat tcaaagcgga agagtatgtt ctcggagact tttgctttct aaggataaga    300
accaagggag ggaatactgc catcctgaac cgagaagtga gagaccatta cacactggta    360
atcaaagcag ttgaaaaagt cacagatgcc gaggcccgag ccaaggtcag ggtgcaagtg    420
ctggatacaa acgacttacg gccgttgttc tcacccacgt cctacagcgt ttctctgccg    480
gaaaacacag ccataaggac cagtatcgca gagtcagtg ccacggatgc ggacattgga    540
accaacggcg aatttactta cagctttaaa gacagaacgg acatgtttgc catccaccca    600
accagtggtg tggttgtttt gactggcagg cttgatgtcc tggagaccca gcgctatgag    660
```

```
ctggagatct tggctgtgga ccggggaatg aagctgtacg gtagcagtgg ggtcagcagt      720
ctggccaagc tgacggttca cgtggagcag gctaacgagt gtgcacccgg gataaccgcc      780
gtgacgttat caccatctga gctggacaag gacccaacgt acgccattat cactgtggag      840
gactgcgatc agggtgccaa cggggagata gcatctttga gcattgtggc tggcgacctc      900
cttcagcagt ttaaaacggt gaggtctttc ccagggagta aagcattcaa agtgaaagcc      960
gtcgggggcg tcgactggga cagccatcct tatggctaca acctgacagt gcaggctaaa     1020
gacaaaggaa ctcctccgca gttttcccct gtgaaagtca ttcacgtcat ttctcctcag     1080
ttcagagctg gcccggtcaa gtttgaaatg gatgtttaca gagctgagat cagtgagttt     1140
gcccctccac atacacccgt ggtcctggtc aaggctattc ctagttattc ccatttgagg     1200
tacgttttta aaagcactcc tggaaaaccc aaattcggtt taaatcacaa cacgggtctc     1260
atttccattt tagaaccaat taaaaggcag cacacatccc attttgagct tgaggtgaca     1320
acaagtgaca gacgagcctc caccaaagtc gtggtcaaag ttgtaggtac aaacagcaac     1380
cccccggagt ttacacagac ctcgtacaaa gcatcctttg atgagaatgc accgtcggt      1440 accccggtca tgagggtgag cgcggttgac cctgacgagg gggagaatgg ctacgtgact     1500
tacagtattg caaacttaaa tcacgtgcca tttgtcatcg accactttac gggtgctgtg     1560
agtacctctg agaatctgga ctatgaactg atgcctcgag tctacacgct gaggattcgt     1620
gcttccgact ggggcttacc gtaccgccgg gaagttgaag tccttgccac aattactctg     1680
aataacctga atgacaacac cccctgtttt gagaagacaa actgtgaagg gacaattccc     1740
cgagacctgg gtgtagggga gcagataacc acggtttctg ccattgacgc tgatgagctg     1800
cagttggtcc ggtaccagat tgaagctgga atgagttgg atttgtttgg cttaaacccc     1860
agctctggtg tgctgtcatt gaagcactcg ctcatggacg gcttgggtgc aaaggtttcc     1920
tttcacagct tgagaatcac agctacagac ggagaaaatt ttgccacacc attatatatc     1980
aacctaacgg tggctgccag tcgcaagcca gtaaacttgc ggtgtgagga gaccggtgtt     2040
gccaaaatgc tggcagagaa actcctgcag gcgaataaat acaccatca gggggacgcg      2100 gaggatattt tctttgattc tcactccgtc aacgcccatg ccccacagtt taggggttct     2160
cttccaacag gaattgaggt aaaggaggac ctcccagtgg gcgccagtat actattcatg     2220
aatgctactg accttgactc tggcttcaat gggaaactgg tctatgctat ctctggaggg     2280
aatgatgaca gttgctttac tgttgacatg gaaacaggaa tgctgaaagt cctctctcca     2340
cttgaccgag aagtaacgga caaatacaca ctgaacatta ccgtgtatga ccttggtata     2400
ccccagaggg ctgcctggcg ccttctggat gtcaccgtcc tggatgccaa tgacaacgcg     2460
cccgagtttt tacaggagag ctattttgtc gaagtgagcg aagacaagga gataaacagt     2520
gaaatcatcc aggtagaggc caccgataaa gacctgggcc cagcggaca cgtgacatac      2580 gccatcctca cggacacaga gaagtttgcg atcgacaggg tgaccggtgt ggtgaaaatt     2640
atccagcctt tggatcgtga agtgcagcgt gtacattacc tgaagatcga ggccagggac     2700
caagccacag aggaaccctg gctgtcctcc actgtgcttc tgaaagtgtc actcgatgat     2760
gttaatgaca acccacctag gttcattcca cccagttact ccgtgaaggt tcgagaagac     2820
ctaccggaag gaaccatcat catgtgggtt aaagcccatg accctgatgt aggtcagtcc     2880
agtcaggtga gatacagcct cctggaccac ggagaaggcc acttcgatgt ggataaactc     2940
agcggggcag tgagaattgt ccagcagctg gactttgaga agaagcaact gtataatctc     3000
```

```
accgtgaggg ccaaagacaa agggaagccg gcgtctctgt cttccactgg ctacgtggaa    3060
gtggaggtcg tggacgtgaa tgagaactta cacgcgccag tgttctccag cttcgtggag    3120
aagggcacag tgaaagaaga cgtccctatg ggctcatcag taatgaccgt gtcagctcac    3180
gatgaggaca ccgggagaga tggagagatc cggtattcca tcagagatgg ctctggtgtt    3240
ggtgttttca ggatagatga agaaacaggt gtcatagaga cctcagatcg actggaccga    3300
gagtcgactt cccactactg gctcaccgtc tacgccacag atcagggtgt ggtgcctctg    3360
tcatccttca tagaggtcta catagaggtt gaggatgtca atgacaacgc accacagaca    3420
tcagagcctg tgtattatcc tgaaataatg gagaattcac caaggatgt atctgtggtc     3480
cagattgagg catttgaccc ggattccagc tccagtgaca agctgacgta cagaattaca    3540
agtggaaatc cccaagggtt cttctcaata cacnctaaaa caggtctcat cacaaccaca    3600
tcgaggaagc tggaccgaga gcagcaggat gaacacattc tggaagttac tgtgacagac    3660
aatggtgtac ctcccagatc caccattgcc agggtcattg tgaaaatcct ggatgagaac    3720
gacaacaggc ctcagttcct tcagaagttt tataaaatca ggctcccgga gcgagaaaaa    3780
gctgatggag accggagcgc gaagcgcgag cctctctacc gagtcatagc cgcagataag    3840
gatgaagggc ccaatgccga gctctcctac agcatcgagg aagggaacga gcacggccgg    3900
ttttccattg aacccaagac aggagtggtc tcatccaaaa agttctctgc ggctggagaa    3960
tacgacattc tttctattaa ggcaattgac aatgggcgcc cccagaagtc atcgaccacc    4020
agactccata ttgaatggat ctccaaaccc aagccgtcct ggagccgat ttcgtttgag     4080
gaatcggttt tctcgtttac tgtaatggag agtgatccgg tggctcacat gatcggcgtg    4140
atctccgttg agcctcctgg catgcctctg tggtttgaca tcatcggggg caactatgac    4200
agtcactttg atgtggacaa gggcactgga accatcattg tggccaagcc ccttgacgca    4260
gagcagaagt ccagctataa cctcacagtg gaggcgacag acgggacctc cactatcctc    4320
acccaggtac tcatcaaagt aatagatacc aatgaccacc gccctcagtt ttctacctcg    4380
aaatacgaag tctctgttcc cgaagacaca gagccagaaa cagagattct gcaaatcagc    4440
gccgtagaca gggacgagaa aaacaaactg atctacaccc tccagagcag catagatcca    4500
gcaagtctca agaaattccg cctcgatcct gcaacaggcg ctctctacac atctgagaag    4560
ctcgatcacg aagccattca ccagcacgtc ctcacagtca tggtccggga tcaggatgtc    4620
cctgtgaaac gcaactttgc cagaatcatt gtgaatgtca gtgacatgaa tgaccactct    4680
ccgtggttca ccagttcgtc ctatgaaggg cgggtttatg agtcggcagc cgtgggctcg    4740
gtcgtgctac aggttacagc tctggacaga gacaaaggga gaaatgctga agtgctctac    4800
tccatcgagt caggaaacat tggaaattcc tttacaatcg accccatctt gggctctata    4860
aaaactgcca gagaattgga tcgaagtcac caagtagact atgatttaat ggtaaaagct    4920
acagacaaag gggagccacc aatgagcgaa atgacctccg tgcggatctc tgtcaccgtc    4980
gccgacaatg cctctcctaa gttcacatcc aaggagtact cggctgagat tagtgaagcc    5040
atcaggattg ggagttttgt tggaatggtc tctgctcaca gtcagtcatc agtgatgtat    5100
gaagtaaaag atgaaatat aggcgatgca tttaatatca atccacattc aggaagcatc     5160
gtcactcaga gagccttgga ttttgagaca ctgcccattt atacattgac agtacaaggg    5220
accaacatgg ccggcttgtc caccaataca acgtggtag tgcacataca ggatgagaat     5280
gacaaccctc cagctttcac acgggcggaa tattcaggat tcattagtga atcagcctca    5340
gtcaacagcg tggtgctaac ggataagaat gttccgctcg tgatccgagc caccgacgct    5400
```

```
gatcgggaat ccaatgctct gctcgtctat caaattgtcg agccatctgt gcacaactat   5460
tttgccattg atcccaccac cggtgccatc cataccgtac tgagtctgga ctatgaagag   5520
acacgtgtct ttcacttcac cgtccaagtg catgacatgg ggacgcctcg tctgtttgct   5580
gagtatgcag caaatgtgac cgtgcatgtg attgacatca atgactgccc ccctgtcttc   5640
tctaagtcac tgtacgaagc atccctccta ttgccgacgt acaaaggcgt gaacgtcatc   5700
acagtgaatg ccacagatgc cgactccagg gcgttctccc agttaatata ctccatcacc   5760
aaaggcaaca ttggggagaa gttctccatg gaccacaaga ctggcaccat agcaattcag   5820
aacacaaccc agttacggag ccgctatgag ctgaccgtcc gcgcctccga tggccggttt   5880
acaagcgtgg cctccgtgag aatcaacgtg aaggaaagca gagagagtcc tctcaagttt   5940
acccaagatg cctactctgc ggtggtgaag agaaactcca ccgaagccaa aaccttagct   6000
gtcattaccg cgatagggaa cccgattaac gagcctttgt tttaccgtat cctcaaccca   6060
gaccgcagat ttaaaatcag ccacacctca ggcgtgttgt caaccactgg gataccattt   6120
gatcgggagc aacaggagac gtttgttgtg gtggtagagg tgactaaaga acgggagccg   6180
tcggccgtgg cccacgttgt ggtgaaggtc accgtggaag accagaatga taatgcaccc   6240
gtgtttgtca accttcccta ctatgctgtg gtgaaggtgg atgctgaggt gggccatgtc   6300
atccgccacg tcactgccat tgacagagac agtggcagaa acggtgacgt tcactactac   6360
cttaaggagc atcatgacca ctttgagatt ggaccctctg gtgacatttc tctgaaaaag   6420
caatttgagc acgacacctt gaataaagaa taccttgtca cagtggttgc gaaggacggg   6480
gggaacccag ctttctccgc agaagttcta gttcccatca ccgtcatgaa caaagccatg   6540
cccgtgtttg aaaaggcttt ctacagtgca gagattcccg agaacgtcca gacgcacagc   6600
ccagtggtcc acgtccaagc caacagccca gaagggttga agtgttcta cagtatcaca   6660 gacgggggacc cttttagtca gtttactatc aacttcaaca ctggggtgat aaacgtcatc   6720
gcaccgctgg actttgagtc ccacccagcc tataagctaa gcatacgggc cactgactcc   6780
ctgactggcg cccacgctga agtgtttgtt gacatcgtag tagaagacat caatgacaac   6840
cctcccgtgt tgtgcaaca gtcttactcg acaaccctgt ctgaagcatc tgtcatcgga   6900
gcgcctatcc ttcaagttag agccaccgac tctgactcgg aaccaaatag agggatttcc   6960
taccagctga ttggaaatca cagcaaaagc cacgatcact ttcacataga tagtcacact   7020
gggctgattt cactggtgag ggctttggat tacgaacagt tccagcagca caagctgctc   7080
gtaagggctt ttgatggagg aatgccgcca ctgagcagcg atgtggtcgt cactgtggat   7140
gtcaccgacc tcaacgataa cccgcctctg tttgaacaac aggtttacga agctaggatc   7200
agtgagcacg ctgcccacgg gcattttgtg atgtgcgtaa aggcctgtga tgcagatcgc   7260
tcagacctag acaggctgga gtactccatt ctgtccggca atgatcacaa gagctttgtc   7320
attgacgggg agacaggaat catcacgctc tccaacccgc gccgcacac cttgaagccg   7380 ttctatagtc tcaacgtttc tgtgtctgat ggggttttcc gaagctcggc tcgggtgaat   7440
gtcaccgtga tgggagggaa tttgcacagc cctgtctttc accagaatga gtatgaggta   7500
gagctggctg aaaacgcccc cttgcacacc ctggtggtcc aagtgaaggc tactgacaga   7560
gattccggta tctacggcca cctgacttac caccttgtaa atgactttgc caaagacagg   7620
ttttacgtga acgacggagg gcaggtcttc actctggaga gacttgatcg agaggctcca   7680
gcagagaaag tgatctcagt ccgtttaatg gctaaggatg ctgggggggaa ggtcgccttc   7740
```

```
tgcactgtca acgtcatcct cacggacgac aatgacaacg caccacagtt tcgctcaacc   7800
aagtacgagg tgaacgtggg gtccagcgcc gccaaaggga cgtcggtcgt caaggtcttc   7860
gcgagtgatg ccgatgaggg gtcgaatgct gacgtcacct acgccatcga ggcagattcg   7920
gaaagtgtcg aggagaactt ggaaatcaac caactgaccg gcctcattac tacaaaggaa   7980
agcttaatag gtttagagaa tgaattcttc actttcttcg ttagagctgt ggataacggg   8040
tctccgccca aagagtctgt tgttcctgtc tatgttaaaa tacttccccc ggaagtgcag   8100
cttcctaggt tctcagagcc cttttatacc tattccattt cagaagacat gcctattggc   8160
acagagattg acctcatccg ggtagagcat agcgggactg ttctctacac cctggtcaaa   8220
ggcaatactc ccgagagtaa cagggacgag ttctttgtga ttgaccggca gagtgggaga   8280
ctgaagctgg agaagagcct tgaccacgag accactaagt ggtatcagtt ttccatcctg   8340
gccaggtgta ctctggatga ctacgaggtg gtggcttcta tagatgtcag tatccaggtg   8400
aaagacgcta atgataacag cccagttttg gagtccaatc catacgaggc atttattgtc   8460
gaaaacctgc cagcagggag tagggtcatc caggtcagag catctgacct agactcagga   8520
gtcaacggcc aagtcatgta cagtctagat cagtcccaag atgcagacat catcgagtct   8580
tttgccatta acatggaaac aggctggatt acaaccctca aggagcttga ccatgaagag   8640
agagccagtt accagattaa agtggttgcc tcagaccatg gtgaaaaggt gcagctgtct   8700
tccaccgcca ttgtggatgt caccgtcact gacgtcaacg acagcccgcc tcgattcaca   8760
gctgagattt ataaagggac agtgagtgag gatgaccccc caggggtgt gatcgccatc   8820 ttgagcacca ctgacgccga ctctgaagag attaaccgac aagtgtcgta cttcataaca   8880 ggagggatg cattgggaca gtttgctgtg gaaaatatgc agaatgactg gagggtgtac   8940
gtgaagaaac ctctcgacag ggaacaaaag gacagttacc ttctgaccgt cactgcaaca   9000
gatgggacct tctcttccaa gctagagtt gaagtcaagg ttctcgatgc caatgataac   9060
agtccagtgt gtgagaggac cgcatatttct gatgccattc ccgaagacgc tcttccgggg   9120
aagctggtca tgcaggtctc tgccacagat gcagatatcc ggtccaacgc ggagatcact   9180
tacactttat ttggctcagg tgcagaaaag tttaaactga atccagacac aggtgaactg   9240
agaacattag ccctccttga tcgtgaggag caagcagttt atcatcttct ggtcaaggcc   9300
acagacggag ggggcagatc ctgtcaggca actattgtgc tcacgttaga agatgtaaat   9360
gacaacaccc ccgagttcac cgcggatcca tacgccatca cggtatttga aaacacagag   9420
cctgggacac cgttgaccag agtgcaggcc accgatgcag acgcagggtt gaatcggaag   9480
atttcctact cactgcttga ctctgctgac gggcagttct ccattaacga gcagtccgga   9540
attcttcagt tggaaaagca tttgacagg gaactacagg cagtctatac tctcactttg   9600
aaagcagcgg accaaggatt gccaaggaaa ttgacagcca ctggcacggt ggttgtgtct   9660
gttttggata taaatgacaa cccacctgtg tttgagtacc gtgaatatgg tgccaccgtg   9720
tcagaggaca ttgtcatcgg gaccgaagtt ctccaggtgt acgcagccag tcgggatatc   9780
gaggcgaatg cagaaatcac atacgcaatc ataagtggga acgaacacgg aaaattcagc   9840
atcgattcta agacagggc catatttatc attgagaacc tggattatga aagctcccat   9900
ggctattacc tgactgtgga agccactgat ggaggcacgc cctcgttgag tgacgtggcg   9960
accgtgaaca tcaacatcac agatattaac gataacagcc cagtgttcag ccaggacagc  10020
tacaccacag tggtcagcga agacgcgcc ctggagcagc ccgtcattac aattatggct  10080
gatgatgctg atggccccttc aaacagccac atcctctact ccattataga gggtaaccaa  10140
```

```
ggaagtccat tcacaatcga ccctgtcaga ggagaaatca aagtaacgaa gccctagac    10200 cgcgaaacga tctcaggtta tacgctcacg gtgcaggctg ccgacaacgg caatccaccc    10260
agagtcaaca ccaccacagt gaacatcgat gtctccgatg tcaacgacaa tgctcccctc    10320
ttctccagag acaactacag tgtcatcatc caggaaaaca agcccgtggg tttcagcgtc    10380
ctgaagctag tagtgacaga caaggactcg tcccacaacg gcccccttt ctcctttgct     10440 attgtgagtg gaaatgatga caacatgttt gaggtgaacc agcacggggt cctcctgaca    10500
gcggcaacag tcaagaggaa agtgaaggac cattaccttc tgcacgttaa ggtggctgac    10560
aatgaaaagc ctcagctgtc ttcgttgaca cacattgaca tcagggttat tgaggagagc    10620 atccacccctc ctgccatttt gccactggag attttcatca ctgcttctgg agaggaatac   10680
tcaggcgggt tcataggaaa gatccatgcc acagaccagg atgtgtatga cacccttgacg  10740 tacagtctgg atccccacat ggatggcctg ttctctgttt ccagcacggg gggtaaactg    10800
attgcacaca gaaagctgga tataggccag taccttctta atgtcagcgt gacagacggg    10860
aagtttacaa cggtggctga catcaccgtg cacatccagc aagtgaccca ggagatgctg    10920
aaccacacca tcgctatccg atttgcaaat ctcaccccgg aagagtttgt cggcgactac    10980
tggcgcaact tccagcgagc tttacgcaac atcctgggca tccggaagaa cgacatacag    11040
attgtcagct gcagccctc cgaaccccac tcccaccttg acgtcttact ctttgtagag     11100
aaatcagggg gcacccagat ctcaacgaaa caacttctgc acaagatcaa ttcttccgtc    11160
acggacatcg aggaaatcat tggcgtgagg atactggatg tgttccagaa actctgtgca    11220
gggctggatt gcccgtggaa attctgtgat gagaaggttt ctgtggatga aaacattatg    11280
tcaactcata gcacagccag actgagtttt gtgactcccc ggcaccatag aacagccgtg    11340
tgtctctgca aagatgggac atgcccgcct gtccaccaag ggtgcgaaga taaccctgt     11400 cctgcaggat ccgaatgtgt cgctgatccc cgagaagaga agtacagctg tgtgtgtcct    11460
ggtggcgggt tcgccaaatg tccagggagt tcatccataa cttttaccgg cagcagcttt    11520
gtgaaatatc gtctgatgga aaatgaaaac cgactggaga tgaagttgac catgcgcctg    11580
agaacctact cttcccacgc ggttgtgatg tacgctcgag gaactgacta cagtatcctg    11640
gagattcata ctgggagact gcagtacaaa tttgactgtg gaagtggccc tgggatcgtc    11700
tctgttcaga gcattcaagt caacgatggg cagtggcatg cagtgtccct ggaagtggag    11760
gggaattatg caaaattggt tctagatgaa gtccacactg cctcgggcac agccccagga    11820
gctctgaaaa ccctcaacct ggataactac gtaattttg gtggccacct ccgccagcaa     11880
gggacaaaac atggacgaaa cacccaggtg gccaatggtt tcagggctg catggactct     11940 atttatttga tgggcagga gctacccttg aacaacaaac caagagccta tgcacacatc     12000
gaagaatggg tggacctagc tcatgggtgc ttgttaactg ccaccgaaga ctgttccagc    12060
aacccttgtc agaatggagg cgtctgcaat ccctcgccca ctgggaggtta ttactgcaag   12120 tgcagtgcat tgcacgcagg gacgtactgt gaggtgagcg tcaacccgtg ctcctccaac    12180
ccctgcctct acggaggaac gtgcatggta gacaacggag gttttgtttg ccagtgcagg    12240
gggctgtaca ctggccagag atgtcagctt agtccgtact gcaaagatga accctgtaaa    12300
aatggtggaa cgtgttttga cagtttggat ggtgctgtct gtcagtgtga ctcaggcttt    12360
aggggagaaa gatgtcagag tgacattgac gagtgtgctg ggaacccctg tcggaacggg    12420 gcccttttgcg agaacacgca tggctcctat cactgtaact gcagccagga gtacagaggg    12480
```

```
aagcactgtg aggatgccac tcccaaccac tacgtgtcca ccccgtggaa catcggactg    12540
gccgaaggaa tcggaattat tgtgtttata gccgggatat tcttactggt ggtggtgttt    12600
gtcctctgcc gaaagatgat cagtcggaag aagaaacacc aggcggaacc tgaagacaag    12660 cgtttgggc caaccacggc tttcttacag agaccttact ttgattccaa gccgagcaag    12720
aacatttact ctgacatccc gccccaggtg cccgtgcgtc ccatttccta cactccgagc    12780
attcccagtg actctagaaa caatctggac cggaactcgt ttgaaggctc ggcaatccca    12840
gagcacccag aattcagcac ttttaacccc gagtctatgc acggacatcg gaaagccgtg    12900
gctgtgtgca gcgtggctcc aaacttgcct cccccacccc cttccaactc tccctcagac    12960
agcgactcca ttcagaagcc cagctgggac ttcgactacg acgctaaagt ggtggatctt    13020 gaccttgtc tttccaagaa gcccctggag gaaaaaccct ctcagccata cagtgcccgg    13080
gagagcctgt ccgaggtgca gtcccttagc tccttccagt cagagtcctg tgatgacaat    13140
gggtaccact gggatacatc agactggatg cccagtgttc ctctgccaga catacaagag    13200
ttccccaatt acgaggttat cgatgagcac acgcccctct actcagctga tccaaatgcc    13260
atcgacactg actattaccc tgggggttat gacattgaaa gtgactttcc acccccacca    13320
gaggacttcc ctgcacccga tgaactgcca ccattgcctc cagaattcag cgaccagttc    13380
gagtccatac acccacccag agacatgccc gcagcaggta gcttggggtc ttcctccagg    13440
aatcgtcaga ggttcaacct gatcagtac ctgcccaatt tctaccccgt cgatatgtct    13500
gaacctcaga acaaggcgc tggtgagaac agtacctgta gagaacccta cactccctac    13560
cctccagggt atcaaagaaa cttcgaggcg cccaccatag aaaacatgcc catgtctgtg    13620
tacacctcta cggcttcctg ctccgatgtg tcagcgtgct gcgaagtgga gtctgaggtc    13680
atgatgagtg actacgagag cggggacgac ggccactttg aagaggtgac cattccccg    13740 ctagattccc agcagcatac ggaagtgtga                                    13770

<210> SEQ ID NO 13
<211> LENGTH: 14118
<212> TYPE: DNA
<213> ORGANISM: Yarrowia lipolytica

<400> SEQUENCE: 13
atgaagatta aaaatatgt aactcctgta aaaagaaaag ctttcaccat actccaatgg     60
atttcactac tgtgtagtct atggttgatc cccactgtac aaagcaaggc cgatgagaag    120
cacacggcga ccctggagta tagactagag aaccaactgc aagatctata taggtttagc    180
catagtgtat ataatgttac cataccagaa aatagtctgg gcaagactta cgccaaggga    240
gtattgcatg aaagactggc cggcctgaga gttggcttga acgcagaggt taagtatagg    300
ataattagtg gcgataagga gaagctattt aaggccgagg agaaactggt cggagatttt    360
gccttcttag cgattcgaac gcggacaaat aacgttgtgc taaacagaga aaaaactgag    420
gaatacgtta agagtgaa ggcacatgta catttgcacg accgaaatgt atcaagctat    480
gaaacggagg cgaatatcca catcaaagta ctggatcgca atgacctgag tccgctgttt    540
tatccgaccc agtacaccgt tgttattccg gaggacacgc ccaaatatca agtatttta    600 aaggtcacag ctgacgatgc tgacctcggc atcaatgggg aaatctacta cagcctcctg    660
atggatagtg aatactttgc tatccatcca acaactggcg aaattactct cctgcagcag    720
cttcagtatg cggagaactc gcacttcgag ctcacggtgg tggcctacga tcggggatca    780
tgggtgaacc atcagaacca ccaggccagc aagacgaagg ttagtatttc ggtgaaacag    840
```

```
gttaactttt  acgctccaga  gattttcacg  aaaaccttct  cgagcgtgac  gccaacatca   900
aaccctttga  tttatggaat  tgtacgagta  aacgacaaag  acactgggat  aaatggcaac   960
ataggggcgat tggaaatcgt  cgatggaaat  ccggatggca  cgtttcttct  gaaggcggcg  1020
gagaccaaag  acgagtacta  catcgaattg  aatcagtttg  cccatcttaa  ccagcaacat  1080
ttcatttaca  acttaaccct  actggcggag  gacctcggaa  ctccccgtcg  attcgcctac  1140
aaatccgttc  cgattcaaat  caagcccgag  agcaaaaata  tacccatatt  cacacaggag  1200
atttacgaag  tatccattcc  agaaacggca  cccattaaca  tgcctgtgat  aaggctcaaa  1260
gtaagcgatc  cagatttggg  caaaaatgca  ttggtctact  tggaaatcgt  gggtggaaat  1320
gagggcgacg  agttccgaat  taatcccgat  tcgggaatgt  tgtacacagc  aaagcaactg  1380
gatgccgaaa  agaagtcaag  ttataccctta acagtctccg  ccattgatca  ggcaaatgtt  1440
gggtcgcgga  aacaatcttc  agccaaggtg  aaaatcagcg  tacaggatat  gaacgacaat  1500
gatcccattt  ttgagaatgt  caataaggtc  attagtatca  atgagaacaa  cttggctggc  1560
tcgtttgttg  tgaagcttac  tgccaaggac  agggattctg  gtgaaaattc  atacatatcg  1620
tatagtattg  ccaatctaaa  tgcggttcca  tttgaaatcg  atcactttag  cggtatagtt  1680
aagaccacat  cactgcttga  cttttgaaaca atgaagcgta  actatgagct  gataatccgt  1740
gcatccgatt  ggggattgcc  gtacagaaga  cagacgaaa  tcaaactgtc  catcgtcgtc  1800
aaggatatca  acgataatcg  gccgcagttt  gaacgtgtga  actgctatgg  caaagtgacc  1860
aaatcggcgc  cgatgggcac  cgaggtattc  gttacctcag  ccattgactt  tgatgcaggc  1920
gatataatat  cctataggtt  gagcgacggc  aacgaggatg  gctgctttaa  cttggacccc  1980
acatcggggtt  ccctgtctat  ttcctgcgac  ctgaagaaaa  caaccttaac  aaaccgtatt  2040
ctcaaagttt  ccgccacgga  cggcacccac  ttttccgatg  acttgatcat  caatgtacac  2100
ctaatgcccg  aagatttggg  tggagattcc  agtattctac  atggttttgg  atcctttgag  2160
tgccgggaaa  ccggcgtggc  caggagattg  gcggaaacat  tatcgttggc  cgaaaaaaac  2220
aatgtaaaga  gtgcatcgcc  atccgttttc  agtgacttgt  ctctaacacc  cagtcgatat  2280
ggccaaaatg  tgcatagacc  agagttcgtg  aacttccctc  aggagctgtc  cattaacgaa  2340
agtgtccaat  tgggcgaaac  agttgcttgg  atagaggcca  agatcgcga   tttgggctac  2400
aatgaaagc   tggtatttgc  aatttcagac  ggggactacg  attcggtttt  tcgtattgat  2460
ccagaccgcg  gtgaactgca  gattattgga  tatttggata  gagagcgtca  aaatgaatat  2520
gttctcaaca  tcaccgtcta  cgatctgggt  aacccgacca  aatcgacgtc  aaaaatgttg  2580
ccaataacga  tcctcgacgt  gaacgataat  cgcccggtta  ttcagaagac  gttggccacc  2640
ttccggctga  ctgagagcgc  caggatagga  actgtggtac  actgccttca  tgccacggat  2700
gcggattctg  gaatcaatgc  tcaggtgaca  tatgccctgt  cggttgagtg  cagcgatttc  2760
acagtaaatg  ctactacggg  atgtcttcgt  ctgaacaaac  cactggatcg  cgagaagcag  2820
gataactacg  ctcttcacat  aactgccaag  gatggtggca  gtcccgtgct  atcctcggag  2880
gcattggttt  acgtcctggt  cgacgatgtc  aacgacaacg  cgcccgtttt  cggagtgcaa  2940
gagtacatat  ttaaggtgcg  cgaagatctg  ccccgtggaa  cagtgttggc  cgtaatcgag  3000
gcggtggacg  aagatattgg  acccaatgcc  gagatccaat  tctctttgaa  agaggagacc  3060
caggatgagg  aactattcag  aatcgataag  cacacgggtg  caattaggac  tcaaggatat  3120
ctggactatg  agaacaaaca  agtgcacaac  cttattgtca  gtgccatcga  tggcggagat  3180
```

```
ccctctctaa cttcggacat gtccatcgta ataatgatca tcgacgtcaa cgagaaccga    3240
tttgcgcccg aattcgacga ctttgtgtac gagggaaagg taaaggagaa caagccgaag    3300
ggaacgttcg taatgaatgt cacagcacgg gatatggaca cggtggacct gaactccaag    3360
atcacgtact caataacagg tggcgatgga ctgggaattt ttgcggttaa cgaccaaggt    3420
tcaataactt ccttgtcgca actcgatgcg gagacgaaaa acttttactg gctgacgctc    3480
tgtgcacagg attgcgcaat agttcccctc agcaattgtg tggaagttta catacaagtc    3540
gaaaacgaaa acgataacat tcctcttacg gacaaaccag tgtactacgt taatgtcacg    3600
gaagccagtg tggaaaatgt ggagatcatt accctaaagg ctttcgatcc cgatatagat    3660
cccactcaga ctataacata taacatagtt tccggaaatc ttgtcgggta ctttgaaatt    3720
gattcgaaaa caggagtgat taagacgaca gaacgcaaat tggatagaga aaatcaagcg    3780
gaacatattt tggaggtggc tatatcagat aacggatctc cagtactatc ttctacatcg    3840
cgaatcgttg tgtcagtact ggatattaac gataacagcc ccgagtttga ccaaagggtc    3900
tacaaggtgc aagttccgtc ttcagccaca gtcaatcaat ctattttcca ggttcacgct    3960
atcgacagcg acagtggcga aaatggtcga attacctact caattaagtc cggaaagggt    4020
aagaataaat ttcgcatcga tagccaaagg ggccatatac atatagcaaa accattggac    4080
tccgacaatg agtttgagat tcacatcaag gctgaggaca acggaattcc taaaaagagt    4140
caaactgcta gagttaatat tgttgtagtt cctgtaaatc ctaattccca aaatgcaccg    4200
ttgatagtca gaaagacatc cgaaaatgtc gttgatctta cggaaaatga caagcctgga    4260
tttttggtca ctcaaatttt agctgtcgat gatgacaacg accagctgtg gtacaacatt    4320
tccaatggca atgacgacaa tacctttttac attggccaag acaacggaaa catactgctt    4380
tcaaaatatt tggactacga gacccaacag tcctataatc tgactatcag cgtcactgat    4440
ggcacattca cagcgtttac taatctttg gttcaagtga tcgatattaa tgacaacccc    4500
cctcagttcg ctaagatgt gtatcatgtc aatatatccg aaaatattga agaggaatca    4560
gttataatgc aactccacgc cactgacaga gatgaggaca agaagctatt ctatcacctg    4620
cacgcaactc aggatccgtc gtcgctggca ttgttccgaa tcgattccat aagtggaaat    4680
gtcattgtca ctcagagatt ggattttgaa aagactgcgc agcatatact catcgttttt    4740
gttaaggatc aaggagcgcc tggaaaaaga actatgccag agataattgt aaacgtgcat    4800
gaccacaacg accatcatcc agaatttact gctaaaataa ttcaaagtaa ggttcccgaa    4860
agcgcagcta ttggctctaa gttagccgaa gtgagggcca tagatagaga tagtggtcac    4920
aatgccgaga tccagtactc gattatcacg ggtaacgtgg gtagtgtgtt tgagattgat    4980
ccgactttcg gtataatcac attggctggc aacttgaata tcaacaagat ccaggagtac    5040
atgcttcaag tgaaggccgt agatctggga aatccaccgc tgtcatcgca gattccggta    5100
cacatcattg tcaccatgtc cgagaacgat cctccgaagt tcccaaccaa caacattgcc    5160
attgaaatat tcgaaaacct gcccatcgga acatttgtta ctcaagtcac cgctcggtcg    5220
tcgtcatcca tattcttcaa tattatttcc ggcaacatca acgaaagctt ccgcattaac    5280
ccatctactg gagttattgt tatcaatgga aatatcgact atgaatccat caaagtattc    5340
aaccttacgg ttaaaggaac caatatggca gccgagtcat cctgccaaaa tataattata    5400
catatcctag atgctaacga taatattccg tatttcgttc aaaatgaata tgttggagca    5460
ttacccgaat ccgccgctat tggatcttac gtactgaaag tacacgactc atcaaaagat    5520
catttaacat tacaagttaa ggatgcggat gtcggagtaa acggaatggt tgaataccac    5580
```

```
atagttgacg atctggcaaa aaactttttt aaaatagatt cgacaactgg cgctattgaa    5640
ctgttacgac aattggacta tgaaacaaac gctggttata cctttgacgt tacggttagt    5700
gatatgggaa agcccaaact acattccact acaactgcac atgtgacgat tcgtgtcata    5760
aatgttaacg attgtcctcc agtatttaat gagcgtgaac tcaatgtaac tttgttcctt    5820
ccaacttttg agaatgtgtt tgtaagacaa gttagcgcaa aggatgctga taacgatacc    5880
ttaaggtttg atattgtgga tggaaacacc aacgaatgtt tccagatcga aaatacacc     5940 ggaataatta caacacgaaa ttttgaaata ctaaataacg aaaatgatcg ggactatgcc    6000
ttgcacgtcc gtgcctccga cggaattttc tctgcaattt taatagttaa aattaaggtt    6060
ttgtccgcca tcgattcgaa tttcgcattc aacgtgaat cgtacagatt ttctgcattt     6120
gaaaataaca caaggtagc taccattgga ttggtaacg taataggaaa cacactggac      6180
gaaaacgttg agtatcgcat cctgaaccca acacaattgt ttgatattgg aatcagttcg    6240
ggagccctaa aaaccactgg agttattttc gatcgcgaag taaaggattt gtacagactc    6300
ttcgtggaag caaagtcaat gctatacgac ggcatgaatt caaatgttcg cagagcagta    6360
acgtccatag atatatccgt cttggatgtg aacgacaatt gccccttgtt tgtcaatatg    6420
ccctattatg ccacagtctc tattgacgat ccaaaaggaa cgattattat gcaggtcaag    6480
gccattgact tggacagtgc agaaaacggc gaagttcggt acgaacttaa gaagggcaat    6540
ggggagttgt tcaaactgga ccgcaaatct ggggagttat ccataaagca gcatgtcgaa    6600
ggtcataacc gaaactatga attgacagtg gctgcctatg atggcgccat aacaccatgc    6660
tcctcggaag ctcctctgca ggttaaggtt atagatcgtt cgatgcccgt ttttgaaaag    6720 cagtttata ctgttagcgt caaggaagac gtggaaatgt actcagccct ttccgtatcc     6780
attgaagcag aaagtcccct gggaaggagt ttaatttaca caatatcttc cgagagtcaa    6840
tcgtttgaaa ttgattacaa cacgggatca atttttgtcg taaatgaatt ggattacgag    6900
aaaataagct cacacgatgt ttccattcga gcgactgaca gtctttctgg tgtttatgct    6960
gaagtcgttt tatctgtttc cattatggat gtcaatgact gctatccaga aattgagagt    7020
gatatataca acctaaccat tccggaaaat gcatcgtttg gaacacaaat tctgaagatt    7080
aatgcaactg ataacgactc gggagcaaat gcaaaacttt cctattacat tgagtccatt    7140
aatgggcaaa ataattcaga actgttttac attgacgtca cagacggaaa tctgtattta    7200
aagactccat tggactatga acaaatcaag tatcatcata tagtcgttaa cgtaaaggac    7260
catggatcgc catcattaag ttcccgatca aacgtattta taacaggtag aattctatgt    7320
cgctttatct cttacaaact aatttatgat tctattattc cagttaaaga cttaaacgac    7380
aacgctccat gtttcgttga gccgtcgtac ttcaccaaag tgtcagtggc agctgttcgt    7440
ggacaatttg ttgctttacc taaagcatac gataaggata tttccgatac cgattctctg    7500
gaatacaaaa ttgtttacgg aaatgaattg caaacctata gtattgataa gctaacagga    7560
gtgatttccc ttcaaaatat gttaaatttc actgataaaa gtagcacagt cttgaatatt    7620
tccgtctccg atggagttca tacggcatat gcccggctca aaatatcctt attgccagaa    7680
aacgtttaca gtccactgtt tgatcaaagt acttatgagg ctcaagtacc tgaaaacttg    7740
ctacacggtc ataatataat cacggtaaaa gcatcggatg gagactttgg cacctacgcc    7800
aatctttact acgaaatagt ttcggaggaa atgaaaaaaa tctttctcat cgaccaaacg    7860
acgggtgtaa taacctcaaa agtaactttc gaccgtgaaa aaaaggatga gtacgtggtg    7920
```

```
ctactgaagg tgtccgacgg tggcggaaaa ttcggatttg cctctctcaa ggtcatagtc    7980
gtcgacgtga acgataacgt tccttacttc ctattgaagg aatacaaaat ggttgttagc    8040
acaacagtgg aagcaaacca aactatcctg acggtcaaag ccaaagacga cgatattgtt    8100
gataatggat cggtgcattt ccaaattgtt caaaaatcca acgataaggc agtaaaggat    8160
gtaatcgaaa tcaacgagaa aactggggat attgtgttta aaagcaaggc ggaatcttac    8220
ggagtgaact catatcagtt tttcgttcgc gcttccgatc gcggtgaacc tcaatttcat    8280
tcggaagttc cagtgtcaat cgaaataatc gagactgatg ccaatattcc cacttttgag    8340
aaatcgtcag ttctactaaa gatcatagag tcaacgccac caggaaccgt gctaacgaag    8400
ctacatatga ttggaaacta tacgttcaaa ttctcaatag cagcggatca ggatcacttc    8460
atgatatccg atagtggtga actgatcctt cagcagacat ggacaggga gcagcaagag    8520 tcgcacaatt tgattgtagt ggcggaaact tccacggttc ccgttttttt cgcctacgct    8580
gatgttttga ttgacgttag ggacgaaaat gataactatc ccaagtttga caacacattc    8640
tacagtgcca gtgttgcgga aaacagtgaa aaggtgatat ccttggtgaa agtatcggcc    8700
acagatgcgg acactgggcc aaatggcgac attcgctact acttggaaag tgatactgaa    8760
aacattcaaa atatttttga cattgacatt tactctggct ggatcacctt gctaacctcc    8820
ttggacagag aagttcagtc cgagtacaat ttcaaagtaa ttgctgccga taatggccac    8880
ccaaagcatg atgcaaaagt acctgtaact atcaaaatcg tagactataa tgataacgca    8940
ccagtattta agttgcctat cgaagggctt tctgttttcg aaaacgcgct gcctggcacg    9000
gttttaatca acttactcct aattgatccc gatatcgaga acaggaaat ggatttcttt    9060 atcgtttctg gggacaagca agcccagttt cagatcggta agagcggaga gttatttatt    9120
gccaaaccat tagatcgcga acaactcatg ttctacaact taagcataat agccactgat    9180
ggaaaattca ctgccaaagc caatgtggaa atagatgtaa aagacataaa cgacaatacg    9240
ccttactgcc taaaaccccg ctatcatatc tccactaatg aatcaatctc gattggaact    9300
acactcgttg aggtcaaggc gattgacttt gattttcaaa gcaaactgcg cttctatctt    9360
tcgggcaaag gtgcgacga cttcagtata ggaaaggaaa gtggcatcct gaaggtggca    9420
agcgcactgg atcgggagac aaccccccaag tacaaattgg tcgcacatgt acaggatggc    9480
aaggacttta cgcaagagtg tttctcggaa ataatcatca cggtcaatga cataaatgac    9540
aatatgccca ttttctcaat ggctcaatat agagtgagtg tacccgagga tgcacaactg    9600
aacacattga tcacgaaagt gcacgcgatg gataaggatt tcggggtaaa tagacaaatc    9660
aaatactcgc taatgggtga aaaccatgat tatttcaaaa tatcaaaatc gactggtatc    9720
ataaggctgc acaaaagtct cgatcgtgaa acaatttcat tgtttaatct cactgtgaag    9780
gcggaggact gtggcgttcc aaaaactacac tccattgcaa cagttgctgt gaacatattg    9840
gacattaatg acaatccacc cgagttcagt atgcgtcagt attcgtgcaa aattctggaa    9900
aacgccacac acggcacaga agtgtgcaaa gtttatgcca cttcgataga tattggggta    9960
aatgcggata ttcactactt cataatgagt ggcaacgagc aggggaagtt caaaatggat   10020
tccacgacgg gcgacttggt gctaaatgca accttggact atgaaatgtc caagttttac   10080
ttcttgacca ttcaagcaat cgatggcggc actccaccgc ttagcaacaa tgcatatgtg   10140
aacatctcta ttctggacat taatgacaac agtcccacgt ttctgcaaaa cctgtaccgc   10200
attaatgtca atgaagatat tttcgtgggc tccaagattc tggacgtcaa agccacggac   10260
gaagattcag atgtaaatgg tcttgtaact tacaacattg aaagaggcga caatataggc   10320
```

```
cagttttcaa tagatccgaa aaacggaaca attagcgttt cgaggccatt agatcgtgag   10380
actatttcgc actacactct tgaaattcaa gcctgtgatc agggagatcc tcagagatgc   10440
aacagtgttc caatcaatat aaacattttg gacactaacg ataatgcacc catattttcc   10500
agctctaact acagtgtagt acttcaagaa aaccgacttc tgggctatgt attccttacc   10560
ttcaagatat cagacgcaga cgaaacaccc aataccacgc catacacctt cgatattagg   10620
tctggaaatg agggtgggct tttccggctg gagcaagatg gttccttgag aacgcctcg    10680 cgatttaatc acaatctgca ggacgaattc gtgattcaag ttcgagtttt cgacaacggc   10740
acacctccat tatattccga tgcctgggtg gttgtgaaaa taattgaaga aagccaatac   10800
ccgcccattg tcacacccct agaagtaacc ataaattcat tcgaggacga ttttcgggc    10860 gcattcattg gcaaagttca tgcctcggat caggacaagt atgatgaatt gaactttagt   10920
ttggtgtccg gtcccgatga catgtatcag agctcgaagc tgttcaacat tccaacaac    10980 acggaaaga tctatgccat atccaacctg gatattggtc tgtacaagct aaatgtgtcc    11040
gtttcggatg gtaaatttca tgtgttctcc attgtcaaaa tcaacgtgga actggtaacc   11100
aatgatatgc taaagagtc ggttgtcatt cgattcagaa ggatttcagc atctgagttt    11160
ctgctgagtc acaggaaaac ctttatgcgc tccattcgca atataatgcg atgtcgccaa   11220
aaggatgtaa ttctcatcac ccttcaatcg gattatcaaa aagcatcaca acatgctgtg   11280
ggtaatcgac gagccaggtc cattgactcc gatttgaacg tggtgtttgc agtgcgaaag   11340
cagcaaataa tacccgattc cgatgaattc ttcacaagtg atgaaattcg gcagacactg   11400
atagacaaga agaacgagat tgaaaacgaa accaacctgg tggtggagga tgtactacca   11460
tccacctgtc aaagcaacaa aaacgactgc gttcacgggg aatgcaaaca gatattacag   11520
atcctgaaga acaacgttac caccacccttt acggatgtga ttagttttgc tgctccatct   11580
tacattccgg tgaatacgtg tgtctgtcga ccaggattcg atggaaagca ctgcaaagag   11640
actgtgaatg cctgctccac ggatccatgt tccccgcaga ggatctgcat gccgtctggc   11700
tcggctttgg gttaccaatg tgtgtgtccc aagggatttt caggaaccta ctgcgagcgg   11760
aagtcttcga agtgcagcaa tgagtcctgt gacatgggtc tattcactgc ggtgtccttt   11820
ggcggaaaga gctatgccca ctacaagatc aacaaggtga aggcgaagtt cacgctggaa   11880
aacgggtttt cctactccct gcagataaga actgtgcaac aaactgggac tctgctgtat   11940
gccagcggca aggtggacta caacatcctg gagatcataa acggagctgt tcagtacaga   12000
ttcgatttgg gctcgggcga gggagtcatc agtgtgtcca gcattaacat ctctgacggc   12060
gagtggcatc aaatcagcct agagcggtcc ctcaatagtg ccaaagtgat ggtggacaac   12120
aagcacgtct cccatggcag tgctccgggt gtgaatggca tcctgaacat ccagtcgaac   12180
gatatctttg taggcgccga ggttcgtccg catccatcga taattggcta cgaggatatt   12240
cagcgtggct tcatcggttg catggcaaac atcaaaatag ccaaagagtc gctgccattg   12300
tacatttccg gtgggagtac cattgctgcc ttgaaacgtt ttacgaatgt cgagttcaag   12360
tgcgatccgt cgaatgttct ggtgcgcctg gcatttgcg gatctcagcc gtgtgccaat    12420
agtggaatct gcaaggaact cgatacggac gtgtttgaat gcgcctgtca gccccgatat   12480
tccggcaagc attgcgagat tgatttggac ccttgctcat cgggaccctg cttgtttggc   12540
ggcaggtgcg actaccacgg accgaacaac tacagctgca cgtgtcccat ccacttatcc   12600
ggaaagaggt gtgagtacgg caagttctgc acgccgaacc cgtgcaaaaa cggtggcatt   12660
```

```
tgcgaggaag gcgatggaat atcgcactgc atgtgccgcg gctacacggg acccacttgt    12720
gagatcgatg tggatgagtg cgagaaccag ccgtgcggca atggagcgac ctgcatcaat    12780
gaacccggaa gtttccgttg catttgtcca tcttatctca caggagccag ctgcggcgat    12840
cccctgtatt cgaactctat ttctacaaag ctgaagaact tttctataga gcacattagc    12900
gggatcattt ccggcgtggc cgtggtactg gtcatcatca gttgtgtcct gtgttgcgtg    12960
gtgttgaaga ggagttcctc ttcaaagcga aggaaccgac tagaaaagga caagaacaag    13020
tcgtcgtaca aggaggcgaa cttgaactca ctggtggaca aggacaatta ctgcaaacca    13080
aacgtaaagt tgagtaactt ggaggttaac cagcgtccaa ttagctacac agcagttcca    13140
aatgacaacc tagtcctgag caataggaat tttgtaaata acttagacat cttgcgtagc    13200
tacggttcgg ccggcgatga actgaaaaat gtgccattcg agtaccgaaa ggttaatcga    13260
aacaaacagc atgtgaacat aaactcctgc cattcaaccg atgcagataa tgcctacaaa    13320
caagaatggt gcgagcaaat gcatttaaga accttcagtg aaaataaact gaacaatgaa    13380
cttaaacggg atttcggacc atctgtgagt cgcttttcaa ctgggaaact aatccaagtt    13440
gaaatgccca acgtgtgcca ctcttccagt gcgaatttcg ttgattattc agctcttgcc    13500
aatggtcagt atcattggga ctgttccgac tgggttcgca aaagccataa tcccttgcca    13560
gatataaccg aagttcctgg agcagaaata gctgattcgt cgagcttaca cagcaacgat    13620
agcaacgagt ccaagtcgaa gaaagccttt ttcgtgcaca gggaagacgg agatgttgat    13680
ccgacgaggg atatagccgc gttgaatgag gatatcggat cggagtattt ggactcggag    13740
gcagagagct gcttggagcc gtttatgttg ccaagatcaa gtaatcagcc actttcaaga    13800
ctgagttctt ttaataatat cgagaatgaa gactataaat caaatacagg caaagtatat    13860
ttaagcatca ctgattcgta tttaccgacg atgcattttc caagtgagac cgatggggaa    13920
agctctatga ccgaggggcc gatttctagg atggaaataa aaaccaggag gacgataagt    13980
gaaaattcag aggaggcata cctatttcca tgcactgtcg gagaaattgg atccaacagc    14040
aacatttcgg ttcgactgtg tgaaattgaa gattctgagt tggaggagtt tttaccacaa    14100
caacaaacaa acaattaa                                                 14118

<210> SEQ ID NO 14
<211> LENGTH: 1632
<212> TYPE: DNA
<213> ORGANISM: Saccharomyces cerevisiae

<400> SEQUENCE: 14
ctacaactta ctcttatttc tgctgctctt agcaaaagtt tctgcgataa ctcttctctg      60
gattttacct gtagcggttt ttggtagctt atcaacaaag tacaccttgg ttggaatttt     120
gaaagaggct aggtgcttct ttaagaagtt caccagttct tcgtaggtca ttttttctcc     180
cttcttcaaa acaatggcgg cttgaactac ttggccgtac atatcgtcgg gaacaccaaa     240
tgcaacggct tcatcgatct ttggatgcga tagcataatg ccgtcgagct caatgggtga     300
aatcttttca ccacccctgt tgataagctc tttgattctg cctgtaagga ccaaaaaccc     360
ctcagggtcg aaataacctt ggtcaccggt tctgaaatag ttctctctct tggtgaagtt     420
ctccttgtta gcttttggat tattagcata ccccaaagtg acgttttcgc ctctgatgga     480
aacttcgccg actttgcccg ggggcaagac attgtcattg tcatctagaa tgacgacggt     540
gactccttgt ggctggccca cagtaccagg ctttctcttt cctggaggca gattgtttga     600
ggtcatttga tgtgatgctt cggtcatcgc ataggcctcc aagacaggtg cattgaattc     660
```

```
cttctccagc ttatggaacg ttgctggagc caaagcagaa gaacacgatc tgatgaatct      720
aatgtgtggg aaagggtttg gtttgggcat gttcagcata atcatgctta ttgtgggaac      780
gcaactgaac caattacagt tgtacttaac aaattggtcc cagaataact ttggatggaa      840
tccatcggga accacaacag aaccctgagt tctaaaagtg gaaagtaaaa caccaattaa      900
cccatggacg tggaaaagag gcatcacgac ataagatctg tccaagggcg ttagcttgta      960
agtgttagca atgttcaacg tgcttctcac aatgttcaaa tgtaacaaag gcaccgtttt     1020
tggagtggag gtggtaccac tggtatgcaa aatcagggca acgtcactgg aacgggcaaa     1080
cccagggaat ttaacgggat ttgtgttgac aaatttggcg ttgttcaaag accggtaaat     1140
aacccttttg tagttgtcct ctggagagta tatatcatac tctaccctaa acctggtcgc     1200
atcgaaggcc agctctacga taaaacatcc aaacgtggag gcagatttta gaatttcaga     1260
actctgtaac tttgtggtac cctttgggac gcaaatcgcc ttagatttca ggtcattcaa     1320
ataaaaattg aactccttt ccttataatt gggattcaag ggcgcgccaa ttttagcgtc       1380
catagtagca ccgaggaaag cgacgataaa ttccagccca ttacgcatgg atatcgccac     1440
tgtatcttgt ctgaaaacag ctccgtacaa tggagaatta ggatttgtga acatggtctg     1500
gaagtgaccc accatgtggg atagatccct gtaggtcacc tgagtgtccg tttcaggaac     1560
aataacggcg acattatcgg atacgctaaa agtatcgttg aacgaagcag taacagtagc     1620
ggcacttgtc at                                                         1632

<210> SEQ ID NO 15
<211> LENGTH: 3473
<212> TYPE: DNA
<213> ORGANISM: Homo sapiens

<400> SEQUENCE: 15
gcgagccgat gggggcgggg aaaagtccgg ctgggccggg acaaaagccg gatcccggga       60
agctaccggc tgctggggtg ctccggattt tgcggggttc gtcgggcctg tggaagaagc      120
tgccgcgcac ggacttcggc agaggtagag caggtctctc tgcagccatg tcggccaagg      180
caatttcaga gcagacgggc aaagaactcc tttacaagtt catctgtacc acctcagcca      240
tccagaatcg gttcaagtat gctcgggtca ctcctgacac agactgggcc cgcttgctgc      300
aggaccaccc ctggctgctc agccagaact tggtagtcaa gccagaccag ctgatcaaac      360
gtcgtggaaa acttggtctc gttggggtca acctcactct ggatgggtc aagtcctggc       420 tgaagccacg gctgggacag gaagccacag ttggcaaggc cacaggcttc ctcaagaact      480
ttctgatcga gcccttcgtc ccccacagtc aggctgagga gttctatgtc tgcatctatg      540
ccacccgaga agggactac gtcctgttcc accacgaggg gggtgtggac gtgggtgatg        600
tggacgccaa ggcccagaag ctgcttgttg gcgtggatga gaaactgaat cctgaggaca      660
tcaaaaaaca cctgttggtc cacgcccctg aagacaagaa agaaattctg gccagtttta      720
tctccggcct cttcaatttc tacgaggact tgtacttcac ctacctcgag atcaatcccc      780
ttgtagtgac caaagatgga gtctatgtcc ttgacttggc ggccaaggtg gacgccactg      840
ccgactacat ctgcaaagtg aagtggggtg acatcgagtt ccctcccccc ttcgggcggg      900
aggcatatcc agaggaagcc tacattgcag acctcgatgc caaaagtggg gcaagcctga      960
agctgacctt gctgaacccc aaagggagga tctggaccat ggtggccggg ggtggcgcct     1020
ctgtcgtgta cagcgatacc atctgtgatc tagggggtgt caacgagctg gcaaactatg     1080
```

| | |
|---|---|
| gggagtactc aggcgccccc agcgagcagc agacctatga ctatgccaag actatcctct | 1140 |
| ccctcatgac ccgagagaag cacccagatg gcaagatcct catcattgga ggcagcatcg | 1200 |
| caaacttcac caacgtggct gccacgttca agggcatcgt gagagcaatt cgagattacc | 1260 |
| agggcccccct gaaggagcac gaagtcacaa tctttgtccg aagaggtggc cccaactatc | 1320 |
| aggagggctt acgggtgatg ggagaagtcg ggaagaccac tgggatcccc atccatgtct | 1380 |
| ttggcacaga gactcacatg acggccattg tgggcatggc cctgggccac cggcccatcc | 1440 |
| ccaaccagcc acccacagcg gcccacactg caaacttcct cctcaacgcc agcgggagca | 1500 |
| catcgacgcc agcccccagc aggacagcat cttttctga gtccagggcc gatgaggtgg | 1560 |
| cgcctgcaaa gaaggccaag cctgccatgc cacaagattc agtcccaagt ccaagatccc | 1620 |
| tgcaaggaaa gagcaccacc ctcttcagcc gccacaccaa ggccattgtg tgggcatgc | 1680 |
| agacccgggc cgtgcaaggc atgctggact ttgactatgt ctgctcccga gacgagccct | 1740 |
| cagtggctgc catggtctac ccttttcactg gggaccacaa gcagaagttt tactgggggc | 1800 |
| acaaagagat cctgatccct gtcttcaaga acatggctga tgccatgagg aagcacccgg | 1860 |
| aggtagatgt gctcatcaac tttgcctctc tccgctctgc ctatgacagc accatggaga | 1920 |
| ccatgaacta tgcccagatc cggaccatcg ccatcatagc tgaaggcatc cctgaggccc | 1980 |
| tcacgagaaa gctgatcaag aaggcggacc agaagggagt gaccatcatc ggacctgcca | 2040 |
| ctgttggagg catcaagcct gggtgcttta agattggcaa cacaggtggg atgctggaca | 2100 |
| acatcctggc ctccaaactg taccgcccag gcagcgtggc ctatgtctca cgttccggag | 2160 |
| gcatgtccaa cgagctcaac aatatcatct ctcggaccac ggatgcgtc tatgagggcg | 2220 |
| tggccattgg tgggacagg tacccggggct ccacattcat ggatcatgtg ttacgctatc | 2280 |
| aggacactcc aggagtcaaa atgattgtgg ttcttggaga gattggggc actgaggaat | 2340 |
| ataagatttg ccggggcatc aaggagggcc gcctcactaa gcccatcgtc tgctggtgca | 2400 |
| tcgggacgtg tgccaccatg ttctcctctg aggtccagtt tggccatgct ggagcttgtg | 2460 |
| ccaaccaggc ttctgaaaact gcagtagcca agaaccaggc tttgaaggaa gcaggagtgt | 2520 |
| ttgtgccccg gagcttttgat gagcttggag agatcatcca gtctgtatac gaagatctcg | 2580 |
| tggccaatgg agtcattgta cctgcccagg aggtgccgcc cccaaccgtg cccatggact | 2640 |
| actcctgggc cagggagctt ggttttgatcc gcaaacctgc ctcgttcatg accagcatct | 2700 |
| gcgatgagcg aggacaggag ctcatctacg cgggcatgcc catcactgag gtcttcaagg | 2760 |
| aagagatggg cattggcggg gtcctcggcc tcctctggtt ccagaaaagg ttgcctaagt | 2820 |
| actcttgcca gttcattgag atgtgtctga tggtgacagc tgatcacggg ccagccgtct | 2880 |
| ctggagccca caacaccatc atttgtgcgc gagctgggaa agacctggtc tccagcctca | 2940 |
| cctcggggct gctcaccatc ggggatcggt ttggggtgc cttggatgca gcagccaaga | 3000 |
| tgttcagtaa agccttttgac agtggcatta tccccatgga gtttgtgaac aagatgaaga | 3060 |
| aggaagggaa gctgatcatg ggcattggtc accgagtgaa gtcgataaac aacccagaca | 3120 |
| tgcgagtgca gatcctcaaa gattacgtca ggcagcactt ccctgccact cctctgctcg | 3180 |
| attatgcact ggaagtagag aagattacca cctcgaagaa gccaaatctt atcctgaatg | 3240 |
| tagatggtct catcggagtc gcatttgtag acatgcttag aaactgtggg tcctttactc | 3300 |
| gggaggaagc tgatgaatat attgacattg gagccctcaa tggcatcttt gtgctgggaa | 3360 |
| ggagtatggg gttcattgga cactatcttg atcagaagag gctgaagcag gggctgtatc | 3420 |
| gtcatccgtg ggatgatatt tcatatgttc ttccggaaca catgagcatg taa | 3473 |

<210> SEQ ID NO 16
<211> LENGTH: 1086
<212> TYPE: DNA
<213> ORGANISM: Mycobacterium bovid subsp.bovis

<400> SEQUENCE: 16

| | | | | | | |
|---|---|---|---|---|---|---|
| atgagtcaga | cggtgcgcgg | tgtgatcgca | cgacaaaagg | gcgaacccgt | tgagctggtg | 60 |
| aacattgtcg | tcccggatcc | cggacccggc | gaggccgtgg | tcgacgtcac | cgcctgcggg | 120 |
| gtatgccata | ccgacctgac | ctaccgcgag | ggcggcatca | cgacgaata | cccttttctg | 180 |
| ctcggacacg | aggccgcggg | catcatcgag | gccgtcgggc | cggtgtaac | cgcagtcgag | 240 |
| cccggcgact | tcgtgatcct | gaactggcgt | gccgtgtgcg | gccagtgccg | ggcctgcaaa | 300 |
| cgcggacggc | cccgctactg | cttcgacacc | tttaacgccg | aacagaagat | gacgctgacc | 360 |
| gacggcaccg | agctcactgc | ggcgttgggc | atcggggcct | ttgccgataa | gacgctggtg | 420 |
| cactctggcc | agtgcacgaa | ggtcgatccg | gctgccgatc | ccgcggtggc | cggcctgctg | 480 |
| ggttgcgggg | tcatggccgg | cctgggcgcc | gcgatcaaca | ccggcggggt | aacccgcgac | 540 |
| gacaccgtcg | cggtgatcgg | ctgcggcggc | gttggcgatg | ccgcgatcgc | cggtgccgcg | 600 |
| ctggtcggcg | ccaaacggat | catcgcggtc | gacaccgatg | acacgaagct | tgactgggcc | 660 |
| cgcaccttcg | cgccacccca | caccgtcaac | gcccgcgaag | tcgacgtcgt | ccaggccatc | 720 |
| ggcggcctca | cggatggatt | cggcgcggac | gtggtgatcg | acgccgtcgg | ccgaccggaa | 780 |
| acctaccagc | aggccttcta | cgcccgcgat | ctcgccggaa | ccgttgtgct | ggtgggtgtt | 840 |
| ccgacgcccg | acatgcgcct | ggacatgccg | ctggtcgact | tcttctctca | cggcggtgcg | 900 |
| ctgaagtcgt | cgtggtacgg | cgattgcctg | cccgaaagcg | acttccccac | gctgatcgac | 960 |
| cttttacctgc | agggccggct | gccgctgcag | cggttcgttt | ccgaacgcat | cgggctcgaa | 1020 |
| gacgtcgagg | aggcgttcca | caagatgcat | ggcggcaagg | tattgcgttc | ggtggtgatg | 1080 |
| ttgtga | | | | | | 1086 |

<210> SEQ ID NO 17
<211> LENGTH: 1713
<212> TYPE: DNA
<213> ORGANISM: Homo sapiens

<400> SEQUENCE: 17

| | | | | | | |
|---|---|---|---|---|---|---|
| agttcctgga | gaaagatggc | gacagccgag | aagcagaaac | acgacgggcg | ggtgaagatc | 60 |
| ggccactaca | ttctgggtga | cacgctgggg | gtcggcacct | tcggcaaagt | gaaggttggc | 120 |
| aaacatgaat | tgactgggca | taaagtagct | gtgaagatac | tcaatcgaca | gaagattcgg | 180 |
| agccttgatg | tggtaggaaa | aatccgcaga | gaaattcaga | acctcaagct | tttcaggcat | 240 |
| cctcatataa | ttaaactgca | ccaggtcatc | agtacaccat | ctgatatttt | catggtgatg | 300 |
| gaatatgtct | caggaggaga | gctatttgat | tatatctgta | agaatggaag | gaatctgat | 360 |
| gtacctggag | tagtaaaaac | aggctccacg | aaggagctgg | atgaaaaaga | aagtcggcgt | 420 |
| ctgttccaac | agatcctttc | tggtgtggat | tattgtcaca | ggcatatggt | ggtccataga | 480 |
| gatttgaaac | ctgaaaatgt | cctgcttgat | gcacacatga | atgcaaagat | agctgatttt | 540 |
| ggtctttcaa | acatgatgtc | agatggtgaa | ttttttaagaa | caagttgtgg | ctcacccaac | 600 |
| tatgctgcac | cagaagtaat | tcaggaagaa | ttgtatgcag | gccagagggt | agatatatgg | 660 |
| agcagtgggg | ttattctcta | tgctttatta | tgtggaaccc | ttccatttga | tgatgaccat | 720 |

```
gtgccaactc ttttttaagaa gatatgtgat gggatcttct atacccctca atatttaaat    780
ccttctgtga ttagccttt gaaacatatg ctgcaggtgg atcccatgaa gagggccaca    840
atcaaagata tcagggaaca tgaatggttt aaacaggacc ttccaaaata tctcttttcct    900 gaggatccat catatagttc aaccatgatt gatgatgaag ccttaaaaga agtatgtgaa    960
aagtttgagt gctcagaaga ggaagttctc agctgtcttt acaacagaaa tcaccaggat   1020
cctttggcag ttgcctacca tctcataata gataacagga gaataatgaa tgaagccaaa   1080
gatttctatt tggcgacaag cccacctgat tctttcttg atgatcatca cctgactcgg    1140
ccccatcctg aaagagtacc attcttggtt gctgaaacac caagggcacg ccatacccctt   1200 gatgaattaa atccacagaa atccaaacac caaggtgtaa ggaaagcaaa atggcattta   1260
ggaattagaa gtcaaagtcg accaaatgat attatggcag aagtatgtag agcaatcaaa   1320
caattggatt atgaatggaa ggttgtaaac ccatattatt tgcgtgtacg aaggaagaat   1380
cctgtgacaa gcacttactc caaaatgagt ctacagttat accaagtgga tagtagaact   1440
tatctactgg atttccgtag tattgatgat gaaattacag aagccaaatc agggactgct   1500
actccacaga gatcgggatc agttagcaac tatcgatctt gccaaggag tgattcagat    1560 gctgaggctc aaggaaaatc ctcagaagtt tctcttacct catctgtgac ctcacttgac   1620
tcttctcctg ttgacctaac tccaagacct ggaagtcaca caatagaatt ttttgagatg   1680
tgtgcaaatc taattaaaat tcttgcacaa taa                                  1713

<210> SEQ ID NO 18
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 18
aatggtgaaa aacgtggacc aagtgga                                           27

<210> SEQ ID NO 19
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 19
atggatccct aagcagccat gccagacata c                                      31

<210> SEQ ID NO 20
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 20
aatggagccc agcagcaaga aggtga                                            26

<210> SEQ ID NO 21
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 21
```

-continued

```
aatgggtacc tcacacttgg gagtcagcc                                              29

<210> SEQ ID NO 22
<211> LENGTH: 21
<212> TYPE: DNA
<213> ORGANISM: Artificial sequence
<220> FEATURE:
<223> OTHER INFORMATION: syntehtic polynucleotide

<400> SEQUENCE: 22
agagaccggg ttggcggcgc a                                                      21

<210> SEQ ID NO 23
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 23
cagcgtcttg agcgtacaaa                                                        20

<210> SEQ ID NO 24
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 24
aatgatcatc aacggcaagg tct                                                    23

<210> SEQ ID NO 25
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 25
ttatttctga ccctggaggt agaag                                                  25

<210> SEQ ID NO 26
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 26
aatgctgaag ttccgaacag t                                                      21

<210> SEQ ID NO 27
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 27
cgatggtacc tcactcgatc tccaggatg                                              29

<210> SEQ ID NO 28
<211> LENGTH: 2040
<212> TYPE: DNA
```

<213> ORGANISM: Artificial sequence
<220> FEATURE:
<223> OTHER INFORMATION: recombinant polynucleotide

<400> SEQUENCE: 28

```
ccaacagacc gaccatagaa atggattcga ccacgcagac caacaccggc accggcaagg      60
tggccgtgca gccccccacg gccttcatta agcccattga gaaggtgtcc gagcccgtct     120
acgacacctt tggcaacgag ttcactcctc cagactactc tatcaaggat attctggatg     180
ccattcccca ggagtgctac aagcggtcct acgttaagtc ctactcgtac gtggcccgag     240
actgcttctt tatcgccgtt tttgcctaca tggcctacgc gtacctgcct cttattccct     300
cggcttccgg ccgagctgtg gcctgggcca tgtactccat tgtccagggt ctgtttggca     360
ccggtctgtg ggttcttgcc cacgagtgtg gccactctgc tttctccgac tctaacaccg     420
agagaccggg ttggcggcgc atttgtgtcc caaaaaacag ccccaattgc cccaattgac     480
cccaaattga cccagtagcg ggcccaaccc cggcgagagc ccccttcacc ccacatatca     540
aacctccccc ggttcccaca cttgccgtta agggcgtagg gtactgcagt ctggaatcta     600
cgcttgttca gactttgtac tagtttcttt gtctggccat ccgggtaacc catgccggac     660
gcaaaataga ctactgaaaa tttttttgct ttgtggttgg gactttagcc aagggtataa     720
aagaccaccg tccccgaatt acctttcctc ttcttttctc tctctccttg tcaactcaca     780
cccgaaatcg ttaagcattt ccttctgagt ataagaatca ttcaaaatgg ccaagttgac     840
cagtgccgtt ccggtgctca ccgcgcgcga cgtcgccgga gcggtcgagt tctggaccga     900
ccggctcggg ttctcccggg acttcgtgga ggacgacttc gccggtgtgg tccgggacga     960
cgtgaccctg ttcatcagcg cggtccagga ccaggtggtg ccggacaaca ccctggcctg    1020
ggtgtgggtg cgcggcctgg acgagctgta cgccgagtgg tcggaggtcg tgtccacgaa    1080
cttccgggac gcctccgggc cggccatgac cgagatcggc gagcagccgt gggggcggga    1140
gttcgccctg cgcgacccgg ccggcaactg cgtgcacttc gtggccgagg agcaggactg    1200
atccatggcc tgtccccacg ttgccggtct tgcctcctac tacctgtcca tcaatgacga    1260
ggttctcacc cctgcccagg tcgaggctct tattactgag tccaacaccg gtgttcttcc    1320
caccaccaac ctcaagggct ctcccaacgc tgttgcctac aacggtgttg gcatttaggc    1380
aattaacaga tagtttgccg gtgataattc tcttaacctc ccacactcct ttgacataac    1440
gatttatgta acgaaactga aatttgacca gatattgttg taaatagaaa atctggcttg    1500
taggtggcaa aatgcggcgt cttttgttcat caattccctc tgtgactact cgtcatccct    1560
ttatgttcga ctgtcgtatt tcttattttc catacatatg caagtgagat gcccgtgtcc    1620
tggccatcac ctacctgcag cacaccgacc ccactctgcc ccactaccac gccgaccagt    1680
ggaacttcac ccgaggagcc gccgccacca tcgaccgaga gtttggcttc atcggctcct    1740
tctgcttcca tgcatcatc gagacccacg ttctgcacca ctacgtgtct cgaattccct    1800
tctacaacgc ccgaatcgcc actgagaaga tcaagaaggt catgggcaag cactaccgac    1860
acgacgacac caacttcatc aagtctcttt acactgtcgc ccgaacctgc cagtttgttg    1920
aaggtaagga aggcattcag atgtttagaa acgtcaatgg agtcggagtt gctcctgacg    1980
gcctgccttc taaaaagtag agctagaaat gttatttgat tgtgttttaa ctgaacagca    2040
```